(12) United States Patent
Ryan

(10) Patent No.: US 8,039,602 B2
(45) Date of Patent: Oct. 18, 2011

(54) ISOLATED GENOMIC POLYNUCLEOTIDE FRAGMENTS FROM THE P15 REGION OF CHROMOSOME 11

(75) Inventor: James W. Ryan, Augusta, GA (US)

(73) Assignee: Ryogen LLC, Suffern, NY (US)

( * ) Notice: Subject to any disclaimer, the term of this patent is extended or adjusted under 35 U.S.C. 154(b) by 702 days.

(21) Appl. No.: 09/999,121

(22) Filed: Oct. 31, 2001

(65) Prior Publication Data

US 2003/0039982 A1 Feb. 27, 2003

Related U.S. Application Data

(60) Provisional application No. 60/244,705, filed on Oct. 31, 2000.

(51) Int. Cl.
*C07H 21/02* (2006.01)
*C07H 21/04* (2006.01)
*C12Q 1/68* (2006.01)
*C12P 19/34* (2006.01)
*C12N 5/00* (2006.01)

(52) U.S. Cl. .................. 536/23.1; 536/24.3; 536/24.33; 536/24.5; 435/6; 435/91.1; 435/325; 435/375

(58) Field of Classification Search ................ 536/23.1, 536/24.3, 24.33, 24.5; 435/6, 91.1, 325, 435/375
See application file for complete search history.

(56) References Cited

U.S. PATENT DOCUMENTS

| 5,591,623 A * | 1/1997 | Bennett et al. ................ 435/375 |
| 6,184,212 B1 * | 2/2001 | Miraglia et al. ................ 514/44 |
| 6,566,135 B1 * | 5/2003 | Watt .............................. 435/455 |
| 6,812,339 B1 * | 11/2004 | Venter et al. ............... 536/24.31 |

FOREIGN PATENT DOCUMENTS

| WO | WO95/20678 | | 8/1995 |
| WO | WO 99/18198 | * | 4/1999 |
| WO | WO/0015795 A | | 3/2000 |
| WO | WO0162778 A | | 8/2001 |

OTHER PUBLICATIONS

Oren et al. TAPA-1, the target of an antiporliferative antibody, defines a new family of transmembrane proteins. Molecular and Cellular Biology, 1990 vol. 10:4007-4015.*
Waterston, R.H., (PubMed sequence AC026645, submitted Mar. 22, 2000, bases 2312-4001).*
Burge et al. Prediction of complete gene structures in human genomic DNA. J. Mol. Biol. 268:78-94.*
Altschul et al. Gapped BLAST and PSI-BLAST: a new generationof protein database search programs. Nucl. Acids Res. 25: 3389-3402.*
Virtaneva et al. Chromosoma localization of three human genes coding for A15, L6, and S5.7 (TAPA1): all members of the transmembrane 4 superfamily of proteins. Immunogenetics, 1994 vol. 39:329-334.*
Siebert et al. An improved PCR method for walking in uncloned genomic DNA. Nucleic Acids Research, 1995 vol. 23:1087-1088.*
Bowie et al., 1990. Science, vol. 247, pp. 1306-1310. Deciphering the Message in Protein Sequences: Tolerance to Amino Acid Substitutions.*
Ngo et al., 1994. The Protein Folding Problem and Tertiary Structure Prediction. Computational Complexity, Protein Structure Prediction, and the Levinthal Paradox.*
Human Chromosome 11p15.5 PAC clone pDJ915f1 containing KvLQT1 gene, complete sequence, Accession AC003693, PRI Sep. 30, 1998.*
601346329F1 NIH_MGC_8 Homo sapiens cDNA clone IMAGE:3679567 5-, mRNA sequence, Accession BE560890, Entry Created: Aug. 10, 2000.*
601174248F1 NIH_MGC_17 Homo sapiens cDNA clone IMAGE:3529954 5-, mRNA sequence, Accession BE295955, Entry Created: Jul. 5, 2000.*
Andria et al. (J. Immun., 1991 vol. 147:1030-1036).*
Burge et al. Prediction of complete gene structures in human genomic DNA. J Mol Biol. Apr. 25, 1997;268(1):78-94.*
Altschul et al. Gapped BLAST and PSI-BLAST: a new generation of protein database search programs. Nucleic Acids Res. Sep. 1, 1997;25(17):3389-402.*
Alders et al., Human Molecular Genetics, 1997, 6:859-867.
Westerman et al., Placenta, 2001, 22:511-518.
Database EMBL 'Online! 1997, "Human chromosome 11pac pdJ1075f20" see nucleotides 17080-34380.
Kenmochi et al., 1998, Genome Research 8:509-523.
Reik et al., 1997, Trends in Genetics, 13:330-334.
Lee et al., 1999, Hum.Mol.Gen., 8:683-690.
Koi et al., 1993, Science, 260:361-364.
Pileri et al., 1998, Science, 282:938-941.
Segade et al., 1996, Life Sciences, 58:277-285.
Witherden et al., 2000, J. Immum. 165:1902-1909.

* cited by examiner

*Primary Examiner* — Terra Cotta Gibbs
(74) *Attorney, Agent, or Firm* — Cheryl H. Agris

(57) ABSTRACT

The invention is directed to isolated genomic polynucleotide fragments from the p15 arm of chromosome 11.

18 Claims, No Drawings

SEQUENCE LISTING

<160> NUMBER OF SEQ ID NOS: 14

<210> SEQ ID NO 1
<211> LENGTH: 193
<212> TYPE: PRT
<213> ORGANISM: Homo sapiens

<400> SEQUENCE: 1

Met Asp Gly Gly Thr Leu Pro Arg Ser Ala Pro Pro Ala Pro Pro Val
1               5                   10                  15

Pro Val Gly Cys Ala Ala Arg Arg Pro Ala Ser Pro Glu Leu Leu
            20                  25                  30

Arg Cys Ser Arg Arg Arg Pro Ala Thr Ala Glu Thr Gly Gly Gly
        35                  40                  45

Ala Ala Ala Val Ala Arg Arg Asn Glu Arg Glu Arg Asn Arg Val Lys
    50                  55                  60

Leu Val Asn Leu Gly Phe Gln Ala Leu Arg Gln His Val Pro His Gly
65                  70                  75                  80

Gly Ala Ser Lys Lys Leu Ser Lys Val Glu Thr Leu Arg Ser Ala Val
                85                  90                  95

Glu Tyr Ile Arg Ala Leu Gln Arg Leu Leu Ala Glu His Asp Ala Val
            100                 105                 110

Arg Asn Ala Leu Ala Gly Gly Leu Arg Pro Gln Ala Val Arg Pro Ser
        115                 120                 125

Ala Pro Arg Gly Pro Gly Thr Thr Pro Val Ala Ala Ser Pro Ser
    130                 135                 140

Arg Ala Ser Ser Pro Gly Arg Gly Gly Ser Ser Glu Pro Gly Ser
145                 150                 155                 160

Pro Arg Ser Ala Tyr Ser Ser Asp Asp Ser Gly Cys Glu Gly Ala Leu
                165                 170                 175

Ser Pro Ala Glu Arg Glu Leu Leu Asp Phe Ser Ser Trp Leu Gly Gly
            180                 185                 190

Tyr

<210> SEQ ID NO 2
<211> LENGTH: 132
<212> TYPE: PRT
<213> ORGANISM: Homo sapiens

<400> SEQUENCE: 2

Met Gly Arg Thr Trp Cys Gly Met Trp Arg Arg Arg Pro Gly Arg
1               5                   10                  15

Arg Ser Ala Val Pro Arg Trp Pro His Leu Ser Ser Gln Ser Gly Val
            20                  25                  30

Glu Pro Pro Asp Arg Trp Thr Gly Thr Pro Gly Trp Pro Ser Arg Asp
        35                  40                  45

Gln Glu Ala Pro Gly Ser Met Met Pro Pro Ala Ala Ala Gln Pro Ser
    50                  55                  60

Ala His Gly Ala Leu Val Pro Pro Ala Thr Ala His Glu Pro Val Asp
65                  70                  75                  80

His Pro Ala Leu His Trp Leu Ala Cys Cys Cys Leu Ser Leu Pro
                85                  90                  95

Gly Gln Leu Pro Leu Ala Ile Arg Leu Gly Trp Asp Leu Asp Leu Glu
            100                 105                 110

Ala Gly Pro Ser Ser Gly Lys Leu Cys Pro Arg Ala Arg Arg Trp Gln

```
                115             120             125
Pro Leu Pro Ser
        130

<210> SEQ ID NO 3
<211> LENGTH: 290
<212> TYPE: PRT
<213> ORGANISM: Homo sapiens

<400> SEQUENCE: 3

Met Val Thr Leu Thr Tyr Phe Gly Ala His Phe Ala Val Ile Arg Arg
1               5                   10                  15

Ala Ser Leu Glu Lys Asn Pro Tyr Gln Ala Val His Gln Trp Ala Phe
            20                  25                  30

Ser Ala Gly Leu Ser Leu Val Gly Leu Leu Thr Leu Gly Ala Val Leu
        35                  40                  45

Ser Ala Ala Ala Thr Val Arg Glu Ala Gln Gly Leu Met Ala Gly Gly
    50                  55                  60

Phe Leu Cys Phe Ser Leu Ala Phe Cys Ala Gln Val Gln Val Val Phe
65                  70                  75                  80

Trp Arg Leu His Ser Pro Thr Gln Val Glu Asp Ala Met Leu Asp Thr
                85                  90                  95

Tyr Asp Leu Val Tyr Glu Gln Ala Met Lys Gly Thr Ser His Val Arg
            100                 105                 110

Arg Gln Glu Leu Ala Ala Ile Gln Asp Val Phe Leu Cys Cys Gly Lys
        115                 120                 125

Lys Ser Pro Phe Ser Arg Leu Gly Ser Thr Glu Ala Asp Leu Cys Gln
    130                 135                 140

Gly Glu Glu Ala Ala Arg Glu Asp Cys Leu Gln Gly Ile Arg Ser Phe
145                 150                 155                 160

Leu Arg Thr His Gln Gln Val Ala Ser Ser Leu Thr Ser Ile Gly Leu
                165                 170                 175

Ala Leu Thr Val Ser Ala Leu Leu Phe Ser Ser Phe Leu Trp Phe Ala
            180                 185                 190

Ile Arg Cys Gly Cys Ser Leu Asp Arg Lys Gly Lys Tyr Thr Leu Thr
        195                 200                 205

Pro Arg Ala Cys Gly Arg Gln Pro Gln Glu Pro Ser Leu Leu Arg Cys
    210                 215                 220

Ser Gln Gly Gly Pro Thr His Cys Leu His Ser Glu Ala Val Ala Ile
225                 230                 235                 240

Gly Pro Arg Gly Cys Ser Gly Ser Leu Arg Trp Leu Gln Glu Ser Asp
                245                 250                 255

Ala Ala Pro Leu Pro Leu Ser Cys His Leu Ala Ala His Arg Ala Leu
            260                 265                 270

Gln Gly Arg Ser Arg Gly Gly Leu Ser Gly Cys Pro Glu Arg Gly Leu
        275                 280                 285

Ser Asp
    290

<210> SEQ ID NO 4
<211> LENGTH: 145
<212> TYPE: PRT
<213> ORGANISM: Homo sapiens

<400> SEQUENCE: 4

Met Lys Phe Asn Pro Phe Val Thr Ser Asp Arg Ser Lys Asn Arg Lys
1               5                   10                  15
```

```
Arg His Phe Asn Ala Pro Ser His Val Arg Arg Lys Ile Met Ser Ser
                20                  25                  30

Pro Leu Ser Lys Glu Leu Arg Gln Lys Tyr Asn Val Arg Ser Met Pro
            35                  40                  45

Ile Arg Lys Asp Asp Glu Val Gln Val Val Arg Gly His Tyr Lys Gly
        50                  55                  60

Gln Gln Ile Gly Lys Val Val Gln Val Tyr Arg Lys Lys Tyr Val Ile
65                  70                  75                  80

Tyr Ile Glu Arg Val Gln Arg Glu Lys Ala Asn Gly Thr Thr Val His
                85                  90                  95

Val Gly Ile His Pro Ser Lys Val Val Ile Thr Arg Leu Lys Leu Asp
            100                 105                 110

Lys Asp Arg Lys Lys Ile Leu Glu Arg Lys Ala Lys Ser Arg Gln Val
        115                 120                 125

Gly Lys Glu Lys Gly Lys Tyr Lys Glu Glu Leu Ile Glu Lys Met Gln
130                 135                 140

Glu
145

<210> SEQ ID NO 5
<211> LENGTH: 236
<212> TYPE: PRT
<213> ORGANISM: Homo sapiens

<400> SEQUENCE: 5

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
                20                  25                  30

Leu Trp Leu Arg His Asp Pro Gln Thr Thr Asn Leu Leu Tyr Leu Glu
            35                  40                  45

Leu Gly Asp Lys Pro Ala Pro Asn Thr Phe Tyr Val Gly Ile Tyr Ile
        50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
        115                 120                 125

Gln Ala Leu Gln Gln Ala Val Val Asp Asp Asp Ala Asn Asn Ala Lys
130                 135                 140

Ala Val Val Lys Thr Phe His Glu Thr Leu Asp Cys Cys Gly Ser Ser
145                 150                 155                 160

Thr Leu Thr Ala Leu Thr Thr Ser Val Leu Lys Asn Asn Leu Cys Pro
                165                 170                 175

Ser Gly Ser Asn Ile Ile Ser Asn Leu Phe Lys Glu Asp Cys His Gln
            180                 185                 190

Lys Ile Asp Asp Leu Phe Ser Gly Lys Leu Tyr Leu Ile Gly Ile Ala
        195                 200                 205

Ala Ile Val Val Ala Val Ile Met Ile Phe Glu Met Ile Leu Ser Met
210                 215                 220

Val Leu Cys Cys Gly Ile Arg Asn Ser Ser Val Tyr
225                 230                 235
```

<210> SEQ ID NO 6
<211> LENGTH: 329
<212> TYPE: PRT
<213> ORGANISM: Homo sapiens

<400> SEQUENCE: 6

Met Ala Glu Ala Gly Thr Gly Glu Pro Ser Pro Ser Val Glu Gly Glu
1               5                   10                  15

His Gly Thr Glu Tyr Asp Thr Leu Pro Ser Asp Thr Val Ser Leu Ser
            20                  25                  30

Asp Ser Asp Ser Asp Leu Ser Leu Pro Gly Ala Glu Val Glu Ala
        35                  40                  45

Leu Ser Pro Met Gly Leu Pro Gly Glu Glu Asp Ser Gly Pro Asp Glu
50                  55                  60

Pro Pro Ser Pro Ser Gly Phe Leu Pro Ala Thr Val Gln Pro Phe
65                  70                  75                  80

His Leu Arg Gly Met Ser Ser Thr Phe Ser Gln Arg Ser Arg Asp Ile
                85                  90                  95

Phe Asp Cys Leu Glu Gly Ala Ala Arg Arg Gly Pro Ser Ser Val Ala
            100                 105                 110

His Thr Ser Met Ser Asp Asn Gly Gly Phe Lys Arg Pro Leu Ala Pro
        115                 120                 125

Ser Gly Arg Ser Pro Val Glu Gly Leu Gly Arg Ala His Arg Ser Pro
130                 135                 140

Ala Ser Pro Arg Val Pro Pro Val Pro Asp Tyr Val Ala His Pro Glu
145                 150                 155                 160

Arg Trp Thr Lys Tyr Ser Leu Glu Asp Val Thr Glu Val Ser Glu Gln
                165                 170                 175

Ser Asn Gln Ala Thr Ala Leu Ala Phe Leu Gly Ser Gln Ser Leu Ala
            180                 185                 190

Ala Pro Thr Asp Cys Val Ser Ser Phe Asn Gln Asp Pro Ser Ser Cys
        195                 200                 205

Gly Glu Gly Arg Val Ile Phe Thr Lys Pro Val Arg Gly Val Glu Ala
210                 215                 220

Arg His Glu Arg Lys Arg Val Leu Gly Lys Val Gly Glu Pro Gly Arg
225                 230                 235                 240

Gly Gly Leu Gly Asn Pro Ala Thr Asp Arg Gly Glu Gly Pro Val Glu
                245                 250                 255

Leu Ala His Leu Ala Gly Pro Gly Ser Pro Glu Ala Glu Glu Trp Gly
            260                 265                 270

Ser Pro His Gly Gly Leu Gln Glu Val Glu Ala Leu Ser Gly Ser Val
        275                 280                 285

His Ser Gly Ser Val Pro Gly Leu Pro Pro Val Glu Thr Val Gly Phe
290                 295                 300

His Gly Ser Arg Lys Arg Ser Arg Asp His Phe Arg Asn Lys Ser Ser
305                 310                 315                 320

Ser Pro Glu Asp Pro Gly Ala Glu Val
                325

<210> SEQ ID NO 7
<211> LENGTH: 17290
<212> TYPE: DNA
<213> ORGANISM: Homo sapiens

<400> SEQUENCE: 7

| | |
|---|---|
| gcccctgcct ggatcacaac aggcaggacg gctgagcagg cacacatctg tctctccctc | 60 |
| tgctgatctg tggccttgga caggggctac tctgggggag ctgacaggtg acccccccag | 120 |
| gaggcccctc cctgcctctg ggctgggaat ccacctctgt ggagccctg gaatggcct | 180 |
| gtttcaaata cgtaagtggg agcaaggtct catcctcagc gggggacatc gctgggggca | 240 |
| aggccagtgg gtgggtggga aggtttctgt ggcactgggg cctcctgttg attgattcac | 300 |
| ccaattaatc acagccagca gctggggagg gggtaggaag gcggtgaagg gaaaaggagc | 360 |
| ccacagccgg gaggccctgg gaggttggca gaggcctgca cctgcctgca gccagccctc | 420 |
| cggcccagcc ctcttccctc ctttcggagg gccagagca tggggtgcta agggctcagt | 480 |
| ctttaaccc tccccagctc tcagggagcc cctcccatgc tccccaggcc tctgcccac | 540 |
| ttgcacctcc ccgggcccca gggcacagga cgctttcccc acccttggg aggctgaggg | 600 |
| tgtcaggagg cctgggctga gtgctggctt ccgtctcact ggcttgcaga caagaccctc | 660 |
| catttcggtg gaaaaacagc aagaacagca ccccctcca ggcagaccca agggaggcat | 720 |
| cggtgtgagg gcttcaagct ctgtactgtg ggtttaagcc ttgcacctct ggatacctgt | 780 |
| gggcctcggg cagatcactg agcctccctg catctggaag tcggggtgag acccctcaga | 840 |
| gggggctggg aggaggaagg gcccctcttg atgggcagcc cccaccctcc acctactgcc | 900 |
| ctgccctccc agccttcagg gtcctcccca gcttctgtgg gctcccaggt ggacctgggc | 960 |
| caccctgag accccgaaga gctcaaggcc agctaatagc ccacaggctc aggacagcac | 1020 |
| tggacaggcc tctgggccca cctgccccca ctcccgattt tatgggaac aaagactgaa | 1080 |
| ggtgtggccc caaaggaacc acccctcccc cagtgccccg ctgctgggaa aagggtcagc | 1140 |
| agagtttggg tctcccccca caagccctct gggctgtgcg tgctacagct gaggacatgg | 1200 |
| cgttgagggg caggccgcct ccaacccccgt ccaccttgcc ctgtctagct ctgtccaagg | 1260 |
| ctctctccgg ctggctaatc acctctgggc acagctgtgc tgctgaggtc tctgggatga | 1320 |
| ctgaaggtct ttgaaggcca cttgggaga agcgaaggtg catggacacc agggaccctg | 1380 |
| ctcacagcga gtgtccctgc cccatcccctt tctgcattga gtgggacaag cttgcttcca | 1440 |
| tttgggggat cgccatctga ctattccact tgtcttaggg tggggcagag attaggtgat | 1500 |
| gtggaggggc ttctctacat ggccccctg ccccagctct gaggggtagc accagagtgg | 1560 |
| gtttcaccag cgtagggcac gtaggccccg ccatgaacag ggcccaacc ttggtttaat | 1620 |
| gctttgctac tgccatctta aagttcttt tttatttt attttgcttt attttttatt | 1680 |
| agagatgggg tctcccagtg ttgcccaggc tggtcttgaa ctcctggctc aagcaatcct | 1740 |
| ccggcctcag cctcccaaag cactgggatg acacgtgtga gccaccttgc ctggcctttg | 1800 |
| gaatctgact actttatct tctaacttgt tttgcaggtg caggccaacg gcatacagca | 1860 |
| gcactcacat aagcaaagga gagcgtgcac aaggcgccaa atgtatatcc accctcactc | 1920 |
| gtcccccac ttgagtagcg catccacgat gcccacagac accaggccac acagaaaagg | 1980 |
| tgccagggac ccacagcagt gcaaggcagc gtgtcacacc tacgcatgag caagccgggc | 2040 |
| gctgatggcc accgagcagc cacgttttcc attcaaatcc gcacttgcta aggatgcagc | 2100 |
| aggaagccag tggtgttcta caaacgtgc aggacccggg aacctgtcat gtcctttctt | 2160 |
| acttgtgcga cttctctgtg ttagccgagg tctcttgctg atggatctac ccacagtgcc | 2220 |
| ttttgtcttt gaacttgtcc cttcctcct tcctcgccca tcagcgagca ggaggtggag | 2280 |
| ggtgctggtg gaacaagcct gcgtcaagga gtgaaatcag ctgatttcat ttttgtgcag | 2340 |
| tttccactgt tctagtagca aatgaaatag agacgcctgt gccaggacaa aacacacact | 2400 |

```
gtgtcattcc agtgattccg catagaagtt aaatgctctt atgcttgcat tttaaactgg    2460
catcacataa tataaagatg gataaactaca ttcacgctag tcacttaaat tcctaatctt   2520
tcttactcag aatggcatta aatagtgagt ataaaataag aagtataaaa tagtaagtca    2580
agaggttgac tatagaagaa agaaaaatgc tttatatttt agcaccttga acatgacatc    2640
acgatcacct tctccctgga atcagtttct aacttccagg tggggactag gcctggacca    2700
tgagctccta gcagagccct gctgccccca cagcagagcc caggacaggc tggcacctgg    2760
gccaggtgag gctctgtcca ggctcactga tctcaaatgc tgaactgcta aggatgtcat    2820
gtccccaaag gagccgccag gctcagcctc acttcctgga aggcgtgaac attgcaagaa    2880
tgtggaagtg aaagagtcca gggcttaaat ctcaattctc atcattttca agctgagtcc    2940
aagggagaga agacagtcat ggattcttag tttctgtttc tggttgagcc agcagggtcc    3000
cttcctcatc cctctttcct gcttatcact agagacagaa actaaaacca tgactttagg    3060
ctgctgagag cctaaaacaa aacgacagca agagaaggtg ggttggacca gcttgcctgt    3120
gacttcaggc acttcatctt tactgggcac tgggtgaatg acagtgtggg gagggtctt    3180 cataacacgg caatcagcag cccactgtgc ccaggagact cgcctgtggt cctggttatc    3240
aaccacagcc ctttccagtc tcaaaaatgt ccccgctggg acagcaagtt acatcgtcgc    3300
tacaagtcct gtctcctggg agatgcagtc cagcagcact acatcctctg agcagcaggt    3360
gccaagtggg atgaactgga taaggactgc attcggggaa acgcccgtgt gaaaggaaat    3420
acacaggaag gaggtggcaa cgggtgggaa gccactagac cacgacgcga ttctgcccca    3480
gtgaaggcga ggggatagcc tgggcctaga tcgctgtgag gtctatggaa gtttccacaa    3540
gcttgctggg tagttctcga ggcaaactcg gaaaggagt cccttgtctc cctggaacgg    3600
atctttcttg gcatctctgt cacactcatt aggtgggcct ggtgtcaacc ccatttgcag    3660
gccaccccaa acttgatcaa aggtccgctt ctggcacccc ataccctgtc ctacaggaaa    3720
tacagggaca ggctcccaat aacaacaccc agcacggtgc catcaacacc accacgcaca    3780
cgggggctca acggaacaga catctccgct tcttcaatga agacactgga gggaaattgc    3840
ttacaaggcg cttaagagac ctattaagca aacttgatgt gtggacctgc ggcggatccc    3900
gattctataa ggccaactgc acaaaaccac gagaccccct gaggactgcg ccattggctg    3960
ggtccccgat gatatgaaag aacggtggt catttgagcg ggtgatgttt ttgcggtttc    4020
ctttagaggc acacgtgaaa catgacgggt gaaaggattc aaagtctggg atttgcttca    4080
aagcaacgca gggatggcgt gggggatgga tgggcagga agggccttga aactggtgct    4140
ggaggcttcc cagggctgcc ctggagccca gtgcgtcctc caccggccag actgtacaac    4200
ggttggatcc tgtgtccact gctaggaccc aggctccacg agcacgggct tgtgtggcac    4260
acggatgcac cctaagtcct ggcacagaga ctgctcaaca aaggcctcgg tgcttttgtg    4320
tatgtttgaa attttccata ataaaatgaa aaatgggaaa atgggaaaac aaaaatggca    4380
gcactactta ccctctgcag agttttgtcc gcttcacgcc agtgggtggc agtcgtttcc    4440
tctgccctgg ccttccatcg tttcccccct accctcttca cccacccaac agccccctgt    4500
ggtcctggca gctgtgggcc tttccttgag gtcaaggtgt ggagtcctgg ggagggctca    4560
gggaggccac cgaccgggt gtggattctg ggagaagcct gtgggatgtc cctccctggg    4620
tgaccacggc aatgtgcccc ctcctgtccc ttggccaagg ccagttccct gagccctgca    4680
gccccaagcc acagctggtc cactgacccc agttgagcct ggtcctcatc agaccagctg    4740 accccttga ccccgctac agactcggct ttgaccttgg ctgctgagga gccccacct     4800
```

```
ggactgaggc tgcagctggc gagagaggag ccctgagctc tctgataag aagggacctg    4860
gccagcctga cgtttgagac ccaggcatcc cggtagcctg ggtgtcctgt tgccgtggtt    4920
attcaggagc cacccactct gggacaacac cagctgctcc cacctcgcag ggctcccacg    4980
gctctgtccc aaccactcct ttctgaagga aggggtgcct ctgcgcccta agaaaccgg    5040
gggagcccca caacccctcc cccaccagga cactaaaagg cagctttcgg tacagtgaga    5100
catcaaagcc tcctaggccc tgagtcaaag gtatagccgt gtaatatccc agtgccagct    5160
ctccggctgc ggggagcctg gcgcaaagct tccaagcctt ccttgttcct ttcaagagcc    5220
gctcttagaa ttcaggtgag cggagacctg cagggcctcc ccagtgcggg caaaacccaa    5280
agctagcgag agggcagcct ccaggcacct ctcactaact cctcccagag gccgttgagg    5340
tgggtctggt caaacccatt tgcaagttaa cccacttgcc ctgggctgcc cagctgccac    5400
gttagtggag atctgagcgt ggtggcctgc gcaggagccc atgccctcag ccccacagcc    5460
ggtgctctct ggtcagacca cctcagccta gccccacacc cagcacttac cccagccctc    5520
gggatgggtc agcagcctcc agcctgcagc ttccaagcca gcgagtagcc ctgtctggac    5580
aacccaccag cccaccacct cctggaggat gcccccagcc tcacaaggtg tcccaatggc    5640
tccgctatca acggcctggc tgcactccag atctcaccca gacccaccct acggaggagg    5700
cagcagggtt tgaggagtag tgaccacgga agtctggccg tcacctggga agtgtaggtg    5760
ataggagcca ctggtaaaca gaactgattt atttataaag ttcacgctcc cttgaagagg    5820
tgtgccccac acaggcttct ccctagcaga gcagcagtgc ccacaaaccc accccagggt    5880
gggctgtcac gggggcctca cgccagggac cccgcccctc agggactgct cgtgtccaga    5940
tcttggccag catggaaaac tccagatagt gggggcaggg gtccaggtca tctttattac    6000
gccccaggtc aagggttctt tgtacaaaaa taggtctccg tttgccagca gtgtccctcc    6060
agcagctcaa gttaatgtgt agaaaatgga ttctctgtgc ccttagaaaa tcctctcccc    6120
tccggaaaaa tctccaagtg ttggtgcccc ccgccccact gcagtcgaga agctgtgggg    6180
aggggcggcg tcgaggaag ccgccagccc ttatggggcc agctccaagc ccgtttccac    6240
cgcggcattg gtcaggctgg gccggacgaa cgaggcggcc tcggcggtgc gggggtggt    6300
gggtgggtcc ccggctcgct ggggggcggag cgcgggccgg tccacctggc gggctccccg    6360
gcgatgagcg cgccggccgc tcgctcggct tccggggctg aggctgcggg gggaaggtgg    6420
ggaaccaaac gcgcgtcaac gcgggcgcgg gcccggggca gaccccgccc gggccggccc    6480
tgcccgcacc tcccccaagc gaactcggca gtttcgtttg ctcggttggt tttggagtct    6540
tgagtccgtg ggtgccgcga ctcggtctga gacacggcgg gggcggggcg ggcgctcgga    6600
gccgcggtga gtcagggctc cgcgcccgcc gactcatttc tgccgccccg gcccgggagc    6660
gcgatttgca atgcaaagtc acccgcctc cagcacccca atctgcccca ggatccgcca    6720
gcactagaga cctcaacggc ccgacggccg ctccctcc ctcgtctacc cctcccctcgt    6780
cggcggctga gccgcgaggg gaagttttgc aatcccggac aaacaaacgc cggtcttgca    6840
cgggcttgaa aaactttggg ggaaatgaag agtgagcgaa atcgaagcca tcgctcgggc    6900
ctggcgctcg gctccgcggg ctcctggggg cgcgacccgc cgggcctgcc caccccgtcc    6960
ctccaccccg gccccggcc ctccctcctc cctgcctccc ggctgttacc tcataggtcg    7020
agggcgctca gtagccccct aaccagctgg agaagtcgag tagctcgcgc tccgcaggac    7080
tcagcgcgcc ttcgcagccg ctgtcgtccg acgagtaggc ggaacgcggg gagccgggct    7140
ccgagctgcc cccgcggccc ggggacgaag aagcgcggga gggcgaggcg gcgaccgggg    7200
```

```
tggtccctgg cggcccgcgg ggcgcagacg gccgcacggc ctgcggcctc agccctcccg   7260
ccagcgcgtt gcgcacggcg tcgtgctcgg ccagcaggcg ctgcagcgcg cggatgtact   7320
ccacggctga gcgcagcgtc tccaccttgc tcagcttctt gctggcgccg ccgtgcggca   7380
cgtgctgccg cagcgcctgg aagcccaagt tcaccagctt cacgcggttg cgctcgcgct   7440
cattgcgccg cgctacggcc gctgcgccgc ctccggtctc tgcggtggcc ggtcgccgcc   7500
gccggctgca gcgcaacagt tccggggacg cgggtctccg ccgggcagcg cagccgacag   7560
ggacgggggg cgcagggggc gcggacctgg gcagtgtgcc gccgtccatc gcgcctgcat   7620
ccacccgccc gctccaggtc ccggcgcgcc gcaggaaggt gcaggcagag gaaccggagg   7680
cgacggggaa aactgtggcg ccccaagggg gcttctggca cggcgccgcc aggcaactcc   7740
ccagggcacg cgtcctaggt cgtctggagc ccggggatag gaggcctagt ggtggcaggc   7800
cgtacgcgcc agggagcgtg ggacgctcgt gtcccgcgcg tgcggccgga ctctcccagg   7860
tctccgcagg cgcggcgcag gcggctggtt tttaaatgta tagataaccc tcctccgcgc   7920
cgccgccgtc gcctttctca cgccctcctt ccttcgcctc gccctcccgc cacgcttcgc   7980 cctcccctc gcgcgatcac attctgtaag gcccaaagcg tgcgcatgtc ccctagccc    8040 atcccccgga cgcagtccac agatccccag tgcgcccaac tggcgaaatc tgcgagttcc   8100
cggtgcgccc cctgctcccg gcaggtgctt agtgcgcccc caaagcaagg tacgcaggtc   8160
ctgggttgag ccttcccgta cccccaccct aaccccgcgc gcagcccgc cagtcccaag    8220 agccgccaga ccttcgcacg cgcagcgcgc gctgtgggag ggaaggcgcg gccctggcga   8280
caacacggct gttcgggagg cgcgcaagat cccccggggc agcacgcgcc gcgcagccca   8340
cacccacgcc ccaccctcct ggggccgagg aggcggggc cagggtctca gccaatcgtg    8400
ggccacccgt ttggccaatc gcgcagggcg cggctccacg cccggcccca ttgaggaagc   8460
gcgtacgcgt ggcgcgtggc tcacggggag catcgctaac aaagctgggt tcctgctggg   8520
ccccgccctg ctcctcgccc ccgcgactgg gctgggcgcg ctgtcccta gcgcagctat    8580 gtcccgagcg cgcccccacc tgtgcgttaa tctactggga atgggggtgg actgcgcctt   8640
acctggggcg gggtggggct taaggagtgg tcgagactga ggcggggtgg gaggttcagg   8700
ttccgggggc gccttcccca acccgccccg ctttccccgt ccctccacgc gcaccctgcc   8760
tgtggtttcc gtgcgccccc ggcctgaggg ctctgggcgg caccttaacc cggagggcct   8820
ggaggtctgc acccgaccgc cttgtgccag gacggtcagg tccacgccct ccccaccgt    8880 ggctccctcc atctgcagta tcccccacct ccagccgtc ctgccctcct gttctccgtc    8940
tcgcttcccg tcggtgcctc cgggatctca cagccctcgc acctctttg tgacccaggc    9000 tgtttttctg cacccccctc tcccctgagg gcactgagat tgggccattg gcctgaaggt   9060
ctctgggagc agcacccttc caggggaggt gggacgtcga gaacttctcc ctaagagatg   9120
cggggaaatg gtggggcctg agagtgcaaa cactgcagaa atgcgaaaaa tgtagtgtta   9180
acggaagagt ttaggtcctg cctcactgtc cgggaaacgc gtgccctcgg gggagccttt   9240
gccaagccgg ttttttcccga aggtgaccag atgctcctgg ccactgcct ctgagacctc    9300 agggaacgga gattttgtg gacccagctg cctggagctg ctttcctgtt ccggccggag    9360
gaggtgaggc ccaagacccc tcctgggagc ctggggcag atagccagtg tttactgcca    9420 gcctcgggt gcccacctgc tcccattacc ctgcaggatg ctgctggctg cccacctgg     9480 gcccccagca cacctgtgtc tcgagtacgc ctggccctcc tgccttggga ggggccggaa   9540
gagtagcacc tgcctgggag ctggtggtct gcggtctcta tttggcagat gaggaagccg   9600
```

```
acttggagag aaccctggat gtgtccacag tcactcctcc gcccagtgga gcgatccagg   9660
cagaaatcgg ggccctgagt ctgaatccgg gttctgcaac cagggcagat gcgggcttgc   9720
ctctgctccc tgtccctggt ctgagagccc attcttccca gatggtcact tggcaaatca   9780
cagcctggca tggattgttc tgccctcctt ctgctgcctc cctccttccc cttgtcaagg   9840
ctgcaagacc aggatctagg aacgatcctg gagccctgca aactaggcct tggaaatccc   9900
tgctggattt ccacctcccg ggctgggagc ccctcggtca tctgttgctg tgtaaggagc   9960
caccaggatt ttagcggtct gaacaacgat gtattatttc tcaggattct gtgacttgat  10020
gggtgggccc tctgctgctc tgggtgtggc tgcatacacc ccgggggtca cagggacga   10080 gcggtacagc ggctggggttg ctctctaccc ggtcttcgtc caagcccctc cacagctggt  10140
aagatctccg gagcaggacc tgcaagccct cttcagatca ccccagaact tcctgtctaa  10200
aaactgaagc ctctcactgc ccaggcatgg cttcttgcta ccctgccctc aggcacagtc  10260
ctgcacccac ctgcgtctgc tgtgccatgt ccaggccagt cccccccac caccaacacc   10320 tctctctatc ttcatcctct tcccaatctg gtcctccac cgctgtggaa accccgtctg   10380
cccccaaagc ctagcttaaa aataattccc tagggacctg tgtctctccc tgcctcggcc  10440
cctccttcat tcctgggtgc ctccggctgt gcagcatttg acactgcagc acccccctta  10500
attcggaagc atgctgtctc ctggactggt gagtctccac actatctgag ccgtcttctc  10560
tggaactctt ggcctctcag tccgttctga aatacagcc ttggtaagca cggtgcccac   10620
atgaatgttt ccagcagcag gattcaaaat agccacatgt ccatcaacag atgagtggat  10680
aaacaaaaca tggtccagaa taatggaaga ttactcagcc ctaaaagag cgaagctgg    10740 tgaacctcga gaacacgagg ccgcgtgaac gaagccagac accgaggacc acgtagcgtg  10800
agactctcag tctatgaaat gtgcggagtc gataaattca cagagacaga aaggagattc  10860
acggttgcca ggggctgggg agtgacaaca gagggatggg ggtgactgtg aaagggtacg  10920
tggtttcttt cccagaggat aagaacgttc taacatggcc tgtcctgttg gcttcacagc  10980
tctgtacaac acacaaaaaa accattgaaa tgtacacttt gtggaatgtg aactgtatct  11040
tgataaagca gttagaagac cttcgaacat aagcatgcgg cctcatgggg cctttgcctg  11100
ggcaccctgg cacctctccc aggctctacc tatctccgac ttcattcctg agctcttgaa  11160
caggggtaag gcaaactttt tctgcaaagg aacacgtggt aagtattttc ggccttgacg  11220
gtcacatgtc tctgccacga gtcgtctgcc ttggggcgca aatgcaggct gggcaggga   11280 agaaataaca aaacttgctt cctggtcact gaaacatgaa gtccaggtca cactcactgt  11340
tacaaaatac tccgaatttt cagactgtgg ttcaatacac atgacataaa atggaccttc  11400
ttaaccattt gtaagtgcac ggttccgtgg aattcagtat attcatgtgg ctgtgcaatc  11460
atcaccacca tccatctcca aaagtttctc attttcccaa accgaaagtc tgtccccatt  11520
aaacagcagc ttcccatgac ccttccccca gcccctggca cccaccatcc actctgtgtc  11580
tgtagatttg actgctctgg agacctcctg taagtggaat cctacagcat ctgtcttttt  11640
gtggaccgga ttcttacact gatgctgatg ccctcgagct tcatccatgt cgtagcctgc  11700
ataaggattt cctctctttt tatgggtgaa taatattcca ctgtatgggt agaccacggt  11760
gttgatccgt tcctccgtca gtggatgctg ggtggtttc cacccttggg ctaccgtcag  11820
tgacgctact gtggacatgg gggtacaaat atctctttga gatcctgctt tcagttcttt  11880
tggggataga cggagaagcg gagttgccag gtcatacggc aaacctctgt ttaacctttt  11940
gagggaccac catgttgttt tccgcagtgg ctgcccacag tacattcctg ctgcgcacga  12000
```

```
ggttctgatg tctccacatc cccgcccaca cttggtgctt tctgggtttg tttcgtttcg    12060
ttttgttttt gtttgttttt gagacggagt ctcgctctgt ctcccaggct ggagtgcagt    12120
ggcgcaatct tggctcactg cgacttctgc ctcccgagtt ccagccattc tctagtttca    12180
gcctcccgag tagctgagac tacagatacg tgccaccatg cccggccaaa ttttatttt     12240 ttgtagagat agagtctgac tatgttgccc agcctggctg aggtgataat agttttttga    12300
tgatagctaa tgggtatgga ttttaatttt ttaaccactt aagaatttaa agaaaattcc    12360
tagcttttgg gcaatacaaa agcaggccag gggctggatc tggcccatgg gcctcggtct    12420
gctgacagct gctccagagg actggtatgt ccacgtgaca cctggcccga ccccatcct    12480 cctgcagctc ctcaaactca acttgttgca ggttgaactc ggcctccttt cctctaagga    12540
aagatcccct ccgcagcaga gaacaccagg tcggcagtgt gggcactgcc cttcctctcc    12600
cctgccctct gctgtacgtc agcccagccg cttctccagc caggtcccca tcttgccttg    12660
gacactgccc ctgcctctgc cctggtctcc tgggttctca gtttgctgct tctgtctgtg    12720
caccgcctgg aagtggggggg gccttaccca gcatccagcc cagctagatc atgtccgggc    12780
cctcggggtt caggcccagc accctcacgt gccatcactc actgcctcct ctccagctcg    12840
gacgttgtat ctcctggaag ccttccctga tcccagtggc ctcctgaagc ctcctcgccc    12900
ctgtgctcca cagggagctg tgctgcccgg gcctgctctg tccaataggc taacctgacc    12960
tgctccttcg acatctaagg tgctgctcat gtgtattcat gacctgggtg gatgttgggg    13020
agcccaggcc cagcaaagag gggcaggagc aggcagttcc ggggttggcg atggcccagg    13080
ggaagctttc ggcctggttg gtcagagctc ctggtgacca agggtgactt caaagtcaac    13140
gtgagcctca ctcacatgag atgagcctag agcgtccaag aacagctctg tagctggcca    13200
gccgggagct gcagccctcg gtcctgctgt cccccggggg agccggctcc tgctccaggg    13260
atgagcaagg ctcaaattga ctttgaagtc tcccacaggc cgtttggaac tggggtgcag    13320
gagctggaag tgtggggcac cctggggagt cacgaagcct gactgattgt caggcagatg    13380
tgtggcggga gttggggaga tgcggtagga cacagggggg atctgggggg tgccagtgtg    13440
ggccgcgggc tgggaggtat catcagtaac ttcagatcgt ttcgtagcga cacttaaaaa    13500
atacctgaag agggacgggt ggaatgaact tcaacatcat acccaaaata ttagcatttc    13560
aacatgtaat cagtataaaa attacttgag agctgtttca cattttcttt tcataccaag    13620 gttttgaaa tccggcgtgc gtcttttac actcacagta cctctcactg tggaccggcc      13680
acgtctcaat gctcagtggc acccaggct ggtggctccc gtcttagaca acacacatct    13740
ggaccgggag agcctcaggt cccctgtgat accagttttc tagtctctgt atctgacagt    13800
gtgacatctt ggggacttgc tgactatgaa gggccacccc tcccaggata aactaattcc    13860
tagagacagt gaaggagacc cttttcatgg gcaaacccac caacgcagag cccaacccct    13920
tcctctatca gggtcttacc tttgagggca ctacacctgc ccttgttacc ccaagggaag    13980
gtcccagaca accagcagcc cctaggccct agagttctga acttatgtca gcctggccaa    14040
tcctaaaccc atatccctg ccttgcccat tccttctaca gaaaccacaa gaaaggttct     14100
tgcccaggtc tccctgtggc tcccccacct tctgaccgac cctgtgcctg tgcccgcccc    14160
gctgcctgtg catgccacc cgctttgaga actgtgagct aacaattatc tcttctatgg     14220
caattgactc tcgatctgtt ggcctcacca tacctgaata ataacggaac tacattttag    14280
aaagccagta gaaagccatt gcctcgcatg acagaccagg aagctgggc ccagagaaaa     14340 gccacgtgct caaggctggc cagtgagtga gaggcagaga ctcaggagtg gatcatgggc    14400
```

```
ttcccttggt tcagcctcct ttacatccgt cccttaccc caccgtggag gcttggggct    14460
gagagggaga ttctgtggct gcactccaag gactggccag ttccaggcag gaggcggcac    14520
tcccagctgg ctggaaaaga agaggctgct tctctgtcaa gctcatgtca ttcccccatg    14580
aaactgaaag ctgcccgggt atgagaccat ggagaagaca ggtctcattc tctgggccac    14640
gtttcctaac cacagtacaa taaggctaga agaaaaccc caaagtccca gctctaacat     14700
ggcaaatgca tgaagaaaag aacagtcttc taaacaactc ttaggtttaa gaagaatgaa    14760
aacagtgatc atgggccttt cgaaaatcaa cagccaaaaa actttataac ctcaaacaaa    14820
ttcctccgaa acaagaaact ctgaacaaaa gtgaacaaag cattcaactc taggagatca    14880
ggaaaacaaa acccgaaata tgtgtgaaag aagtaataag ggctaattaa tgatgaggag    14940
gagagaaatt aacaaggcag aaaagtgaac tgttaactaa gttgatataa tgaaaaactg    15000
ctgtttttta aaagaccaac aaaataggcg catttaaata agaagaaga cacatttta     15060
aaataccaga aagggtgaaa ggtgacttaa gtacaaatat gtaaaagatt aaaaacagga    15120
tgttcattta tgaccacgat ggagtaacag ggactgaatt tactgctctc ctcccgcccc    15180
ctccaaaaca acaataacaa caaaaaggat caaattcagg aaacaacagt tttcaataca    15240
ctgcacatac gacaacaaag gacagtagtc ctcaagagat ggcaaacagg tgaacggggc    15300
cctacagctt cccagctgct cccctgagtt tcccaaccat ggcccagaag gaggtacctg    15360
ggcagagccc agtggagtac ttggaggagg agacagagct cagagccaag gaggcccagg    15420
cagctgggtt ctcaggacag aggagtggat tggagagagc tgcatagagg gagagcccta    15480
gagagctgca gaaagttcct ccaaggactc agcagagaac tgatcaggga tgtgtgtgaa    15540
gagccagagg ctagggaaga aattgtccgg aaggatcaga gagaagtgcc cagttctcac    15600
tcaggactgg aggagggctg tcctaaccag cccacatggg aaactcatag ttcatgaggc    15660
cgtggacaga gtatacagca ggctcttgcc tcactggcgg ggatcatttg ccctagactg    15720
gacaccgttc caatcccacc tcaccccaaa aaatcaagtg tttctaagta actcaactat    15780
gccccaggca aaactaaaaa ataggaatac aaaaatatct ggcatctaaa aagataaaga    15840
ttacaatgta tgatatttaa taaaaaatgc caagcatgca taaagcagaa aaatatgcca    15900
tctaataagg atatagataa aaagtaaata aatatccaga gctgacaaag gcattaacaa    15960
ggaaagaaca tcaaaacagg tgttatgact gtatttccta tgttgaaagc caagtggaga    16020
catggaagag atgtatatat attacatatg tctcttctat gtctctagtt agggggattc    16080
tatggctgca ctccaaagac tggccaatca ctggccagag gcagcacccc cagcctgctg    16140
gaagaggaga ggctgcccct ctgtcaacct catgtcattc tcccatgcaa ccagaagctg    16200
tccgatatg agatcatgca gaaagtgacc atatactcag gacaggacag gttcatttgg     16260
gactatttat ttatttattt agagatgata gctacaatgt ctgagacaaa gaatacactg    16320
agctggaaaa acagtaagga tattatgaaa gaaaaggtta atgaacttga agacattgca    16380
atagataata ttcaaaatta agcatagaga gaaaacagaa ttgtttaaaa gtgaagagag    16440
cagcagtgag ctatgaaaaa attcaagtgg tctaatatac atgtaatcaa agtccctgaa    16500
tgaaaggaca gaagagacag aaaaagtatt tggagaaaat aaatgacaga aaattttcca    16560
aagttgatga aaattataac acacagatct gcaaagctca acaaattctg ataaggagga    16620
acttgaagaa aatgacagca tcaagacaca tcttctttgt atatcttcat cttttctgag    16680
atagggtttc actcttgtcg cccaggctgg agtgcaatgg tgcgatctcg gctcaccgca    16740
acctctgcct cctaggttcc agcgattctc ctgccttagc ctcccgagta actgggatta    16800
```

```
caggcatgca tcaccatgcc cagctaattt tgtatttta gtagagatgg ggtttctcca    16860
tgttggtcag gctggtctca aattcccgac cttgggtgat cctcccacct tggcctccca    16920
aagtgctggg attacaggaa gacatatctt aatcaaattg cttgaaacca gtagtaaagc    16980
aaaataaaat aaaatgaaat aaaaccttaa agcaaccag aggaaaaaag atacatttac    17040
atatgtacaa aagaatgact tatatacaga ggaatagaaa taaggatgaa acaatatttg    17100
tacacctgtg ctcatagcag cactatttac aatagccaaa aagtgaaagc aaccgactat    17160
ccattgatga tgaatgaata aacaaaatgt ggtccatcca tgcagtggaa tattatccag    17220
ccttaaaaag caagggaatt ctgatacatg tcaacacata tgatgaacctg gaggacatta    17280 tgctgagtag                                                           17290

<210> SEQ ID NO 8
<211> LENGTH: 25970
<212> TYPE: DNA
<213> ORGANISM: Homo sapiens

<400> SEQUENCE: 8
aataagccag acacaaatat tgtatggttc cgcttacatg aggtagcatc attaaatcca      60
taaaggcaga cagtaaaatg gtggttgcca aggcctagga gttagtgatt aatgggatcg     120
agatacagtt tggaaagatg aaaaagttct ggagatggat ggtgataatg gctgcacaac     180
aatatgaatg tacttaatac cattgagtta tatacctaaa aatgattaag gtagtaaatt     240
tgtatgtcat gtatattta ccacaattaa aaaattagac aaaatacaaa ataaaaaag      300 gatgatacaa atttctcact ggaaacaatg caaggagaag acaatggagc aacatcttta     360
aagaactaaa aaaatactgt caacctagaa ttctataccc agtgaaaata tctttcaaaa     420
gtacagatga atcgtttgt tcagacattc aaaagctgaa agaattcatc accagcagac     480
ctgcactaca aaaatattaa aggaagtctt tcaggaagaa ggaaaattat atgagataga     540
attatagaat tagcaaacgg atgaagagca ccagaaatgg taactatatg gataaataca     600
tataaatttt tgttgctatt taaatatttt taaaaaatag gtgactactt aaacaaaaac     660
agtaactgat agggagttga taccatatgt aaaaatagat catatggcaa taccacaaag     720
gcaaggaggg gagaaatgga ggtatactat cataaaattc tcatactgta tgtgaagttg     780
tatcatttca ctttaaggtt gactgtgata agttgaagat gtaagctata taccctacag     840
gaagcactaa attaaaaaa aagaattaca gtaaataaat taattaaaaa ttaatggaat     900
cattaacaaa ttattcaatt aattcttacc accaaaaaaa aaaaaaaag aaacagaaaa     960 agagacgaaa tgggacaaag acagatagaa cgaatagaaa tgacaggttt atatactcag    1020
gcctaaccat aacaataaac acattaaatg tcaatggtct aaatacccag ttaaaacctc    1080
atagtcaggt tggataacaa agtaatacct aactgtctgc tgccttcaag aaacatgctt    1140
caaatataaa tatataaata tgtttaatgt aagatggtgc tatggtaagt ggcttttaag    1200
gaggcccgaa gcatcttagt attcacatcc atggctggga ctaggggag gcaagtaagc    1260 cacttgcctc ggtcatgaaa ttcaagaag gaccacaaaa ttcagtaatc aagacaaata    1320
atatttcaat gcaatatttt taaaaataca aattaatgca aaaatatatg aagaccaaat    1380
tttcagaatt ttaaataaag acaggatgag taacagtacc atactatgct gagcctctgt    1440
tggagcctga agcaaaaggg aaaattcagc cttctgagaa gccctgattc ggaggcacca    1500
agataaactg tgcttagttt cctgcccac aggaatctgt gagataagta tctgttgttt    1560
taagctacta gttttgggg tatttgttag acagcagtag atagtatgaa gttcaggatt    1620
```

```
ctatgtcaaa accaatcaaa agaaagcaga agtggccatt ttaatagatt tcaggataaa      1680
gaatattacc aggcattaag aaggtcactt cagaacaatt aaggggccat tcatgagggc      1740
atgacaatcc caaatgttaa cgaataaagc aaaagcatca tgatagacct acaaggagaa      1800
atagattaac ccacaattac agtcagagtc ttcaacactc ctttctagat acttgataga      1860
ataaatagac agaacatcat aaaaaatata gaaaaggtaa acaacactat caacttgctt      1920
gacctaattg acattaatgg aaaatcccac ctgttaacag caaaatacac attcttttaa      1980
agtgcacgtg aagtatttac caaggtaaat tgtcttatgg gcaatagaac aagtcttgga      2040
aaatgtaaaa gaggattcaa gtcatacaaa gtatattctc tgaccataat gaagttaaat      2100
tctgctaata acagagatat atgaaaaatg cccaaatatt tggaaataaa taaaatagat      2160
ctaaataacc catggtttaa caaataaatc aaaagagaaa ttagaaacta ttttaaacca      2220
agtaaaaatg aaaacacagc atttcaaaat ttatgcaatg cagtacttgg aggggatttt     2280
agacagctaa acacatatat tagaataaa taaaagcctg aaatcaatga caccagctcc      2340
ttagaaacta ggaacacaaa cccaatgtaa gtgcaaggag tacaaaataa gaatcagagt      2400
agaatcagtg aaacagaaaa aaatagagct atcagtgaaa cacaaagctg gttcattgag      2460
aaggtcagta atatcaataa aagccagaat ggtcaggagg aaaaggaaaa agatgctatt      2520
tgccaatatc atgaatgagt gagaggtcat cattacagat cctacaggta ttaaaagtat      2580
aataaaagaa tattaggaac aactttatac caataaattc accgacttag atgaaataga      2640
caaaatcttt gtgagacaca aactaatagc acttacttaa gaagaattga ataaccagaa      2700
tagcaccata tttattcagt aaattaaatg tgtaggtaaa atccttcctt caaagaaaac      2760
cccaggccta tgtgatatca ctagtgaatt ctatcaaata tttaaggaag agataaaacc      2820
aattctacat aaataaatcc agaagaattg aaaaagatgg aatacttta aattcattct      2880 ataagaacag cattaccctg ataccaaagc cagacaatca caacacaagg gaagaactac      2940
aggctgatat tcctcatgaa cgtagatgca agaattctaa aaaaagttt agcaaattga      3000 acccaaccat atacaagtgg ggcctattca aggaatcaag gtgcgtttaa cattcaaaag      3060
atcaactcaa cgaattgacc atattaaatt taaaagaag gaccatataa taatgtcaat      3120
agcacagaaa aagcatttga caaaatccag tggccattca tgattttaa aatctcagcg      3180 aactaggaat agaaagaagg acaatttctc agcctgtaaa gggtatcaaa cttaatggta      3240
caagactggt tacttttcctg ctaaaacaca tagacaagac aaaggtgtcc tcataatttc      3300
tatttagcaa tgtcctagag gttttagtca gtggaacaaa gcaagaaaaa ggaacaaaag      3360
ccttccagtt tggaaggagt aaaactatcc tcattcacag aaaatgatca gctgtgaaga      3420
aaatctgacc aaatctgcaa aaacactaca ttaattaaag tgagtttagc aaggttgcag      3480
gatacaagat caatctagat aatcaattgt atttccatat agtagcaaag aacaattgga      3540
aattgaagta aaaatgcca tttgcaaaaa catcaaatat taaatactca gctataaata      3600
tggcaaaaga tttgcaaacc tgtacactga aaactgaaaa acattgatga gggacattaa      3660
agaagactta tctaagtgga gagatatgct gtgttaatgg attggaaaat tcagtattaa      3720
gatgtcaatt ttcctcacgt taatctatga attcaacaca attcaaataa aaaaaatatc      3780
agaaggcttc tttgtagaaa ctggcaaaat ggttttaaaa tctgtaaatt cttaatttcc      3840
catacgaatg tattttcgtt cttcaactga cattttatct gtaaaaatct gagaagtgtc      3900
aggttggcat ggagcatatc ataatttttc acattaaaaa tattgaaaat attttttgttt     3960 aattgctttt tctttcacag aagggcagtt atgaatgaat gtatatctct atataataca     4020
```

```
tatacatata tataatacat atatagtata cataatatat atataatatg tattgcatgc    4080
atatattcag agacagaatc tcactgtgtt gcccaggctg gagtgcagtg gtgcgatcat    4140
agctcactgc ggcctcaaac tcctgacttc aagatatttt cttgcctcgg cctcccaaag    4200
cactgtgatc acaggcatgt gagccactgc acccagccta aatggatgtt tgtaagtgtg    4260
gaatatgtgc atacaggagt ctgcctccaa actctctacc cctctgtctt tggtctaact    4320
ttcctcttat gccaatccca tgggattttc ctattaggct tcactgtatg tcttcatatc    4380
agacagagca aattcctctc tttttgttct tttcaatcaa agttgacatg taacaggcat    4440
atgccagaca tcactgtgga aacgctatac tcaactgagg actttggtag atttacggag    4500
agtacgcaga cagacatttc gtgtgggaat gccttaatat tacaaagctg tcaaaccccc    4560
ctacatgaac gtaaggatcc agtgcaatcc cagtccacat ctcagctggg gtgtggcaaa    4620
cgctccacga ccttactcca acactaagat cgaagtgtag aagtccgtga gtagctcagt    4680
cagctttgag tgtttgcaaa gtgagtgttt cagtggcaaa tattcctaat attctctgag    4740
gcttggtgtg cctaagggta ttttcatctc gctgctgcat ttaaacaata atcatacccg    4800
taaaatcctg tgttcaaagt taccttccac gcctttgaaa tattattctt ttgtcttctc    4860
acatccggta tcgctcttga gaagaatgat gcgattcttt cttgctcttt ttaggcaatt    4920
ctgccgattc tctatgggcc aattcaggac tttgatattt taaaacttca ccgtaacgca    4980
tctatgttct ttcttatctg tcctcgccgg cctgtcaaga gcccttgcgt gtgtttctgt    5040
aattctgggg tatttatttt cattatttct ttaaatacct cctctcttcc tctgctttct    5100
gagactcttc ctagccaatc cactactttc tccttttctc ctcaaacgtc tctgcttccc    5160
ttttaagttt ttttctcatt attgctcctg aaccttctag aacaattcca ccacacttga    5220
tattttatct cacttgtttc ctagcagcac ccatgctgtg atgtacccca ttcactgttg    5280
aactggcatc ttcctcacac tcagtatttt cccccagctc cttgtatatg cctcttcatc    5340
ccatttcaca ctgtgccagc accatccctt atgtttttga gggttttttt ctttcaagtc    5400
tggagtgcag tggcacaatc ttggatcact cagcctcaat ctcctgggct caagcaatcc    5460
tcctgcctca gcctcccaag tagctgggac aacaggcacg aaccgccatg gttggttaat    5520
gtttgtatgt tttgtagaga tgggatcttg ctacgttacc caggctggtc ttgaactcct    5580
cagcccaagc gatgcgctca cctctgcttc ccaaaatgct gggattatgg catgaatcac    5640
tgcacccagc catgttttg agtttctacc aggattgctt tagcctcaca gttcatgttt     5700
ttcagcagtt cttgtctgta tgcaatgtga tgatcagatt gctgcctttc cattctcgca    5760
ggtatgccca tgagttcagg ctccacctga agtgacggtg actgcgtcgg gcagtgtgtt    5820
gggggaggaa ccaggcctg gccctggctg gccatcccca ggccgtggaa tgtagggacc     5880
agccccacag ggtcggtggg tctctccccg tgtgcggcga cgagagagtg taaaaataaa    5940
gacacaggac aaagagataa aagaaaagac agctgggccc gggggaccac taccaccaat    6000
gcgcggagac cagtagtggc cccgaatgtc tggctgtgct gatatttatt ggatacaaag    6060 caaaagggc agggtaaaga gtgtgagtca tctccgatga tagataaggt cacgtgggtc      6120
acatgtccac tggacagggg gcccttccct gcctggcagc cgaggcagag agagagggga    6180
gacagagaga gaaacaactt acaccattat ttctgcatat cagagacttt tagtactttc    6240
actaatttgc tactgctatc tagaaggcag agccaggtgt acaggatgga acatgaagga    6300
ggactaggag cgtgaccgct gaagcacagc atcacaggga gacggttagg cctccggata    6360
actgcgggtg agcctgactc atgtcaggcc ctccacaaga ggtggaggag cagagtcttc    6420
```

```
tccaaactcc accagggcaa gggagactcc ctttcccggt ctgctaagta gcggatgttg   6480
ttccttgact cttttttgcta ccgctagacc acggtccgcc tggcaacggg cgtcttccca   6540
gacgctggcg tcaccgctag accaaggagc ccttctggtg ccctgtctg ggcataacag    6600 aaggcttgca tgcttgtctt ctggtcactc ctcactatgt cccctcagct cctatctctg   6660
tatggcctgg ttttcctag gttatgatta tacagtgagg attattataa tattggaata    6720
aagagtaatt gctacaaact aatgattaat gatattcata tataatcatg tctatgctcg   6780
agatctagta taactcttgt tgttttatat attttattat actggaacag ctcgtgccct   6840
cggtctcttg cctcggcacc tggatggctt gccgcccacc gtggaagaag aggaaagcgt   6900
tcctcttccc ttcccttccc cttttccttta acacttaaaa catatttatc cctcccctcc   6960
catctcccct cccaactcat aaatatagta ggattccaac taataaacat agaaggcatt   7020
tggcaaccag cacagcaatt atttaggcac aaatcctcaa ctgatgctaa aacgagtgag   7080
taaaagtcta agaagcaaca ggaagttaca cggcatcacg tttctcccca caaactggaa   7140
attacaaagc acagaacatc aacgtgacat tggagaaacc tgccagctac aattttaacc   7200
gtgttccaag ttaacactgc cggtccttc ttcctctttg ggccgtgata gagcagttag    7260
gaccacacgt ggccttcact gcacacaacc agcaaccagg atgcagtcac acagtttgtg   7320
aggcaagttc tcaaacgctg acagcgcgc cgtgggtggt ctgtgaagga cgtgaaacca    7380
gccgggggag cctggtgatc ttccagccga ccgagagtct ctgggctggg ccctgggtct   7440
cactgaggtg aggagacaga ggtcagagct cagcgaggat gaggcaacta gaattttcag   7500
ggtagatctt tgaagaggag gtgggggaaa gagagaaaga cagaggagag agacagaggc   7560
agagatacgc agagagggag agagagagag cgggagaggg agagaggggg aagagaggga   7620
ggaagagatg aagaaagggg gagaaacagg gatacagaca gggagagaga taactaggca   7680
gagagagtta gaaaggggag aagagagaga tagagaaaga cagagagaga gagagaaaga   7740
gatacagaga gagagagaga gaaaaaaaaa aactccaggg atctgcagag accctcaggt   7800
ccttggctga atatggatcc acacatgcat gaagataaac cacctgaggc cagagaaaaa   7860 accccgtag ctcaggtcac acggtctgga gacagtttgt gttcccacaa aactatataa    7920
tacacaggat gtcgggaagg gtcctcataa gagcctctct tgagtgctga ttctaaacca   7980
accctagact aaaggcagcc ctggattcac cctacaaagc atagaagcaa agctccaaag   8040
atccgatggg tatcaggaac tcatggatgc cagaacaaaa tccgacagca attaaaggaa   8100
tacaacaaaa tctagcaacg gactgtgcaa tatttgcaaa aaaaaaaaaa aaggccaggc   8160
atgcagagga acagggaaac gtgacccaga accaggagaa aagccagtca gtggaggcag   8220
gtgcagaaag gccagaggtg ctactgtgac cagacaagga ttgaaacagc tgttttagag   8280
gggccctacg tgtaagaagg tccagtaata gaaagagggt gataaagcaa tggtggtagg   8340
gtgctcacag ttggagaata gcggaggta caggaatcct ttgtactatt aatgaagctt    8400
ttctgcacat tggaaatgat acaaaacaaa aagttaaaaa atgaaagaga ggtggggtga   8460
gcctagagca tggagcccca ggacccatag aattttgttg attcctctta gtgttcctgc   8520
tagccaggca ccttgtgtga aatttgccat taactctctg gaaaaaatcc gctttgggag   8580
gaggccactg cccgtgtggc cacctccagc cttgagacca gagcagaagg atacaggagc   8640
aactgcttgg agacggctgg cagatctgca cgtgtttcta tccatcccac ttcccctctg   8700
taaggttcta actctgccct gctgttctcc ctgctgtcca ggccattgct gctgatttct   8760
gcagtgacgg ggccagcaac aactgtctca aggcagcttg ggaaaagaca agcctgcctc   8820
```

-continued

```
caactgttgc tcttgtcact gcttctagct gtctcctccc caggttgcag ttcccaacac   8880
cacacacacg tgtgcacaca catgcatgca tgcacacaca tgcacatata gcacagcatt   8940
catgcataca catgtaccca cacacgcaca cacttgcaca cacatgcaca atgcatacac   9000
atgcacatac atgtgcacat gcacaccagc tcaccacagc ctgtagtctt tttttttga    9060
gacggagtct cactctctcg cccaggctgg agtgcagtgg tgcaatcttg gctcactgca   9120
agctccgcct cccaggtttc accattctc ctgcctcagc ctcccgagta gctgggacta    9180
caggcacgcg ccaccacgcc cggctaattt tttgtatttt tagtagagac ggggtttcac   9240
cgtgttaacc aggatggtct cgatctcctg acctaatgat ctgcccacct tggcctccca   9300
aagtgctggg actacaggcg tgagccaccg cgccctgccg cctctagtat tcttagagat   9360
gtgccacatt gttgattttt cctcaaggct gtttctccct ctagatgctg gagcttctcc   9420
agcattgatt ttggggacgg aagcctgggc gaggtacaca ttccggcagc cagtgccagc   9480
tcttagaagg tcacactgcc tattgtgtgg acagattaga tggggtgggg gtgggacttg   9540
tgagtccagc aaggggcta ttgtaggcag agctgcaaga ggcaccagca ggctgcatgg   9600
gctccaggag agaggtgcga cctgagagcc attctggaca ctgggctcag tgaaagaagc   9660
cggtcagaaa aggacaaatc ctgtgtgatt ccctgggtag aaggtcccta gggtggtcaa   9720
atccatagag acagaaagtg gatggtgggt gccagggcct aggagagggg atggggaacg   9780
agtgtttaat ggggatagag tttcagtttg gaagatgag aaagttctgg agatgaaggg    9840
tggtgacagc tgcacaacag cacgaatgtg tctaatgacg ctgaagtgta gtttaaaatg   9900
gttaagatgg tcagttttgt attatgtcga ttttaccaca ctgtttttaa aaagaagcat   9960
cctggagaaa gcgtcagtac tgctcatggg ggtggggtga ggagtcagct ccagtggctg   10020
ctgggctctc gtccgagagg agaagggagg ctggccctcg ggggaagggc tgcagggatc   10080
cagggttcct gggtggatgt gcggagtctg gggtacctgg gaactatccc cacagaaatg   10140
ggaggccacc actgaaattc caatgagggg ctcgaagtta aaacttaaca catgaaagat   10200
aagtggggtg acagcgtgga gccccaggac ctgttgattc ctcttaccgt tgctgagggg   10260
ctaatggaag gggctgggct ggagggtccc ctgcagtcag tggcaactca gcccctgggc   10320
actgagggac catgcaagaa gcgggagaga gaacagaaaa ggcaggaaga gcccttttcc   10380
tccactgagg gagtaggcag agtcagggag tggctgagaa agggcaacac agtcagcaac   10440
gggaaatgca aggaagacat gaggacccgg tccccccatg cctggagggc tggagtgagg   10500
acagaggggg cctgctggac ccaggagcgt ggagctcact ggtgactcct gagagtcagg   10560
ggactcccag gaatggcgtg gaatccagga tgccacttcc tcctgcctgg cagcagggca   10620
ggcagctggc tggggcccag actcccagga ggatgccact gctgcccaga cctactgcag   10680
tgcacagcag agcggcaagg gccctggtg cgttgagcaa acttccaggc ttaaaaagag    10740
cgtggctgcc tcatccctcc accacccaga gctggctcag gccacgtgtg acccacccta   10800
cccttaacaa ggcagctccg ggagtcctgg aagatgaaca tcccgctcag ctagggcgac   10860
actgtgccaa tccctcccat gggcttccac ctgtacctct tgtttctac acagctttat    10920
tgaaatataa ttcacatact ataaaattca ctgttttaac tgtaccattc aggggctttt   10980
agtatattca cagaagcatg cctccctcag cacccccaaa aacaactccc cgctttagta   11040
tattcgcaga ggcgtgccac ccgcagcacc cccaaaaaca actccccact ttattcgcag   11100
aggcgtgcct cccgcagcac ccccaaaaac aactccccgc tttagtatat tcgcagaggt   11160
gtgcctcccg cagcaccccc aaaaacaact ccccgcttta gtatattcgc agaggtgtgc   11220
```

```
ctcccgcagc accccaaaa acaattcccc gctttattca cagaggcatg ccacccgcag    11280
cacccccaaa aacaactccc cgctttagta tattcagagg cgtgccaccc gcagcacccc    11340
caaaaacaac tccctgcttc agtatattca cagaggcgtg cctcccgcag cacccccaaa    11400
aacaactccc tgctttagta tattcagagg cgtgcctccc tcagcacccc caaaaacaac    11460
tccccgcttt agtatattca cagaggcgtg ccacccgcag cacccccaaa aacaactccc    11520
cgcttcagta tattcacaga ggcgtgccac ccgcagcacc cccaaaaaca actccccgct    11580
ttattcacag aggcgtgcca cccgcagcac cccaaaaaac aactcccac tttattcgca     11640 gaggtgtgcc tcccgcagca cccccaaaaa caactcccg ctttagtata ttcacagagg     11700
cgtgccaccc gcagcacccc caaaaacaac tccccgcttt agtatattca gaggcgtgcc    11760
acccgcagca cccccaaaaa caactcccg ctttagtata ttcagaggcg tgccacccgc     11820
agcaccccca aaacaactc ccgctttag tatattcaca gaggcgtgcc acccgcagca      11880
cccccaaaaa caactcccg ctttagtata ttcagaggcg tgcctccctc agcaccccca     11940 aaacaactc ccgcttcag tatattcaca gaggcgtgcc acccgcagca cccccaaaaa      12000
caactcccta cttcagtata ttcacagagg cgtgccaccc gcagcacccc caaaaacaac    12060
tccccgcttt agtatattca cagaggcgtg cctccctcag cacccccaaa aacaactccc    12120
cgctttagta ttttcacaga ggcgtgccac ccgcagcacc cccaaaaaca actccccact    12180
cactagcagc cgctcccctt gccccagcct ctgccaaaca ctgacccact tcccacctcc    12240
atggagttgc acgttctgga catttcatac aaatggggtc ctctgattcc ccacccacaa    12300
tttttaatca tacttaactt ccaaataaag acaaagtcaa atccctcttc cacccaacaa    12360
gatgtggcca agcgtataca agagaacagc atgtcccccct ctccccagaa gaagaggaga    12420 gccctgatc ctgattcatc tctgggtgtt cttcccctta aaaaaaaaa aaaaaatca       12480 aaggggaat aggattcagc tggaatggga ttcagctgat tctcattctc cctttgatat      12540 cctaatttt tttttttttt tttttttttt tttttgagac agactctgtc agccaggctg     12600
gagtgcagta gtgcaatctc ggctcactgc aacctccacc tcctgggttc aagcaattct    12660
cctgcctcag cctctcacat agctgggata acaggcacgg ccatcacgc ccggctaatt     12720 tttgtatttt tagtagagac ggggtttcac cacattggcc aggctggtct caaactcctg    12780
acctcaggtg attcgcctgc ctcagcctcc caaagtgcta gattacatg cctgagccac     12840 cgtgcccagc ctgatagcct aaaatttaaa cactgagatg tttgaaataa ttaaatatca    12900
actactatca aacgtacact tcatacacta gtaccgtatg aagtggtagg gaatggaaga    12960
ggagaagaaa cagtggctaa tgtggtccta cccaatacac tcggatcaaa ataagaaaca    13020
cgcacacctg tgataggctt cgtttctgca gcagccgagc agcgggaact agcgtttcag    13080
cctccgtctc ccgcatagcc ttcgcctccg caagcactca gctgatgtgg ctctttgcct    13140
ggtgggatgc cctaagcctt cattcctgga gagcctgggt cctgaatgac cctgcttgga    13200
tcaggggtga tggttttcca tgattttaat cacaggacat gggaaccttα agaggcgctg    13260 caggggaccc tccgcattcc agacgtgctc ctcctcatcc tccttgtgca acccggccga    13320
ttccgcccga taaaatcagt cccgtggccc gggcagtaac tgcctttttt acctattgat    13380
tctctgcagt gaggatccca aaatggcctg gtgcaatctc accttccagt ctggtggagc    13440
cgttggtgtc tctgcgggaa actctcctcc ctcgagaact cagacttcta caccaagagg    13500
acctagagtt gtggggacag ggagcaaaca catcaccagc agaatgtcat gagggtgaag    13560
agaagccatt gccacttccc cttctggact cccagaaccg tgaggtctgg gcggcaggag    13620
```

```
aaaccgctcc atagactgac tctaattcag agcctggacc gcctcctgga ggacacggcc   13680
ctctctgcaa agcgtcccca ctcagcaggc gccgtgtgag tctcccgaag gccattccac   13740
ggtcctgttc gtgagctgct tcggggagag gaggaccacg gaagacctcc aaggtcacaa   13800
gcattgggcc tttgccctac tccattaact gtggtgaatt ccttgagcag cagtgtgaga   13860
atgccgaatg aggcgctcca gagtccacag gtggtttcgg caaaagcacc gtgggcaagg   13920
agggccagtc cacctgcaga gcaagcctct atcctggtga agcgcagcg gtgccagttc   13980 catgccggca gctgtctcat atcatccact ccacctggag gctggcagat cccctgcaac   14040
actggggcag gcgggcactt agtggatggg ccttggtgag tggagcccct gtgccgatcc   14100
catgtgtgac ctccatccct gctaccacag tctctatctt caccagcctg ctgacaatga   14160
cagggtggct ggggaaggag cctgactgat gcccaaagaa agggccatct tgtctacctg   14220
gtcactgagc ttctcctcgg ctgaggcggt tgccctttgg caaatgtcac atgggctgcg   14280
aggatcttca cgctctgccc tttcagagac ctctaaccac acaacacttc cccacacctc   14340
ctgctaccgt tttcccaaat gtgttccttt caagtccctg accatccatc tggccaagcc   14400
aggagcaact gaccatgagt gggtggcacc tgtagctccg aactctcctt ccaggaaaaa   14460
tgaaaacacc taggggccct gcccagagta tggaccacgg gtgttggaac cacttttca   14520 tgtaacttgc ttgtgacttc agggcctgcc tgagccccgg gttgtatatt gctgcttcca   14580
cttgaagaca gaacacagct gtgcatgccc aactctgtgg ctcgctgggt ccagcaacat   14640
cccactcatg acgtacagtt cagatcacgt ggcgacttag tggcctgtcc agtctctatg   14700
gaggcctgga cgcaatccac agagttatcc agagaggatg gcagagcttg actccaaaat   14760
cctaagggcc ctgggctgtg attcacctgc aggagcctat catggccccc acgcagcatc   14820
cttacctgcc acagacacct caaatgccat gggatctgtt ggtcccgtgg ctcaagtggc   14880
tcagcagctt tcatgaccac atgcacttgc tgcagagcct tctcttgttc tgggactccc   14940
agaaagcaga cagcatttta ggtcattcct acatgggttt tcctacccat gtcttcctac   15000
ctacccgtgg gtcatatggc ccatgttgca aaacattttg gaaaaggcaa aactatgcag   15060
acaatgaaat gatcagtggt ttccaggagt cagtggggag ggagggaaga ataaatggag   15120
cacagacgga ttttagggca gtaaaataat tctgtgtgac actgtaatag tggagatatg   15180
ccattacaca tttgcccgaa ctcacagcat gtacaacaag aagagtgaac cctcatgtaa   15240
cctgatcaat gactaggtca atattggttc atcaattgca aagatgtatc acagtaattc   15300
aagatatgaa taataaggga aactgtgtgt agggagagat gctatatgag gactctcaaa   15360
tatgctcaat ttctctgtaa acatgaaact gctctgaaaa ataaaatcta tattaaaaat   15420
taaagctttc accagatcaa tggctgtaga ccaggtgtcc ggggatgctt tgatttgccc   15480
cagtgatcag tagtcatatc tggaacagca gttgcaattg gagtcctggt taagtttacc   15540
aggattcact gtccttcttt ctccgggacc ccctgtctt ccacacaagc caattagacg   15600
agtggaacga ggctgcagtg ggggtcacca ccctgcatct tccaagtcct cgatggcggc   15660
actgaccttt gcagtccctc cagggctgca ggttgctttt gactgacaat tttcctaggc   15720
agagttcacc ccaatggctt ccacctggcc tttcccagca tagtagcccc caccctcagg   15780
tcagggaaca aatgtggggg ctctgctggc tgccacatac gtctgtttac tcacccatct   15840
gaggctaggg aagtgacctc tgcacccacc gagggttgga cctgagctag aactccgtga   15900
gcccactgac ctccatacgc ccctcctctg actattagat ccgatgggtg tttgtgtccc   15960
caggagtggg tgtcaggtta gagttagagt ccagtaatcc ccctgagtct gatgatcccc   16020
```

```
ctttccacta gccaccccag caaatggctg caggtccctg aggggagact ggggaaagaa    16080
gaataatgta aatttgtagg agtatggcaa ggtccttcct caggggcacc cagtcctcct    16140
tcactcaggc accaggcaag ggaggccacc cattgctcca gctcccgtgg caccgtgagc    16200
caccggccaa ggccacaggg ctccatgggc tggactgttc caatcactgc cggtgccagt    16260
tgccatctca gccacaggcc cggggcctcg tggccacccc cactgggctg tgccctgcct    16320
ccttaaagac tgtgagcgag ctcccaactg ggacacccct gaccagctca ctcttatttt    16380
gtctgccctg gccctgatgc tggtgtttga gatatcagaa ctcacctcaa accaccctaa    16440
gcagagatca ctccggctga cgcaggggtg cggcccacat gtgagggacc ctcaggctgg    16500
gcagcattgg ctgagccccc accgcacctt ccctcccacc ctggggtcct cagcctccgc    16560
ccaaggcagg ggggacactg ctggcaactg gtcacccaga gagcatgggc tgcagggatg    16620
gccctgagta ggacacacag ctcccgagac ccctcactgg ggacacaggg gggccctgca    16680
gccagggtgt cagtgtgggg acagcccagc agacccccaag ccaccactg aggttgcttc    16740
tcagggagc accactggtg ggctgtcagc tcctgcctgg gccccggcct cttgcccctg    16800
tcccacctcc cacctgcacg gcctccagca ttgcccaaat tcactgcctt cactcccaag    16860
tccacagagg tgtctcatcc aggcgggtga acactcgtgt gttgggaggc tggtgaagcc    16920
tggcattggg gggcaccacc catctcccett ctttgtctca ctgccttgaa acaccccaca    16980
tctatcacct ctgccccga ggctccccag gttcacccca tgccagcctc agcccaacaa    17040
ggcctgtgct tctgaccagc accgctgggg ttctcagggc atctacccctt tccgctgtag    17100
cccactgtct ctaaacatat ttcacacgtt gctggggca gtgtgtgtga ctcactgctt    17160
cccagagcca gcccagagct gtttagtaga catgaggtga gtgaatgaat gaatgaatga    17220
atgagtgctg ggagctgtct cagttagctc caatctgcca taaggaagca ctgcaggctg    17280
ggcatgtaaa cagcaggtgc ttatttcttg cagttctgga ggctggaagt ccaatatcaa    17340
ggtgctgctg attccagtct tggtgagggc tctcttcctg gcttacagat ggctgccttc    17400
tctctgtgtc ttcatacagc tgtccttcag tgcatgtaag gagagagaga gagaagaggg    17460
agctcctaaa tgtctcttgg tataagggca ctaatcctat gggaccaggg accttcatgt    17520
cctcatctgt ccctaattac ctcccagaga tccacttcct aacactatct cattgcgggg    17580
cagggcttca acctatgaat tttgcaggaa cacgattctg tccatagcga acactgacac    17640
tgaacccgcc tcctaaagcc ttctctcacc atattcctca tgctgctcaa agatcctctg    17700
caaccttgtg cccctcccaa gggtccctgc acctgtccca gagagagggc agcctggcaa    17760
tgggcctggg ccctgacgct tgagcatcgg ggtctggcct gaaaggggat gggcgttcac    17820
ttctaggttc ctgagagagg caacactgca ccttttaaagg tgtcaggagc tcactgcccc    17880
agctggtcat gaaacagtct cttcatcaag ggctaaataa agcacgctga ccaccaggaa    17940
tggggcagga agcttctgcc ctgcagcctg ccttgtctgc acgggagtg tggggaccat    18000
taggggagg gtccgatgtg cattttctg ccagcgggac cttcccctgc cccagtcct    18060
gcccaggccc gggggtcac tctgaaggca tctggctctt accccaggca tctcctgcct    18120
ctgccccact cctccacccc cacggggtgc cgagtctcag cccaggctgg ggtggcccag    18180
gcaggacagc aggcttggtg gtgcccggcc ccacatacta gtgggtggca cagcgtggat    18240
gtggatagag acgcctcccc tacagtctgt ccctggtatc tgtgacgcag gtgtggggtc    18300
cctttagact cccctgggag acagctgtgt ctatgaaggg gcagccatcc ctgggtcccc    18360
tctgccctca ctgagggcag agcctaggct ccttgggggg ggaagcaggg tgcccctcag    18420
```

```
tgcccactgg agttggccag cggaggcagc agcccacggc actgagaggg aaggcccggg   18480
cagccatgcc ccagaaactc ccttggttgg gagcagagca gtgcccagag cccagaaccc   18540
agtttgagta tggtcttggc tctcaaggga caggccaggg tgcctccagg ggaaggggc    18600 tgcccaggca gtaggggttc aaaggtcccc tggggcccac ccagctgacc caggcctagg   18660
gtaatccaga aggggagctg ccctcctcct ccctgggctc aggagaggct gcaaaggcag   18720
ctcctgggac gtggatttca gaatcagggc aaaggacaga catgagccag attcaggtgc   18780
ccgcgtggcc cccacaggtc tcttcaagct ccaggcccca ctcgctgtga cgcaggtggg   18840
aagctcttga gtgcctcccc ggtgggaggg ccgcgctca  cagacagcac aggggccccc    18900
aggctccagc ctcagagccc ggctgctcac ctctgatgga cagaaaggg  tccctgtctc    18960 aggaaggtag aggctgccac ctcctggccc gaggacacag ctttccagag gaggggcctg   19020
cttctaagtc caagtcccat cccagccgga tagccagggg caactgccca ggtaaactga   19080
gacagcagca gcaggcaagc cagtgcagag ctgggtgatc cacaggttca tgagcggtgg   19140
caggtggaac aagggcacca tgggcggagg gttgggcagc tgcaggtggc atcattgagc   19200
caggggcctc ctggtgggta aggacattgt agagtgagcg ggcgcacctg gacccagga    19260 attcacagga aggagagagg aaaaaggaag tccctggcgg gtaaacacat atgcatgcac   19320
acacatccac gtctgcacac gcatccacgc ctgcacacgc atccatgcct gcacatgcat   19380
ccacgcccaa tctcttccct ggaaataaag ccaggggccc ttaggccagc ttgcagtggg   19440
gcccagccct taggacaggc tccttggtgg ggtaggggtg ggggcagctg tcctcctggg   19500
ccagctcctt ggggctgaac ccgctgctcg aggggtcttc caggctccca gcggccggca   19560
ccacctctag agcaggtggg caggggtgtg tggggtgggc aggggtttgt gagggtgggc   19620 agggggtgtgt ggggtgggca ggggtgtgtg gggtgggcag gggcatgtgg ggtgggcagg   19680
ggtgtgtgag gttgggcagg ggcgtgtggg gtgggcaggg gtgtgtgagg gtgggcaggg   19740
gtgtgtgggg tgggcagggg tgtgtaaggt tgggtagggg tgtgtggggt gggcagggat   19800
gtgtggggtg ggcagcggtg tgcggggtgg gcagggtgt gcggggtggg caggagggtg     19860
tggggtgggc agcagcctgc acagtggctt cccctcaaca agccacttcc tcttgcagag   19920
ggaatgttgg ggtgggaggg tgtggctcag caaagggcgt gggggttcca ccggctccct   19980 gccccccgctg gtggggcaca gtgagggggg ctgtggtcag acctggtctc tggagggcca   20040
gccgggggtt cccgtccacc tgtcaggggg ttcgacgcca ctttgagatg acaagtgagg   20100
ccacctgggc acagcgctgg tgtgagaagg aggccatcag gacaggtcaa gaacccaggc   20160
ccgccctgct ccgaaattct tcagacctga tgaagaggtg tcccagaagc gggtggtgct   20220
ccaggcccgc ctcaccagct ccaggaggt caaggttgga gagagacaat tctaggggcg     20280
aaccagacat agccaagagc agctcatctt ccctggagag gacgggctgc ccacttgcac   20340
agcccggggg cctcctgccc ctagacctgg taccttcact cttgttgcca cccctacatt   20400
catacctgcg ccccagtctg agccacacct aggcccccag ctgaagtgac actgtgggtg   20460
ccaggcatct gaggtctcca caagccccca cagactcagg gtgggaattc ctgggggcca   20520
gagctgcaga gggtgctgcc tgggggtgct gggctggacg ggggtcctgg ttgtccctcc   20580
tggttctcct ggttctccct ccgcagaggg agggaggcgg tggcctcagc agttcctcca   20640
gcagcgttcc tgagcgggcg gcagctgggc cctcttccca cagccacgct ggggttgcca   20700
tgcctgcagg tcttgggggcc ccctccccct tgatgaggtc ctgaccaaat gcaggaggag   20760
caattccagc accgaggggc gagcagagcc gcctgttagc actcctggga gggcccggag   20820
```

```
tggtccctga atgatggatt cacctggaac attttcaccc tcttcaggcc caccctgccc   20880
cagaggccca cggaaaccct gcctgtactg gggccgcagc gctgccccca cccatacgta   20940
attacacggc tcgtgtaat tgcaaattcg aggtttacaa agcctccccc tggaggcccc    21000
acgtgagtgt gagcgaggcc ccagcccacc cctgtggccc caagaaggct ctgcgacaaa   21060
atatccatga gtgccgccca cgaaggcatt aaaaccaacg accttctcaa aacttaagct   21120
gtcacaggac atttcaaagg gtgtttccta agaacacctc aataatgatg ttccaaggag   21180
accccatcca aattcctcca aggattacgc ccccaaggcc cagtccacac ttgctcactc   21240
ccaggacggg gagctcacct cctcctcccc gggcgccgtc tcctccacat cccacaccag   21300
gtcctgccca tgactttccc cctctcagcg ccgtcctcag tggccacacc aagaacgagg   21360
ccatgtcttc ctgggaaggg cctcagatgt cagcaaatgc cctggtgtct gggctgggc    21420
tgggggcacc agggtgaggt ggtgggggga gccaacctca ctgcccctcc ccttcctgcc   21480
tgcccttctt ccggggcacc cagcagctcg gtcctagggc gatgttgaca gacagacaga   21540
ggggcggatg cagcctacct cctgggcagt gagctgcggt ctgaggcccc tgcccagctg   21600
gaaaccacag ggaggggaag ggaggggagg agaggagagg agaggaaccg tcatggggcc   21660
ttggagtcga gtcagggttg ccaaatgcca gatgctggtc acctgcttct ttatcttggt   21720
aacaggcagg tcgggcagga gtgggtggtg ggtggggtg agcaggggtg aggggtggca    21780
gggcctcagc acagggatta tccctcccct gacacacaca ccagccctac tgtccctgtc   21840
ctgcccttgc agacatgtgt cctgcccttg cagacagccg caggcaggca gggaccacca   21900
tgagcaaccc cgtctctcct cctgagggc agcacagagc ctggaggagg cctgagtggg    21960
gctgaggcct ggggcgagct ggggtggagg ggcactggct gccgggctcc agggatcttc   22020
tccccttcct gccccggagg gtgctggcac aggggtgggg ctcactccca ctccgtagac   22080
acaatgatca gaggtcctgg gtgtctgggg aagctgggct gtgcgtgtat gcgtctacca   22140
tgtggggtg cctgtgagtg tgctggggcg tctgcagtga aggcctcctg agaccactcc    22200
acggaaacac cgggaatccc tgcagctgag cctgtctctc acgggaccgg gaagctggag   22260
agagccccaa ccctgcccgc tggggccgag ctccctgctc ctgcagcagt cccatgcccc   22320
acactctgag tctgccctat ccacagctgc tgggcctctc tgtggccacc atggtgactc   22380
ttacctactt cggggcccac tttgctgtca tccgccgagc gtccctggag aagaacccgt   22440
accaggctgt gcaccaatgg ggtaagtgag gtccaggcct ggctgcatcg ggaggggcct   22500
cgggtgcaag ggtggctggc acgagcccag ctggacgcct cacagccaga atggtgccag   22560
gccctaggca ggagccagag gtggtcaggg gcagggaggg gctgccctgg agtcctagct   22620
cccctgggca gggcctcggg tctgggtgac agccagtgtt cctgcctggt tctcgtgccc   22680
cacaggagcg tgggcacagt gtgggtatat gtcgggcagg gtcaggaagt ggctctgtgc   22740
ggtcaggacc tggctctgtg cagtcagggc tcagtcccag gcaggcctgg gactggcctg   22800
gggctgggca cagcaggtcc atgagggctc acatggctg atgttccact caggacctgg    22860
gatgtgggtg gggaggggt gggggctgct ctagccagac gcctccctgc agggactcag    22920
cagcgactta tccaacatcc agagagcggg agcgagggcc agagcctgct ggggccactc   22980
aggggtaagg ctgaggaagg cccctttaat gaggggatgt cagagccaga tctgcagggg   23040
actctcaggc aggagctcag ggggcccagg aaggctgcag cccggtgggc agatgtaggg   23100
aaactgaggc ccaggaggtc agggatactg ccttagaacc caatgctttt ccccaagtcc   23160
taggaccagg gcctccctgg aggaggacgc ctggggccca ggtccaggtc cggactgata   23220
```

```
agattacagc tccagtccgg ccacttgtca ctaggacatg gcaggaggat gcctggggcc   23280
caggtccagg tccagactga taagattaca gctccagtcc ggccacttgt cactagggca   23340
tggcagggag catgtggctt ccaagatagc cccacaggca tggagggcag ggaggaaaag   23400
agggaaggag gggcagtccc ccaggctgaa cgagtcccac ctccctcctc cttccctcag   23460
ggccgtctga tggagagaca ggcccattca gagcccccca ggagtccctc acggcccctg   23520
actcccaagt tagatttcac acccaggctg tgtgcactca ggacctgtcc tgggcacccc   23580
taaccctcct cctctctcct cccaaccagc cttctctgcg gggttgagcc tggtgggcct   23640
cctgactctg ggagccgtgc tgagcgctgc agccaccgtg agggaggccc agggcctcat   23700
ggcaggggtg agttcattgt gttcccagat gcccaggccc ccagaaaaga attagaaagg   23760
agtgaagagc tggcagggct gtgtgccacc cccacacctg agtgaccagg cagaaccaga   23820
ggccccaggg atgctggcca gccgagaccc ccacgtcaac cccacacctg agtatctagg   23880
cagaaacaga ggcccca ggg atgctagcca gccgagaccc cctacctggg tagccaaggc   23940
ccctccacca ggccctacct caccctgtca tctacacgcc caacaagggt tcctatagga   24000
gctctgaaag agagacgg ccctcctgac cctgggagct gtttccaaag tccctgggag   24060
ggtctggttc tattgcccag caagctctgg gagggcactg ggagcatccc atttcctgtt   24120
cggaggaggc cgggccaggc tcaggaaacg cccttgagc tctccagcct gggctctccg   24180
gagctgcaca ctctccttcc cagctgccgg aggtgtctcc ccagcccga ggtcccatag   24240 gcccctccac cccaccccat agcagtggcc tcttgtcacc ctcattccta ctcctcccca   24300
tgggcttctg tcttggtccc tgccactcga tggtcatcgc agaccccacc tggcggcagc   24360
ctccccacgc ctgtcctgcc cctgctaggc ccacagccct cttctctcac cccagctggg   24420
gcagctcctc cctggcgccc cgggctccca cctgtccctc tagcctcccg tctccccttt   24480
ccagccatga ggagcttgtg ctggggg ctt tgcttccctg tttagcctgt gaagctggac   24540
cactctgggg gtccctgagg gcagagcctc ctggtcccc agggctggca gggttttcag   24600
ctcagccttc aagttcagca aatgcttgtt taatgaccct ggtttataaa tgtctccaag   24660
aataggaata gagtcacctc ctggagctgc tgccgggcca accagccctg ggtgggccca   24720
tggtgggcag aggaggaccc agcagctcca gcactagcca ggattcctgc tccggggcac   24780
acgagcatgg gcaggga caa ccccggcctg tgctatctgg cttcagggcc aggtggg agg   24840 ccccagtggg gagatgacaa ggcaggtagt ctgcccccc ccccagaggg tgtgtggcct   24900
gcaaagggac acctggatgg aagaaaaggt tggcaacagg gccaggccaa ggggtccagg   24960
tcagagctgg aggcccagaa agaaccagcg ctgggctgc agtaccgtcc accaggggt   25020 gccatggtgc tgggcttgag gccacatatg cagaagccag ccgctgggcc acggggctcc   25080
tgtcccagtc accagccttt cccaccccac cttgccccg tgcacaaacc agtctagcac   25140
cctcatctgt ggccaaggcg gtcagggagc acctgggctc aggttctgtg tccccagcca   25200
gccccaaggc cagggtgact tgacatgtgg gtcaggcctg tagagcagcc ttggaggccc   25260
ccaactggat gcctgcactg ggctggggtc ctgaggacac tccagtccca gctgggtggg   25320
ctccagcaca gctcccaagc cccaatgcac ttagacccag cctggatggt gagctcagca   25380
tggccacagc agggagctgg gagacccag tcaagagacc tgctccattg agctgcatgc   25440
atgtgtgtgc atgagggtga gcctatgtgt atgcgtgtgc aaatatacat gtgtgtgtgc   25500
atgtgcatga gtgtgtgtgt gcatgtgtgt gtgcgtgtgc aggtgcctct gtgtgtgtgt   25560
gtgtgtgtgt gtgtaagtat ctgtcaccgg tcttcacctg cccctgttgc catacgggtg   25620
```

-continued

| | |
|---|---|
| tggtgtctgc gtgttgcatc tggcacatct gtatgtgtgt ctgcacgcat gagcacaagt | 25680 |
| gaagggcta gggaagggga gcagggagtg gaaagatttt ttccaatggg ctgggcgcct | 25740 |
| ggatgctccc cacaaagccc cttcctgcct gcccccaccc ctccggcctc tccctagct | 25800 |
| ggcctctcgc acaggaaatg aaagagcttg ctgggctgag agagcagagc tggcagcgcc | 25860 |
| gcccaaggaa gcacattcaa ttcgcttatg tatctattta tttatttcca tttagaatga | 25920 |
| ggagaaagaa aatggccagg gcagacctga ccacccagca gcctctgatg | 25970 |

<210> SEQ ID NO 9
<211> LENGTH: 30196
<212> TYPE: DNA
<213> ORGANISM: Homo sapiens

<400> SEQUENCE: 9

| | |
|---|---|
| tggtgagggc tctcttcctg gcttacagat ggctgccttc tctctgtgtc ttcatacagc | 60 |
| tgtccttcag tgcatgtaag gagagagaga gagaagaggg agctcctaaa tgtctcttgg | 120 |
| tataagggca ctaatcctat gggaccaggg accttcatgt cctcatctgt ccctaattac | 180 |
| ctcccagaga tccacttcct aacactatct cattgcgggg cagggcttca acctatgaat | 240 |
| tttgcaggaa cacgattctg tccatagcga acactgacac tgaacccgcc tcctaaagcc | 300 |
| ttctctcacc atattcctca tgctgctcaa agatcctctg caaccttgtg cccctcccaa | 360 |
| gggtccctgc acctgtccca gagagagggc agcctggcaa tgggcctggg ccctgacgct | 420 |
| tgagcatcgg ggtctggcct gaaagggat gggcgttcac ttctaggttc ctgagagagg | 480 |
| caacactgca cctttaaagg tgtcaggagc tcactgcccc agctggtcat gaaacagtct | 540 |
| cttcatcaag ggctaaataa agcacgctga ccaccaggaa tggggcagga agcttctgcc | 600 |
| ctgcagcctg ccttgtctgc acaggagtg tggggaccat taggggagg gtccgatgtg | 660 |
| cattttctg ccagcgggac cttccctgc ccccagtcct gcccaggccc ggggggtcac | 720 |
| tctgaaggca tctggctctt accccaggca tctcctgcct ctgccccact cctccacccc | 780 |
| cacggggtgc cgagtctcag cccaggctgg ggtggcccag gcaggacagc aggcttggtg | 840 |
| gtgcccggcc ccacatacta gtgggtggca cagcgtggat gtggatagag acgcctcccc | 900 |
| tacagtctgt ccctggtatc tgtgacgcag gtgtgggggtc cctttagact cccctgggag | 960 |
| acagctgtgt ctatgaaggg gcagccatcc ctgggtcccc tctgccctca ctgagggcag | 1020 |
| agcctaggct ccttggggg ggaagcaggg tgcccctcag tgcccactgg agttggccag | 1080 |
| cggaggcagc agcccacggc actgagaggg aaggcccggg cagccatgcc ccagaaactc | 1140 |
| ccttggttgg gagcagagca gtgcccagag cccagaaccc agtttgagta tggtcttggc | 1200 |
| tctcaaggga caggccaggg tgcctccagg ggaaggggc tgcccaggca gtagggttc | 1260 |
| aaaggtcccc tggggcccac ccagctgacc caggcctagg gtaatccaga aggggagctg | 1320 |
| ccctcctcct ccctgggctc aggagaggct gcaaaggcag ctcctgggac gtggatttca | 1380 |
| gaatcagggc aaaggacaga catgagccag attcaggtgc ccgcgtggcc cccacaggtc | 1440 |
| tcttcaagct ccaggcccca ctcgctgtga cgcaggtggg aagctcttga gtgcctcccc | 1500 |
| ggtgggaggg gccgcgctca cagacagcac aggggccccc aggctccagc ctcagagccc | 1560 |
| ggctgctcac ctctgatgga cagaaaaggg tccctgtctc aggaaggtag aggctgccac | 1620 |
| ctcctggccc gaggacacag cttttccagag gagggcctg cttctaagtc caagtcccat | 1680 |
| cccagccgga tagccagggg caactgccca ggtaaactga gacagcagca gcaggcaagc | 1740 |
| cagtgcagag ctgggtgatc cacaggttca tgagcggtgg caggtggaac aagggcacca | 1800 |

-continued

```
tgggcggagg gttgggcagc tgcaggtggc atcattgagc caggggcctc ctggtgggta    1860
aggacattgt agagtgagcg ggcgcacctg ggacccagga attcacagga aggagagagg    1920
aaaaaggaag tccctggcgg gtaaacacat atgcatgcac acacatccac gtctgcacac    1980
gcatccacgc ctgcacacgc atccatgcct gcacatgcat ccacgcccaa tctcttccct    2040
ggaaataaag ccaggggccc ttaggccagc ttgcagtggg gcccagccct taggacaggc    2100
tccttggtgg ggtaggggtg ggggcagctg tcctcctggg ccagctcctt ggggctgaac    2160
ccgctgctcg agggtcttc caggctccca gcggccggca ccacctctag agcaggtggg    2220
caggggtgtg tggggtgggc aggggtttgt gagggtgggc aggggtgtgt ggggtgggca    2280
ggggtgtgtg gggtgggcag gggcatgtgg ggtgggcagg ggtgtgtgag gttgggcagg    2340
ggcgtgtggg gtgggcaggg gtgtgtgagg gtgggcaggg gtgtgtgggg tgggcagggg    2400
tgtgtaaggt tgggtagggg tgtgtggggt gggcagggat gtgtggggtg gcagcggtg    2460 tgcggggtgg gcagggtgt gcgggtggg caggagggtg tggggtgggc agcagcctgc    2520
acagtggctt cccctcaaca agccacttcc tcttgcagag ggaatgttgg ggtgggaggg    2580
tgtggctcag caaagggcgt gggggttcca ccggctccct gccccgctg gtggggcaca    2640 gtgagggggg ctgtggtcag acctggtctc tggagggcca gccggggtt cccgtccacc    2700 tgtcaggggg ttcgacgcca cttgagatg acaagtgagg ccacctgggc acagcgctgg    2760
tgtgagaagg aggccatcag gacaggtcaa gaacccaggc ccgccctgct ccgaaattct    2820
tcagacctga tgaagaggtg tcccagaagc gggtggtgct ccaggccgc ctcaccagct    2880 ccagggaggt caaggttgga gagagacaat tctagggcg aaccagacat agccaagagc    2940
agctcatctt ccctggagag gacgggctgc ccacttgcac agcccggggg cctcctgccc    3000
ctagacctgg taccttcact cttgttgcca ccctacatt catacctgcg ccccagtctg    3060
agccacacct aggcccccag ctgaagtgac actgtgggtg ccaggcatct gaggtctcca    3120 caagcccca cagactcagg gtgggaattc ctggggccca gagctgcaga gggtgctgcc    3180
tgggggtgct gggctggacg ggggtcctgg ttgtccctcc tggttctcct ggttctccct    3240
ccgcagaggg agggaggcgg tggcctcagc agttcctcca gcagcgttcc tgagcgggcg    3300
gcagctgggc cctcttccca cagccacgct ggggttgcca tgcctgcagg tcttggggcc    3360
cccctcccct tgatgaggtc ctgaccaaat gcaggaggag caattccagc accgaggggc    3420
gagcagagcc gcctgttagc actcctggga gggcccggag tggtccctga atgatggatt    3480
cacctggaac attttcaccc tcttcaggcc caccctgccc cagaggccca cggaaaccct    3540
gcctgtactg gggccgcagc gctgccccca cccatacgta attcacggc tcggtgtaat    3600 tgcaaattcg aggtttacaa agcctccccc tggaggcccc acgtgagtgt gagcgaggcc    3660
ccagcccacc cctgtggccc caagaaggct ctgcgacaaa atatccatga gtgccgccca    3720
cgaaggcatt aaaaccaacg accttctcaa aacttaagct gtcacaggac atttcaaagg    3780
gtgtttccta agaacaccct caataatgatg ttccaaggag accccatcca aattcctcca    3840
aggattacgc ccccaaggcc cagtccacac ttgctcactc caggacggg agctcacct    3900 cctcctcccc gggcgccgtc tcctccacat cccacaccag gtcctgccca tgactttccc    3960
cctctcagcg ccgtcctcag tggccacacc aagaacgagg ccatgtcttc ctgggaaggg    4020
cctcagatgt cagcaaatgc cctggtgtct tgggctgggc tgggggcacc agggtgaggt    4080
ggtgggggga gccaacctca ctgccccctcc ccttcctgcc tgcccttctt ccggggcacc    4140
cagcagctcg gtcctagggc gatgttgaca gacagacaga ggggcggatg cagcctacct    4200
```

```
cctgggcagt gagctgcggt ctgaggcccc tgcccagctg gaaaccacag ggaggggaag    4260
ggaggggagg agaggagagg agaggaaccg tcatggggcc ttggagtcga gtcagggttg    4320
ccaaatgcca gatgctggtc acctgcttct ttatcttggt aacaggcagg tcgggcagga    4380
gtgggtggtg ggtggggtg agcaggggtg agggtggca gggcctcagc acagggatta    4440
tccctcccct gacacacaca ccagccctac tgtccctgtc ctgcccttgc agacatgtgt    4500
cctgcccttg cagacagccg caggcaggca gggaccacca tgagcaaccc cgtctctcct    4560
cctgaggggc agcacagagc ctggaggagg cctgagtggg gctgaggcct ggggcgagct    4620
ggggtggagg ggcactggct gccgggctcc agggatcttc tccccttcct gccccggagg    4680
gtgctggcac aggggtgggg ctcactccca ctccgtagac acaatgatca gaggtcctgg    4740
gtgtctgggg aagctgggct gtgcgtgtat gcgtctacca tgtgggggtg cctgtgagtg    4800
tgctggggcg tctgcagtga aggcctcctg agaccactcc acggaaacac cgggaatccc    4860
tgcagctgag cctgtctctc acgggaccgg gaagctggag agagcccaa ccctgcccgc    4920 tggggccgag ctccctgctc ctgcagcagt cccatgcccc acactctgag tctgccctat    4980
ccacagctgc tgggcctctc tgtggccacc atggtgactc ttacctactt cggggcccac    5040
tttgctgtca tccgccgagc gtccctggag aagaacccgt accaggctgt gcaccaatgg    5100
ggtaagtgag gtccaggcct ggctgcatcg ggagggcct cgggtgcaag ggtgctggc    5160 acgagcccag ctggacgcct cacagccaga atggtgccag ccctaggca ggagccagag    5220 gtggtcaggg gcagggaggg gctgccctgg agtcctagct cccctgggca gggcctcggg    5280
tctgggtgac agccagtgtt cctgcctggt tctcgtgccc cacaggagcg tgggcacagt    5340
gtgggtatat gtcgggcagg gtcaggaagt ggctctgtgc ggtcaggacc tggctctgtg    5400
cagtcagggc tcagtcccag gcaggcctgg gactggcctg ggctgggca cagcaggtcc    5460 atgagggctc cacatggctg atgttccact caggacctgg gatgtgggtg gggagggggt    5520
gggggctgct ctagccagac gcctccctgc agggactcag cagcgactta ccaacatcc    5580 agagagcggg agcgagggcc agagcctgct ggggccactc aggggtaagg ctgaggaagg    5640
cccctttaat gagggatgt cagagccaga tctgcagggg actctcaggc aggagctcag    5700
ggggcccagg aaggctgcag cccggtgggc agatgtaggg aaactgaggc ccaggaggtc    5760
agggatactg ccttagaacc caatgctttt cccaaagtcc taggaccagg gcctccctgg    5820
aggaggacgc ctgggcccca ggtccaggtc cggactgata agattacagc tccagtccgg    5880
ccacttgtca ctaggacatg gcaggaggat gcctggggcc caggtccagg tccagactga    5940
taagattaca gctccagtcc ggccacttgt cactagggca tggcagggag catgtggctt    6000
ccaagatagc cccacaggca tggagggcag ggaggaaaag agggaaggag gggcagtccc    6060
ccaggctgaa cgagtcccac ctccctcctc cttccctcag ggccgtctga tggagagaca    6120
ggcccattca gagcccccca ggagtccctc acggcccctg actcccaagt tagatttcac    6180
acccaggctg tgtgcactca ggacctgtcc tgggcacccc taaccctcct cctctctcct    6240
cccaaccagc cttctctgcg gggttgagcc tggtgggcct cctgactctg ggagccgtgc    6300
tgagcgctgc agccaccgtg agggaggccc agggcctcat ggcagggtg agttcattgt    6360 gttcccagat gcccaggccc ccagaaaaga attagaaagg agtgaagagc tggcagggct    6420
gtgtgccacc cccacacctg agtgaccagg cagaaccaga ggccccaggg atgctggcca    6480
gccgagaccc ccacgtcaac cccacacctg agtatctagg cagaaacaga ggccccaggg    6540
atgctagcca gccgagaccc cctacctggg tagccaaggc ccctccacca ggccctacct    6600
```

-continued

```
caccctgtca tctacacgcc aacaagggt  tcctatagga gctctgaaag agagagacgg   6660
ccctcctgac cctgggagct gtttccaaag tccctgggag ggtctggttc tattgcccag   6720
caagctctgg gagggcactg ggagcatccc atttcctgtt cggaggaggc cgggccaggc   6780
tcaggaaacg ccccttgagc tctccagcct gggctctccg gagctgcaca ctctccttcc   6840
cagctgccgg aggtgtctcc ccagccccga ggtcccatag gcccctccac cccaccccat   6900
agcagtggcc tcttgtcacc ctcattccta ctcctcccca tgggcttctg tcttggtccc   6960
tgccactcga tggtcatcgc agaccccacc tggcggcagc ctccccacgc ctgtcctgcc   7020
cctgctaggc ccacagccct cttctctcac cccagctggg gcagctcctc cctggcgccc   7080
cgggctccca cctgtccctc tagcctcccg tctcccctt  ccagccatga ggagcttgtg   7140 ctggggctt  tgcttccctg tttagcctgt gaagctggac cactctgggg gtccctgagg   7200
gcagagcctc ctgggtcccc agggctggca gggttttcag ctcagccttc aagttcagca   7260
aatgcttgtt taatgaccct ggtttataaa tgtctccaag aataggaata gagtcacctc   7320
ctggagctgc tgccgggcca accagccctg ggtgggccca tggtgggcag aggaggaccc   7380
agcagctcca gcactagcca ggattcctgc tccggggcac acgagcatgg gcagggacaa   7440
ccccggcctg tgctatctgg cttcagggcc aggtgggagg cccagtgggg gagatgacaa   7500
ggcaggtagt ctgcccccccc ccccagaggg tgtgtggcct gcaaagggac acctggatgg   7560
aagaaaaggt tggcaacagg gccaggccaa ggggtccagg tcagagctgg aggcccagaa   7620
agaaccagcg ctgggctgc  agtaccgtcc accagggggt gccatggtgc tgggcttgag   7680
gccacatatg cagaagccag ccgctgggcc acggggctcc tgtcccagtc accagccttt   7740
cccaccccac cttgccccg  tgcacaaacc agtctagcac cctcatctgt ggccaaggcg   7800
gtcagggagc acctgggctc aggttctgtg tccccagcca gccccaaggc cagggtgact   7860
tgacatgtgg gtcaggcctg tagagcagcc ttggaggccc ccaactggat gcctgcactg   7920
ggctggggtc ctgaggacac tccagtccca gctgggtggg ctccagcaca gctcccaagc   7980
cccaatgcac ttagacccag cctggatggt gagctcagca tggccacagc agggagctgg   8040 gagacccag  tcaagagacc tgctccattg agctgcatgc atgtgtgtgc atgagggtga   8100
gcctatgtgt atgcgtgtgc aaatatacat gtgtgtgtgc atgtgcatga gtgtgtgtgt   8160
gcatgtgtgt gtgcgtgtgc aggtgcctct gtgtgtgtgt gtgtgtgtgt gtgtaagtat   8220
ctgtcaccgg tcttcacctg ccctgttgc  catacgggtg tggtgtctgc gtgttgcatc   8280
tggcacatct gtatgtgtgt ctgcacgcat gagcacaagt gaaggggcta gggaagggga   8340
gcagggagtg gaaagatttt ttccaatggg ctgggcgcct ggatgctccc cacaaagccc   8400
cttcctgcct gccccaccc  ctccggcctc tcccctagct ggcctctcgc acaggaaatg   8460
aaagagcttg ctgggctgag agagcagagc tggcagcgcc gcccaaggaa gcacattcaa   8520
ttcgcttatg tatctattta tttatttcca tttagaatga ggagaaagaa aatggccagg   8580
gcagacctga ccacccagca gcctctgatg gtgaaggccc tggggaggtc tgggtgggcc   8640
catccaccac ccaagatcct ctctgcgcgg gaggttggtg gtgggggag  agagagaaag   8700 agagaaagag agaaagagag agagaggccg tggatgctct ttctcctgag gaatgaaatg   8760
gtttctggaa aatgctggtc tcctgagctg gctcagggcc tcaagcctgg gaggcagcat   8820
tgagtgatag cttccagatg gggatggtgg ccctcagcca gcaaggagga ggaggaggag   8880
gacgaagaag gaggagggca gaggagaagg agggagaaag agggagaggg aagaggagga   8940
aaaggaggga aaggggggga gaaggagag  ggagaggggg agggagaggg aggggagggg   9000
```

```
gggagaagaa ggagggaggg ggagaaggga agaggaggga gaaggaggga ggacaaggga    9060
ggaggagatg gaggagggg  aaggaggaga aggaggaggg agaaggagga ggaaagagaa    9120
aagaggaaag aaggtgagga gaagaaagaa ggggagggtg gaaggaggag gaggaagagg    9180
aggaaggagg aggagagaga agagaggagg aggaggcagc tcccaggcca tcccccatca    9240
ggccttgcag cctccagggc aggcaggagg gccatgagga gccgccagcg ccctgtccct    9300
gcagggctgg aggcccatg  ctcacgcctg tgcttggggg ccagcagggc tccccagctc    9360
tttccacgcc cctctggccc agcttcccct ggcatgccag cgttgtcgct gcccacctgc    9420
cagcatgtgt gggtctccgt ctatcccacg ggcacccatg ctcctggcat caccctgaat    9480 ggggcccag  ggtttgaagg gcccagaccc aacctgctcc agcctgtgga ccacccaggc    9540
gggcacagtg ctgcctgagg gggctggcgt tcaccggggg cctcaggact cctgggggag    9600
ctgcccggtc ggtggctaga ctcaccgtca ggtactccag gtcctcaggg caccagcatg    9660
aaggcaaagg cggctgccca gaccctgagt gggaggacat ccccagggtt cttagcctgg    9720
gtgacctctg ccaccatcca taaaactgta tcgggggcat ctgtatgctc tcagaggagg    9780
ggtctctcgt gttccttagc ttccgcaagg gggctctcaa aagcctggaa gccttgaccg    9840
agagaacaac gggcaagtgc cgggggcggg tgcgcagacg tttccaccag agaacgcccc    9900
actccacgac taggggcacg ggcatcagtg agagagaggg gacagtggtt ggccgggcca    9960
tggagaccca ggcagagtat ggagagaaag tgaggtgagg gaggtgggct caactgcaaa   10020
gagagaggcc acagcatcct gagcaggcac cacacctgtc ccaagcctca ccagcactgg   10080
gctagctggt gccttgtttc agaaaagaag gcaaaacaga agatcctaca gccccggccc   10140
tggagaggct caggctcagg ggagactctg cccggccctg tccaggtcca tgcccctcag   10200
gaagcagccc cagtgggcag aggtctccat ctttctcaggg gtgccctgcc cctgctgggc   10260
aggggtgcag tgttgccatc aacaggcccc tgggggccaa aatgggagaa caagggatga   10320
attcccaaaa agcgcagggg aaggggatgg gaaggtgcta tggaacccac gcacccagcg   10380
cccacgctct ccccaggcca agtctccctc tcaggcagtg gggagcggga ctcagaccca   10440
cacctcgacc aagcatcctg ctgggggcgc agctgaggg  cactgccctg cccaggcctg   10500
ccaggcccca ccaggcccg  cagtgactgc ccccaccccc gcagtgacca ccccccaca    10560 gtgaccggcc ccccgcagtg accagccccc cgcaatgacc agcccccaac agtgaccagc   10620
cccccatagt gaccggcccc ccacagtgac cagccccccg caatgaccag ccccccaacag   10680 tgaccagccc cccatagtga ccggcccccc gcagtgacca gccccccgca atgaccagcc   10740
cccaacagtg accagccccc catagtgacc ggccccccac agtgactggc cgcccacag    10800 tgaccggccc ccccagcag  cgaccagccc ccgcagtga  ccagccctca acagtgacca   10860
gccccgctct gcccccaggg cttcctgtgc ttctccctgg cgttctgcgc acaggtgcag   10920
gtggtgttct ggagactcca cagccccacc caggtgagca ccagctgccc ctaccctgca   10980
gtggagggtc ccccagtaag ccagtgggca cctggggact ggggagcagt cctgggagga   11040
gcagccccag cttccaggct tgtgctgacc gggtgggggtg ggggagaccg cagcctgggt   11100
tccctctgcc tgaggcttca gggaggccaa gcgctggagg tgggtgaggg ccagcagctc   11160
cctggtgggg agggacctat gctgtacccc tgccttcgcc ccagtctcat tttcttaaag   11220 ccccctcagcc cacccctcc tgagctgatg cccctcgggt ttgagggagg gaatgaggag   11280
gaagaagaag gaaagccact ggcttggcct taggggttga ctagaaggag cagagtgttc   11340
cagaaaatga gacctgaggg ccagcgctcc tgatggcctg gtggggcaga cggtaccagt   11400
```

```
ggggaaggga cctggagacc cgcggactgg ggtgtcgcag cctccacccc ctccacggaa    11460
cagcacccat ccttccgtcc tggatgctga cctgcctgga ggagggtccg gcctagctga    11520
ccgtgggcag gggccaaggg cgtccccgtg gaaaggccag cagcttggag aggaaggagg    11580
cctccctggc ccagcagaga atgagagctc ggtagcagag ccagcccac cttcccttg     11640 agagccagac ctggtgagag cccccagggc agccgggcgg caccagggac agccacgggc    11700
agggtcatgg agtggggcag gagagcctgg caggtcacaa gaggtgattt cttggagccc    11760
tagctggagt cctagtggcc tcgtgtattc aagtgcctgg ttgcccaggg ccctcaaaca    11820
caggcttggc catgagagat accgaggctg gtagcaggca ggtcctctgg ctgagctctg    11880 caggggcct gctgtgcagt ttcttgagct gtgctggcag cctgagtgtg gtggtcccca     11940
ccgtggtttg caaatggggg gactcaggcc ctctgggggt gggggagct caaggttacc     12000 ctggcagtgc cggggctgga tgggggctcc aggcttacga caaaggctct tggccccaaa    12060
gtgcccaccc acccctggca tcatttggga ggaaccgcct gaaccaggtg ggagaaacac    12120
cattttatca ggcccagaag gatcccagag gggctgagcc cccagaagag ggctgtggct    12180
ttgaggactg gcacaggagt cttaccaggg tggtgagctg ggccaggtcc gtgtttcggc    12240
ctcacgtttc ctgtccactg aggggtggtc tggctcattt gaggtctggg tcacagtgtg    12300
ggtggccgag gtcaagacag ctgccagggt tccccgggct cgtctggggc agctgcggcc    12360
catgccccat gcttctgtgt gtttatggct ctgatcgtgg agccacaatt ctggagggga    12420
gggggccata caggggccac aggacagaac gcagctgggg cctgctctcc aggaagggaa    12480
gggggtgcaa gaagatagat gccccagccg ggctcaccta tggcctgtcc cagccccagg    12540
cagcatcccc cacacacatg gtccttgtct ggcccgtgcg cccagctgcc cttcaggggt    12600
cagttctcag ggccttgcct gacccaggc agggactgg ggcttcctcc tgggcctctg      12660
gtccccatct gcccctccca gtgggtcttg acttctggca tcatctgtgt caggcctggt    12720
ggccatggag gtggcctggg tgaaggagct ctgaatatga agtcagtgtc cttgggccgc    12780
ccttgggcaa gccactttaa cttcctgggc ctcagtttcc ttttctgtga agggagcacc    12840
aagatccagg ggctgcatgg gtgggaatgg ccaggtgtgt gcaaagactc ttcctcctca    12900
cctgcgtgcc tcctgccgtg ccccgttgcc caggctggtc ctccaggacg tgggacttgc    12960
tcgaagctgt cctgggtgtg gatggagtgg cttttggtgcc agggcccggg ccctgagcag    13020
gaggggcggc tgcacatccc gtctcctgcc ctccacccctc agggcccacc agagccgaat    13080
gggcttcaac cttgggctcc ctgtccaaca aagtcctgct ggcagcctag acagtggcaa    13140
aggccaaagg ccccaagctg ttggcaccgg aaacgtcgag gtgagagccg ggggcccaga    13200
gcccagcccg gcccattcac ccattccccc tgtccctccc cacagggcca ctgaggtgtc    13260
ctgaacacag ggtcagggtg actcatgtgg tgcccctgcg gatgggaagg cagaggacag    13320
aggagggaag ggaccagcca catgcccttg gtggtgccct gtggcacag acccgggccc      13380 agagctgaaa gtgggtgcc cctccacctc cccaactctt gccccaggga gtcctggctg     13440
ccacttccct gggatgctca tgcgggcagg aggcgtggac cggcttcag ggatgaatgt      13500 ggagcttgag ggctattaat tacgttctcc tcgagggctg agccacttt gccttaacc      13560 ctcccctgt gccctgacga gtctgcttcg ggaataattc atgctcaaat taagtacagc      13620
agtgtggggt gcagcctcgt cctcacagtc tgccccaccc tggagccact accctccctg    13680
gatcctccag ccgccgagtg ggctcaggcc agagccagct ctgtaccgtg tggggctggtc    13740 cacaggcctc ctgcagctcc tggtccccac ctgccgttca ggacctgtct gtaccttcct    13800
```

```
gagcactttc agcagacaca ggatggggtc gccaagccca ggcagacacc agggaagatc    13860
tggtcatggg gaaaagcccc cgggcaccgg aagacggagc ttagtgcgtt gatacctgtc    13920
aggcagcacc ttcccccagg tgtcctgaga aacacaggcc ccaggctcct tcagagcccc    13980
cagagcctgg aatggagaca gacggtgaag catcacctag gagcccaggc cccgtggaga    14040
gcagccggcc cggcctccag ggccctccag ggccagacaa ccggctttgg ggtaggaggc    14100
ctacctcgct gagctctgct tccccagtcg tggggagagc tgcttggcag agccaggcag    14160
ggcaggaaga gccaggcagg gcaggcaggg caggcagggc aggcagagcc aggcagggca    14220
ggcagagcag gccccctcagc cactagcagg agttgtcact ctcgcccatg ctgtggtaat    14280
aatgacacct tgctcacagc ctcagaggca ccttttgtcct ccttgggcca tggcaggcgc    14340
ctgacaatgg gaacagtcat tggagttggg agggaagcag gaggggaggt ccgagccaac    14400
ccccgggccc actccgctgg gcctccagtc ctcaccagga cctccaccca cgaggacaca    14460
atggccaggc cagactccac ccccatttca cactcacaga cgctgaggct gaacaaggcc    14520
cccgccctgg ccgacagtgg tgtggccagc ttggtgcctg cccgcccctg ggcactgcgg    14580
ggaggacaag gctggctgag tcggggatga ctcacggaga gtggtctgac ttttattagc    14640
atcaatggga gggatgcatt agggtcagga gccaagtttg gcctggaaag tccatctgac    14700
tcctgttggg gcctccaggc ttgggcaggg ctgaccgaga gcctccactg cccactgccc    14760
gcccagttgg ccgctgtcag ggcctgccac gggggctggg ccccagtgca atgaggaccg    14820
ccgtaagcca ccccttcctt ctggagggca ggtgtgagtg gctagagcgg gcctggggct    14880
tccatcctcc cccagcccttt tggggcagct gctgagcacc cccttcatgt gtcttgactg    14940
tcagcatggc atttggggga gaactgaggg cctctgaggc aggaaggaga catcagaggg    15000
cagggacctc aaagagggcc tcgccctgtg ccaggagacc agcgactcct ggagcagtca    15060
cagaagcctt cctgtaggag gcgagattcc agtttgtctt tgaaggagta acttggcagg    15120
ggagagcatc ttgcttagga gggtggagac atgaggtcca ggtgttggtg aggtgtggag    15180
cgcaggcagc acatccagcc aggccccgtc accttccacc ttcttcaccc cctgccccac    15240
agtggcctcg tccacccaga tctggcctca ggtgcccaag gcttctctgg tcaaaagcct    15300
tacccggagc ccagctgccc gggcttccag aaggcagccg ggtgattctt gggaaagatc    15360
tagaatcccc aagcttttctg ggagctgagg tcctggcaca gggtctctca gcctttttcc    15420
accaggccca gccccatccc ccatttccgg gtcaacagta gcgtgctgga aacttctgtg    15480
ggccaacctt gtaagaccac agcggaggcg gacgcagagc ttggcctctg ctttatcctg    15540
cgggaccctc tgggggcagg agggccactc tgacggccat tgtgtgaagg ccccatcgtt    15600
gatgttggga agcactgtga ctggctgccc agggacccag gttccgcttt ggggagatcc    15660
acctgctaca aggagggcag tgctgggacg tcactcagca ctaagggccc actagcgttt    15720
gggatgtcgt ggggaggggg ctgtgtcccc ggatctccca ccaggccag gacctccctg    15780 tggtctctcg gtgcaggtgg aggacgccat gctggacacc tacgacctgg tatatgagca    15840
ggcgatgaaa ggtacgtccc acgtccgcg gcaggagctg gcggccatcc aggacgtggt    15900
gagcgtgggg acggctgggt ggcagggcgg tcagcttctg cttggactgc agttcagaga    15960
acaggcgcag ggtggccagt gagaggtctg gccaggcacc gagggggttc caggacacag    16020
gccagagttg cccctcaggg ctgggggcaa aaagctccca ccctctgtct gcccaggaca    16080
aggccgccta ccagattctc gaggcccagt gcaaaacgag agggcagggc cctgtattca    16140
gaaacactga aggatttcaa gagcattaaa gcaaatacgg ggccgaacat agtggctcac    16200
```

```
acctgtaatc ccagcacttt gggaggaggt tgaggcaggt gaattgcttg agcccaggag    16260
ttcgagacca gcctgagcaa catagggaga ccttgtctct actttaaaaa aaaaaaaaaa    16320
agaaaagaaa aaataaaagc acatacagcg cacaggccct gtgaacaggg cggggaagct    16380
gcctggctcc agcaggtgtt ctgtcaccag caggcaggca gcgcagcttg agagagctcc    16440
ccttaccagg gcccggctgt gcaatggctg agccccagc agaagcagct gcaataccag     16500
tagccccagc cctggcctgc agggaacccc acctggatac ttgtggtgcc tcagtttccc    16560
catatgtgct gcccgcctcc tggggtctcg ggagcacatc accactccct cccttctgtt    16620
cctgtagttt ctgtgctgtg gaagaagtc tcctttcagc cgtctgggga gcacagaggc      16680
tgacctgtgt cagggagagg aggcggcgag agaggtgagg gggggacctg gatgctggcc    16740
aggcaagacc ctcgggggct ggacaccctg gggcccaacc ccaagaccca gggccatcct    16800 cccacccccac cccttggcct ccccagaccc ttgggaactg ccgctgaagg gctcagggaa   16860
ggttctgatg tgatcggagg ctagttaggg ttcatggtac gccaagccca ttgggtggcc    16920
aggctgggct caagacataa acacaggccc ctttgcccag ctggacgcag ccccatgcg     16980 ccattcactc cttcaagcca gttccagcct ggggacttcc caaggccagc taagtccaca    17040
gaagcctctt ggagtgcacc catgagggct ctgtgccaag ggctgcaggg ctggtgtggt    17100
gggctctgtc taggggggaag ggtgcaggcg tcctgggggg catcagaagg agttgaaggg   17160
cactcagagg agaagaagta ggccagggtg tggccagggc ttcagcaaca acagagcggg    17220
gcccgaggcc aggaagcctt tcctccccag ggccctggga gagactgggc cctcctctct    17280
ttctcctggt gcccggcagc cctcccccag cccaccctgc ccctccctg ctcccctccc     17340 cgctcccctc ccctactgtc ctggaaacaa acccaccctca tctcacagtg ggaggcacct   17400
ggcgaccctc caagaaacag aggggaggag agcaaatggc tggaggcctg gtgagggtg    17460 gagccacagc caaggctctg agggcagaag ggctggcgct gaggatggtg ctggggaggg    17520
accagcggca ttgggggcag ggctaacagt caggaccct gtgccaccca aggagagact      17580
gaaaaggccc ccgactgaaa agcaggagcg agggcctgcc tcgagcaccc ttgggatggc    17640
agggccatgg gcccgactgc aaagcctcct ggggagccgg aagagccagc acaggcggca    17700
ggcacggagc cacccagatg ggctggcatg ggcgggaggg aggcagacct gcctgcgggg    17760
gacaggaggg tgagccctga gaccctgcgg aggcctccac aggccgcccc agttgccatc    17820
atctccaggg ttcagagaca ggcctgccac ctcccttttc tgaaaagatg cctctgggtg    17880
ccatgccctg gggtggcact ggaagcctgg gatggaacca ggaagctggg actgtgcggg    17940 gaccccctc acacccctcc accagctggc ttcctgccct ccctgttagc catcacccctc    18000 tggtcaccaa ggtgctgtgc ccggcctgg gctggatgct gggaacccag agtgaattcg     18060
aagtggcccg gcccagggga gccaacgtgt ggcccaacat ggacgctcag gacagctggg    18120
agacggcacc ggccgggccc agggcagtgc cagagtgccc acagaggcca gccctgtccc    18180
actgggcttc acctgctcgt gctgcctttc cctagagccc tgggggcttc ctaggaatgt    18240
gccgcacccg ccgccctgct gccctggcat tggcctaggt gggcgctgca gctccatggc    18300
cccacagagg ccgcttgtcc aggcagggag ggccgctcag ggcgggtacc atgcctgctg    18360
ccctctcaca ggactgcctt cagggcatcc ggagcttcct gaggacacac cagcaggtcg    18420
cctccagcct gaccagcatc ggcctggccc tcacggtacc ctctcgcctc cctcactgcc    18480
ccttcccacc tcctgcccct cagcctgccc agccccgac tcagatggaa gggtgacccg     18540
ggacaggatc tctggtcttg agcctcactg gctgccaacc tcagggagct gctctggtgt    18600
```

```
gacagggcct gcctcctaca gctgggccgc ccccttacac tgcagagtcc tgatgcttcc  18660
tggggagggg cgcccgcacc ctggggcagt ggggcagccg cgggtgtctc cctcccaggt  18720
gtccgccttg ctcttcagct ccttcctgtg gtttgccatc cgctgtggct gcagcttgga  18780
ccgcaagggc aaatacaccc tgaccccacg gtagggcccc ctgcctgccc ccacacccct  18840
c tggaagggtc ctccagctct gctcgagagg catctgctct gccagctgct aggagggagc  18900
cccgggacca gccccaggc tgacactgta gaggaaacgc tttgggggtg gctgagcacc   18960
agggtggggt gggagacctg gagagtttcc agacccaatg caccgcaccc catggcccac  19020
atggggaccc ccctttgctt acccccaggc cttaccaaga cctggagatg gatgcttctg  19080
ggcctccagg ttatagcccc aggccaggat ctctgtgctt gaataccca gagctcctca    19140
tgcttagggg gcagggaggg tccaacccac agccaggcag ctcttcctgc ccccacggag   19200
cctggcccgt ctctgcctgc catgcccatt aacccaccca cttgctcttc ctggccatcc   19260
aagccctcat ccctgggtcc tctgcattct acaatagcct cacagtcccg tctagaacat   19320
tctgcaacag cctcacagtc ccctagaac attccacagc agctccataa tccctccag    19380
aacattctgc aacagcccca tgatcccctc tagaacattc cacaatagcc tcacaggtcc   19440
cctgtagaac attccaccac agccccatga tccccttgct cctcagagca tgtggccgcc   19500
agccccagga gccagcctc ttgagatgct cccagggtgg acccacacat tgtctccact    19560
ccgaagcagt tgctattggt ccaagaggat gctcgggtag tcttcggtgg ctgcaggaga   19620
gcgatgctgc gcctctgccc ctctcctgcc acctggctgc ccacagaggt gaagacgccc   19680
ctgctgtcag ccctcatggg atccctgagg ggagggtccg agctgtgagg agggaaggga  19740
gtgaaggccc agccagagag ccaggctcca ttgggaacag atgcaagggt aaggggtagc   19800
tcaccaaatc cctccatggg aacgggctgg gagcaagcac aaaggaaacc acactggagg   19860
cagcagccca gggcagactg caagacactg gtgggccacg gcctgagggg ctccacccag   19920
acacaagctg cactggtttt ctatgctgcg taagaagcag catggatgta aggactgcaa   19980
gcagtgccca tttatgatct cgcagctctc cagggcagaa gtcgcggtgg gctcagtggg   20040
tgccctgagc ggggtctctc agactgacgt caggccttgg tgggctgcac tctcacctgg   20100
aggctccggg gaagcatctg cctccaggac cattcaggct gttgacaagt caactcctca   20160
tggctgtagg actgaggatc ccaagtcctt gtccctggtc ctgtggtccc tccaccttca   20220
aaccagcaat ggtgcattga gcaaattgtg gtcaaatata catcacatca aatttaccat   20280
cttaaccatt gttaagtgta tggtttgtgg cattaaatac attcacattg ttgtgcaacc   20340
atcaccacca tctatctcca gaactttcca tcttctcaag ctgaacctct gtccccagta   20400
aacaccaact cccattctct gccccggtcc ctggcaccca ccatccactt ttcgtctcta   20460
tggattcagc tgctccagga acctcatatg tgtggggtca cacaggattc atccttttgt   20520
gtctggttta tgtcacttac tgttatgtcc ataaggtcca tccgtgttgt agcctgtgtc   20580
agaattcttg aaagagaaat cttatcagct ttcccatcat ctcacagcca catggtccgt   20640
gattaaggca ggacatttag tgggaagcgt ggagcatttt agatattctg cctgccacac   20700
ccactcttac tggacgttca gaccacgttg atgacgaatt agctctaatg gtccctaaat   20760
gtttgcacaa tttgctcaaa attctaagtc ctgggtggaa cgccaagttg gcccagccta   20820
ggccaaggtc ctaatgaagc cgacaaaaga gaaggaatgt caaggccctt ctaacttcca   20880
tagagggtgt gtggccccat ctcccaccaa caatcctgta atcccaacac tttgggaggc   20940
cgaggcagga gactgcttga agccaggagt ttgagaccag cctgggcaac atggcaagat   21000
```

```
cttgtttcta caacaacaac aaaaagaaaa cattagccag gcatggtggc acacacctgt    21060
ggtcccagcc actcagggg  ctgaggtggg aggatctctt gagcccagga tgtcgaggct    21120
gcagtgagcc atgatcacgg taccgcactc cagcctgggt gacagagtga gaccctgtct    21180
caaaatataa acaaataggc gggggggcagt ggctcacgcc tgtaatccta gcactctggg    21240
aggccgaggc aggcagatct cttgaggtca ggagttcaaa gccagcctgg ccaacatagt    21300
gaaaccccat ctctactaaa aatacaaaaa aaattagcca ggtgtggtgg cgggcgtctg    21360
taatcccagc tactgagcag gctgaggcgg gagaatcgct tgaacttagg aggcagaggt    21420
tgcagtgagc cgagatcgca ccattgcacc cagcctgggt gacaagagc  aaaactccat    21480 ctcaaataaa taaataaata ataaaaataa ataaagtaca aaaaaattag ctgggcatgg    21540
tggtgggtgc ctgtaattcc agctactcag gaggctgagg cagaagaatc acttgaagtc    21600
aggaggtgga gggtgcagtg agccaagatt gcgccactgc actccggcct gggtgacaga    21660
gcaagacacc atctcaaaaa aaaaaaaaaa tttaatatat atatatatat gtgtgtgtgt    21720
gtgtgtgtgt gtgtgtgtgt gtgtatacat atatacacat atatgactaa ctaaataaat    21780
aaatgctaat aaataaaata aataaattaa aataaatctc caaactagaa gagtaaggac    21840
taacagggcc aagaggtaaa cttttgtgaa tgttccaacc ataagtgctg ccctcactct    21900
cacccgtagg ccccccggcct gtggattctg gtttagggga acggaccat  tcaccagggt    21960 ccagggtcat atgctgtagg actctctgca gtcttgtggt ggcatcttcc agctgagctc    22020
ctaaataatc ctgagtggtc ctgagaagcc agatcaccat cccacagggg tgggtcctgt    22080
ggagggacag ggtacatgga accctagtga atcccatggg gtctcccac  tgccctgtcc    22140 tttggctgta aaggcgatgc cttggctgga aacagcagta cgtgcaggag caggcagtag    22200
gctgggaagg aaagtgccgg tgccggagga agcagtgcta gtggaggggga gtgggtccag    22260 atcaagaagg gttaagtgca gtcatctttc ccatcatctc atagttgcac ggtccaggga    22320
tgaagacagg acagttagca aggagagggg aaccggatca tttaagacca cagctggaag    22380
atgtccctga atgtttgcac aatttgttga aggttctaag tcccgggtcg aacaccaagt    22440
tggcccagcc taggctgagg ccctaatgta gcttggctaa caagagagaa ggaatgttgg    22500
ggcccttcta acctccatag ggggtgtgg  ccccccatga agtggaaata gtgccagtgg    22560
gggagcatca aggagcaggg ccatatccta taggacttca ctgcagtctt gcggtggcat    22620
ctcccagctg tgctcctaaa tgattctgtc ccctccgcac taaatgtcct cccttcgtcc    22680
ctgggaaaag ctagaccctc tccatgaagg aaggcgtcca aagccagtca gcccttggcc    22740
aggtgaccaa tcggtctccc atgagatgtg gtgcgcttct gcgggcggg  acggcacact    22800 gctgaccttg atcgggcatc ggctgcagtg caggggtgtc tggaagagct tggtaagctg    22860
agtccctgtg gctgggccac ggcggctccc ctcccctcca tgtctgcctc agggcagcaa    22920
cagctccctt ggggcagagg ctgcctgtct gccacgggtt ccaagaacct tattagagta    22980
cagtacccca tgcgcttgac agtatgccca gcctgtccag ctacaggact cagcagacaa    23040
acaacaccca ggtcagacta cacctgatgc ccatagacag ggctcagtct ccacccaggc    23100
ccaggggaaa ccgagcgctg tatatccaag cgagaagagg tcctggacac agagggcaaa    23160
ctctgctctc ctcgacgggc actgtggcct ccaccatggc ttggctcagg ctccgagggc    23220
gccttggtca gccaagaccc caagaggacc cttaggtccc tgggtcacaa ctgagtggct    23280
cagtccacac aggaacaaga ccacatgggc atcgtcactg gctgtgcctc ctgcagaaag    23340
caggccaccc ctggcgtgcc tggacacagg ggaagcacac acccaaatgc aggctgtgtt    23400
```

```
tcctccaaag agtgctgcgc acggatgact cagggtgcag gactggtcct tcaccaccac   23460
ggagtaggca tgcccggctt cgttggaccc cagagagagc ttcaggagaa agcaggagtc   23520
tctgttttta cagggtttcc ttctcaccct gccactcatg gttttgtta aagcaaccta    23580 caacttcctc acctccaggt catatcagcc caatgtcctg tgggctgggg agacggtcaa   23640
ggtccacatg ggctaaattg tggctgagag ctaggttatt catgtaatcc caaggcaggt   23700
ccacgctgct gtccctccca ggtgagagca aaccaccttt atggttttct atatgttggg   23760
atagactgaa aaacaacaac aaaacaggtg tttgctggcg aaatagctgc ttgccagtac   23820
aaatgcctgt gctgatttgt tccaattaag aagaaaactg gtgcttgctt cagccacaca   23880
tacactaaaa ttgaaccat acagagaaga ttagcatggt cctccctgcg caaggatggc    23940
acgcaaattc ttgatgcatt ccatattttt ggaacatacc tcaaaataat aagagccata   24000
tatgacaaac ccacaaccaa tatcgtactg aatgggcaaa agctggaagc gttccccttg   24060
aaaaccagcg caagacaagg atgtcctctc tcaccactcc tatttaacat agtagtggga   24120
agttctggcc agggcaatca gacaagggaa agaaataaaa agtattcaaa taggaagaga   24180
ggaagtcaaa ctatctttat ttgcagataa catgatccta tatctagaaa accccatcat   24240
ctcagcccaa aagcttctta agctgataag caacatcagc aaagtctcag gatacaaaat   24300
caatgtgcaa aaatcgctag cattcctgta caccaacaac aggcaagcca aatgaactct   24360
cattcacaat tgccagaaaa agaataaaat acttaggaat acagctaaga agggatgtga   24420
aggacctcct caaggagaac tacaaatcac tgctcaaaga aatcagagat aacacaaaca   24480
aatggagaaa cattccatgc tcatggatag gaagaatcaa tatcatgaaa atggcctcac   24540
cgcccaaagc aatttatgga ttcaatgcta ttcccattaa actaccattg acattcttca   24600
cagaattaaa aaaactattt taaaattcat atggaatcaa aaaagagcct gaatagccaa   24660
ggcaatccta agcaaaaaga acaatgctaa aggcatcatg ctacccaact tcaaactata   24720
ctacaggaat acaataacca aaacagcatg gcactggtac aagaacagat acgtagactg   24780
atggaacaga ataagaaca cagaaataaa actgcacacc tgcaaccatc tgatctttga    24840
caaacctgac aaaaataagc aatggggaaa ggattcccta tttaataaat ggagctgtga   24900
gaactggcta gccatatgca gaaaattgaa actggacccc ttccttacac catatataaa   24960
aatcaactca aggtggatta aaacgtaaa tgtaaaccc aaaactttaa aaccctaga     25020 caaaaaccta ggcaatacca ttcaagacac aggcatgggc aaagatttca taacaaagac   25080
accaaaagca attgcaacat aagcaaaaat tgacaaatgg gatctaatta aactaaagag   25140
cttctgcaca gcaaaagaaa ctataaacag agtaaacaca cagcctaagg aatgggagaa   25200 aattttgca acctatgcat ctgacaaagg tctaatatcc agtgtctata aggaacataa    25260
acaaatgtac aagaaaacaa acaaacaaac aaacaaccc attaaaaaag tgggcaaagg   25320
acttgagcaa atacttctca caagatgaca tacacgcggc caacatttga aaaaaagctc   25380
aacatcactg accattagca aaatgcaaat gaaaaccaca atgaaatact atcccacacc   25440
agtcagaatg gccattatta aaagtcaaa aataacaga tgctggtgag gttgtggaga   25500
aaaaggaatg cttttacact actggcagga gtgtaaatta gttcaaccat tgtggaagac   25560
agtgtgataa ttcctcaaaa acctagaggc agaaatatca ttctacccag caatcccatt   25620
gctaggtata tacccaaagg aatataaatt gttctgccat aaagacacat gcacgtgtat   25680
gttcacttca gcacaattca caatagccaa gacatggaat caagccaact gctcatcaat   25740
gatagactgg ataaagaaaa tgtggtacat atacaccatg tagtactatg cagccataaa   25800
```

```
aagaaacgag ttcatgtcct tgcagggac atggatggag ctggaggcca ttatcttcag    25860
caaactgaca caggaacaga aaccaaata ccgcacgttc tcacttataa gtgggagcta    25920
gatgatgaga acacaaggac acatgggggg aaacaacaca cagtgggacc tgttgttggg    25980 ttggggtgg gaggagggag agcatcagga agaatagcta atggatgctg ggctgaatac    26040
ctgggcgatg gaatgatctg tgcagcaaac cgccatggca catgtttacc tatgtaacaa    26100
acctgcacat cctgcacatg taccctgaa cttgaaagct ggaattttt tttttttt      26160 ttttacttt taagctcttt tgttaaaaac taagacacaa acacacatag cctcggcctg    26220
cacagggtca gaatcatcag tttcactgtc tttcactgtc acatcttgac cagttttgtg    26280
accggaaggt cttatgggca gtgacatgca tgcaactgtc atcttacgtt atagcaatgc    26340
cttcttctgg atacctcctg aagaaactgc ctgaggttgt tttacattta acttgtttta    26400 tataagta gaaggagtac actctaaata aaagtatag taaatacata aacgagtaac      26460
gtagttgttt gttatcattg tcaagtactg tgtgctgtgc ataaatatat gtgccagatt    26520
tttatatgac tggtagcacg gcaggtttac ttacaccagc attgcacaaa acacaggagt    26580
aattgatacg gtttggctgt tccccaccg acatctcatc ttgaatcgta attcccataa    26640
tccccatgtg ttctgaaagg gacccggtgg gaggtaattg aatcatggag gtggttaccc    26700
ccatgctgtt ctcgtgatag tgagtgagtt ctcacaagat ctgatggttt tataaggagt    26760 ttttcccct ttcatttggc acttctcctt gctgctgcca tgcgaagaaa gacctgtttg    26820
ctcccccttc caccatgatt gtaagttttcc tgaggcctcc ccagccatgc ttaactgtga    26880
gtcaattaaa cctctttcct ttataaatta cccaagttcg ggtatgtctt tattagcaat    26940
gtgaggatgg actaatacaa aatgcattgt gctacaacat cattaggtga taggaatttt    27000
tcagctccac tataatctta tgggaccact atcacacatg tacccgttct tgaccaaagc    27060
atcctcatgc tgtgcacaac tgtactcagc caccggctga gtccccacat tggtttcctg    27120
acgtgtgggg tgagggccac tattgtgggc caactggaag ccattagagg tgcctctacc    27180
tagaaaaata gtcaaaagcg atacaataat agtcagtcaa aagctgcatt tccagaggaa    27240
tttcagaggt tagtgccacc atcaaatacc tgaaagatgc aggggcagtg atccccacca    27300
cagccccatt ccactcacct atttggccag tatggaagac aggcgggtcc tggagaatga    27360
caagggattg tcctaagctt gactccaact gcagctgctg ggccagattt ggttccattg    27420
cttgagcaaa ttagctcatc tcttgctacc tggtgtgcag ttattgatct ggcgaatgtg    27480
tccttctcca ccctgtcca caaggcccag cagaagccag ccagcaatg caccctcact    27540 gtcccacctc aggggcctct cgcctctcca gcctgtgtca gaggtaatcc tcagggtct    27600 ggatcaccct tcccttcccc ggcatgtcac actggcccat tacactgatg acattatgct    27660
aactggacat aaggcacaag aagcagcaat tattctatac ttgttggtgt cagagggtgg    27720
gaaataaatc caactaaaat tcagaaccctt ctacctcggt gaaatttta ggagtctagt    27780 gctgtgggc ctgctctaag gtgatacata gattgttgca actgaaccct cccacgatca    27840
aaagagaacg acaccaggtg agcccgtttg atgtgaggaa gacaggttct tcctcattta    27900
ggtgtctgac tctggcccat ttactgagtg atttgaaaag ctgctagttt tgaatgtggc    27960
ccagcagcag gtccaggctc tgtgcaagct gttctgccac ctgggccaat gacccagcag    28020
atccagtctg aggtgtcagt ggcagacagg gacactgtgt agagcctttg ccaagcccca    28080
gtaggtgact catagctcag gcccttacag ttttggagca aggccctgtc atcatccaca    28140
gataaccact ccgtttgag aaacaggttt tggactgtgt attagtctgt ttcacactgc    28200
```

| | |
|---|---|
| tataaagata ttacctgaga ctgggtaatt tataaagaaa aggggggttag ttgactcact | 28260 |
| gttctgcatg gctggggagg cctcaggaaa cttacaatca tggcggaagg gaaagcagac | 28320 |
| acattttaca tggcggccag tgggagaaga atgagcaaga caggaactac caaaacttat | 28380 |
| aaaaccatca gatctcgtga gaactcactc attgtcatga ggacagcatg gaggaaacag | 28440 |
| cccccacgat ccagtcacct ccggccaggt ctctccctta acacctgggg attacaattc | 28500 |
| aagatgagat ttgggtgggg acacaaagcc taatcatatc agcctgtgtc taggtcttca | 28560 |
| tagaaactaa acacttgacc aagggccacc aagttaccac atggcctgag ctgcccatca | 28620 |
| tgatctgggg attatctgac ccatgttgct ataaagttgg gcgtgcacag cagcgctcca | 28680 |
| tttgaatgaa agtgatgtat tgtgatcagg ctcaagcagg tcctgaaggc aaaagtaggt | 28740 |
| tacgtgaaga agtggcccaa atgcctgtgg cccccactcc tgctccaggt gccttctctc | 28800 |
| tccccacctg catctgttgc tgcacaggga ggtccctctc atcaattgac atgggaagag | 28860 |
| aagactcagg ccatacttac aagtggtctg ctcgatatgc aggtgctatc agaaaatgga | 28920 |
| cagctgcagc cctacagccc ctgcggcaga ggcaaaggat ggaaaattcc attccaaaca | 28980 |
| cgagaaatgg gaaggaaagg actaactgag catgaccaaa tccaaaaccc aacaggacaa | 29040 |
| aattaaatct taaagctgaa gaataatttt ctttgactct ttgtcctacc ttctggacac | 29100 |
| actgggacaa ggctcctggt ggccccactc ctacggcttt gtgtgcctgt ggctttccca | 29160 |
| ggctggtggt gcatgctggt ggctctacag gtcccgagtg tcctctgctc ccttgggcac | 29220 |
| cactacacat tgtcctgtgg ggactctcca tggcccaaac ctgtagcagt tctcggcctg | 29280 |
| ggccccaggg tctccatgac acccagtgga atccaggagc aggaactttt cctccacagc | 29340 |
| acgtgcactc cgtgcatctg cagagctggc accgtgctga caccatcgag gtttaccgcc | 29400 |
| tgcgccttct gggctggcag cccaaggaac acctgtaccc acgtgagcct ccatgggggt | 29460 |
| gggccaggag tgatgcacca gcttgcaggg aggaacagag attgaggcaa gtctgggcag | 29520 |
| cacgccccga ggtctcatgg aggccctggg cccttctttt gaagccattc tgccctcaag | 29580 |
| accccggcac cctgagcctg tgatgggcat gacagtctgg aaggtctcgg aaatgccttg | 29640 |
| ggggtcattc tcccattgtc ttgatgagca gcttctgacc tccttctacc cgtactaatc | 29700 |
| tccttatcca aatttgcttg actacaccct tgctattctc tcctgaacat gctttcttat | 29760 |
| tctttttttt tttttatta tactttaagt tttagggtac atgtgcacaa tgcgcaggtt | 29820 |
| tgttacatat gtatacatgt gccatgctgg tgtgctgcac ccattaactc gtcatttagc | 29880 |
| attaggtata tctcctaatg ctatccctcc ccgctccccc cacccaaaa cgggcccag | 29940 |
| agggtgatgt tccccttgac gtgggcaggc taagagtttt ccaagtcttt aagttttgtt | 30000 |
| tcctttctat tatcaattct ttaactcatt tctcttttct cgccttttgc tataagcggt | 30060 |
| caacagaagt catgcagtac ccggagtgct ttgcttagag atttcttcca acaaatattc | 30120 |
| tagttcatcg cttttaaatt ctgcctccca caaagcccca gggcatggac acaattcagc | 30180 |
| caagttcttt gccact | 30196 |

<210> SEQ ID NO 10
<211> LENGTH: 21630
<212> TYPE: DNA
<213> ORGANISM: Homo sapiens

<400> SEQUENCE: 10

| | |
|---|---|
| tgttgttggg ttgggggtgg gaggagggag agcatcagga agaatagcta atggatgctg | 60 |
| ggctgaatac ctgggcgatg gaatgatctg tgcagcaaac cgccatggca catgtttacc | 120 |

```
tatgtaacaa acctgcacat cctgcacatg taccoctgaa cttgaaagct ggaattttt    180
ttttttttt ttttactttt taagctcttt tgttaaaaac taagacacaa acacacatg     240
cctcggcctg cacagggtca gaatcatcag tttcactgtc tttcactgtc acatcttgac   300
cagttttgtg accggaaggt cttatgggca gtgacatgca tgcaactgtc atcttacgtt   360
atagcaatgc cttcttctgg atacctcctg aagaaactgc ctgaggttgt tttacattta   420
acttgtttta tataagta gaaggagtac actctaaata aaagtatag taaatacata      480
aacgagtaac gtagttgttt gttatcattg tcaagtactg tgtgctgtgc ataaatatat   540
gtgccagatt tttatatgac tggtagcacg gcaggtttac ttacaccagc attgcacaaa   600
acacaggagt aattgatacg gtttggctgt ttccccaccg acatctcatc ttgaatcgta   660
attcccataa tccccatgtg ttctgaaagg gacccggtgg gaggtaattg aatcatggag   720
gtggttaccc ccatgctgtt ctcgtgatag tgagtgagtt ctcacaagat ctgatggttt   780
tataaggagt ttttccccct ttcatttggc acttctcctt gctgctgcca tgcgaagaaa   840
gacctgtttg ctcccccttc caccatgatt gtaagtttcc tgaggcctcc ccagccatgc   900
ttaactgtga gtcaattaaa cctctttcct ttataaatta cccaagttcg ggtatgtctt   960
tattagcaat gtgaggatgg actaatacaa aatgcattgt gctacaacat cattaggtga  1020
taggaatttt tcagctccac tataatctta tgggaccact atcacacatg tacccgttct  1080
tgaccaaagc atcctcatgc tgtgcacaac tgtactcagc caccggctga gtccccacat  1140
tggtttcctg acgtgtgggg tgagggccac tattgtgggc caactggaag ccattagagg  1200
tgcctctacc tagaaaaata gtcaaaagcg atacaataat agtcagtcaa aagctgcatt  1260
tccagaggaa tttcagaggt tagtgccacc atcaaatacc tgaaagatgc aggggcagtg  1320
atccccacca cagcccccatt ccactcacct atttggccag tatggaagac aggcgggtcc  1380
tggagaatga caagggattg tcctaagctt gactccaact gcagctgctg ggccagattt  1440
ggttccattg cttgagcaaa ttagctcatc tcttgctacc tggtgtgcag ttattgatct  1500
ggcgaatgtg tccttctcca cccctgtcca caaggcccag cagaagccag gccagcaatg  1560
caccctcact gtcccacctc aggggcctct cgcctctcca gcctgtgtca gaggtaatcc  1620
tcagggtct ggatcaccct tccctttccc ggcatgtcac actggcccat tacactgatg  1680
acattatgct aactgacat aaggcacaag aagcagcaat tattctatac ttgttggtgt  1740
cagagggtgg gaaataaatc caactaaat tcagaaccttt ctacctcggt gaaatttta   1800
ggagtctagt gctgtgggc ctgctctaag gtgatacata gattgttgca actgaaccct   1860
cccacgatca aaagagaacg acaccaggtg agcccgtttg atgtgaggaa gacaggttct   1920
tcctcattta ggtgtctgac tctggcccat ttactgagtg atttgaaaag ctgctagttt   1980
tgaatgtggc ccagcagcag gtccaggctc tgtgcaagct gttctgccac ctgggccaat   2040
gacccagcag atccagtctg aggtgtcagt ggcagacagg gacactgtgt agagccttg    2100
ccaagcccca gtaggtgact catagctcag gcccttacag ttttggagca aggccctgtc   2160
atcatccaca gataaccact ccgttttgag aaacaggttt tggactgtgt attagtctgt   2220
ttcacactgc tataaagata ttacctgaga ctgggtaatt tataaagaaa aggggttag    2280
ttgactcact gttctgcatg gctgggaagg cctcaggaa cttacaatca tggcggaagg    2340
gaaagcagac acatttttaca tggcggccag tgggagaaga atgagcaaga caggaactac   2400
caaaacttat aaaaccatca gatctcgtga gaactcactc attgtcatga ggacagcatg   2460
gaggaaacag ccccacgat ccagtcacct ccggccaggt ctctccctta acacctgggg    2520
```

```
attacaattc aagatgagat tgggtgggg acacaaagcc taatcatatc agcctgtgtc   2580
taggtcttca tagaaactaa acacttgacc aagggccacc aagttaccac atggcctgag   2640
ctgcccatca tgatctgggg attatctgac ccatgttgct ataaagttgg gcgtgcacag   2700
cagcgctcca tttgaatgaa agtgatgtat tgtgatcagg ctcaagcagg tcctgaaggc   2760
aaaagtaggt tacgtgaaga agtggcccaa atgcctgtgg cccccactcc tgctccaggt   2820
gccttctctc tccccacctg catctgttgc tgcacaggga ggtccctctc atcaattgac   2880
atgggaagag aagactcagg ccatacttac aggtggtctg ctcgatatgc aggtgctatc   2940
agaaaatgga cagctgcagc cctacagccc ctgcggcaga ggcaaaggat ggaaaattcc   3000
attccaaaca cgagaaatgg gaaggaaagg actaactgag catgaccaaa tccaaaaccc   3060
aacaggacaa aattaaatct taaagctgaa gaataatttt cttttgactct ttgtcctacc   3120 ttctggacac actgggacaa ggctcctggt ggccccactc ctacggcttt gtgtgcctgt   3180
ggctttccca ggctggtggt gcatgctggt ggctctacag gtcccgagtg tcctctgctc   3240
ccttgggcac cactacacat tgtcctgtgg ggactctcca tggcccaaac ctgtagcagt   3300
tctcggcctg ggccccaggg tctccatgac acccagtgga atccaggagc aggaactttt   3360
cctccacagc acgtgcactc cgtgcatctg cagagctggc accgtgctga caccatcgag   3420
gtttaccgcc tgcgccttct gggctggcag cccaaggaac acctgtaccc acgtgagcct   3480 ccatggggt gggccaggag tgatgcacca gcttgcaggg aggaacagag attgaggcaa   3540
gtctgggcag cacgccccga ggtctcatgg aggccctggg cccttctttt gaagccattc   3600
tgccctcaag accccggcac cctgagcctg tgatgggcat gacagtctgg aaggtctcgg   3660
aaatgccttg ggggtcattc tcccattgtc ttgatgagca gcttctgacc tccttctacc   3720
cgtactaatc tccttatcca aatttgcttg actacaccct tgctattctc tcctgaacat   3780
gctttcttat tcttttttt tttttatta tactttaagt tttagggtac atgtgcacaa   3840
tgcgcaggtt tgttacatat gtatacatgt gccatgctgg tgtgctgcac ccattaactc   3900
gtcatttagc attaggtata tctcctaatg ctatccctcc ccgctccccc caccccaaaa   3960 cgggcccag agggtgatgt tcccccttgac gtgggcaggc taagagtttt ccaagtcttt   4020
aagttttgtt tccttttctat tatcaattct ttaactcatt tctcttttct cgccttttgc   4080
tataagcggt caacagaagt catgcagtac ccggagtgct ttgcttagag atttcttcca   4140
acaaatattc tagttcatcg ctttttaaatt ctgcctccca caaagcccca gggcatggac   4200
acaattcagc caagttcttt gccactttgt aagagggaca gccctccccc agtttctaat   4260
aagatagttc tcatgtctgt ctaagacctc acgagaatgg ctttgactgt gtggatctcc   4320
accagcattc tgatcacgac cactgagatc attgctacca gcccagaggc tctctctaca   4380
gccctgccct cctcggcctg cactggagtc accttagcac caactccgtt cgcaggagtg   4440
tgtgcttttc cagcgtgcac ttcaaaacgt ttccagcctc tcccgtgacc cggttccggc   4500
tctgctgcca cattttcagg tgtttgttac agcaacagcc ccgcttcctg gtagcaatgt   4560
ctgtcttagc ctgtttgtgc tgctgtaaca aagcaccata gaataggtca tttatacgtc   4620
atagaaattg attgctcaca gttccagagg ctgggaatcc tgcactgcag gtgatgtctc   4680
gagaggacct tcttgccgcg tcctcacatg gcagaaaggg aaagggcaca caggcaccga   4740
gctcattcct cgcccttttc taaagcactg atcccaccca ggagggcgga gccccacgg   4800 cctcatcgcc ttccaaaggc cccacctctc actaccgttg cgttgggac ttttcaacat   4860 gaattttgga gggacacaaa tattcagacc acagtaagcc atgactaatg cacacagaaa   4920
```

```
actgaagttt caggatgtat ttgctctcat tcctctccat caactcaatg gcagctgtca   4980
gaaggctctc agacttgaat gggccttaat cccatctttg tcttctgttg atcggtccaa   5040
gtcaggcatt ttattgggcc tttgtctccc aaagcttgtt aaaatcctaa ctcttggagc   5100
agttggtttt tctgcccttg cggtgctctg aatttctgga tccatctctc tgttcacttt   5160
catctctgct tgtaagctgg gccttctttc tcaagctggt ctccgtctcg tgttgcggga   5220
cctaacacaa aactcgcaat gtggtgtttt cccacttcgc cccttatgct cctggctgag   5280
ccttcttgta ttcagcctgc caggtcacca ggagtgattt tagcaagttt gctgctccag   5340
ctccaccaag tccccatcac tcgggccccc ggtgcctgct ctcttggcag cagctgggtt   5400
tgggggttcc gactgctacc acaatacagc ctggcctgtc ctgactaata cagaagcagg   5460
ctctgtgaag gagggtgctg ccataagaag aaacgcaaat taacacgtat ctacacagtc   5520
tccgtggtgc acaacagtca gcttttcctg cttatgtgtc tgggctctgc ttgactgatc   5580
ttggctgggt gcattcccaa gacagcaagt cgtggctggc ctcgggcaca ggaaagggcg   5640
agagactggg gtcacagata caatctagca tagggggaca gataactcaa tgtttaaatt   5700
catagggtgc tggaccaaga gagggcatat ccaaacctga tgtgctcatc catcggagat   5760
gctgggtctg gagaaggtgt agtgactggg tggactttgg caggtcaaca gaggggtgga   5820
tggcggaaca gacgatacca tgtgttcacc acactgtttc ttcctcctag gcaaatggaa   5880
agactgcatt tcccagtcac ctctatggtt agtgtggttg catgagggtc atgtgaccga   5940
gttctgacct gtgggatatg ggaggaagca acgtaagcta cttcccaatc gcccttccct   6000
ttccaaggtg accttacagg acacacgttc ccaaagtcag ctcaaagatg aagagtcact   6060
tgaccaccat atgcaagtga aaataacccc gagacctca gggggtattt gttaactgca   6120
acgtagccta ctttcaaagc atggttcctg gaccagctgc atcacccggg aatgcggtag   6180
aaatgcagat tctcaggccc tgcccaggcc tccaaaatta aggatgctgg ggtggagcct   6240
agcaatctgc gtctaaaaag ctctccaggg caatctgaag gctgttcctg gccaggaaca   6300
gtggctcatg tctgtaatcc cagcactttg ggattacttg agaggacctt cttgccgtgt   6360
cctcacatgg cagaaaatga aagggcacac agggggatcg aggcgggtgg atcacttgaa   6420
gtcaggagtt ggagacaagc ctggccaaca tgatgaaacc ccatctctat aaaaatcaca   6480
aaaattagcc aggtgtggtg gtgcatgcct atagtcctag ctactcagga ggccgaggca   6540
ggagaattgc ttgaacccag gaggtggagg ttgcagtgag ccgagatcgt accactacgc   6600
tcccgcctgg gcgacagagc cagattccat ctcaaaataa ataaataaat aaaggctgtt   6660
ccaactatat aggagttcag gatactggca agggtgtgat taaagtgaag gaccaggtgt   6720
tcccagctgt gcaggcaaag aagtgcagtg aggaaagcat gcagtacggc tgcgtagagc   6780
actcccagca aagcaggtgg gcaaagcaaa cacacagggc ctggaggtgt ggaaggggtg   6840
caaggtttgg actttaaatc tcagagagga agcaacccaa aattaaagag accccaggga   6900
tggtgatggg cacagtgggg cagatgaagt tcactggaca ggggaggtca ggggcctagg   6960
ggccgtggtg tggggttgct tgtcccagct gggatggaca caggaattgg gctggagaag   7020
atgtacatga ggtggtcttg tctaaaccct gcacatccag ctccaagcat gcaggtaaat   7080 tccccccggaa ccaactccca tgccaacgtc agactcgaac aagtccaagg atgctgagta   7140
acagtcaggg ttctccagag aaaccgagtc agtaagatgt gtacatacac acagagagag   7200
attattgtaa ggacttggct cacacaatta cagaggctga gcagtcccaa gatccgtagt   7260
tgggaacctt ggagacccag gaggactgat ggtgtaagct cccgtctgaa aggcagcagg   7320
```

```
ctcaagaccc aaggagagcc aatgtttcag tttgagtttg aagacaggaa aaaaccaatg    7380
tcccagctca cccaggtaag aggacttccc tcttatttgt cacgcgcctc tgtgtgaaga    7440
gaccaccaaa taggttttgt gtgagcaatg aagcttttta atcacctggg tgcaggcaga    7500
ctgggtccaa aaaaggagtc agcaaaggga gataggggtg gggcagtttt ataggatttg    7560
ggtaggtagt ggaaaattac agttaaaggg ggttttctt ttgtgggcag gggcgggggg     7620
gttacaaagt gctcggtggg gaccttctga tactcattga ccaggagaag gaatttcaca    7680
aggtcaattg attagttagg gtggggcagg aacaaatcac catggtggaa tgtcatcagt    7740
taaggcagca actgtctact ttcacttctt ttgtggttct tcagttgctt caggccatct    7800
ggatgtatac atgcaggctt gggctcagaa ccctgacacc actcagccat tttgttctat    7860
gcaggccttc agtgggtggg atgaggccct ctagaaaata aaaggtttcg ctctccctct    7920
ccctctcctt ctccctctcc gtctccctct ccctctcccc acggtctccc tctcatgcgg    7980
agccgaagct ggactgtact gctgccatct cggctcactg caacctccct gcctgattct    8040
cctgcctcag cctgccgagt gcctgcgatt gcaggcacgc gccaccacgc ctgactggtt    8100
ttggtggaga cggattttg ctgtgatggc cgggccggtc tccagcccct aaccgcgagt      8160
gatccgccag ccttggcctc ccgaggtgcc gggattgcag acggactctc gttcactcag    8220
tgctcaatgg tgcccaggct ggagtgcagt ggtgtgatct cggctcacta caacctacac    8280
ctcccagccg cctgccttgg cctcccaaag tgctgagatt gcagcctctg cccggccgcc    8340
accccgtctg ggaagtgagg agtgtctctg cctggccgcc catcgtctgg gatgtgagga    8400
gcccctctgc ctggctgccc agtctggaaa gtgaggagcg tctccgcccg gccgccatcc    8460
catctaggaa gtgaggagcg cctcttccca gccgccatca catctaggaa gtgaggagtg    8520
tctctgcccg gccgcccatc gtctgagatg tggggagcgc ctctgacccg ccgccccatc    8580
tgggatgtga ggagcgcctc tgcccggccg agacccgtc tgggaggtga ggagcgtctc      8640
tgcccggccg ccctgtctga gaagtgagga gaccctctgc ctggcaacca cccgtctga      8700 gaagtgagga gcctctccgc ccggcagcca ccccatctgg gaagtgagga gcgtctccac    8760
ccggcagcca ccccgtccgg gagggaggtg gggggggtca gccccccgcc cggccagtcg    8820
ccccatccgg gagggaggtg ggggggtca gcccctgcc cggccagtcg ccccatccgg       8880
gagggaggtg gggggtcag ccccagccc ggccagccgc cccgtctggg aggtgagggg       8940
cgcctctgcc cggccgtccc tactgggaag tgaggagccc ctctgcctgg ccagccgccc    9000
cgtccgggag ggaggtcagg gggtcagccc ccgcccggc cagccgcccc gtccgggagg      9060 tgagggcgc ctctgcccgg ccgcccctac tgggaagtga ggagcccctc tgccctctgg      9120
gcccgtctgg gaggtgtgcc caacagctca ttgagaacgg gccaggatga caatggcggc    9180
tttgtggaat agaaaggtgg gaaggtggg gaaagattg agaaatcgga tggttgccgt       9240
gtctgtgtag aaagaagtag acatgggaga cttttcattt tgttctgcac taagaaaaat    9300
tcttctgcct tgggatcctg ttgatctgtg ccttacccccc aaacctgtgc tctctgaaac   9360
atgtgctgtg tccactcagg gttaaatgga ttaaggtgg tgcaagatgt gctttgttaa     9420
acagatgctt gaaggcagca tgctcgttaa gagtcatcac caatccctaa tctcaagtaa    9480
tcagggacac aaaacactgc gaaggccgga aggccgcagg gtcctctgcc taggaaaacc    9540
agagaccttt gttcacttgt ttatctgctg accttccctc cactattgtc ccatgaccct    9600
gccaaatccc cctctgtgag aaacacccaa gaattatcaa taaaaaaata aattaaaaaa    9660
aaaaaaaaag ttactcagga gacccttta gaaatactta gggaaagata agctgtctcc     9720
```

```
ttgggatgac tgggctggtg tctgtgcata tgccttctct ggatccaagt gactttacca    9780
caccaagcct taagactgcc agactgttct ctccattgaa agccattctg caccactggc    9840
catacagaag gaatctcata ttccaggaga ctggcccaaa caggactgtt gagtggcctc    9900
taaggctttt agacgtcaaa agggtttata agaataatca tcataatata gttatgaatc    9960
agaaacatgc atacattttc ttaaatgacc ctgtgggac tggagttaaa aaggggaggag   10020
tacccagatg caggcgtcta gcagaatgga cttgcttgag aatatcaagc aagacagcca   10080
aagaggactc ctaggattgt ctcaccagga cttctgaggc gactctaatg aaatgactta   10140
aaagtgtggt ggagtggctt ctgtggctcc cacaccggcc taatcctggt tgatattgca   10200
caaccagggt gcactgacaa tctctgggaa aaaagcaagg tctaatattc aaagcttggc   10260
aaacatgacc aagactttt ctcttttcctt tgaattattt tagttcccta atttttttgtc   10320
ccatatgcca cttaattctt tttatttttgt attaaaagtt gtgctcttgt ctcaaccttc   10380
tttctagatt ggatcctgca tgtttttttt atcattatac ttttggcagc cctaccacta   10440
ggcttcctga aatatagcac ctttgttttt gtttgtttgt ttgtttgttt tgagaccgag   10500
tttcgctctg tcacccaggc tggagtgcaa tggcacaatc tcagctcact gcaacctctg   10560
cctcctgggt tcaagcgatt ctcctacctc agcttcctga gtagctggga ttacaggtgc   10620
gtgccaccac ccccggctaa ttttttgtgtt tttattgaga tggggtttca ccatgttggc   10680
cagactggtc tcaaactcct gatcccatga tctgcctgcc taggccttcc aaagtgctgg   10740
gattataggt gtgagccacc gcgcctgcc tgcacctttg ttatatagaa aattcttatc   10800
aacattattg tctacttta gactttattt tgttctattg aactattctg gttctagtac   10860
catacattaa aattatagct ttataatact ttttaacatc tgacaggatg tgctcccctt   10920
atcatccttc tttttcaata ttttatcatt ctcacagttt ttctcagatc aacttcacat   10980
gtaatttaca aaagaaatta aaattacatt ggtatttagg tggaaattat gttaaattta   11040
tgtactaatc tggagaagtc ttgttttgta ataataattc ttaccatgaa ggaaaatagc   11100
ttctctctcc gctgattcat gttttttctc atgtctctca gtagagttta tagcttttt   11160
tgtataagtt ctcataattg cttgaatata ttcctaatta tttaaaaaaa aaaaaagaa   11220
aataaaaggt ttccactttc aaagttcccc ttcttgttaa agaatgaatc ataagtgtta   11280
gaaataacag tttctttttt ttttttttg gaagcatttc ccatttttat tcataaaatt   11340
attacttaaa attgcaaaag tagatttaca gagccacagg taacaaaaca ggaaatgaaa   11400
tgttccagac attccgaaaa gttcgaaaga aacacaccct agcctcaaaa tctccggtta   11460
aaccgtggtt gcacaacagg ttctatttat tcctgcattt tctcaataag ttcttcttta   11520
tatttgcctt tctcttttcc aacttgttga gacttggctt tgcgttcaag aattttttc   11580
cgatccttgt ccagttttag cctggtgata accaccttgc ttgggtgaat gcccacgtgg   11640
acagtcgtgc cgttggcctt ctcacgctgc accgctcga tgtagatgac atatttcttt   11700
ctgtacacct ggattacctt gccaatttgc tgacctttgt agtgtcctcg aactacctgg   11760
acctcgtcgt ccttgcggat gggcatggag cggacattgt acttctgccg cagctccttg   11820
gagagcgggg atgacatgat cttcctgcgc acgtgtgagg gggcattgaa gtaacgtttg   11880
cggtttttac tgcggtccga ggtaacgaag ggattgaact tcatggtgac cctccggcta   11940
ctagctgcct cagaccctca acagtttctt ttaaagacta actttcttca agcctccttg   12000
ctttgtgcta ataactcttt gttaagctct atcctatgta actgttggac atcctcacca   12060
acatattcca gctcacagcc tatgccccctt ccttatttgg tgatgttatt gcctcctgag   12120
```

```
acttttcata agcaacttat ttgttcttcc ctgcacttac ctatttagga aagtttcagg    12180
ttattagcaa atcgggtatc actttaagat tgtgaggtcc cactccagcc aatggatgca    12240
ggacatagca gtaaggacaa cccaaatgcg taagggataa atacatctgc ttttcctttg    12300
ttcaggtgtg ctctcaccat tgttccatct gcgactgagc accatttctg caaaaagtaa    12360
agatggcctt gctgagagat cttttgtctc tgtgctgact tttcttcacg gcactgatta    12420
tcttttctca acaattttgg tggcaattgt atggggatat acttcctcc aggggcgtct     12480 ctagtcctct ctcacgaggg ggcactctgc tgcctcttgc agtggcctca ggggtaaggg    12540
accgagaccc atccggtgtg accaataaac ccggactctc agcaatgtgg aaagaaactg    12600
gccaacaacc tggggtaaag gatcctcaca taccgaggtg acgactctgt gcacagacca    12660
acgaaggaga agccacggga gccggtaaag tacttcttgg tggtcagatt ctgggggct     12720 gaatgtgtgt gtgcacgtga atgatcacag acaaccctgc ttgcggtgtt gtgtggatgg    12780
tgacaaatcc tactgctgga cggagtgttt gggtcctctc tgtgcttcca gagcaacctc    12840
agatggctta gggcagatcc tgccatggga tttatactgg cacgccaact ctaagagggg    12900
cctagctctc ccttgggga gtggccagag aggacaacac aagtgggaag tgtgcaaggg     12960
accttcagag gaggaaaggg aggaaacagg tcaacctctc acggcaggca aggcaagaca    13020 cccctggtt tgaggggtc ttctgcaaat ttcaggagt tgaacctcat acaaacctcc       13080
ggtagtaaga aaaatattca gagttctcct ttcccttctt ctcggggaa gaaagaggct     13140 aagctccact ccgcttgtcc cttccctagg ggaaggggaa ggagaaggga gaatagcagc    13200
ataagcgact ggcagaggca gggaaagacc ggcagaaagg aaagagaaac tgggagagga    13260
agtcagagag agagagagac aaagaggag tcaaagagag agaaagagag agacagagag     13320
tcagagagag agaaagagag agacagagac aaagaggag ttagagagag aaaaagagag     13380
acagagagta agagagagag agtcagagag agagaaagag aagtagtaaa gagaaaacag    13440
tgtaccctat tcctttaaaa gccagggtaa atttaaaacc tataattgat cattgaagat    13500
cttctctgtg accctagaac actccaatac tgcctgtaaa gaagcaagac gagtcacacc    13560
agtgactgca agaccctaga gctattaacc agttagtcca aactaccac cctgttgtta     13620 cagtaataga tgtaaaagat gccttctggg cttgtccatt tgcagaggac agccaggacc    13680
tatatgcctt tgagtgagaa gaccctcact ccggtgaaa atggtaatac caatagacg      13740 tcttacccca agggtttacg gagtctccaa atttatttgg tcaaatattc aaataagtca    13800
tttaattagc aaaggtaaac agaaaattga gcttgaatgg attgaaggca tcacattctt    13860
gcctctgctg gagactaaat aagagcttag aaaattttgg gattagttgt atggataccg    13920
tcgtctatgg gtagactcat gccctaaaaa caaaactctt acacaaaaag ctcacacgag    13980
acagaccaaa cccctcatg tggcaattac agaaatcca acaggtggga aggttaaaac       14040
atctattagt aactgcccct gtcctagctt tactctcctt aagcagccat tccaccttgt    14100
tggtggtgta acaacggcg tagcccaaaa acactgaggc cactgacaac ccatagcctt     14160
cctaatcaaa aatccttaac ccagtaaccc gcggatggtc caaatgcatt caatctgtag    14220
cagcaacttc tttgctgaca gaagaaagta gaaaaataac tttgagaaga aacctcattg    14280
tgagcacacc tcaccaggtc agaactatcc taagtcaaaa aaaaaaaaaa aaaagaaaa     14340 gcaaaaggt agcttactaa ctcaaaaaat ttaaaatatg aagcgattct gtcagaaaaa     14400 gatgattta cattaaccac tgatcattcc cttaacccag caggtttgct aacagggat      14460 ctaactctta atgaattacc atacaaaggt ccaaccagac ctagaaggaa ctcccttcaa    14520
```

```
gacaggacaa tagatggttc ctcccaggtg aatgagggaa aaagccacaa tgggtattca    14580
ttaagtaatg gggaaatagg agtagagtta ggaaaattgc ctaggagttg gggagttgtt    14640
tgcactgagc caagccttaa gatactgaca gaatcaggaa ggagtcattg tgaaaagtga    14700
agtagagttt acctcctcaa aagactttcc tccccatct aatcaggaat aaatagtaac    14760
ttctcttagt agcaaaatgt attcaaagac cagcgctaac attcttaaat atctgctaga    14820
cgtaataaag aaatcaatgt actttatgtc cttagctccc acaatttagt ctaaatgttt    14880
gctctggcat gcttatactg gtccaggcaa gcattaggtc ctatcctgtt cctcttcctt    14940
gtttgtgtct cacatgtccg tgtgaaaaga ccaccaaaca ggctttgtgt gagcaacaag    15000
gctgtgtatt tcacctgggt gcaggcgggc tgagtccgaa aagagagtca gcaaagggtg    15060
gtggattatc attagttcct acaggttttg gggtaggcgg ttgggttagg agcaatgttt    15120
tgccagcagg gggtggatct cgcagagtac attctcaagg gtggggagaa ttacaacgaa    15180
ccttcttaag ggttggggag attacagagt acattgatca gttagggtgg ggcagaaaca    15240
gatcacaatg gtggaatgtc atcagttaag gctattttca cttcttttgt ggatctttgg    15300
ttgcttcggg ccatctggat gtatacgtgc aggtcacagg ggatatgatg gtttagcttg    15360
ggcccagagg cctgacagtt tgaaggtgtt tttacctttc tcagcattcc acgagttact    15420
tcttcctttg ttctcctctg cctttgcctc ttttaaaaag ttctaagttg ctagccagtc    15480
gggacaaatg cagaatgtca ggcctctgag cccaagctaa gccatcgcat ccctgtgac    15540 ttgcacgtat atacgcccag atggcctgaa gtaactgaag aatcacaaaa gaagtgaata    15600
tgccctgccc caccttacct gatgacattc caccacaaaa gaagtgtaaa tggccggtcc    15660
ttgccttaag tgatgacatt accttgtgaa atcccttctc ctggctcatc ctggctcaaa    15720
aatctccccc actgagcacc ttgcgacccc ccactctgct cgccagagaa caactccact    15780
ttgactgtaa ttttcctta tctacccaaa tcctataaaa cggccccacc cttatctccc    15840
ttcgctgact gtcttttcgg actcagcccg cctgcaccca ggtgaaataa acagccgcgt    15900
tgctcacaca aagcctgttt ggtggtctct tcacacggac gcgcgtgaaa cagaatgtga    15960
ggtcccgttc cagccaatgg aaaccagaca cagcagtagg gtggacgcgt caggttataa    16020
atgaccctgt ctcctttgct cagtgtactc tcgtggcaaa actgctgccg agtgtaccct    16080
ttctacagaa agtataaaaa tgaccttgcg taggaaatta aatttatgtt caagtgccat    16140
ttctttatgg caccggggag caagcatttc aaacatcatt tgtaccaatt ctaagttaaa    16200
tttggactaa acaaggtctt attaatagca aaggataatt gaaatcccaa acttacaagg    16260
ttttcaacaa aagtaaagtt tgctaaaagt taacagtata acatgtatta tcctaacttc    16320
taatgttgtg accttaggct gtctagtcca cagacataaa ggaagttcgc tttggaaaag    16380
aatggttatc atctttgaga gaaaaaaaat tgtttcgaag gtttaagcaa gttttgaaat    16440
attcattgta aaggaaacat attggctaaa gttaaagggg tatcttccag tttttctgtg    16500
aactggacat taaaataaaa gcccagtggg ttttcttaa agcgctaacc tgctctttaa    16560
caaaaattac gaaaggttaa aaattataaa agtttaaaaa aagagtctgg aaatctcacc    16620
ttgtggtcag accttaaaat tggatacata tgtctacaag gttttattaa aatgaagttt    16680
aacacgaata acacactaat gtaaaggtga aatttagctg atctggtata aaatcacaca    16740
ggaagcactg tcaaatataa aatggtgttt ggctttcttt ggtctaaaaa ctaataaaaa    16800
taggtactaa aggaaatttc tcagcaagaa ggcactaagg actataaaat ccactgctga    16860
tgtccccacc tttaaaacaa aagatcaatt tttagaaatg atatacttgg tttatcctcc    16920
```

```
acccttaaaa caaaaggtct tctagcacag gccctgccct gagagtttcc agtacatcag   16980
caccagcctg gggatcccgt tctcatcaaa gggtggaaag aagggaaact ggagccagcc   17040
tgggaaggac cctgccttgt gctgctgact accgagattg ctattcgtac aacggaaagg   17100
gggtggacac gtcccaccag agtcaagcaa gcaccattat caacagaatc atgggccatt   17160
gtttctggat caagccctac caaattaaag ctaaggaaag ctgagtctat ctctttcctt   17220
tccttttccta acccagtgcc tatatccatg actattccta ccactagcaa ctctaacccc   17280
actttagaga gtttctgtgg tttgggagca gaggtcactg gaagggatcc tataggcttc   17340
aaggtgcgct ttgttctccc tcctccacct cctacgactg ccccttccc aaacctacaa    17400
catcaaacta tgcctcgcct catgccaaat gacacaagca agttcttaga agtagaaata   17460
ggagacccaa ggcaaaccct agccattgaa agagggtata agacataaa tgccggttaa    17520
aacggattaa atatcccgtt cgcactttaa gcaaagtga ccattaagct tgtgggcgcg    17580
gtaggccaga ggctcaggat gcctcctttc cactgggacg gtcctcaaat caagcggaca   17640
tggagtgcgt ggtagctctt ttcgaagatt ccaccacctg gaataacgaa ttgtgccaag   17700
ctctttctct gctatttcct gaagttcagt gccctgtggg tcagccccg agggccatcc     17760
agccttcatc ttccaaaacc aatttttacct cgtgtctcca acaacgaggg gaaaaaactt   17820
ggcattcctt ggagacttaa aaggttgcag taaagtcagg cacctccaaa agctgaccca   17880
tcggtctgcc cttattcatc cctgagcgga tgtatggtgg tattatggag gacctttact   17940
ggacactctg ccaaataatg agagcagtac tgatgctgta gttcagttgg ctatcccttt    18000
tactctggca tttcatcaac cagaaaaaga aaaaaaatg tagcctcaat tcttacctct     18060
ttaacaacgc taataagtat actctttctt cgtaggtgtt atgtcgtacc atacatccag    18120
gagttcatca aaacaactaa gccaagacat gctaagaaag tttgaagagg aaaactatac   18180
agtaaaagag gagggaattg taggaagtaa aaagtttctg cttcaaagtt cccccttcttg   18240
ttaaagaata aatcataagt cttagaaata atagattctt ttaaagacta attttcttca    18300
agcctccttg ctttgtgcta ataagctcttt gttaagccct atcctatgta actgttggac   18360
atgctcacag acacattcca gctcacagcc tatgccccctt ccttaattgg aaatgttatt   18420
gcttcctgaa accttttgta agcaacttct ttgttcttcc ttgcacttac ctatttagga    18480
aagtttcaaa tcgggtatca gtttaagata gtgaggtccc actccagcca atggatgcag   18540
gacacagcag taaggacaac ccaaatgcgt aagggataaa tacatctgct tttccttgtt    18600
tcaggtgtgc tctcaccatt gttccatctg cagttgagca ccctttctgc agaaagtaaa    18660
gatggccttg ctgagagatc ttttgtctct gtgctgactc ttcttcgcag caccgattat    18720
ctatttctaa caattttggt atttctaaca ggcccacaca cactgtgtgg gccaagctgc   18780
ttcactcagt ccactgatca aatgctcatc tcatcctcac agacacaccc aggatactgc   18840
ttgaccaaat atctggacaa cccatggccc agtcaagtcg acagaccaaa tgaactgtca    18900
cagacagctt ctgtccttgg aacggggtgg gattccacgg actctctccc ttcacagtgg   18960
agatgctcag tcagcaagct gccagaagtt cagagctggg gaagatataa agaggactgg   19020
gcatggaagc tgcaggaact agtcaggaac tgggagtacc taggagtcag ctcctgagtg   19080
tgcaggatca tggtgaaata gaagttagaa gaaggaagag tgtgtcaata tcagagcatt   19140
gtcttatagc acaggactta accctctcct aaggttccag ggagacagtg ccaaatcatc    19200
acttgagtgg tgcttagaag cttcagggca aaagagccaa ccctaagtac atttgtctac    19260
tggggctgcc atcacaaagc accgcagaca gggtggctta tacaacagac tcattgtctc    19320
```

-continued

```
acaatcctgg cggctggagt ccaagatcaa ggttttgcaa ggctagctcc tcctgaggcc   19380
tctcttggct tgtagatgac cggggccttc tctctgtgtc ctcacagggt cttccctcag   19440
tgcgtgtccg tgtcctcacc tcctcttgta agactccagt cctatgagat taggacccac   19500
tgtcatgaac tcatttactg ttgattacct ttgttttatg ttttttgttt ttttgagaca   19560
gggtcagtct ctgtcaccca ggctggagtg cagtggtgca atcatggctc actgcagcct   19620
caaactcctg ggctcaagga atcctcccac ctcaatctcc caagtagctg ggactacaga   19680
tgcataccac tgtgcctggg tgtattagtc tgttattgca cagctataaa gaaatacctg   19740
agagtgggta acttataaag aaaggaggtt taattggctc acggttcata gctgcttctg   19800
gggaggcctc aggaaagttt cagtcatggt ggaaggtgaa ggggaagcag acacgtctta   19860
cacggccaga cagttcctcc tacactggct gacactctct cctgccacct tgtgaagaag   19920
gtgcctgctt ccttttctgc catgactgta agtttcctga ggcctcccca gccatgtggg   19980
actgtgagtc aattaaacct cctttgttta taaattgccc agtctccggt agtatcttta   20040
taacagtgtg aggatgagct aatacacaca ggaagcagca atgccatcaa agagccaggg   20100
gccttgactg gcagaactag tgagaccatc accaaaacat ggcattcctt gggcaaggca   20160
ggtgcgcagc cagcaaggta ttgcttaatc tacatgatca aaagacatca ggatggttgt   20220
tcaggaggct gagaacagcc atcctattat ggctgagttg tgtccctca aaatttatat    20280
actgaagtct taaccccca ggacctcagt gtgtaagtat ttggagaaag gcctttaaa    20340
gatgtagtta aattaaaatg aagacattag ggtgggccct aatccaatct gactggtgtc   20400
cttgtaagaa gaggagatga ggacacatgc agaggcatga ccacatgagg acacagggag   20460
aaggtggcca tctgcaaatc aaggagtgag gcctcgggag gaaccagcac taccaacacc   20520
ttgatctcgg acttccagtc tccagaacca tgagatgatg aaagtctgtg tttaagctgc   20580
ccagtctgtg atattgtttt gcaaccctaa tagatgaata catacccca tgaaaaagca    20640
tgatctcttg cccagtttct gcacctgaga cagttttcaa acccaaaccc cactgattga   20700
aggagggatt aggtcccagg aggacggacc ctgcagtacc atagcaggct cccccagtcc   20760
ttcccccaccc caccactaaa ggtgtatttc agtaactgtg cactaggaaa agggcaatgc  20820
ccagggctgg gggactccgg gaccaagttg acactgagag ctggagtcaa ggtaccatca   20880
tgggcccact agagtagggc gtatggaggc cagcaaagtg caatcctggt ccacctctag   20940
ctcacactga gtcatccctt tgcattccca gaatgctgca tattccccca gaccctaaaa   21000
gtacactcag acaatcttgg tagttggcag aatcctcacg taggctcatt gtcctgtagg   21060
gtaaaaacta tcatagtgtt accaagtaga aacttctgaa actgcccacc accttagcca   21120
aggcaataca ccaaaaagaa aatctcattg gtggggaatg gcagagatgt gggcccctt    21180
ggaagacttg aaggttgcag gtgaggcgat tcccatcatc tcccccattt tccagagaat   21240
gctaacagac tactgtcaac ttgtgatggg aaatttatg cgtccacttc actgggccat    21300
ggtgcccaga tgtttggtta acattattc tgggtgtgtc tgcaaggtgt ttctggatat    21360
gcttagcatt tgaatctgtg gactgagaaa agcaggtcac tctctctggt aaaggtgggc   21420
ctcatccaat cagttgaagg tctgactaaa acaaaaagat taagcaagag aaaattcgct   21480
ctccctgcct gtcttagtct gtttatgttg ctataaagga atattggagc ctgggtaatt   21540
gataaagaaa agaggtttat ttggctcatg gttctgcagg ctgtacaaga aacatgacat   21600
ctgcatctgc tgctggtgag ggcctcaggc                                    21630
```

<210> SEQ ID NO 11

```
<211> LENGTH: 37113
<212> TYPE: DNA
<213> ORGANISM: Homo sapiens

<400> SEQUENCE: 11
tgtgggctcc cctctgctga tgggttcccc tctccagctg tggcttccct ctgctgatgg      60
ggtcccctct ccagctgggg ctccctccac tgatggggtt ccctctacag ctgtggctct     120
ctccactgat ggggtcccct ctccagctgg ggctccctcc actgatgtgg tccctcttc      180 agcttgggct ccctccactg atggggtccc ctcttcagct ggggctcctc tccactgaca     240
gggtctcctt tccatctggg gctcccttgg ctgatgaagt cccttctcca ggtgaggctg     300
ctctctgctg acagggtccc ctctccagct aggtctcctc tctgttgata gggtcccctc     360
tccgggtggg ctcccctctg ctgacggggt cctctgatgg ggtccctact ccagggggc      420 tcccctccat agatgagctc cccttcctgg gttgggtgac ccctccgccc tatctgtgtc     480
tgcaggttgg ggctaggcag tgctggccag catctgacaa cctcccctttt ctgttcttgg    540 gcactgctca cttattcagg tctcagccag gcagcccctc caatggtaat cttcagagtc     600
cccttcagca acacagcttc ccctctgtgg cccagctcat gctgaagtaa acaaggcaat     660
gtcattaacg gctggtatca gcttgtacgg ggaaccagtg gccccagaag cctctgggga    720
ggcccaggct gtgaggatca ggggtccgga agagcctcta gagcgggaga aagaggcctc    780
aggggtccct cctcacaggg gatggtgaca acacggtagg gaatggaggg gtcagggctg    840
ggtccaggac acggtgaccc tggccagaaa aggccgggcc tggctggcac ccgcacgaag    900
ggaacggagc cagtgtggaa aagcaggccc gcgtcctctt ctgcactccc agcccctta    960 aactacacac agcttgtagg aaggggatca gaggcccctg ggcgtcccat ggctatgctg   1020
cacctgggga catgaagcct agggtagctc agccagctct ggtcacggct gacagacagc   1080
ctcaccccaa cagcctcacc catccctcct cagggaacag gtcctaaca agctgctttc    1140 cccatcccag tgttgaacaa aaactcatgg gtttagacaa gagtgaaggt gactcctcca   1200
ccacccatcc cacctccagc aggcagccac cccaaaaatt attgatttat taataaatca   1260
atgacaggtg ccagccagcc ccacctgtcc ccaacctgca aatgcagaca ggggtcactt   1320
ggtccaggga gaggagaccc tcagtggagg ggagacaccc tggagagggg accccatcag   1380
caaaggggag cccagctgg agacagtaaa taggcagact attcactgtc ttccccctca    1440
agccaggccc acagagtcac agagtatagc caccagcctc ctgggcccac ccgggaggcc   1500
ccaaccacac tccccctgct cagctcagcc cggatttctg gattctgctg cctgccaggg   1560
atcctgagga ggagatggta tcagagcctc accagccctt ctcatacccc ggagtcctca   1620
tgatgataac agtgtgtgcg ccaggctgtg caggtgctgg ccgggatcct ctgagggac    1680 gagatctcca tgggagggca ccactctgat gtccatcctg ggcttccgtg ccctgcctg    1740 gccactgccc gctgctcttg gtcaagatca tggaccctca gaggccaacc aggcctcagc   1800
ctgtgcctac agcatcctct ctactgccgg gcttctgaat tgctccttcc tcctgtctcc   1860
cacccagagc aagaacgaag gggaggcccc cagagcctg cagcgccggg agagactccc    1920
atccccaccc cgcatgccat caacacaaac tgccggagag tttaggggat cccacgactt   1980
ggggtctcca aagagacccc cggacatctt catcgagacc ccctgggca ctgcatgctc     2040 aggcttccca ccctggccc accccatggg gtgtgcccag tcccgcatct caccccatat    2100
ccatgcatgc atgcatgaac ctgaaagcac cccacaccct ctggtgctca gtcctcccct   2160
cctccctggg gtcccctccc ctccctgccc ccaagccctt gcatccccct gcaaacctca   2220
```

```
caaggggtgaa ctatttctgt cctgaaagca gagagggccc ttttcttggg acctctccgc   2280
catctctgcc tccactccca gctgctgtca gctctggcct ggcccctgca ggaagcaatc   2340
actggtctcc ctgtttccca tctggcccca aggtctgttc ttgcccttcg accagagagg   2400
tttgaaagca caactcgggc cctgcgtgcc ctgctcccca gggctccaca cctctgagca   2460
cccgcgcagt aacggaggct cccagccccg cctcgcccca gggtcccctc caacactctc   2520
tggccttggg cctttgctat acccgggggcc tggaagggcc ccctcatccc caagtgtca   2580
ggcaaaggtc tcagagcact gtccctgccc ggcgtgcttg gtcctgactg ctaggcccca   2640
aatcattcct tttcccatta cctcttggtt tctctgtagc tggggtcact accccaaatt   2700
cttgaattga ctgacgtgtc caactatttc atgttttccc cctctacact gggagcccta   2760
caagggcagg gccccctggg caagaatagt gccagccagg agcccctgga gaagatagct   2820
acacatgtgc cccaggcccc agatggcact cagccctgcc tgtcaatgct ggacataggg   2880
cagtttttat cctggctttc tacacaagga ggaaagacta accatgccag cgggcagcgg   2940
ccggatcacg tatgtcagta gaactctgac ccctgagaag cctggaagcc aaaccacacc   3000
tctgtagcaa tcacgccaca gactcaggcc acggctaacg gctgcagtt cacctatttt   3060
tgcccccaac tcaagaccaa ctggaggaag gcaaatatgt ccctgacgaa gggtggccgc   3120
ctccagcctc cccagcccag agcctcagcc tccccagccc actgcctcca gcaacacaca   3180
tctgaagcct tctctgttgg ttggttttat tggtattttg gaagattgtt tgttttttgt   3240
tatgagatgg agcctcgctc tgtccccag gctggagtgc agtggcgcga tctcggctca   3300
ctgcaagctc cgcctcctgg gttcaagcca ttctcctgtc tcagcctccc gagtagctgg   3360
gactacaggc acccgccacc gtgccaggct gattttttg tatttttagt agagacgggg   3420
tttcaccatg ttagccatga tggtcttgat ctcctgacct catgatctgg ccatctcggc   3480
ctcccaaagt gctgggatta caggcgtgag ccactgcacc tggcctttgg aaggtctttt   3540
ataccttttat tgagataaaa ttcttatgac ataaaactta gcataaactg tagacttagt   3600
tggtgtgact ttagagtagt ctcagaattg tgcaaccatc accactgcct acttttagaa   3660
cattttcaac atcccaaaga cagaaccccg taggcacctg ttagcagcca ctccccaccc   3720
agtccacgaa gccccaggca gccactcacc aatctacttt ccattaattt gcccattcta   3780
aacacttgaa aaaatggta tcacaatggt cttttgggtt tggcttcttt ccctcagcat   3840
catacccctca aagttcatcc atgttgtagc tcgtatcggt acttcattca tttttatggc   3900
tgaataatat tccactgtat ggatagaccg atattttgtt tatttattta ttcattgatg   3960
aacatttgaa ttgttcccac ttttttagcta ttaaaactag tgctggctgc gtgcagttgc   4020
tcatgcctgt aatcctagca ctttgggagg atgaggcagg cggatcactt gaggccaaga   4080
gtttgagacc agcctggcca acatggtgaa accccatct ctaataaaaa tacaacaatt   4140
agccagacac ggtcatgcgt gcctgtaatc tcagctactc aggaggctga ggcaggggaa   4200
tctcttgaat ccgggggggca gaggttgcag tgagccaaga tcgcgccact gcactccagc   4260
ctgggcaaca gaccaagact ctgtctcaaa aacaaaaca aaacaaaaca aaacaaacca   4320
gtactgctat gaacatgcat gtgcatattg ttatacagac atatgctttc atttctcttg   4380
gatacacaca cacacacaca cacacacaca cacacacacg tatatctagg             4440
actggaattg ctgattttta tggaaactct atatttagca ttttgagaaa cggccagtct   4500
gttttccgaa gtggctgcac tattttgcat tcccaccagc aatgaaggag ggttccaatt   4560
tctccatacc tctgccaaca cttgttattg tctgtctctt ttatttatag ccatcttgat   4620
```

```
gggtgcatcg tggtatctcg ctgtgttttg atttgcattt ccctgatgac taatgatggg   4680
gacatctttt catgagctta tcggtcatat gtacatcttc tttggagcaa gctctattct   4740
aatcctttgc ccatcattaa aggtaggtgg tttgtcttct tgttgataag ttagagttct   4800
ttacatgttt agatactagt cccttatcaa atagatgatt cacaaatgtt tgctgtcatt   4860
tcttgggttg tctttccact tccttgatgg tgtcttttca cgcacaaatg ttttagctt    4920
tggccaagtc caatttatct attttttctt ttgttgcctg tgcttttggt agtgtatatt   4980
aaaaaccatt gtttaacaca aggtcaccaa gatttattcc tatgttcttt cctaaggatt   5040
ttattttttc tttctttttt tttctttttt tttgagacaa agtctctctc tgtcgccaaa   5100
gctggagtgc aacggcacaa tctcagctca ctgcaacccc tgcctcctgg gttcaagcga   5160
ttcttctgcc tcagcctccc gagtagctgg gattacaggc gcccaccacc atgcccagct   5220
aattttgtg tttttagcag agacggggtt tcaccatgtt ggccaggctg gactcaaact   5280
cctgatctca ggtgatccac tgcctcggc ctcccaaact gctgggatta caggtgtgag   5340
ccactgcgcc tggccttcct aaggatatca taattttagt gcttacattt aggtctacga   5400
tccattttga gttaattttt gtgcacagca tgaggtaggg gtccaacttc attcttttgc   5460
acatggatat ctagttgtcc cagcaccatt ttctgaaaag actattcctt cccccattga   5520
attgtcttgg taccccttgtc aaaaatcaac tgatggccgg tctgaaggta gtgagttatc   5580
tcaattgatt gttcacagtc agttacagat ggaacacctc gttctactct ttcccgcctt   5640
ctcactgctg cacttgaaca gtcttttaaaa aaatcaattg accataaatg caaggatttg   5700
ttcttggagt ctcaacttta ctgcattgat ctgtaggtct atccttatgc cagtaccaca   5760
ttgtcttgat tactgtagct ttgcagtaag tttgaatcag gaaatgtgag ccctccggtt   5820
ttgctcttct ctttctagat tgttttggct attctgaaac ccttgtattt ccttatgaat   5880
ttgaggatca gcttgtaaaa agacagatgg gattttgata gagattgtga agctatagat   5940
gaattcggga gtttggccat cttaacatta tgtctcctga tccatgactg caggatatct   6000
ttccatttaa ttcgatactc tttgattcct ttcaaaaata ttttgtattt ttcagtacac   6060
aagttttatg catcttttgt tgcatttatt tctaggtatg ttctttttgc caatattata   6120
aatgagattg tcttcttcac ttcattttg gatggttcat tgctagtgta tagaaataaa   6180
atcgatgttt gtatattgat cttgtatcct gccacattgc tatgcatgtt tattagtttt   6240
aagggtttta gtggattttc tatatataat gtcatataat cagcaaatag aaagtttaat   6300
gtcttagtcc ttttgagctg ccacaacaga ctaccataaa ctgagtggct tataaacaac   6360
acaaatgtat ttcccacagt tctggagact gggatgtcca agatcaagac acccgtaggt   6420
ttggtgtctg gtcggggcct acttctgggt tcatagatga ctgtcttctc gctgtgtccc   6480
ccccatagtg aaaggaaggg gcccagggtc tttctaaggc ttcttttata aggacactaa   6540
tccaatatag gaaggctctg ccctcataac ctaatctccc aaaggcctca cttccaaatt   6600
ccatcacctg gggagtaaga atttcaacac tgggggaca cagatattca gacatagcat    6660
ttttcttctt cctttctaat atgggtgccc ttgacatctt tttcttacct aattgccctg   6720
ccagagcctt ccagacagtg ttgaatggaa gtggggagca ttcaccccac cttactcctg   6780
atcataggg aagaactatc cggctttcac cactgagcac cacgttagct ggggtatttt    6840
tgtcagcgct ctttatcagg tggaggcagg tcccttctat ttctagtgag ttcagtgctt   6900
tttttttttt ttaatcaggg aagagtgtga gcttgtgttt gggtgccttc cctgcgtctg   6960
ttgagatgat cttacggttt ctgtctctta ttctattgat atggcgtatt tattaccttg   7020
```

```
gttgctttt  ggatgttgat  aacatccaaa  ctcttctgcc  accccttta  atagaaagct    7080
gtacaactcc  ccaacctgcc  tgggcgtgtc  tgcccaagat  gagtgctagt  ggccgactcc   7140
ctgctagagt  gagcactgca  taaacagcct  ctgcttgtcc  tcatttgagt  gatcttcatg   7200
tattccacga  gaaatcaagg  cacagggtc   tcatggtctc  atgaatggct  ccaccaactg   7260
aaggtgtgct  ccatcggggc  tgtgagtcac  ctcacgccag  gcagaaaggt  ctctctgtca   7320
aacatggctt  caaggaacca  gggacctggt  tcctcccaca  ggccaggccc  tgcccctaag   7380
tgcaatggga  atatatgcac  atgtcacctg  tcccaaaatg  ctgggagatg  gcacttctgc   7440
agatggggaa  actgagggac  cagcccgaag  tcacggggag  gggaagactc  ctacacacag   7500
ggaggagaag  aacccagccg  ggctgcaaac  gcctgcccctt  cctcaacgtg  cctccggctg  7560
tgcccacatc  gctccagcag  ctctgccttc  tcaggcata  agccttctca  gggcagggga   7620
ggcccaggga  gcggcgctcc  catcccaggc  cgggctgctg  agcaagcccc  tccccttct   7680
cccctcatcc  tctgacagag  tccacctgaa  tatttgtcct  ggagccagga  tggaagctcc   7740
accaggccca  gctaacaaca  ggaacccttt  cagacgcact  tctgggtgcg  tactgtgcca   7800
gtatcacaca  gacacaagcc  atgtccttgt  cagccatggg  atccccaagg  tccccatgag   7860
gtcacaccag  tgggccactg  ggaagggcac  ttcagatgtg  gagctcccat  gggccaggcc   7920
ctgcgaagtg  gtcctcctac  cccctcatag  ccagtcttcc  ctgtgagcct  gcaagtgact   7980
gtgaatgtga  gttccactct  ggagctaaga  cgggctgctg  ccccccgcaat  cagatgtcag  8040
gcccatgaag  ccctccatca  tcccactgca  gtcagaataa  aatgcagcct  ccctctggcc   8100
tccaggtccc  aaggccagcc  cccctgcctc  ccaggctcac  acctgcccct  aacctgtgtc   8160
cagccccttt  ccctggctc   tgtctcctgc  ttcccttgtg  ttcctccaac  ctcacctgtc   8220
tgtctggagt  gctcctcccc  ggctctgcct  agctggctcc  ttctcaggca  tcagggcctg   8280
gatccactgt  ggctcttcca  agcctctgca  cttggagtgc  ctcagcccg   tggttgagga   8340
gtgccccaac  cctgtgaccc  tctagcaagc  atcctaggaa  ttccgtccct  ccccagcact   8400
gatatgacca  tcgtgctgtg  acacgtgtca  tctccgccag  agttgcagat  cctccagggg   8460
aggggtctgc  tgcctggctc  ccacagccag  ggcctggaac  agtgcctgac  acacagcagg   8520
cacccactaa  atatttgatg  catggctgaa  gaggacaggc  aggctggctg  ctggctgggc   8580
atggcctgct  tctgaggctg  gtggtcaagg  acacagtgtg  catggatctg  cccccctcctc  8640
ccacttcctg  agagtggagc  cagtgtctcc  ctccacctac  cacccccctgc  tgaggacaca  8700
gctcacacct  ttaacgggaa  atgtcccat   cactggggac  agcagggagc  tgatgggaga   8760
gcaggtgtcc  aggacatcca  gagaaatgtt  tcctcacact  ggaacccttt  tctattccct   8820
tctaaacaaa  aagaatcctc  gaagactctc  aagtgaccat  atagtgtctt  ttcttataat   8880
gtcacttcga  caggcacaaa  atgtaaaacc  aggcataaac  tactagtgct  tgcagttctt   8940
acgcaggcat  gaagccaaaa  ccagtttaca  aattaaccac  caagaaaacc  ggtagagcac   9000
agatgatgac  gatagagctg  ttttgtccaa  tgtgagcgct  actggccacc  cagggccatg   9060
tgaatttaaa  ttacgatgaa  acacaatgaa  aaatttggtt  ccttgtggcc  acatttccag   9120
tacccagtag  tcatctgtgc  cagggggtta  tccaggtaca  gaacattccc  atcgttgcag   9180
aaggttctat  cagctagcac  tggggttggac  gacacttgcc  aagacgagct  ggctagagga  9240
tggttctccg  gacctggtcc  cacgtggttc  ccaggtaagc  cccgcccag   gatgcagccc   9300
cgttgtccat  cagtttttctt ggagagggca  tgggaaacct  tcgtcagtgt  gtcatctcct   9360
gcaaaggcct  tcgctccttc  ctctggggag  aaagcaccct  tcactctctg  aatcattagc   9420
```

```
ccaaagcagt aagtgcagca ggcctggccc cacaccttcc ggaagagcca cggtgtgagg    9480
ctggcatccc tggggcacga cacaaccagg atgtagacga aatagatgca atatctggag    9540
gttctcctat aggtgtctct ggcctcctgg acacttcaca ctgttctggg agctgccctc    9600
tcaggcccca gtgacctttt cagatgcaga ctcccacagc atgggtcagc aattctcccc    9660
ttccgtgaga cagggattgg ttacctgtac taggaccttg aggccaacac tgactagggg    9720
gcctcatgcc tgcccaggtt ccagcccggg agagcaatgt gagcaaagct tgctgtcttt    9780
gcaaagccaa ccactgtggc atcaactcct tcaggaagcc ctcccggatt gtccaaggtg    9840
ctcacctcct tgggggagcc ctcccagatt gtccaaggtg cttgagggag ggaggaatgg    9900
gttgttctcc cggcaccggg gctgcactcc tgggcagacg ctgcatgcct gtcctcaggc    9960
gcggccctgc tgccaccccc ttgggggctc ggagcgcgac agcagcttgg ggacgcctcc   10020
cgcgcccagc acggtgcacc tgggccctga gtcctggcc gaaacgcgcc aagttggggg   10080
taggtgcagc gaccccatac ccctcggctg cgcgccctgg cggcaggagg cggggccggg   10140
ggcggggcgt gagctggccg ggggcggggc ctatggaggg gcgggaccgc ggcgccctat   10200
aagtactgcg gagcgcaggc gcgcgcccgg ccagagagcg agcgcgcaac ggcggcgacg   10260
gcggcgaccc caccgcacat cctgccaggc ctccggcgcc cagggcgcac ggcgcgcccc   10320
cgtgccggcg gcccctgcgc ccatttcttg gcgcccccgc ccggtcggcc cgccaggccc   10380
ctttgccggc caccagccag gcccgcgcc ggcccgcccg ccgcccagga ccggcccgcg   10440
ccccgcaggc cgcccgccgc ccgcgccgcc atgggagtgg agggctgcac caagtgcatc   10500
aagtacctgc tcttcgtctt caatttcgtc ttctgggtaa gggctgcgcc gggggccggg   10560
gcgggagggg gcaggcacac actccacgtt gggcaggtcc cgcggcagcg tgctaggccc   10620
cgcgggcgca gcgcgggccg cgaagttgtg gggccacctg tgggctccag gagcggggtg   10680
gggggtcgcc cggggccacc gcgcccccg acattgggc tgaggggctgc gagccgagtt   10740
tcggggcctc tgtgctcggg ggcccacctc tgcggccggg ccggggcttc tggggccgc   10800
cgggcagttc ccgctgtggt ggtgatgggt gcggtggtcg cgggtcggga cccgagtacc   10860
cggccgcccc tcagctaagg aggggcctgc gcgggtccct ggccgcggat tccggactgc   10920
tgcttcgcgg ggacgagggg ggggctcgcg ggcgggactc ctggcgcccc gcccccatga   10980
gctcatcaag agccgccgcc cctggatggt ggggcggggg cgcacacttt gccggaggtt   11040
ggggggcgatc cgcctcactc ttttccccagc ccagctcact ctccaatctg cggtcaccac   11100
ccgagacctt cctgggggtc gcgcctaaaa ggagcgcaga ctcccgccgg gatgcccag   11160
aagctggggt gcgcgcaccc tggccgtccc tgcctgggag ccgatctccc tctcctcacc   11220
cagacacgtt ccagcggagg cctcctccca gaagggctct ggaggcctcg caggagtggg   11280
gatcccgcgg ttctgagttg gcacaaggaa gagagtggca ccaggggcct ggagtggatg   11340
gcagggtccg ggagtggggc cgctgctttg caagagggc cccacgctg gcatctttg    11400
ggtgccagcg tgggtggagg agggtctttt gctgagaatg gctttctcct gaccgcagtc   11460
tttgctgctg ggaagtgact gatgggcttt cgccttttgt ttccatttcc tgtcggtgtt   11520
agaattgggg aggggggtgga aatcccttct tggcctggaa ggactggagt gggtgtccat   11580
ggccgcggcc tccccgtggc cacgcccctg gcatagact gcaagcccct ccccgtgccc   11640
cccaggctgt caccccttcc tcgtggaaga ctcggctgat gtcccagtgg accgagtgtt   11700
tctcaagttg aggcagggag ggcaaacttt ttaaatggcc cctggagcca gtgtgtggga   11760
ccagagacat ctgtttccca tctggacggc tgaggatccc agtgcggatg attatttgga   11820
```

-continued

```
gggggaagga cggaggctga actgaactct cagctgggag atgagtgggg cagtcacatc   11880
ccaccttccc caagccgggc tgttctgcac agcctgcttg ggacgctggt gggagtcact   11940
gtggctttcg gcactgccct ggcagtgggg gcagctaggc catttgggag gggctcgctt   12000
tccccaggcc gggccctggg acctcagccg ttgcttagtg gtggcctgct tcagcccagg   12060
catgtgggag aggcaccaga cacaggatgt ccctctgcca gcccctgaag ccccgtcccc   12120
tgacgaggcg agtgtggacc tggggtgggg gctgaggga gactgtggac ctggggtgg    12180 gggctgaagg aaggtgtgga cctggggca ggggccgagg aaggtgtag gcctgggggt    12240 agtaggggct gagggagagt gtggacctgg gagtaggggc tgaggaggg tgtaggcctg   12300 ggggtggggg ctgagggaga gtgtggacct gggggtaggg gctgagggag agtgtggacc   12360
tgggggtggg ggttgaggga gggtgtggac ctggggcag gggctgaggg agagtgtgga   12420 cctagggca gaggctgaag gggagtcacg ggagggact tctccggagg tggattttg     12480 ctctctggac ggtgtgtcag cactgggtga gcccctcctg cctgcccagg ctgagaggtc   12540
tccctggcag cccctggga gtgtcgccag ggcgggcctg gaagtttccc aggcagctgg   12600
ggtggagacc tgacacatcc caagggtgct tgttattaag gctcaaggaa atgtctctga   12660
ggcctcaccg ctcctctccc cagggcctgc tccctgcaaa gcattgagaa ctgagtccgt   12720
ccacagtcac tgtggaccca cccatccact ggggctcagt ggtagccagc aatgccaggc   12780
tgggtgaggt ggggttggtg ggcaccaccc tggtggaccc ccctccaccc tggtgtcgca   12840
gggtgtgtgg ctgagagcac agtgccatgg gcttgggcct ccttggtgga gtccccaaca   12900
cactgctctg gtcctgggcc tcggccttcc ccgtctgcag tgggggccca cagtgagcct   12960
acctcctggt ggtgttggtg gatttgctga catgcctgag tgttgacagg gggcttggtg   13020
caggaagggc tcagggcgtg ggtgttggcc aggggtccaa agggacctct gcctcagaga   13080
gcccagccca gacaggcagg atgtgcagtg gggaaggggc tgcgggaacc ctgcagggtc   13140
cagaaggaca cagtgcagtc ctgtgggctc tggggaggct ggtggggagg aggttgacaa   13200
tggatatctg ggtggggcac ttgttagaag ttccatttta gagaggaaag aggccttgcc   13260
tgtgggagaa ggcagctggg gtagcctgac ctctttccca ggaaggagcc cacacacaca   13320
cgcacaggca ctcacacaca cgaatgtgca cacacacaca ctcccaccttt cacacacact   13380 cacactcttg ctgtctccct tcccaagcca aggtgcgagg gggaaggtct gggcagcatg   13440
cacctgcgcc ctgaccgctt tgggggccag tgagaactgg gctccctggg tgcgcggcgg   13500
gcccaagcag ggaggacatt gcagatgccc tggccaagca gcgtggaaat cctgtccctt   13560
gggtgggtct cggagcctcc atcagaggcg gctggcacct gagacccacc tgctgccagg   13620
agcagggcag gagagtttgt gtcccgggac agggaactgg cctgtgggag ccttgccttc   13680
ctcatctgtg taatggatat aagagtcttc tcctcggggg ctggccaggg agtccagaag   13740
aggtgtcacc agtccccgca gggagaagag cggtgtcccc cgcctgggac tggctgctcc   13800
cccaagctaa tgcagctggt agccacctcc cagtggcagg gcagccaaac ccggccggga   13860
aagagactga ttagaagcct cgctcacggg tatttctcgc ttccagacag cacatgactg   13920
tcatttggca cgtctttcgc cgtccttccg ggagagggc tgcaaccctg gcaggcgctg    13980
tgggggaggg ggctaggaca tcctgtgcct ggtttcacca agtgggtgtg tggactttcc   14040
ctggctcccc caggctgtct ggctgcacag ctttgggaa acggccactg ggtcaagcgg    14100
gccgagaaga ggaagtctgt ggtttgtctc tgctacagac tggccccagt gaggctgtcc   14160
agcagtgcag ggcacagagc aaaagcaggg aggtatgggc ctacttcccc ggtcgcccct   14220
```

-continued

```
gtggctggct gtggctctgc cgggtgctga caagtcactc gccctccctg cggtcaccag    14280
ggtgcatgcc cgaaagccct ccattctttc ctgggtttga gggtccttct cctgcaccca    14340
ccccagcgcc cagttcagct caactttcag aaatctggtt cacccccaat cccctttctca   14400 taactgcttc caagcccaga caaggagaca gaccccaaaa gatccctacc cctatttccg    14460
cacctgaaat cgcaccacgg gaagagcttt gctcatagag tcaataaggc ttagagtcca    14520
ggcgcctgtg cgagggagca ggtcatcacc cttgtaccca ccgtggtttt agacaggacc    14580
ctgaggttgg ggtggggctg gggctggaga ggagccaggt gccctgcccc ttgcttgggc    14640
cccgtgtccc tgtgatccag gctgggcgtg ctatgggtgc tgggtgatat ccagccctg    14700 caggtgtccg ccttgttccc agcacccctc tgggcaagaa gaaccaggct ctcccagaaa    14760
tgggcttcag tgatctccac ttccaagtcg tccccacctg ccttgtagga cacagtggta    14820
cctggtatgc tgggcagcct tccaggaacc tctggactta ctcagtgtcc cccagcccta    14880
cacaccattc tttgtgtttc tgggcccaaa ctaagccccc caacctgggc tgcagagcaa    14940
gtgctgaatc atgagagacc cttgagggtc ctccaggtag gcccccagtg ctggaggagt    15000
cccctcaggc aggggccac gcccaagggt gtggaaggtc agctggcagc cggatctcac     15060 tttttggggct gtaggcttcc tgcactggcc gccaatgcca tggccgtggg atggccagga   15120
taaggcatct gcccccacc cccacccccc gcacaaggtc tttgagggct gcgggctcaa     15180
ggagttggcg gtagggctgg gggaccaggg gcacagagct tgtaagcgcc tctctccagg    15240
atgtgggtgg cccagcaggg gagctttgag agtccaggtg tgagattcca aatgctaggg    15300
gcctgagagg agggagccac cagcttggcc agagcctggt ggatcacgcc cccaccacgc    15360
cttgcccttc tctctggtca tgtgctctcc caccacgttt ggaaagttac tgcttccctc    15420
ttcctcagcc cctcgggctc ccagttatgg aagtggcgtg attcagagaa ggtaaaggat    15480
gggagggaga gggctgggtg atgggggacc ccgcagggcg ccctgtgctg ttacatggag    15540
ctccaggatc agggcaggtg ggcagcctgg ggtcctcact tctctcccca gccaggccag    15600
gtccctcaca gccctgccag gagcatgata tccgctgcgg tgcagaacta atctcaaagc    15660
tcaaacccag gtaacagtgt aggtaaaaca gatgacaggg catgagactc accccaggac    15720
aggcgaagga cccaggccga tgggggccca gaacagtcct gatcctggag ctccttcccg    15780
agtgggaccc cagggggtttc cgaggggctt agagtagggc ttagaggctt agagtagggc   15840
tagggacttc ctggcttccc tgcctcggga acagctggtc ctggaagggg cttggtcctc    15900
ggggcactgg tgcccaccac ccctgatgcc tgggagacac cagcatcctc tgagcatgtg    15960
tgcgtcctcc tggtcccgag ggaagtgact cctcacatcc cccagctggc ggggccagag    16020
ggccagcatc ctcgcctgac acctattttt agatgctgag acaggcggct tcctcggggc    16080
caggggccct gtgagtggag cttccgcttc ctggcctagg agagaattcc tgctcctctt    16140
ccctccatgc tgccttttcg cccctggagg ccacaacggg gtcagagggg cagctgctca   16200
ccacctagga gggcctgaga gggccctacg tcacccaggg aggagtctgg ccccgtcccc   16260
aacctccaca cccaggcctg gcactgcccc ttcttggtgg gcagagagtg aggggttggc    16320
ctgcagggac ccaggctgga ggggccgttc acctccggcc cccagcgtcc cttcctggaa   16380
gcaccttggt gagcccctcc cctccttcac ccagtatctc caggggtact tcctcctttc    16440
cttcctgcct cagggcctca ctgtcctcct ggggagggtg tctcaggccc cagcacctcc    16500
cagtggctga gccgaatggg cacttcccgg tgtgtttccc atatgtgcag tccctaggtg    16560
tcggtgagca ggcacagagc ccgcagcgtg gccctgcctg tggaccccc tccccaagag     16620
```

```
catcaaggga gggcctggac tagagacaca cagatgccca gcctgtacgt aaaggcgggt    16680
gagctgatgt accatcgtcc tcgtccccca ctggggtgcc tgggcaggac ttggggtgac    16740
cacttggccc gtctgggtgg gggtaaggta tgggtggggc gaccagatcc ctgccctttc    16800
ctgcagctgt gggggtgtgt gtgctggcct ggagagctcc cacccgaagt tctggctcct    16860
ggctgtccgg ggcctgcggg ggcagcgagc agctggcatg ggtaggggag ctgacctagg    16920
cctgcccggg cagcgcctgc tgccttttgc tcccttcag ctgcttcttg gaaacagcgg     16980
acaggctggg caggaaccca gtgtgcttgg cagccccct tttaaagtcg attctgttat      17040
ttattaattc ccaggaagga gaaagaaaga aacaatcctt catagagtac aaacactgct    17100
tttagtagcc ttgcaaggag ccctccagga accccacagg ttacctgggc tccatcctga    17160
gagccaccct ccatcccaa tccccagcag agcatcttgt ggggtggggc ggcttgtggg      17220
gcggggcgcc ttgggaggcg gggtgtctcg ggaagcgggg cgtctcggga ggtggggtgg    17280
cttgtggggt gggggcatttc ctggggtggg gcgtctcgtg gggtgggaca gcttgggggg   17340
tggggcatct cggaggcgg ggcgtcttgt ggggtagggc ggcttgtggg gtggggcatc     17400
ttgtggggta gggcggcttg tggggtgggg catcttgtgg ggtgggacgg cttgtggggt    17460
gggcatctc gggaggtggg gcatctctgg ggcccggcca cttgggaggc ggggcatcct     17520
ggggggcgggg catctcagag ggcgcctccg gaggctggag tatcttggga ggtgggagca   17580
ggtggcagag aggcttccca caggtgagct ttgagcaggg aggtgcctgt atggatggct    17640
ctgtggggag aggggtgaca ggagttccag attccggcac ttatgaaacc tcacagtgat    17700
ggagagccga gtgctgctgt gcaggctaag ttgtgtgcat gtcagcttct gcacttttat    17760
ttccttgttt gtagacaagg cagagagaag ctgagatggg cctgaggtcg ccttggtgaa    17820
aggcactcag cagccagggc cttgggctgc cctccctcat caccgtgaaa gcgggactct    17880
cttttaactg acatcgggct ccatagttac tccagtccta actttgatgg atcctaaaag   17940
tgcacttcta aggacgcggc ttcggtgttt cccatgccgc tgcttgcccc tgggaagcgt    18000
tggctctgcc tcggaagaag ttagcgccaa gatggcagcc tggggtcttt ggggcccaga    18060
agaaacactg gccccgggga gttcagtcat cagggactta ggatgtgggg gcttttcaaa   18120
cagctttatt tagacgtgat tgacacacag taaatacaga tgtttaaggg tacaacttgg    18180
taagtttga caaatttata ccccgtgaa accatcacca actccccagg tgcccctggg      18240
gcccttggga tctctgcttc ctgcccctcc tccccgtccc agggcaacca cgggccgtcg    18300
ctgtgggtgc acacagcatg catttcttca acaagcggac tcagaaggca cttgcacatc    18360
gttgctgttc tgcctctttg cttcagcatg attacccaga ggcgcacccg tgccgtggcc    18420
tgcccgtcgt ctatgcaccc gtgctgtggc gtgcccgtcg tctgtgtggc atgcctgtct    18480
gtgcacccgt gctgtggcgt gccggtcgtc tgtgtggcat gcctgtctgt gcacccgtgc    18540
tgtggcgtgc ccgtcgtctg tgcacccgtg ctgtggtgtg cccgtcgtct gtgcacccgt    18600
gccgtggcgt gccgtcgtc tgtgcacccg tgctgtggtg tgccttcgt ctgttccttt      18660
tattgccggg cagggttgca cccacatgtg caagccagcg acggacccca ggttcacccg    18720
ttcaccggtc agtgggcata tgggttgttt cagtttgggg catttacaag aaacgtgcta    18780
gaacatttgt gtacaagtct tgtgtgaacc taagttcatt tctcttgggt aaatacctgt    18840
gcgtggagca gctgggtcat gtggtgaatg tgggtttcac tgcttaagca gcagttttac    18900
ataactgcca aactgttatt caaggtggct ggaccgtttt acagccccg ttgtatgcgt      18960
cccagttgcc tcccccagca gcatgtggtg tggttggtct ttttcgtggc agccagtcca    19020
```

```
ctgggtgcgc tcggcatgtg gctgcagctt gacctgggtt tcctggtccc tggcaaggtg    19080
gagcatctct tcatgtgctt ttttgctgtg tgtggatctt gcggggaagg gtctgttcct    19140
gttttttgcc catctttcaa agattgggtt gccagttttc ttgctgttga gtttggaaag    19200
ctctgcatac gttcagggca caggtccttt accaggctct gccccaggtc tttcggagag    19260
caggtgtctt tcgcattcct gactctgggg aacctctagc cctgccacat ggggtttgtt    19320
atggggcagg ggcacctgtg cctttcccac cacggggctt ggggatttgg tgctgccatt    19380
gccctccctc gtaggtggcc ctagggggt ccctccgcct ccgtttcctc atccagaaac     19440
cggcagtgac catcaccacc attgttgtca cctagctcca gctcaaggtc cctgctgaag    19500
gtcggagagc ttggcatggc cccgtttgtc catgctaggg ctgggaagac caaggctcag    19560
gtgaggcctg tgcccagtgc ctggcactcc ttcttgcccc attttccac ccagggtggc     19620
tcccgactac ttctggtagc ctcggggaca gttgaggtgg acaggctggc gtcaccccca    19680
tttccggctg tccctcccac cccctcctgg cccagctgtt ctgccctatt aaaagtcaca    19740
tgggccctcg ggtccttcct ggtgttggcc caggctcttt caggccctgc aggccaggac    19800
cagccttccc tgcaaccctc ggcagaggcc tgggccggg gcttgtctag ggcagcctc     19860
cccatacggc cctggagtct gaacagaagc cccttcccag agcacagcaa gaagctgcaa    19920
cgtggcctga agtcccacca ttagcaggtt tggggtttag gctgagcttt gccatcacta    19980
cctttctgtt aggacggtat gcccattaga tgggatcatc ccctcagcgc ccaggctaga    20040
ggaggggtgg tccctgccca gccagggagg gctggggtg gatgggcctc tacagagcag     20100
cttccgagcc aggcacggtt ccatgatcag ctctgtttta tagaggggga cactgaggaa    20160
ccggagcct ggggaccttc cagtggcccc acagctcctg tggctgagtc agggtttgtc     20220
accaggcctc tgtggggatg aggctccccc atccacctgc cccactctgt cctggaacag    20280
ctctcaaaac ggtctctgga ccacagtttc aaaagaaaat aagcaatgtt ttcaaaggcc    20340
ctggaggaag ccagagttac cacggcaact ctcggcctcg ccacctcctc ccgccaggct    20400
gcatctggag ccagctcagg agggcagcag ggtgaggaca gccaggctct ctggggccac    20460
cccccagccc ccacccttcc tgcctctcct gcactgtcca cggccctccc tgtgctccca    20520
cgggtataat gggcacagaa gaaccaggag ctgtctgccc ctgcaggatt ctggaagcca    20580
ggggcccctg gcctccctgg ggccttgtca tgtgaggggc acacgtgggg tcccagctgc    20640
cacatggctt ccagcgctgc cgcaggtgt atgttgggcc cttggtgact ctaatgcacc     20700
ttccactcgg cacagaagag cttcagtctg gggcctgggc gggggaagta ggctgccatc    20760
ctcgctaaac caaagtgtga aaattgagtt gaaactccca taggagggca ggaggcacag    20820
ctcctcagaa gaaggtctga gaaaccacag cccaggttgt tgtttcgggt gtgtggagaa    20880
ggtgctctgg cagtcctgct acaggggggac catcaacagc cccttgggg tgagagcccc     20940
gtggctgctg gcaccagcag cccctatgag gcttatttta tttttgagac agggtcttgc    21000
tctgtcaccg aggctggagt gcagtggcac aatcataact cactgtagcc tcaacctcct    21060
gagctcaagc gatcctcctg cctcagcctc caaaggtgct gggattacag gcgcttgcta    21120
ccacgcccag cccccctctgg ccttattgtt tgccaggccc agctcaggtc ccggaggagg    21180
ggagacagga gtgtgaggga aaggggaag aggtatagag ccccagctc ctccaccac       21240
ccgaaccctc accgaggccc tagaccctag accggcctga ccgggggtc ctcaggccgg     21300
ggacttgggt gcaggccatg gtgctgggc ctgaagctca cgctctgctg agcacagccc     21360
cctgcccaac cccaccctgg ggccctgctt ccctggccag ggccattgga acaggagtgg    21420
```

```
ggctgtccag gtggtgttct tgggtccagc cctcagtttc tcttctgcag ttgaccggca    21480
gccctgcatc tgtggtgggg tcggcgcctg gtgctggtga ggcaaggcct cagctgctgg    21540
gacaggacct gcctggcacc cagctggtgg cagagccaag cattccgact cagctctggg    21600
agcagctgcc ttctgggctg gcattctccg ccagggggt tgtgccctcg tggcccccc     21660 cgggtgcctc ctcacctggc tgatttcatc tcctgtcccc ctgcctcctc ctccaggaag    21720
cccccagggc ctggccctcc ttgagagtgg catggaggag gaagaagact cgcccaggcc    21780
catgggagtc ggatggtggc cgcacttgtg gggccctgac cccataggct tcttcagcac    21840
gccctggcct gggtgatccc tgcctgaggg ctgtgcacgg ctcatctgcc agaccagatt    21900
ttaggggatt cttgtactgt cctcctggag cagcagggg taaagcctga cccacccaga    21960
ctgtccagca acaagggcct cctgctgtgg gccaggacc ctggaactga ccaattgtgt    22020
cctagggacg cagagtcccc aggctgctag agggctgtgg ggccctgttt catgcctgaa    22080
gcaggaagaa accccaggag aggtctgaag gggacccagc ccccaccctg tctagcaggg    22140
aggagcctct gcaagaggcc gagggtgct gaagtggagg aggatagagg cagcaggact    22200
cagggtcact ggtcatttat ggggatcaca cggctgcagt gtgccctgca tggtgctagg    22260
caccagggac agcagaggac aagcctgtgt cctctcccac caccagaggg ctgggcactg    22320
cccctaggga gagagggggc cttggtgtgt gcagagggg gcctggggca cgtgcctggc    22380
ctggtcagat gatcagagtg ggctgggctg ggcctggtct ggggcccagt ctcaagggca    22440
gaccccacct ggctagagtt gattgtgtgc acaccggatg accggcgtt gaaggcctct    22500 cctctctgtg agcctcatcc ccacctgcca gactcccagc acagcctgct tcctgcccca    22560
gctgctgagc gacagcgctg ggccggcttc tgcgcgcccc ttccccagc ccatcttgga    22620 aaccacagca gcgtccttcc tcccaagtcc cttcccaggg ctgacatccc acagcaggga    22680
tgtatcccac aaaccccgca ggccctggtg cctacagctt ggcctggtaa catcaaatcc    22740 tacccctctcc tcctggcagc aaagatgggg tgcccccacc ccagagttct cagcaccccc    22800
agacagaagc agtcccccag cgacctcaga actcttgggg cgctgccaca cccttgcagg    22860
agggggcagt gttcctggga tgctcaggtc ctggtatcac ctctggccag atacggaagg    22920
tgaaactaca gggcatccaa ttcaccttga acttcagata aacaccagat tattttttg     22980 tatgtcccgt gcaatatttg ggacacactt accctaaaga agtattctgt tttcatctga    23040
gaggcagatt taaccggcgt cccgtgtctt cctggcagtc ctgccctgga gtcacactcc    23100
acaggtgcag ggcagggcca ggctccaagt agatggcggc caaagcaccc gccccatgct    23160
cctgactccc ggggctcttc agggcattgc gaaaaccagc agcagagctg acacctggtc    23220
cctgctcggg agccagcaag gcaggaggct gcttaggcct tgcgtgtggg gtgggcgcac    23280
tccctgctgc agtgctcttc gtacatgtga cactgttccc gctctttccc agctggctgg    23340
aggcgtgatc ctgggtgtgg ccctgtggct ccgccatgac ccgcagacca ccaacctcct    23400
gtatctggag ctgggagaca gcccgcgcc caacaccttc tatgtaggtg agtgcacatg    23460
tggccgcaga cgcattcagg gagggcttct aggaggaggc aggtcctagc cttttggatg    23520
gggacatgga gggtgaaaga cagtcgggca tggcgtgtcc gggcagggag gcggccctgg    23580
aaagggctct gggcacaagg gttgagatgg aggtgggcct gtggcctgct ggcccttctg    23640
gtctgagcca gggcaggggg tggcagctag gcctgggcag ggactgtgtg gagaccttgc    23700 ttatttaag tgtggggtta tttcggggga ggctccctga aagggtggg gctggatgcc    23760 tgggccacac agagcagccg aggcagctgg cgctgtggag cccgggaggg agggagggat    23820
```

```
ggagctcaag ggatggaacc cagtgagggg tggagacggg gcaggggagg ggtggagagg    23880
ggtggagacg ccccagaggc ggtgtgactc agctgcccct gcaggcagct gcaccttgct    23940
gccttattag gctgcgtgtg ggggactggg ctgccctccc tgcccccagg agcaggagca    24000
ggagtgatgg aggaggagga ggggagggc aaggccagga ggaggaggag ggccatctca    24060
ctgtgcagag agcagcaccc ttcctcctgg tgcccctggc agggctggtg ctggtggggc    24120
tctgggagca tttgttgaga tgcttctggc cttgaaagga ggccctggg atggctctgt    24180 tgccctcaca ggctgagggg tgggtgaggt gggcagcctg tgtgtcccca gtcctcaggg    24240
cttccctcag ccggcaggtg cccccaggcc tggagctgca gggccaggcc ccctgccagt    24300
tacggaggct gcttggcttg gttgctgaac cagggcccca ggaggccgaa atagccccac    24360
acctgcgccg tcccacctct ttgtccagtc accccagggc caggtgaggg ccctggccac    24420
acagcgtgcc cgttccttct tccccatgcc ccgctcatgg gtcagagggc cggtgctggg    24480
gtccagatgg tgtcaacagg gatggtccct gtcctcccca gagacagaag cctgtggccc    24540
acggagggtt tctgggccca gccgatccta gggagggtcc catggccctg cccataggtt    24600
cctggcctct ctcggggccg tggtgccctc acaggtggtg tcaggaagga cgggaaaggc    24660
tgcttgtccc aggggctcat gtggagacca ccccctgcac gcagctgggg cgctcctgcc    24720
tgtgtcctca gaagcactcg gcttagcttt gcccatgtgc ctgggctgtg ggtggcagag    24780
cccggccagc atcctccgat ctccaagggt gcatctctac tggaggcccc tcctgggcct    24840
cttgctcccc gcttcccaga tcattaggat atttggggtc cagaagggcc tcccagccat    24900
cctgggcctt gtcctccggg gccaccagtc cagccagtga caaccacagc atccccggcc    24960
tggaacgagg ctgcccccag cacgttcctc gtactcctgt ccagggacag gaggggctgc    25020
ccctgccacc gagtcccctt ctccaggacc tggggcctgt gggtgtgagg caggtgttct    25080
tggaaggggt cactctccag gcacccggcg gccaaggctt gtggctggag cagctcccgc    25140 tgtgggtcg gcgtcgggcc ccgtgtgcc ggagaggagc tgaagggtca cttagcttcg    25200
ggctggggcg aggacagggg acaccccaga gaggtatgcc aggcctcctt cctgcgcccc    25260
actctcggca gaagcagagg tcacaggctg tgctgaggcc ccatggtgct gccccccatga   25320 tgccagggtg aggctggcgt tggaagcagg tgtctgacct gcatggtgtc accgtggcca    25380
catcagagct ccagccccag agccgccacc cctcggtcct tggctgtggt ttccctgggc    25440
tggaggagcc tgccgttgtg ttggccacac gaccacagga cctgccaccc ccgacgtggg    25500
ctctgcctgg gcccccactg gacagggacc ccttggagct cctctggcca ccaagtcctc    25560
gcccattcca gaatcggcct tctggagcct cttgctgtcc ctgatgcggg ctgggccttg    25620
ccaagggctt ttttttcctgc gccgggaaca gggtggattt gctgggctca ctcccctcag    25680
agacgctgcg ggtgcggtgg gttaggccca agggcgttaa gagaggaggc tggggtgggg    25740
ctggggcctg gcaggggtc tggcagccct gggcctccca cctcctgtca ggaccaaaaa    25800
aggcaacgcg cctctcctga cctgtacccc ggagtgaacc caaccttgca acccaggagt    25860
gtcagggcct gaggggaggg agacctggct cctgggtgcc gtgcccgtaa ggaggtggcc    25920
acctgcaggg cattcctggc agaggcttca tctggccagg taggaggctg ggtggccgag    25980
ccccaaatct gggtgtgttc tctgcctggc ggtgggtcct gccccaggca ccttctcctc    26040
tgggctggct gggcagggac aatgggcctg gctgcgagga gggggcctgg gctgccttct    26100
gcattgcctc ggtgacggga gatggcccct gcctgctgag ggatagggga gtgggcaggc    26160
agtgagagac actgacagct gtcccgcggg tacagggccc tgtctgggtg gccaggccca    26220
```

```
tgtctcgggc ccacagtgcg cccccacce ttggacggcg ccttctccct ccccaggtgc   26280
atgctgccca gccagggagc gtgggggagt tcgggagggc tggcctacac gccctggtcc   26340
agctgtccca ggtggggtgc tgggcttcag ccctcagccc agggcctagg aatccaactt   26400
gatcctcccc acacagcagc caggttcaaa tgcaggtccc gtaacggaag tgctgctgtg   26460
cagcccagat tgggggggcag gagccagcag ggccccccca ccctcttctc gcaccacact   26520
ggggaggcag cattggttcc agttccggtt cctgggctgc cctctcaacc ccggcctaca   26580
gtggggccca ccctgtgcct tctgatgcca ctcccacccc acgccaagtc ccagaggctt   26640
tgggagcggg tgaaggcggt gggtggcggg tggcaggtgc aggcggtggg tggtgggtgt   26700
ggcaggtggc gggccccacc gcaggtgtca tccctgcgaa gcacctgtcg ccagcactca   26760
gagcgctcat gaggtgccca gtccccatgt ggcctcctta gtctccgtcc tgtgtcatgg   26820
aagaggtaac tgaggcacag aaaactcacc aggccaggct gggatgtgag gtcccttgct   26880
gctcatccct ggcagtcagc aaccctacat cttcccagct gggcggcccg tggtgggttc   26940
ggcacccagg accctccggg gtcttgggct gtggcgagtg tgtaggcacc cacctggtgt   27000
ctctctcccc gcaaggcatc tacatcctca tcgctgtggg cgctgtcatg atgttcgttg   27060
gcttcctggg ctgctacggg gccatccagg aatcccagtg cctgctgggg acggtaaggc   27120
agggaggcgg gcctgtgcct gggccgggga ggggctgggg gctgcgtctg gccctgagga   27180
gggggcagag ctggtgctca gggcggagcc tagaattctg ggggaggtgg ctcctgtgcc   27240
ctgcttttcc cgtttggttt ttaaattaaa tcccaccgtg cttggtctcc atcgtggcca   27300
gttcctacgt gaccgctttt ctttgtcaaa aaatagccac aaatataaca gggagcaagc   27360
ctcagctctg aggccagcct cggcgtcccg ggcacaccgc ccctgtggg aagcccaggc    27420 ctggctgtgc catccagggc ctggccagtc caggaagagg gagcctatgc ccgtgtctcc   27480
agtgggggaa actgaggcag atcccatggc tccccttcc gtggggagca ggaacaaggg    27540 ggtgggggaag atcagtcagg ggtcatgctg ctgcacacgc ctccctgggg gctgcagaca  27600
tcctggactc accagcctgt gaccccaaac cacacgcccc gccccatcca ccccgtcctg   27660
tggagcctgg tgccgcgtgg ggacatcctg ggctttgacg gctcctccct gcgctgagtt   27720
ttagcctctg tgccccaggg ctccacacaa gccgctcact cctggtcagg tcgtgggctg   27780
gtggctccca ctagcccctc acagacacgc ctgctgggca cctgggtgtg tgtccttggg   27840
ccccgcctac agcctgccct cttttcctccc tctggccact gcccggctcc agttcttcac   27900
ctgcctggtc atcctgtttg cctgtgaggt ggccgccggc atctgggct ttgtcaacaa    27960 ggaccaggtg agcctgggtg tgcagggaca gggtggggtg ggtgacgggg gcaccctcct   28020
ctcctgtcgc gggtggggt tggctgact catggcttgt gggagctctt tgggctcttc    28080
ctgggtccca cttgccagga ggatctccag gggctttatg gaggaggcag cattgggct    28140 gagcaccagg ccagcctccc gtgtcccagc actcccgggg cagctgagag tgcagagtcc   28200
ttgtcctctg gggtctagcc tcgaagccac cctgcccagg gagagcctgg gaaaagtgcg   28260
tccgcctggg gcgggcggg gtgggggcaa ggagggggag gttcccctg tgcatgtgac     28320 cgcacccctc ccccagatcg ccaaggatgt gaagcagttc tatgaccagg ccctacagca   28380
ggccgtggtg gatgatgacg ccaacaacgc caaggctgtg gtgaagacct tccacgagac   28440
ggtgcggccc cggggggcga gggcgggag cagggccccg gaacccggc ggggtgtgtc     28500 tcgtcctgga tgaatcctgc ctacgcccag acctcaggag caggaggtgc ccttgggacc   28560
tccaggaccc ctggtctcaa ctggtcctcg ggtgggaacc tagtgggcca gggtggccca   28620
```

-continued

```
gggtgcggaa agctctgagc agcgcagctg aggaggaaga aggctggccc ctggatgcat    28680
tctgcagtgg ggagcgctgc gtacccctgg ccacctcccc atgggttccc tagagccacc    28740 gtcccccctgg gcacatccag ggctgacctt gcaccccctgc tctctgcagc ttgactgctg   28800
tggctccagc acactgactg ctttgaccac ctcagtgctc aagaacaatt tgtgtccctc    28860
gggcagcaac atcatcagca acctcttcaa ggtgcgcgag gccggtgggg ccgcgcctga    28920 cccccccgcat gtcccgcccc tgggtggggt cctaggggtg ggcaggtcac acggcagccc   28980
cacagggagc gaccacactg ggtggcatgg cccctgtcag ggctgctctg ctgggagggt    29040
tggggtggga ccgcatctgg cccacgagga aggcaggcgc cctgtgctgc gcattccggg    29100
tgaagaaggt ggaggctctg ggggtggga actcacctgc accccagct ccacgtgtgc     29160 actcgtgggt gtggacgccc ctgacagcct gtagctggca gggcctgcag gccatatagt    29220
gccctgtgga agtttcctgc tgaggcctca gtggaagtcg tcatcagtga tgctttaggg    29280
gtctagtgac accaatgacc gtgatctcag tggaaaaggg cacagtgtgt cccaggcatt    29340
tcgcgtttat gttaaaacgg gtggaagata gcaagccggc agaggccggg ccgctgcacc    29400
cgcctgttcc gaggtgggta gggggtgggg ggctgttccc aggattcccc tctacgcttt    29460
ctgtggtgac cacggattac tgcgtgacaa cgggaagccg ggagccgagg cccggtccct    29520
gaccacgcgt gcctggccac ccctgcagga ggactgccac cagaagatcg atgacctctt    29580
ctccgggaag ctgtacctca tcggcattgc tgccatcgtg gtcgctgtga tcatggtgag    29640 cgggcgcgggg cggagggcct gctctctggg ctgcccccttc cgcggggcct tgtgctgact   29700 gcgccccccca ccaccctcct gcagatcttc gagatgatcc tgagcatggt gctgtgctgt    29760
ggcatccgga acagctccgt gtactgaggc cccgcagctc tggccacagg gacctctgca    29820
gtgcccccta agtgacccgg acacttccga gggggccatc accgcctgtg tatataacgt    29880
ttccggtatt actctgctac acgtagcctt tttacttttg gggttttgtt tttgttctga    29940
actttcctgt taccttttca gggctgacgt cacatgtagg tggcgtgtat gagtggagac    30000
gggcctgggt cttggggact ggagggcagg ggtccttctg ccctggggtc ccagggtgct    30060
ctgcctgctc agccaggcct ctcctgggag ccactcgccc agagactcag cttggccaac    30120 ttgggggggct gtgtccaccc agcccgcccg tcctgtgggc tgcacagctc accttgttcc    30180
ctcctgcccc ggttcgagag ccgagtcgt gggcactctc tgccttcatg cacctgtcct    30240
ttctaacacg tcgccttcaa ctgtaatcac aacatcctga ctccgtcatt taataaagaa    30300
ggaacatcag gcatgctacc aggcctgtgc agtccctcag tgccagtggt gtctgagacc    30360
taggggttgg ccggagggca ggggaatctg acatcggtgg ggcttggctc tgtggactct    30420
gtggggtcca gggtgagggt gggtgggtcg ggatccctgg tgttcaccaa aggagtcact    30480
ctgtaaaatt tggggagtta tttattctga gccaaatatg agcaccggtg gcctgtgaca    30540
cagccccagg tcctgagaac ttgtgcccaa ggcggtctgg ctacttaatt gtatacattt    30600
tagggacata ggacattgat cattacatct aagatgtacg ttggtttagt cggaaaggtg    30660
ggacgatttg aagggaggg actttcaggt cataggcgga ttaaaagatg ttctgattaa     30720
taattggttg atttttatcta aagacctgaa atcaatagaa tggactatct gggttaagag    30780
gagttgtgga gaccaagatt attatgcaga tgaagccgcc agattgtaaa tgtttcttat    30840
cagacttaaa aaggtaccag aatcttagtt aattctctcc tggatcagga aatagacctg    30900
gaaagggagg gggattctct atagaatgta gattttccca agagacagct ttgcagggcc    30960
atttcaaaat acatcagaga aatatatttt ggggtaaaat acttcggttt ctttcagggc    31020
```

```
ctgctgtcac gttggtatct tattactaca gagtctgttt tgtgagtctt aaggtctttt   31080
tatttttaga cagagttttg ctcttgtcac ccaggttgga gtgcaatggc gtgatctcag   31140
ctcactgcag cctcccctcc acctcccagg ttcaagcgat tctcctgcct cagcctcctg   31200
agtagctggg acaacaggca tgcaccaccc acccagcta attttgtatt tttagtagag    31260
acggtgtttc gccacggtgg ccaggctagt ctcgaactcc tgacctcacg tgacacacca   31320
ggttttggga ttacaggtgt gagccaccac accggactaa ggtctctgtt ttaatgtgaa   31380
tgctggtcag ctgtgcctat gaggcatgtt cggccaccca cagtcatcat ggcctcaacg   31440
agcttttcag gttacttta gaatgcattt ggccaagagg tgcccattca gttggttggg    31500
gttgcttaga attttacttt gggtttaaac cagggagcaa ctccaggtag caagggccct   31560
tttgggagc gttctctcta ttctcttttg ggagaggccc tgtgttgcct gcagccactt    31620
ccaccctgcc ccttgggcac acaaggggca cacagtgtaa gcaggtgggc aggaggggtc   31680
gggcagccag ggaatgcagt gagatgggct tggggtaggg gctgggtgcg ctgcaggact   31740
cctcttcctc ctgagggatg gtaaaggatg gacacactgc cccctcccga gcatttgagg   31800
gtctctgccc tgcccatctg ttacctgtaa atgttccttt gaggagctga tggctcaggc   31860
ctgagccaca tctcagaggg tctggagggg aagaaagacc tcatcctact agggagcccc   31920
cccagcccac cagcgagcgg tggttggggg cagacaggct gtggggctaa ggagcccctg   31980
cactcccccg tccttttccc tttgtctgag cacctccagc cagtgggctt ggtctagact   32040
ctcctatctt tccccacatc gtggggtggg gcttgctctg ggttaggcta cttttcccta   32100
gttgtgggga ggggggtgct ggcacatttc actgttccct ggaggaaatg agtgcctggg   32160
aattcatatc tagggctccc agcagcctct ttgcaggcca atttggaaac tgtccccagc   32220
cctgcatttt agggggttac agagtctctc agcaggccct cctcccctgc tgctcccaac   32280
ttgcaagcct gcactggttg ggagaacata atggtccaag gagccccctc tctactttcc   32340
gctgtgttcc ctgtggggag gaagagcag tttaagaaat aaggaatccc aaaggcgcac    32400
agcagaccgg gggccgagga gtgggtcctg cttccccctcc tttttctag gctgagccac    32460
agcaggtcct tgaatcctat ttcccagcgg atgccaggac agcaggccct gggggagttc   32520
tctctcgagc ctttcagagg gaccagaggt ctagcagcca aggagaactc agaatccttg   32580
agtgtgtggg gcaggaactc tcccagctga gaagggggcac aagtgccaa ccatctaggg    32640
cccagtggcc aaggaagacg cggcttgtcg cagggagaat ctgggccctg tcctcccctt   32700
tcagggcggg cagctgacct gcccctgct gcggacaggc gaggccaggc tgctggctcg    32760
caagcatggc ggagcccaaa ccttccctgc tgccgcccgc ccagccacgg ctgacttgga   32820
agcttgagga gcgttcagca gcctccatcc tgcccgggag gaccggggac ctggaagggc   32880
ctggccctcg cttccctgca gcgccctagg gggacgtctc agtgcctccc ggagcccgga   32940
ccaatgcacc agagctgagg gcccaagggt gtgagggtgg ccgggcagtg gccccgagga   33000
cggcgcccca caagtttgcg gccagggccc agcaaacccc taggggtggg aaagcgtcgg   33060
cccagctagc gggtccagca gggctgcccc cttcaccgtg gccagcggt cacgaccca    33120
cgtcctcatc gcgggctggg actgcctctg cgtctggcct gagcgggacc gtgggatcct   33180
ggggagcccc gcctcggtgc actgacgagg cccagaagga gtgacggtta ccgcttccgg   33240
tcaggaccgg aagtgccggg aacggcattc gtcctccgtg cgagatgacg cacttcctgc   33300
ctgaggcggc cgctgttctc gcggcttccg gcaggtggcg ctgagaccac gggaagccag   33360
cctggctgtc ggttagccct cgagcattct gggaattgca ggcctggccc ctcctcttcc   33420
```

```
tgttcttggt caattccggt cttgtttccc caacaaatgc cgtcgtttcc ggggctgctt    33480
ccgagccgga cccaagggcc ggggcgtgga ggagtagagg ggcgagcgca tgcgcacagg    33540
actacacgtc ccgacaggcg tcgggagcgg cggcccagtt ccttgtggga gctgtagttc    33600
tgcaggcgcg gaagccgtgg tgctcggccg gcagagcact cggtttccca gagggctgag    33660
cgcgccgcac ggaggtgcgg cgccgaccaa gatggagact gccgagcagc cttgagccgg    33720
taggtttgtg gtgagggagg acgggccgcg cgggccggcc gagcctccgg gaggtcaccg    33780
agcgcagctt taatacctga gctcgaaggc cccgctgtgc tcgccgaccc ccgtacctcg    33840
cggccgggcc cttgggaccc acagcatcct tgtgaggccc ggaggcctgt ccagcccgac    33900
tggacagtgc cgaggggcac cgagagccag cttggcaccg agagttcgtt tgttctctgg    33960
cggggaggtc ttgctggcac atatagtgga gaaaggccgg gctctgcgtt catgtggaga    34020
aagagacggc ttccttcagc ctacggacat gaaggagtca actctacctt ccactcgttg    34080 ccggcttttcg ccgagaaccc cgagaaacgg actaccggag tccctatctt gcagcccgat    34140
ccccgctacc cgtcggagtg ccccgctgac caggctgctt ctggccgcgg cggcgttccg    34200
ctgcagagga cgggagtgcg aatctgggaa gcagggttct ggttgaactc cagcttcgtc    34260
tgcaacatac tgtgtgactt gggcaaatta tttcccccgc cccgttcctg ccagctttaa    34320
aacggtcatc agtgggggt gctgcgtatc ccctttcact ggggtggctt cttcactgag    34380
gagagtcgcg cctcagagga actgaggtcc tgcctgtgtt cgacctggtg gggggcacta    34440
agagcccctg atagtacccc tgaccccatc cttattgggt gcacaagaca caggtcactc    34500
tgggcgggca aggagttttg gtagcaggag aggagtcggt ggatggatgg ctgaggacag    34560
tgcagaaggg tgtggctggg ccgtcttttt ttgcctggaa attcaagttc tgaggcaccc    34620
agtcactcca gcactaaatg ggtgcaggag gcagcacttg tctgcccagc tggaaaggca    34680
gggtatgtgc tgagtgttac aggtggaagg ccactggagg tcgctccagg agccgcgggg    34740
atttacctct gcctaacagg gctgctcaag gtgatggtcg acaccccact ttcctgagag    34800
cttgaccctc agatgccagg gccttggctg cagattcctt gggagctccc ggggatcttc    34860
cagcaaatag gagcaaatct tttccccgtg gatcaggaag gtgcacgctc tttgtggaat    34920
acgactgctc accccgcaca gcaagcagct tataagtggc cctcctgcct gatttcagcc    34980
ctgggttcaa gccctgggtg gctgcttact accaaaatcg ctcagtagct ccaagcctgc    35040
ctgcagaggg ttggcaccat taaatgaggt aacgagtcaa aagtccctac cctgggtcct    35100
agcctgtcag ggctccgaa aacccaggct caggtcggtc ctgcccggca cctgtttcac    35160
acatgtacac tccggtctga ggttggtcct ctcccccacc ccacccacct gcagttgagc    35220
agctgaacag aggccatgcc ggggcactcc gaggcctgag acgaccacgc ctgtgccgct    35280
gaggaccttc atcagggctc cgtccacttg gcccgcttgg ctgtccaatc acactccagt    35340
gtcaaccact ggcacccagc agccaagaga ggtgagagga gggcttggag ggggaggcgg    35400
gactccaccc tgtgtgggac agttctgtca gttgaccctc cacttgtcca ggggcagtgg    35460
atctgcaggg ggaactcatt ctcaatactg ttcctcctga gaaacaaatt ttctgggctg    35520
ttttggttta ggtgtggcgt ggccctgggg acgcatggct gaggcaggaa caggtgagcc    35580
gtcccccagc gtgagggcg aacacgggac ggagtatgac acgctgcctt ccgacacagt    35640
ctccctcagt gactcggact ctgacctcag cttgcccggt ggtgctgaag tggaagcact    35700
gtccccgatg gggctgcctg ggaggaggag ttcaggtcct gatgagccgc cctcacccccc    35760 gtcaggcctc ctcccagcca cggtgcagcc attccatctg agaggcatga gctccacctt    35820
```

```
ctcccagcgc agccgtgaca tctttgactg cctggagggg gcggccagac gggctccatc    35880
ctctgtggcc cacaccagca tgagtgacaa cggaggcttc aagcggcccc tagcgccctc    35940
aggccggtct ccagtggaag gcctgggcag ggcccatcgg agccctgcct caccaagggt    36000
gcctccggtc cccgactacg tggcacaccc cgagcgctgg accaagtaca gcctggaaga    36060
tgtgaccgag gtcagcgagc agagcaatca ggccaccgcc ctggccttcc tgggctccca    36120
gagcctggct gccccactg actgcgtgtc ctccttcaac caggatccct ccagctgtgg    36180
ggaggggagg gtcatcttca ccaaaccagt ccgagggtc gaagccagac acgagaggaa    36240
gagggtcctg gggaaggtgg gagagccagg caggggcggc cttgggaatc ctgccacaga    36300
caggggcgag ggccctgtgg agctggccca tctggccggg cccgggagcc cagaggctga    36360
ggagtggggc agccaccatg gaggcctgca ggaggtggag gcactgtcag ggtctgtcca    36420
cagtgggtct gtgccaggtc tcccgccggt ggaaactgtt ggcttccatg gcagcaggaa    36480
gcggagtcga gaccacttcc ggaacaagag cagcagcccc gaggacccag gtgctgaggt    36540
ctgagaggga gatggcccag cctgacccca ctggccactg ccatcctgct gccttcccag    36600
tggggctggt caggggggcag cctggccact gcctagctgg aatggaggga agcctgcagg    36660
tggcaccggt ggccctggct gcagttctgg gcagcatcct cccaagcaga gaccttgctg    36720
aagctcctgg ggtgtgggt gtgggctgga agcactggct ccctggtagg gacaataaag    36780
gttttgggtc tttctgagac tttgtgtcta tctgggccct gcttacccaa agggctcagt    36840
tggcagcaag agctccccac acctgaccct cggtgccgga ccactcgagg gtggctgaca    36900
cctgcatccc tcaccagcac atcacccagg tgacagtgag aattggaaac cccaggcctc    36960
ctctagggct tgtggctcag tggcaggtgt ccagtgagtg ccctcaatgg gcctgagtgg    37020
gtacagaatc tgccctcccc caaccaaagc ccacatgatg ccatcagccc caggcctagt    37080
gcagaccaca gcttgggaag cgaaagggag atg                                 37113
```

<210> SEQ ID NO 12
<211> LENGTH: 15540
<212> TYPE: DNA
<213> ORGANISM: Homo sapiens

<400> SEQUENCE: 12

```
agccaagcat tccgactcag ctctgggagc agctgccttc tgggctggca ttctccgcca     60
ggggggttgt gccctcgtgg cccccccccgg gtgcctcctc acctggctga tttcatctcc    120
tgtccccctg cctcctcctc caggaagccc cagggcctg gccctccttg agagtggcat     180
ggaggaggaa gaagactcgc ccaggcccat gggagtcgga tggtggccgc acttgtgggg    240
ccctgacccc ataggcttct tcagcacgcc ctggcctggg tgatccctgc ctgagggctg    300
tgcacggctc atctgccaga ccagatttta ggggattctt gtactgtcct cctggagcag    360
caggggtaa agcctgaccc acccagactg tccagcaaca agggcctcct gctgtgggcc    420
agggaccctg gaactgacca attgtgtcct agggacgcag agtccccagg ctgctagagg    480
gctgtgggc cctgtttcat gcctgaagca ggaagaaacc ccaggagagg tctgaagggg    540
acccagcccc caccctgtct agcagggagg agcctctgca agaggccgag gggtgctgaa    600
gtggaggagg atagaggcag caggactcag ggtcactggt catttatggg gatcacacgg    660
ctgcagtgtg ccctgcatgg tgctaggcac cagggacagc agaggacaag cctgtgtcct    720
ctcccaccac cagagggctg ggcactgccc ctagggagag agggggcctt ggtgtgtgca    780
gagggggggcc tgggcacgt gcctggcctg gtcagatgat cagagtgggc tgggctgggc    840
```

-continued

```
ctggtctggg gcccagtctc aagggcagac cccacctggc tagagttgat tgtgtgcaca      900
ccggatgacc cggcgttgaa ggcctctcct ctctgtgagc ctcatcccca cctgccagac      960
tcccagcaca gcctgcttcc tgccccagct gctgagcgac agcgctgggc cggcttctgc     1020
gcgccccttc ccccagccca tcttggaaac cacagcagcg tccttcctcc caagtccctt     1080
cccagggctg acatcccaca gcagggatgt atcccacaaa ccccgcaggc cctggtgcct     1140
acagcttggc ctggtaacat caaatcctac cctctcctcc tggcagcaaa gatggggtgc     1200
ccccacccca gagttctcag cacccccaga cagaagcagt ccccagcga cctcagaact      1260 cttggggcgc tgccacaccc ttgcaggagg gggcagtgtt cctgggatgc tcaggtcctg     1320
gtatcacctc tggccagata cggaaggtga aactacaggg catccaattc accttgaact     1380
tcagataaac accagattat tttttttgtat gtcccgtgca atatttggga cacacttacc    1440
ctaaagaagt attctgtttt catctgagag gcagatttaa ccggcgtccc gtgtcttcct     1500
ggcagtcctg ccctggagtc acactccaca ggtgcagggc agggccaggc tccaagtaga    1560
tggcggccaa agcacccgcc ccatgctcct gactcccggg gctcttcagg gcattgcgaa     1620
aaccagcagc agagctgaca cctggtccct gctcggagc cagcaaggca ggaggctgct      1680
taggccttgc gtgtggggtg ggcgcactcc ctgctgcagt gctcttcgta catgtgacac     1740
tgttcccgct ctttcccagc tggctggagg cgtgatcctg ggtgtggccc tgtgctccg      1800 ccatgacccg cagaccacca acctcctgta tctggagctg ggagacaagc ccgcgcccaa    1860
caccttctat gtaggtgagt gcacatgtgg ccgcagacgc attcagggag gcttctagg      1920 aggaggcagg tcctagcctt ttggatgggg acatggaggg tgaaagacag tcgggcatgg    1980
cgtgtccggg cagggaggcg gccctggaaa gggctctggg cacaagggtt gagatggagg    2040
tgggcctgtg gcctgctggc ccttctggtc tgagccaggg caggggtgg cagctaggcc      2100 tgggcaggga ctgtgtggag accttgctta ttttaagtgt ggggttattt cggggaggc      2160 tccctgagaa gggtggggct ggatgcctgg gccacacaga gcagccgagg cagctggcgc    2220
tgtggagccc gggagggagg gagggatgga gctcaaggga tggaacccag tgaggggtgg    2280
agacggggca ggggagggt ggagaggggt ggagacgccc cagaggcggt gtgactcagc     2340
tgcccctgca ggcagctgca ccttgctgcc ttattaggct gcgtgtgggg gactgggctg    2400
ccctccctgc ccccaggagc aggagcagga gtgatggagg aggaggaggg gaggggcaag    2460
gccaggagga ggaggagggc catctcactg tgcagagagc agcacccttc ctcctggtgc    2520
ccctggcagg gctggtgctg gtgggctct gggagcattt gttgagatgc ttctggcctt     2580
gaaaggaggc ccctgggatg gctctgttgc cctcacaggc tgaggggtgg gtgaggtggg    2640
cagcctgtgt gtcccagtc tcagggctt ccctcagccg gcaggtgccc ccaggcctgg      2700
agctgcaggg ccaggccccc tgccagttac ggaggctgct tggcttggtt gctgaaccag    2760
ggccccagga ggccgaaata gccccacacc tgcgccgtcc cacctctttg tccagtcacc    2820
ccagggccag gtgagggccc tggccacaca gcgtgcccgt tccttcttcc ccatgccccg    2880
ctcatgggtc agagggccgg tgctggggtc cagatggtgt caacagggat ggtccctgtc    2940
ctccccagag acagaagcct gtggcccacg gagggtttct gggcccagcc gatcctaggg    3000
agggtcccat ggccctgccc ataggttcct ggcctctctc ggggccgtgg tgccctcaca    3060
ggtggtgtca ggaaggacgg gaaaggctgc ttgtcccagg ggctcatgtg gagaccaccc    3120
cctgcacgca gctggggcgc tcctgcctgt gtcctcagaa gcactcggct tagctttgcc    3180
catgtgcctg ggctgtgggt ggcagagccc ggccagcatc ctccgatctc caagggtgca    3240
```

```
tctctactgg aggcccctcc tgggcctctt gctccccgct tcccagatca ttaggatatt    3300
tggggtccag aagggcctcc cagccatcct gggccttgtc ctccggggcc accagtccag    3360
ccagtgacaa ccacagcatc cccggcctgg aacgaggctg cccccagcac gttcctcgta    3420
ctcctgtcca gggacaggag gggctgcccc tgccaccgag tccccttctc caggacctgg    3480
ggcctgtggg tgtgaggcag gtgttcttgg aaggggtcac tctccaggca cccggcggcc    3540
aaggcttgtg gctggagcag ctcccgctgt ggggtcggcg tcgggccccg tgtggccgga    3600
gaggagctga agggtcactt agcttcgggc tggggcgagg acaggggaca ccccagagag    3660
gtatgccagg cctccttcct gcgcccactc tcggcagaa gcagaggtca caggctgtgc    3720
tgaggcccca tggtgctgcc cccatgatgc cagggtgagg ctggcgttgg aagcaggtgt    3780
ctgacctgca tggtgtcacc gtggccacat cagagctcca gccccagagc cgcccaccct    3840
cggtccttgg ctgtggtttc cctgggctgg aggagcctgc cgttgtgttg ccacacgac    3900 cacaggacct gccaccccg acgtgggctc tgcctgggcc cccactggac agggacccct    3960
tggagctcct ctggccacca agtcctcgcc cattccagaa tcggccttct ggagcctctt    4020
gctgtccctg atgcgggctg ggccttgcca agggcttttt ttcctgcgcc gggaacaggg    4080
tggatttgct gggctcactc ccctcagaga cgctgcgggt gcggtgggtt aggcccaagg    4140
gcgttaagag aggaggctgg ggtggggctg gggcctggca ggggtctgg cagccctggg    4200 cctcccacct cctgtcagga ccaaaaaagg caacgcgcct ctcctgacct gtaccccgga    4260
gtgaacccaa ccttgcaacc caggagtgtc agggcctgag gggagggaga cctggctcct    4320
gggtgccgtg cccgtaagga ggtggccacc tgcagggcat tcctggcaga ggcttcatct    4380
ggccaggtag gaggctgggt ggccgagccc caaatctggg tgtgttctct gcctggcggt    4440
gggtcctgcc ccaggcacct tctcctctgg gctggctggg cagggacaat gggcctggct    4500
gcgaggaggg ggcctgggct gccttctgca ttgcctcggt gacggagat ggcccctgcc    4560 tgctgaggga taggggagtg ggcaggcagt gagagacact gacagctgtc ccgcgggtac    4620
agggccctgt ctgggtggcc aggcccatgt ctcgggccca cagtgcgccc cccacccttg    4680 gacgcgcct tctccctccc caggtgcatg ctgcccagcc agggagcgtg ggggagttcg    4740
ggagggctgg cctacacgcc ctggtccagc tgtcccaggt ggggtgctgg gcttcagccc    4800
tcagcccagg gcctaggaat ccaacttgat cctccccaca cagcagccag gttcaaatgc    4860
aggtcccgta acggaagtgc tgctgtgcag cccagattgg ggggcaggag ccagcagggc    4920
ccccccaccc tcttctcgca ccacactggg gaggcagcat tggttccagt tccggttcct    4980
gggctgccct ctcaaccccg gcctacagtg gggcccaccc tgtgccttct gatgccactc    5040
ccaccccacg ccaagtccca gaggctttgg gagcgggtga aggcggtggg tggcgggtgg    5100
caggtgcagg cggtgggtgg tgggtgtggc aggtggcggg cccaccgca ggtgtcatcc    5160 ctgcgaagca cctgtcgcca gcactcagag cgctcatgag gtgcccagtc ccatgtggc    5220 ctccttagtc tccgtcctgt gtcatggaag aggtaactga ggcacagaaa actcaccagg    5280
ccaggctggg atgtgaggtc ccttgctgct catccctggc agtcagcaac cctacatctt    5340
cccagctggg cggcccgtgg tgggttcggc acccaggacc ctccggggtc ttgggctgtg    5400
gcgagtgtgt aggcacccac ctggtgtctc tctccccgca aggcatctac atcctcatcg    5460
ctgtgggcgc tgtcatgatg ttcgttggct tcctgggctg ctacggggcc atccaggaat    5520
cccagtgcct gctggggacg gtaaggcagg gaggcgggcc tgtgcctggg ccggggaggg    5580
gctgggggct gcgtctggcc ctgaggaggg ggcagagctg gtgctcaggg cggagcctag    5640
```

```
aattctgggg gaggtggctc ctgtgccctg cttttcccgt ttggttttta aattaaatcc    5700
caccgtgctt ggtctccatc gtggccagtt cctacgtgac cgcttttctt tgtcaaaaaa    5760
tagccacaaa tataacaggg agcaagcctc agctctgagg ccagcctcgg cgtcccgggc    5820
acaccgcccc ctgtgggaag cccaggcctg gctgtgccat ccagggcctg gccagtccag    5880
gaagagggag cctatgcccg tgtctccagt gggggaaact gaggcagatc ccatggctcc    5940
cccttccgtg gggagcagga acaagggggt gggaagatc agtcaggggt catgctgctg      6000
cacacgcctc cctgggggct gcagacatcc tggactcacc agcctgtgac cccaaaccac    6060 acgcccgcc ccatccaccc cgtcctgtgg agcctggtgc cgcgtgggga catcctgggc      6120
tttgacggct cctccctgcg ctgagttta gcctctgtgc cccagggctc cacacaagcc      6180
gctcactcct ggtcaggtcg tgggctggtg gctcccacta gcccctcaca gacacgcctg    6240
ctgggcacct gggtgtgtgt ccttgggccc cgcctacagc ctgccctctt tcctccctct    6300
ggccactgcc cggctccagt tcttcacctg cctggtcatc ctgtttgcct gtgaggtggc    6360
cgccggcatc tggggctttg tcaacaagga ccaggtgagc ctgggtgtgc agggacaggg    6420
tggggtgggt gacggggggca ccctcctctc ctgtcgcggg tggggggttgg gctgactcat   6480 ggcttgtggg agctctttgg gctcttcctg gtcccactt gccaggagga tctccagggg      6540
ctttatggag gaggcagcat tggggctgag caccaggcca gcctcccgtg tcccagcact    6600 cccgggcag ctgagagtgc agagtccttg tcctctgggg tctagcctcg aagccaccct     6660
gcccagggag agcctgggaa aagtgcgtcc gcctggggcg gggcggggtg ggggcaagga    6720
gggggaggtt ccccctgtgc atgtgaccgc acccctcccc cagatcgcca aggatgtgaa    6780
gcagttctat gaccaggccc tacagcaggc cgtggtggat gatgacgcca acaacgccaa    6840
ggctgtggtg aagaccttcc acgagacggt gcggccccgg ggggcgaggg cggggagcag    6900
ggccccggga accggcgggg gtgtgtctcg tcctggatga atcctgccta cgcccagacc    6960
tcaggagcag gaggtgccct tgggacctcc aggaccctg gtctcaactg gtcctcgggt     7020
gggaacctag tgggccaggg tggcccaggg tgcggaaagc tctgagcagc gcagctgagg    7080
aggaagaagg ctggccctg gatgcattct gcagtgggga gcgctgcgta cccctggcca    7140
cctccccatg ggttccctag agccaccgtc cccctgggca catccagggc tgaccttgca    7200
cccctgctct ctgcagcttg actgctgtgg ctccagcaca ctgactgctt tgaccacctc    7260
agtgctcaag aacaatttgt gtccctcggg cagcaacatc atcagcaacc tcttcaaggt    7320
gcgcgaggcc ggtggggccg cgcctgaccc cccgcatgtc ccgcccctgg gtggggtcct    7380
aggggtgggc aggtcacacg gcagccccac agggagcgac cacactgggt ggcatggccc    7440
ctgtcagggc tgctctgctg ggagggttgg ggtgggaccg catctggccc acgaggaagg    7500
caggcgccct gtgctgcgca ttccgggtga agaaggtgga ggctctgggg ggtgggaact    7560
cacctgcacc cccagctcca cgtgtgcact cgtgggtgtg gacgcccctg acagcctgta    7620
gctggcaggg cctgcaggcc atatagtgcc ctgtggaagt ttcctgctga ggcctcagtg    7680
gaagtcgtca tcagtgatgc tttaggggtc tagtgacacc aatgaccgtg atctcagtgg    7740
aaaagggcac agtgtgtccc aggcatttcg cgtttatgtt aaaacgggtg gaagatagca    7800
agccggcaga ggccgggccg ctgcaccgc ctgttccgag gtgggtaggg ggtgggggc      7860 tgttcccagg attcccctct acgctttctg tggtgaccac ggattactgc gtgacaacgg    7920
gaagccggga gccgaggccc ggtccctgac cacgcgtgcc tggccacccc tgcaggagga    7980
ctgccaccag aagatcgatg acctcttctc cgggaagctg tacctcatcg gcattgctgc    8040
```

```
catcgtggtc gctgtgatca tggtgagcgg gcggggggcgg agggcctgct ctctgggctg   8100
cccctttccgc ggggccttgt gctgactgcg cccccccacca ccctcctgca gatcttcgag   8160
atgatcctga gcatggtgct gtgctgtggc atccggaaca gctccgtgta ctgaggcccc   8220
gcagctctgg ccacagggac ctctgcagtg cccctaagt gacccggaca cttccgaggg   8280
ggccatcacc gcctgtgtat ataacgtttc cggtattact ctgctacacg tagcctttttt  8340
acttttgggg ttttgttttt gttctgaact ttcctgttac cttttcaggg ctgacgtcac   8400
atgtaggtgg cgtgtatgag tggagacggg cctgggtctt ggggactgga gggcagggt    8460
ccttctgccc tggggtccca gggtgctctg cctgctcagc caggcctctc ctgggagcca   8520
ctcgcccaga gactcagctt ggccaacttg gggggctgtg tccacccagc ccgcccgtcc   8580
tgtgggctgc acagctcacc ttgttccctc ctgccccggt tcgagagccg agtctgtggg   8640
cactctctgc cttcatgcac ctgtcctttc taacacgtcg ccttcaactg taatcacaac   8700
atcctgactc cgtcatttaa taaagaagga acatcaggca tgctaccagg cctgtgcagt   8760
ccctcagtgc cagtggtgtc tgagacctag ggttggccg gagggcaggg gaatctgaca   8820
tcggtggggc ttggctctgt ggactctgtg gggtccaggg tgagggtggg tgggtcggga   8880
tccctggtgt tcaccaaagg agtcactctg taaaatttgg ggagttattt attctgagcc   8940
aaatatgagc accggtggcc tgtgacacag ccccaggtcc tgagaacttg tgcccaaggc   9000
ggtctggcta cttaattgta tacattttag ggacatagga cattgatcat tacatctaag   9060
atgtacgttg gtttagtcgg aaaggtggga cgatttgaag gggagggact ttcaggtcat   9120
aggcggatta aaagatgttc tgattaataa ttggttgatt ttatctaaag acctgaaatc   9180
aatagaatgg actatctggg ttaagaggag ttgtggagac caagattatt atgcagatga   9240
agccgccaga ttgtaaatgt ttcttatcag acttaaaaag gtaccagaat cttagttaat   9300
tctctcctgg atcaggaaat agacctgaa agggaggggg attctctata gaatgtagat   9360
tttcccaaga gacagctttg cagggccatt tcaaaataca tcagagaaat atattttggg   9420
gtaaaatact tcggttcctt tcagggcctg ctgtcacgtt ggtatcttat tactacagag   9480
tctgttttgt gagtcttaag gtcttttttat ttttagacag agttttgctc ttgtcaccca   9540
ggttggagtg caatggcgtg atctcagctc actgcagcct cccctccacc tcccaggttc   9600
aagcgattct cctgcctcag cctcctgagt agctgggaca acaggcatgc accaccccac   9660
ccagctaatt ttgtattttt agtagagacg tgtttcgcc acggtggcca ggctagtctc   9720
gaactcctga cctcacgtga cacaccaggt tttgggatta caggtgtgag ccaccacacc   9780
ggactaaggt ctctgttttta atgtgaatgc tggtcagctg tgcctatgag gcatgttcgg   9840
ccacccacag tcatcatggc ctcaacgagc ttttcaggtt tactttagaa tgcatttggc   9900
caagaggtgc ccattcagtt ggttggggtt gcttagaatt ttactttggg tttaaaccag   9960
ggagcaactc caggtagcaa gggccctttt tgggagcgtt ctctctattc tcttttggga   10020
gaggccctgt gttgcctgca gccacttcca ccctgcccct tgggcacaca aggggcacac   10080
agtgtaagca ggtgggcagg aggggtcggg cagccaggga atgcagtgag atgggcttgg   10140
ggtagggggct gggtgcgctg caggactcct cttcctcctg agggatggta aaggatggac   10200
acactgcccc ctcccgagca tttgagggtc tctgccctgc ccatctgtta cctgtaaatg   10260
ttcctttgag gagctgatgg ctcaggcctg agccacatct cagagggtct ggaggggaag   10320
aaagacctca tcctactagg gagccccccc agcccaccag cgagcggtgg ttgggggcag   10380
acaggctgtg gggctaagga gcccctgcac tcccccgtcc tttttccctttt gtctgagcac   10440
```

```
ctccagccag tgggcttggt ctagactctc ctatctttcc ccacatcgtg gggtggggct   10500
tgctctgggt taggctactt ttccctagtt gtggggaggg gggtgctggc acatttcact   10560
gttccctgga ggaaatgagt gcctgggaat tcatatctag ggctcccagc agcctctttg   10620
caggccaatt tggaaactgt ccccagccct gcatttttagg gggttacaga gtctctcagc   10680
aggccctcct cccctgctgc tcccaacttg caagcctgca ctggttggga gaacataatg   10740
gtccaaggag cccctctct actttccgct gtgttccctg tggggaggga agagcagttt   10800
aagaaataag gaatcccaaa ggcgcacagc agaccggggg ccgaggagtg ggtcctgctt   10860
cccctccttt tttctaggct gagccacagc aggtccttga atcctatttc ccagcggatg   10920
ccaggacagc aggccctggg ggagttctct ctcgagcctt tcagagggac cagaggtcta   10980
gcagccaagg agaactcaga atccttgagt gtgtggggca ggaactctcc cagctgagaa   11040
ggggcacaag gtgccaacca tctagggccc agtggccaag gaagacgcgg cttgtcgcag   11100
ggagaatctg ggccctggtc ctccctttca gggcgggcag ctgacctgcc ccctgctgcg   11160
gacaggcgag gccaggctgc tggctcgcaa gcatggcgga gcccaaacct tccctgctgc   11220
cgcccgccca gccacggctg acttggaagc ttgaggagcg ttcagcagcc tccatcctgc   11280
ccgggaggac cggggacctg gaagggcctg gccctcgctt ccctgcagcg ccctagggg   11340 acgtctcagt gcctcccgga gcccggacca atgcaccaga gctgagggcc caagggtgtg   11400
agggtggccg ggcagtggcc ccgaggacgg cgccccacaa gtttgcggcc agggcccagc   11460 aaaccctag gggtgggaaa gcgtcggccc agctagcggg tccagcaggg ctgccccctt   11520
caccgtggcc cagcggtcac gacccacgt cctcatcgcg ggctgggact gcctctgcgt   11580
ctggcctgag cgggaccgtg ggatcctggg gagccccgcc tcggtgcact gacagagccc   11640
agaaggagtg acggttaccg cttccggtca ggaccggaag tgccgggaac ggcattcgtc   11700
ctccgtgcga gatgacgcac ttcctgcctg aggcggccgc tgttctcgcg gcttccggca   11760
ggtggcgctg agaccacggg aagccagcct ggctgtcggt tagccctcga gcattctggg   11820
aattgcaggc ctggccctc ctcttcctgt tcttggtcaa ttccggtctt gtttccccaa   11880
caaatgccgt cgtttccggg gctgcttccg agccggaccc aagggccggg gcgtggagga   11940
gtagaggggc gagcgcatgc gcacaggact acacgtcccg acaggcgtcg ggagcggcgg   12000
cccagttcct tgtgggagct gtagttctgc aggcgcggaa gccgtggtgc tcggccggca   12060
gagcactcgg tttcccagag ggctgagcgc ccgcacggaa ggtgcggcgc cgaccaagat   12120
ggagactgcc gagcagcctt gagccggtag gtttgtggtg agggaggacg ggccgcgcgg   12180
gccggccgag cctccgggag gtcaccgagc gcagctttaa tacctgagct cgaaggcccc   12240
gctgtgctcg ccgaccccg tacctcgcgg ccgggccctt ggacccaca gcatccttgt   12300 gaggcccgga ggcctgtcca gcccgactgg acagtgccga ggggcaccga gagccagctt   12360
ggcaccgaga gttcgtttgt tctctggcgg ggaggtcttg ctggcacata tagtggagaa   12420
aggccgggct ctgcgttcat gtggagaaag agacggcttc cttcagccta cggacatgaa   12480
ggagtcaact ctaccttcca ctcgttgccg gctttcgccg agaacccccga gaaacggact   12540 accggagtcc ctatcttgca gcccgatccc cgctacccgt cggagtgccc cgctgaccag   12600
gctgcttctg gccgcggcgg cgttccgctg cagaggacgg gagtgcgaat ctgggaagca   12660
gggttctggt tgaactccag cttcgtctgc aacatactgt gtgacttggg caaattattt   12720
cccccgcccc gttcctgcca gctttaaaac ggtcatcagt gggggggtgct gcgtatcccc   12780 tttcactggg gtggcttctt cactgaggag agtcgcgcct cagaggaact gaggtcctgc   12840
```

```
ctgtgttcga cctggtgggg ggcactaaga gccctgata gtaccctga ccccatcctt    12900 attgggtgca caagacacag gtcactctgg gcgggcaagg agttttggta gcaggagagg    12960
agtcggtgga tggatggctg aggacagtgc agaagggtgt ggctgggccg tctttttttg    13020
cctggaaatt caagttctga ggcacccagt cactccagca ctaaatgggt gcaggaggca    13080
gcacttgtct gcccagctgg aaaggcaggg tatgtgctga gtgttacagg tggaaggcca    13140
ctggaggtcg ctccaggagc cgcggggatt tacctctgcc taacagggct gctcaaggtg    13200
atggtcgaca ccccactttc ctgagagctt gaccctcaga tgccagggcc ttggctgcag    13260
attccttggg agctcccggg gatcttccag caaataggag caaatctttt ccccgtggat    13320
caggaaggtg cacgctcttt gtggaatacg actgctcacc ccgcacagca agcagcttat    13380
aagtggccct cctgcctgat ttcagccctg ggttcaagcc ctgggtggct gcttactacc    13440
aaaatcgctc agtagctcca agcctgcctg cagagggttg gcaccattaa atgaggtaac    13500
gagtcaaaag tccctaccct gggtcctagc ctgtcagggg ctccgaaaac ccaggctcag    13560
gtcggtcctg cccggcacct gtttcacaca tgtacactcc ggtctgaggt tggtcctctc    13620
ccccacccca cccacctgca gttgagcagc tgaacagagg ccatgccggg gcactccgag    13680
gcctgagacg accacgcctg tgccgctgag gaccttcatc agggctccgt ccacttggcc    13740
cgcttggctg tccaatcaca ctccagtgtc aaccactggc acccagcagc caagagaggt    13800
gagaggaggg cttggagggg gaggcgggac tccaccctgt gtgggacagt tctgtcagtt    13860
gaccctccac ttgtccaggg gcagtggatc tgcaggggga actcattctc aatactgttc    13920
ctcctgagaa acaaattttc tgggctgttt tggtttaggt gtggcgtggc cctggggacg    13980
catggctgag gcaggaacag gtgagccgtc cccagcgtg gagggcgaac acggacgga    14040 gtatgacacg ctgccttccg acacagtctc cctcagtgac tcggactctg acctcagctt    14100
gcccggtggt gctgaagtgg aagcactgtc cccgatgggg ctgcctgggg aggaggattc    14160
aggtcctgat gagccgccct cacccccgtc aggcctcctc ccagccacgg tgcagccatt    14220
ccatctgaga ggcatgagct ccaccttctc ccagcgcagc cgtgacatct ttgactgcct    14280 ggaggggcg ccagacggg ctccatcctc tgtggcccac accagcatga gtgacaacgg    14340
aggcttcaag cggcccctag cgccctcagg ccggtctcca gtggaaggcc tgggcagggc    14400
ccatcggagc cctgcctcac caagggtgcc tccggtcccc gactacgtgg cacaccccga    14460
gcgctggacc aagtacagcc tggaagatgt gaccgaggtc agcgagcaga gcaatcaggc    14520
caccgccctg gccttcctgg gctcccgag cctggctgcc cccactgact gcgtgtcctc    14580
cttcaaccag gatccctcca gctgtgggga ggggagggtc atcttcacca aaccagtccg    14640
aggggtcgaa gccagacacg agaggaagag ggtcctgggg aagtgggag agccaggcag    14700 gggcggcctt gggaatcctg ccacagacag gggcgaggc cctgtggagc tggcccatct    14760
ggccgggccc gggagcccag aggctgagga gtggggcagc caccatggag gcctgcagga    14820
ggtggaggca ctgtcagggt ctgtccacag tgggtctgtg ccaggtctcc cgccggtgga    14880
aactgttggc ttccatggca gcaggaagcg gagtcgagac cacttccgga acaagagcag    14940
cagccccgag gacccaggtg ctgaggtctg agagggagat ggcccagcct gaccccactg    15000
gccactgcca tcctgctgcc ttcccagtgg ggctggtcag ggggcagcct ggccactgcc    15060
tagctggaat gggaggaagc ctgcaggtgg caccggtggc cctggctgca gttctgggca    15120
gcatcctccc aagcagagac cttgctgaag ctcctgggt gtggggtgtg ggctggaagc    15180
actggctccc tggtagggac aataaaggtt ttgggtcttt ctgagacttt gtgtctatct    15240
```

```
gggccctgct tacccaaagg gctcagttgg cagcaagagc tccccacacc tgaccctcgg    15300
tgccggacca ctcgagggtg gctgacacct gcatccctca ccagcacatc acccaggtga    15360
cagtgagaat tggaaacccc aggcctcctc tagggcttgt ggctcagtgg caggtgtcca    15420
gtgagtgccc tcaatgggcc tgagtgggta cagaatctgc cctcccccaa ccaaagccca    15480
catgatgcca tcagccccag gcctagtgca gaccacagct tgggaagcga aagggagatg    15540

<210> SEQ ID NO 13
<211> LENGTH: 25760
<212> TYPE: DNA
<213> ORGANISM: Homo sapiens

<400> SEQUENCE: 13
gatcacgata gccaagaaat agactcacac atgaggacag ctagtttgac aaaggtgcaa      60
agtcagttta atagagaaat tgtatctttt caaccaatga tgctggaaca attggatatc     120
cacctgcaaa aagacaaaat aactttgacc aattcctcaa gctgtattca aattcattaa     180
tgtaaaatga attagtaacc taatataaat gtaaaactgt gaaactgtta gatgaaaaca     240
tggtggaaaa tctttgtgac cttagattag tcacagaaag gatatgacgg caaaggcaca     300
attcataaaa gaaaggtggc taaatggaat gtcatcaaaa tttaaaaatt ccactctttt     360
gaaaggcagt cataagagaa taaagaaagc aagccatcag ctgataggaa atattcacaa     420
atcatattac gatgaaggac ttatatccag aatattcatt gcatattctc tgtgtatttt     480
caaaaatgaa tagtaagaaa acaacccctat aaaaatgagc aaaaaagata tacagatatc     540
tcctacacac ttgaccaaag aagatatatg gataataaat aaggtcatga aaacatgctc     600
aacatcatta atcattagga aaatgaaaat taaaaatcgt aatgagatat cgctacacac     660
ctattagaat ggttaaattt tcttgcttta aaactgatca taccaacttt tggcaaaggt     720
aggagaaact gtaattctca tgcactgtga gtgggaagat taatggtaca accccttttaa     780 aaaatgattt ggtagattct taaaaggtga acacacacc ggccggccat atgatccatc     840
cattccactc ctaggtattt attcaagaaa aatgaaagca tttgtctcca caaagacttg     900
ttcatgaatg tttatagcat tggatcatag atagcccaaa ccagaaacaa tccaagtgac     960
gcctaacaag tgaaggtata agcaaatata cccattcatg ttatttatca ataaaaataa    1020
atgaacgatt gatacctgca acaatatcaa tgaatctcaa aataagtata tggcatgaga    1080
taagccagac aaaagaatac atcctgtatg tgtccattga cataacaccg tagaatgcaa    1140
agaatacctg atagaaggcg gatcagtggt tacctaaggc tggggaggag gggtgggagg    1200
aagggattac acagttgtaa tttaattacg aatttaaaac ttacaagaaa ttgttgacgg    1260
tgatgatggt ctcactgttg tacacatatg tcaaaattca taaaactctg cattttggcc    1320
cagtgtggta gctcacgcct gtaatcccag cactttggga ggctgaggca ggtggatcac    1380
ctgaggtcag gggttccaga cctgcctggc caacgtggtg aaaccctcatc tctattaaaa    1440 atacaaaaaa cttagccggg cgtggtggca cgcacctata gtcccagcta ctcaggaggc    1500
tgaggcagga taattgcttg aaccctagat gcagaggttg cattgagccg agattgcacc    1560
actgcactct agcctgggca acagagagag acctatctaa aaaaaaaaa aaaaaaaaa    1620 aaaaaaaaa acaaaaaaaa acctctatat tttaaatatg tgtagtttat tgtatgtcag    1680
ttagccccca ataaacctat aacttcccag gggaaatggc tgagattgat gccaccttca    1740
aagagttaaa gaaggcctag gtagtaaccc ccaccatctc tctcgtgatt tcccctctct    1800
ggcctctctg cagactggct gaatcagaat agatgattgc agacctcaaa ctcaaccaag    1860
```

```
tagcaacacc aaatgggctg ccaggccaga tgtggtatct tcgtttaatc ttagattaaa    1920
ttagattcat ttaatctaag attaaattaa cactgcccct ggtacccggt atcagtagct    1980
acggattctg tgaatgaatt ctcttccatc tcatcaggag agagtgtgag aagcaatttg    2040
cattcgcaca ggagggacaa cagtacacag tcacagtttt gccccaggga tatgttaatt    2100
cttctgctct ttgtcacagt atagtccaaa gggaaaaggc cctctggaca ttccacagat    2160
tatcacgtta gttcactata ctgatggcag tctgttaact ggatctgacg agcaagcagg    2220
ggaaagtact ctggacgccc aagtaaggc acacgagcca ggctgggaga taaattccac     2280
gaagctttag aggcctgcta catcatgatc ttattaccat gaagttattg ccataaaatc    2340
tggcaaatcc catggtacaa gaggtatttg caatggagaa agacaccaca cacacagagc    2400
ccctggagaa cttcaaagaa gagtcatggc ccagactcct tgggctctgg aagaaggccg    2460
tgcagagaac gataccattc agaaagaggt tcctgctctc ctgtgggaac tctagagaa     2520 agagtttctg gtcatggacg ttaagtgacc atgtggtcag agatgcccat cttgagctag    2580
gatctgttaa acccaccaaa tcagaaggtc aggcaagccc agcagcatcc agtatacatg    2640
ggaaaagaca cctcctggga ctgcgaacaa gcagagggca aaagaaagcg acataatccg    2700
gggatcggaa cccccacgtc atctaccagt gttgcactga cacctcttct tcagtccaca    2760
cctgtggcct cctgcagagg tccctctgac cagccgatgg agaaggaagg ggcctgagct    2820
tcactcattg gcaggttagc tagaaacgtt agtgagcccc caaaggactg ctcctgcact    2880
gcagcccact caggtggtgg tgatggtggc gatggggtaa ccctcccagg gggccgagct    2940
ttgagtgcag gacctggtcg tgcacttgta gggagagaag cgaaccaaat cagtggttct    3000
atttctagca gttttaggct ctacaggggcc attcccagag cgggacgctt ccaccggaag   3060
acgctattaa gacagcttcc acctggtcac ttcgggctcc tggtatcaac aatctggcag    3120
agagaatgaa gttcccatac tggcagggt aactggctgg gagcatcatg agaaggtatg     3180
aatacagtca tcaatggggg cgggcaggtg acccaccagg ggcatctctt ggtgctgcca    3240
tgcacagatc ttcccgcaag tagcaagcgc cacagtgtga gcatgataag gccatggtga    3300
ccacaggctg ctcaaggtcc cggctatctg acacggatgg aggaggaagg ggcggtggct    3360
atcagtcagg gccccaggca atgaaaatgg caatggcaat ggcaggagta ggcactggcg    3420
ttcatcccac tcagcctgtt agtgtcaatt tccctggtg ttgggaccaa tttgatcctg      3480
gagaagctct cctcagggga gcaaacctcc tacacaggtg ggctgtgcgg ggggtggggg    3540
tggagtaagg cgtgttgggt catgggtgct actggtgtcc tccccaactc cttttatctg    3600
gaccgtgtgc ctatccccca gctgttaagt gttgacaact aatggctcaa tgaagagctg    3660
tttagctaaa gggaagcccc acatccggga cgtgtgtgcc ctgggggaca cacagcaaat    3720
gactgacaag gaggaacaga aggcagcctc ttgcttccag tcctgggaga ccatgctgaa    3780
gccctgcctc ctggcttatc tgtatctcct gcacaagaat tccagcccag gctctgtttc    3840
tagggagtgt gccctgagat ccagcgctt gagcttcgag agcacgaggg ggtaggttct     3900 ggtgacagg gaccccggtg tgacgacaac tgcaaggttc accttggacc ctggcactat     3960
cctcccacca ggctggaaaa ggagaccagg acatggcccc agcacagccc caggtgggc     4020 aaaccggcag gctgggctgg ctaagctctt ggtgttcttt gtgtgggggt aggtggggct    4080
ggtgagggcg ggactggctg caggtccttc agcgggtccc tgctggacct ccgtggcggg    4140
gacagggatg aaattaaaac agacccgact ccattcaatc tcagcgatcc atgactcagt    4200
gatgcccgga gctgcctccc tttctcctcc ctgggctccc accccgccgc gccccacccc    4260
```

```
attatgatcc cccccaaaat gcagagagcc cactagaggg aggaggctga gggctccagg    4320
ctgccctggt cagacaacac atcatgttcc ttcacctgca gatagaccct gagcccatca    4380
gtgaaacaag gggccccag gagaatcaga atcctgaccc catcccaccc tccacaccag    4440
ctcaacggac tcccaggctg ccagaaaggc ctcatacgtc aaagtcagcc tcccagtcgg    4500
cctccgtttc caggtgtggg cctggagtgc cgtggcccag gtggtatcag aagctcgcag    4560
ggataggcct aagaggtgac cccaggggag ggccaggcca aggagctgca gagagggctg    4620
gggaagctcc agatccccca cctccttcaa aacacacctg aaacaccagc cagcaccagc    4680
accaccaaga tgagaaaggg ccctggaccg tctccaccag tgtcatgcag cagctgggct    4740
ggtcccctcc cttgggtccc catctgcccc acttgtacag gagctaacga cgcctgctgc    4800
ccacccagga ggacctagca ggagcccagt gtgaaggtgt ttgcaaaact ctggggaaag    4860
tgaaggtcag aggtgactcc cagcttccac ttaggacata gagagctgga aagagcccgg    4920
ctcccatcct taaactgcag cagcaacaaa aggcaccaag caacctgaaa agtcaggact    4980
tttctcaaaa ctctctgaga gctgaggtca cagggcaacc aactaaccca aaacaaaggg    5040
aaggcaggcg cctgcaggag gagacgggat gcaggctgtc accgagacag acgaggccag    5100
acaccaggaa gaagaacaca gccaaaatgt ttaatgagtt ggcaagggtc ggtgtggggt    5160
aatgggagag cacagaagcc ccaggggctg cggagtgaag ggaaatccac atccactgga    5220
aggtccccgt ggatttcacg ggatgctctc tttgtggtgt aggcccagca gaggggaaca    5280
gcagccactg tcccaaaggt acaaaaccta cataggttat tctcctcaat ggaacaaaac    5340
ccttagattg ctggaggaaa ggcaaaaaag gcaaaaaaca ctgtcacact tagggcacga    5400
gtagaaacca tcgaaactgg gggaatccta aaagccctgt gccctgggga gggataagct    5460
acatggtggg cccagagcta cagctgagcg tagggcagga gtcccaagaa tgcttcaccc    5520
acaagaccca aaggacatag ggttaatcag aaaaaaccga acagccccc acctccagca    5580 cctgctgaca agcaccatgt aacaagtgac cctggagtgg gagaggccgc agagtgtggc    5640
ctgggagagt ctgcggagtg tggaaaccct ctccaaggta agcttatagc cgaaggctgg    5700
ttggacactg ggaaaagcct ctctatggta aacacaaagt agtgctggag ggatttgatg    5760
actgtggtgc tccagagata accatgacaa caccaaactg aaacccagct caactctgga    5820
cgagattagc cccaagcccc gcagtaaagg aacagcaaaa agaagggtat gcccatttcc    5880
aaaagcacaa aacgaatttc ttcagtctct actgtcctct gcacgatgtc tggatttcaa    5940
aaaattgatg aggcctatta aaaaaataaa taaataggcc agggtctgtg gctcacgcct    6000
gtaatcccag cactttggga ggccgaggca ggtggatcac gagttcaaga gatcgagacc    6060
atcctggcca atatggtgaa accccatctc tactaaaaat acaaaaatta gccgggtgtg    6120
gtggcacacg cctgtagtcc cagctacttg ggaggctgag gcaggagaat cgcttgaacc    6180
cgggagacag aggttgcagt gagccgagat cgcgccactg cgctccagcc tgggcaacaa    6240
gtgagactcc gtctcgaaaa ataaataaat aaataaataa taaataatag atgaatagat    6300
aacgtgctat caagacaaag caagcaaaat aatcagactg aaaggctggt ctcagtggct    6360
cacacctgga atcccagcac tttgggagac tgaggtggga ggatcgcttg agcccaagag    6420
tttgagacca gcctgggcaa cacagagaga cctacctcta caaaaaataa aaataaaaaa    6480
atcaactgtg catggtggtg cccacctgtg gttccagcta ctcgggaggc tgaagcagga    6540
gaatcacttg agcccaggag gtcaagcctg cagtgagtta agattgtact tctctactcc    6600
ggcccggggc agcagagtga ggccttgtct caaaataata atgataaaaa aagaaacaga    6660
```

```
ctcagatatg acacagccgt cggaactgtc agacaggaca ttttaaatac aataaatatg   6720
ctaaagactc taaggaccct aatggagaag ggggaaaata tgcaagctca gataggtcac   6780
ttcagcaaag agatggaaac tagaagaaga aatcaaatgg aaaagctaaa ataaaaaaca   6840
gtaacagcca tgagaagaag cctctggtgg gctcatgaat gtactagaca cagcaggaca   6900
gggtccgtga acttgaacac agttcagtaa aaaatcccta aaatgcagag gaaaaaatat   6960
tgaaaagggg gaaaaagatg cccaaatctt tccaagaagt gtgggacata ttaagtgatc   7020
taacatatgt gtgaatggaa atctcagaaa gaaagatag aaaacacagt gaaaaagaca   7080
gagttgaaga aataatgggt aagaatttta taaaatcatt gacaaacaat aagccacatg   7140
gccaagttca gagaatacca agcaagataa gtaccacatt ttttttttt ttttgagaca   7200 tagtttcgct cttgtcgccc aggctggagt gcaatggtgt gatctcggct cactgcaacc   7260
tctgcctcct gggtccaagt gattctcctg cctcagcctc ccaagtagct gggattacag   7320
gtgcctgcta ccaggcccgg agtagagaca gagtttcacc atgttggcca ggctggtctg   7380 gaaccoctga cctcaggtga tccacccacc tcagcctccc aaaggctggg attacaggtg   7440
tgagccactg tgcccggccg gtaagtacca tttttaaaa actgaaggca tatcacattt   7500
aaactgctga aaacccaaga caaaagcgaa aatcttgaaa gcaaccagag aatacaggta   7560
cattccatag agacacaaga aaaacagaaa tatggtagca gacttctaaa cttctcgtca   7620
gaaacaaagt cagccaggga tgaaagaaaa acaacaacaa aaaactgtt gattcagaat   7680 tctatatccg gtacaaatat ctttcagaaa aaaggagaa ataaagtctt tctcagacaa   7740
acaaaaactg tagaatttgt tactgaaaga ccttcactat aagaaatgtt aaaggaagtt   7800
cttcaggcaa aaacatgata ccagacagag acttggatct acacaagaa gcaaagtgca   7860 ctagaaatgg aataaatgaa agtacaaata gaatttcttt ctttctcatt tttaattgct   7920 ctaaagata actgactaaa gaaaaaattg tggtcacgta ttatatgtct atagtataat   7980
gtaaaataga atgtatgaca ataatagcac aaacagtggg aggaaggaat tgagaatatg   8040
cagttgtaaa tttattatat aacacacaga gcaaggtaat atcatttggt agacaatgat   8100
tatttaaaga tgtatattat aaaacctaag acaactatta atttaaaaaa taagatataa   8160
atgataagcc aatagtggaa actaaatgga atcataaaaa gtactcagtt aatccaaaag   8220
aaggcagaaa agggagtggg gggacaacag acggaataaa tagaaaagag ttagcaagat   8280
ggtaaattaa atccaagcat atggccagaa gcagtggctc gggcatgtaa tcccaacatt   8340
ttaggaggct aaggtgggag gattccttaa gcccaggagt tcagaggcta taatgagcta   8400
tgatcatacc accgcactcc agcctgggca acagaatgag atcccatctc taaaaaaga   8460 aaaacactcc aaatacataa ataaataatt atattaatct caacacacca atgaaaagag   8520
atgatcaatt tgaataaaca aaagacccaa ctatatgcta tctatatgaa acccactta   8580 aatataaaga cataaataag gttaaagtaa aaggatggaa aatatgtgac acagaagcat   8640
gcgtcaaaat aaagatgcag cagctacatt catctcagac aaagtaggct tcagaacaag   8700
gactattaca agggataagt gagacctcac ataacaataa aggagttgca ttttctgaga   8760
aaacaatcct cagtgtgtag gcacctacca acaaggctg aaaacacaga aagcaaaaaa   8820
tgataaaata aaatgtaaca ctcattcatg attttttaaaa aactgtcaac aaacaaggaa   8880
tgtaagagaa ctgaacctaa taaaaggcga agctgaaata caaaaaaaaa aaaaaaaaaa   8940
gctaacatac taaatggtga aaggctgagt acccctaaga ttgtaaagaa ggtatgatat   9000
cccctctcac acttcttttt ttttttttt gagagtctcg ctctgtcgcc caggctggag   9060
```

```
tgcagtggcg cgatctcggc tcactgcaag ctccgcctcc tgggttcacg ccattctcct   9120
gcctcagcct cccaagtagc tgggactaca ggcgcccacc accacgcctg gctaattttt   9180
tttgtatttt tttagtagag acggggtttc accatgttag ccaggatggt cttgatctcc   9240
tgacctcatg atctgcccgc ctcggccttc caaagtgccg ggattacagg cgtgagccac   9300
tgcacccggg cccctctcac acttctattc catattttac aggaaggcct agccaagata   9360
ttaaggcaag aaaagaaag aaatggtata caaatttgaa aggcagaaat aaaactaagt    9420
caattcacaa tgacatgaat gttgcataga aaattcccca acaactaga gaaaactcct    9480 caaatgaaca ggagagttga gcaagatctc agtataaagt caatatacaa aagtgagttg   9540
tattaatatt tctgtttgct agcaacaaac aattagaatt ttacattttc aaaatagatc   9600
cacttataat aatgctcccc atatgaaaaa cttgggcaca gatgtaacaa aaaaagtatt   9660
ctgatctaaa cgaacagaaa aatatactat gttcatggat tagatgagtc aatattatta   9720
agatgtcagt tctccccacg ttgatctaga tattcataca tcccaataat tttcccagca   9780
gaatgttttg tagatgttga caagttgatt caaaaattca tatggaaatt aaaatgctct   9840
aggatagtca aaataattta ggaaaattat tttctggtca ctatctgatt tcactgatat   9900
gttactatat atttactatt tactacctga tttgactata aagctatagc aatcaagaca   9960
ctgaggtatt ggtgaaggcg tagactcagc tcagtgggat tgaatagaga gcccagaagt  10020
ggatccatat aaatatagtc aagtcaattt tggcaaagat gcaaagggaa atcagtagag  10080
aaagggcagc cttatcaaca aacggaactg gatctattgg atgtccatat gcaaaaaatg  10140
aacctggaca cacatatatc acaccttaca caaaaattaa ctctaaatga atcatagacc  10200
ttaacgtaaa atatcaaact ataaaacttc tagaagaaaa cagagaaaat ctttgtgcct  10260
ataggaaagc cagggtcttc agcctcggta ctgttgccat ttggggatgt agctcctgtg  10320
tgggggctgg tctgtgcacc agggaggttt agcagcggtg tgctccagtt gtgacaacta  10380
acaatgtccc cagacactgc ccaatgtcct ctgggggcaa acaggcctg aattgagaag   10440 agaaagttct cagctgtgac gtggaagcat aacccataac aggaaaaaaa aaagttaata  10500
cacgggactt tgttaaatgt aaaacttttc ttctgtaaat ggccatgtta agatattgaa  10560
aagacaaacc acaggctggg aaaaaatatt tgcaattaca ttatcagatg cagaatttgt  10620
attcagaata cacaaagaac tcgaaactca acaatcagaa aacaaacagc ccaattaaaa  10680
aaatcggcaa agggcttgac agacatgtca ccaaagaagg gaggcagatg gcaaagaagc  10740
cccaaaagat gtgccacagg gttcgtttca gggaaatgca aaccgcaaga gacctgtgtg  10800
ctcctgcgtg ctcccgtgtg ctcctgctta ctcctgtgtg ctcccgtgtg ctcctgtgta  10860
ctcctgctgc gaagggtaaa atgaagcaaa acagcgaaaa ctcacagcac acaacctagt  10920
gccagcgagg atgggagca agtgggcctc acgccctgct gcagagtgca ctatggcaca   10980
gcccctgtgt gtgcctgggg ggctgtggg tgacagggg acaaagaaga ggttggcaga    11040
gatggcagag cagcctcctg gtgctggact tcctcaccca gccaggatgg cctgggcctg  11100
caccagtgct gcctgagaca gcgagtctca acctgctcca ggggcgtgtg cgtttctgcg  11160
tgtgtgtgtg tgtgtgtgtc catgcatgtg tctctatgaa tatatgtgct gtatttgcat  11220
gtgtgtgtgt gtctatgtgt gcatatgtct gtgtctgtgt gtctttctgt gtgtgcggtc  11280
tgtgtctgtg ggtctacacg tgtatatgtg catgtgtctg tgtgtgtcgc agtgtgttac  11340
tgtgtctgcg cgtgtgtgca tgcatatgtg caggagggag ggagggctca ggccttagca  11400
gagtccctgg ggctctggga gtggagggca gtgaggctga ggctggtgca aaggtggttt  11460
```

```
caggcgctca ggtgaagtgg agcagaaaca gaagttggaa tccagcccca gcgggcgggc    11520
ggcagcagca gtgccggccc tgcccagaac aggttcgacc tgagccggca ctgcccggct    11580
gccctggggc tagggaggct gagacagaga agggaagcca gagggtgggg gtgggggccc    11640
ggcactggca gagctgcctg ccctcaacga ccgcccctgc cggagacccc cgccccaccc    11700
gctgtggttc tgctggccca ggtttcgctg gcccactcc cagggtttgg catcactgga    11760
gcccagggtc ccccccgcac cctccccaca gccttggccc tgctgctgcc tgcctcctcc    11820
agggtacccc gaggcccacg tcaggagacc cgcctcaggc agcagtggcc cggtggctgc    11880
ttctgcctag cccgcagcac gtgccaccct gggcgcactg ccttcccgaa ggctctcctc    11940
cctccccggg gcgctccctc ccactctgga atgcctccct gcctgcacag caggagtgtt    12000
tggctgaggt ctgcagcccc gacacaggtc acctcccacg cctatggggg cttcagaaag    12060
tcccggaatc ggccgggcgc cctggctcat gcctgtaatc ccagcacttt gggaggccga    12120
ggcgggcgga tgatgaggtg aggagatcga gaccatcctg gctaacacag tgaaaccccg    12180
tctctactaa aaatacaaaa aattagccgg gcgcggtggc gggcgcctgt agtcccagct    12240
actcgggagg ctgaggcagg agaatggcgt gaacccggga gcggagctt gcagtgagcc    12300 gagatcgcgc cactgcactc cagcctggga gacagagtga gactccgtct caaaaaaaaa    12360
aaaaaaaaaa aaagaaagt cccagaatcc cagacatcta acaggatggg gtcccagaga    12420
ccctccaccc acccatctcc ctgacttcca cacaggcagg gatgaaggac tgagggagag    12480
tgggagaggg taactgtggc ggtcacgaag ggtcctcagg tccccgtcct tatcccaagc    12540
cccatccagg ccagaaccgc ggagtgggtg tgcagagcac tcaggcagcc tgtgaatccc    12600
cacagccact tccctaccct gagacctcag agaatgacct ggcctctgtc tttctgtttc    12660 attttatta tttttatctc cagcttgttt gtgaagttca ggggtaccag tgcaggatgt    12720
gcaggatcct tgtcacaagc atccttctca cgaccctgcc tcactccaaa aggggtatca    12780
ggtaggtgag cagaaacgcc ccttcctgaa tgcctgtcct tgtcccacca caaggatgag    12840
gatgcctgct cagagggcac agggagaagc caatggcata gggtgcacag cagcgagggc    12900
caagggacaa ggagtgggg gcccccacct gcccagcgtg acctgctgac cacagctcct    12960
cagcggcggg acaaagcctg cccatggggc cctcagtggc caccctggat gcaaacacgg    13020
ttaatggtca ggcccagcct gtcccctcct gcgcacaaac tcagggcaga gcagagagct    13080
tacatccacc aagacccaga caaaagaaag ccccaagaac acccttaaag gcagccaaac    13140
cctggagctg cctcgggccc atcgatggga gcacaagagg tgaatcctgc tacgggcacc    13200
gtggccgtct acgcgaccgc agcaaagagg aacatggacg actcacagac gcagagacgg    13260
ggggtccatg ctgtgtggtg atgttcacct gcagctcagg acaaacccct acctacggtg    13320
acagatgtca ggaggggtga agggtgaggg agggagggcc tgttagctgg agcgggtctc    13380
agggatgcct gctgctgctg ctggaaacat tctgcacagg ggttcgggtg gaggttctgg    13440
gagtgtcacc cgtgcacact tgtcagcatg ctctccaggt cctgcatttg aggtgcctgt    13500 acccccagtgg aaagatgacg gacagagctg ctcaaccact gccctggacc gcattctgca    13560
gggtgcctta gaaggcccag gaggaaaggg gactccaggc tgggcaccgg tggtccacag    13620
gcttccagag cagcccagct tggccgttgt gtcccagtca ctgggagcta acgaggacgc    13680
accctcatgg gggtatgtgc ccacccagtc ccctccgtag agagcctggg agcctctgtg    13740 ataggggcgtc ctggcccagg gctcccaagg ccaagtatga agtctcattc ccccagacaa    13800
ccttcacctc caggctgcat aacctctact gaccccctc aatcccacct cttcttttg    13860
```

```
tccatgaagg cagtcgggaa atgcagcctg tgcttcggag aggcgggcag ggctggggtc   13920 accccgccc caggcagtgg gataggagat gcgccagggt caggtcccctt gctgcaagcc    13980 tgcaacccgt gcctgtatgt gccagccggg cctgccaatc catccttcac cctgcaggac   14040
cctcccgtct acaggtccca gctctgtgtg ggcctggcca gccctgggc catggctgag    14100 acctgagtcc tcaaaggact gccccttctg agagcagaat cctgctgccc ccagaagacc   14160
aggtgttcaa cctgagccct gatcctaaaa cccatggtcc tctctctcct ccagaatccc   14220
tctgccagcc tccaagagcc gcctgctgct ctcctggtgc ttctcacacc cctgggggat   14280 ggcaggggg cggggagccc agcagaaatt ggagcagaga ggacatggag ggctgagggg    14340
tgagggggca gaccgaatgt atcctctctg cccatgcgtc ttcccccagg atgctacctg   14400
aggtctcggg agaggggcat ctgggaaggc ttcctggagg aagatgagtg cctctctctc   14460 atgaggagg ggctccaggg aggtcagtgt gaacttgtgt tggcacaaag gcagccctgg    14520 ccgaggggc gaaggcagtg tgaagtggga ctcacttccc ccaaagatgc agagggatgt    14580
cgggagacct ggcaggcggc cctgggcagt tcagttgacc ccaccttacc ctaccaggct   14640
gcaggaagcc cctgccccca cctggagccg ctacgggttt tcctagctca gcctaaagg    14700 ctcagcccga ctagatacag gccaactaga gaggtcatgt cagggctgag ggggtggctg   14760
ccaggggtgg ctgctgtggg gaagagcatc ccagcccgca ggccctgcta ccccaggcag   14820
agctgcccgt tgtgtcccgc acgaagagct ttccctgcct gggaatcccg ctctgccccc   14880
caccagccag tggctttgga agttcgtcca gcaaccctgg agtctcagtt tccatgcctg   14940
taatatgggc acagcactca ctccaggatg aacagaagcc gggccaggaa agcagtccct   15000
ggcctggcac cacagcaggg gctgtgaggg ggatggttcc acagttgctg gaggtcgaca   15060
gggaccgaag cacacatgag tgccagatgg gccccacgat gggattccgg cgagggtggt   15120
gcagggagcc acctatacag aggacaattg actgcagaag tgccaggctc atgccctcca   15180
cggatggaga ggccgtcacc tccggggat gccccagggc cgcataccccg tgcagtggcg   15240 ctggagtggc agtgggcgcc tgccccacac taatgcacac acacatcagt gcacacccac   15300
agccacgcca gagaaagcca caggccctga ggggctgccc catgccagcc tgccagctgc   15360
cacacccctc ccacaaagcc tggctctggc ccgggacaca gggagcccag acccatccag   15420 ctttccccctc aatgccccgg gtcctcccac aaattcatcc tgcctcaagc ctcagtctcc   15480
acttccgaca aatgggtctc aagctctctg ctctgtccac cctgcatggc ggtgtgggca   15540
gcacagagcc agcctggtgg gggctgggga ctctggaagg ggtgctcagg gaggggccgg   15600
gctctggggc ccagaaggcc ttggaaggta gtccaggcgg gtcccggaac aagtgttgca   15660
tgagcaccaa atggctcaga gctcccgaaa cctggcgtgc ctgtgagagc cgttgagacc   15720
ccttttcaag gccctgcctg acagcccaca aaagacattc aaatgagaga caaatatttg   15780 gggcccaag gttgagccca gcccagcctc tcaggcccag cccaagctgc tcccaggctc    15840
tcatttgggt attaattgca tttcgtttag agatttgcat gcttatcacg cgggtggtgg   15900
ccagccgtgg gggcctggcc agcctggaca gaatcccaag gctcgtaggc aaatgccagg   15960 aggaggggt gggcagagga cccaggagcc tcccgaatgg tatcaggaga gcaagcctgg    16020
gctaggctgc gggccatcag cgtgggccct gggccacgac ctggcatcca tgtgacctg    16080 agcacgacaa caggacaagc agagaaaaaa gtggatccca aaaacagggc tcccaggcca   16140
acttctccct aacaccagct cccagcaccc caccggggac tgcagcccct ccatggtcaa   16200
tcagggtagc cctggggtcc ctgtcacatg acgtatgccc accctccgac agccctgcag   16260
```

```
cctgtgggac ggcccgtgtg ctcgccgagg cgcttggaac cttggagggc aggctctcag    16320
aagattggct cagggaccct ctggtccacc ctctcggcat cccagggtgt cctggtccca    16380
ggagatgcct catcccaggc cacacggggc cctaggcctt tccgtcctca gccctgtcta    16440
ctctaccctc tacaagagag gtccagaagg ggcagtgctt gacccaagaa gaagaggctg    16500
taactatgga gaggttggga gggggaagtg gccctaaggg ctggagtttt agaaagccct    16560
cttgttcctg cccattatgg gttggatttt atgccctcca gactcacatg tggctgtttt    16620
tggagccagg gcctttaaag aggtaattaa gttaaagtga ggtcattggg gggaccctaa    16680
tcccatgtga ccgatatcct tagtaagagg aggtgaagac acagacacgc acagagggat    16740
ggccacgtga agacacaggg agaaggcagc gtctacaagc caaggagaga ggccttcgga    16800 ggtgggggc ctgcggaatg tgtgagagact aatttctgct gtgtaggccc cctagtgtgc     16860
ggggcttttt cacgcagcac aggccaaccc attgcagcct ctcctgctgt taggacccca    16920
agtccatcct cagggacatt aattaacata ggaacttttt atcctgatgg tgtcacctcc    16980
taggcagaac agggacccgg aggcaggcct agctgcgaac ccccagccct ccctgtcctt    17040
ctcgcaggac agcgggtctg gggctgaagg ctgtgacgct gcccctgcct ggatcacaac    17100
aggcaggacg gctgagcagg cacacatctg tctctccctc tgctgatctg tggccttgga    17160
caggggctac tctgggggag ctgacaggtg accccccccag gaggccctc cctgcctctg    17220 ggctgggaat ccacctctgt ggagccctg gaatggcct gtttcaaata cgtaagtggg     17280
agcaaggtct catcctcagc gggggacatc gctgggggca aggccagtgg gtgggtggga    17340
aggtttctgt ggcactgggg cctcctgttg attgattcac ccaattaatc acagccagca    17400
gctggggagg gggtaggaag gcggtgaagg gaaaaggagc ccacagccgg gaggccctgg    17460
gaggttggca gaggcctgca cctgcctgca gccagccctc cggcccagcc ctcttccctc    17520
ctttcggagg ggccagagca tggggtgcta agggctcagt cttttaacccc tccccagctc    17580 tcagggagcc cctcccatgc tccccaggcc tctgccccac ttgcacctcc ccgggcccca    17640
gggcacagga cgcttttcccc acccttgggg aggctgaggg tgtcaggagg cctgggctga    17700
gtgctggctt ccgtctcact ggcttgcaga caagaccctc catttcggtg gaaaaacagc    17760
aagaacagca ccccctcca ggcagaccca agggaggcat cggtgtgagg gcttcaagct     17820
ctgtactgtg ggtttaagcc ttgcacctct ggatacctgt gggcctcggg cagatcactg    17880
agcctccctg catctggaag tcggggtgag acccctcaga gggggctggg aggaggaagg    17940
gcccctcttg atgggcagcc cccacccctcc acctactgcc ctgccctccc agccttcagg    18000
gtcctcccca gcttctgtgg gctcccaggt ggacctgggc caccccctgag accccgaaga    18060 gctcaaggcc agctaatagc ccacaggctc aggacagcac tggacaggcc tctgggccca    18120
cctggcccca ctcccgattt ttatgggaac aaagactgaa ggtgtggccc caaggaacc     18180 accccctcccc cagtgccccg ctgctgggaa aagggtcagc agagtttggg tctcccccca    18240
caagccctct gggctgtgcg tgctacagct gaggacatgg cgttgagggg caggccgcct    18300 ccaacccgt ccaccttgcc ctgtctagct ctgtccaagg ctctctccgg ctggctaatc     18360
acctctgggc acagctgtgc tgctgaggtc tctgggatga ctgaaggtct ttgaaggcca    18420
ctttgggaga agcgaaggtg catggacacc agggaccctg ctcacagcga gtgtccctgc    18480
cccatccctt tctgcattga gtgggacaag cttgcttcca tttgggggat cgccatctga    18540
ctattccact tgtcttaggg tgggcagag attaggtgat gtggagggggc ttctctacat    18600 ggccccctg ccccagctct gagggtagc accagagtgg gtttcaccag cgtagggcac     18660
```

```
gtaggccccg ccatgaacag ggccccaacc ttggtttaat gctttgctac tgccatctta  18720
aagttctttt tttattttt attttgcttt atttttatt agagatgggg tctcccagtg    18780
ttgcccaggc tggtcttgaa ctcctggctc aagcaatcct ccggcctcag cctcccaaag  18840
cactgggatg acacgtgtga gccaccttgc ctggcctttg aatctgact acttttatct   18900
tctaacttgt tttgcaggtg caggccaacg gcatacagca gcactcacat aagcaaagga  18960
gagcgtgcac aaggcgccaa atgtatatcc accctcactc gtcccccac ttgagtagca   19020
catccacgat gcccacagac accaggccac acagaaaagg tgccagggac ccacagcagt  19080
gcaaggcagc gtgtcacacc tacgcatgag caagccgggc gctgatggcc accgagcagc  19140
cacgttttcc attcaaatcc gcacttgcta aggatgcagc aggaagccag tggtgttcta  19200
acaaacgtgc aggacccggg aacctgtcat gtcctttctt acttgtgcga cttctctgtg  19260
ttagccgagg tctcttgctg atggatctac ccacagtgcc ttttgtcttt gaacttgtcc  19320
cttccctcct tcctcgccca tcagcgagca ggaggtggag ggtgctggtg gaacaagcct  19380
gcgtcaagga gtgaaatcag ctgatttcat ttttgtgcag tttccactgt tctagtagca  19440
aatgaaatag agacgcctgt gccaggacaa aacacacact gtgtcattcc agtgattccg  19500
catagaagtt aaatgctctt atgcttgcat tttaaactgg catcacataa tataaagatg  19560
gataactaca ttcacgctag tcacttaaat tcctaatctt tcttactcag aatggcatta  19620
aatagtgagt ataaataag aagtataaaa tagtaagtca agaggttgac tatagaagaa   19680
agaaaaatgc tttatatttt agcaccttga acatgacatc acgatcacct tctccctgga  19740
atcagtttct aacttccagg tggggactag gcctggacca tgagctccta gcagagccct  19800
gctgccccca cagcagagcc caggacaggc tggcacctgg gccaggtgag gctctgtcca  19860
ggctcactga tctcaaatgc tgaactgcta aggatgtcat gtccccaaag gagccgccag  19920
gctcagcctc acttcctgga aggcgtgaac attgcaagaa tgtggaagtg aaagagtcca  19980
gggcttaaat ctcaattctc atcattttca agctgagtcc aagggagaga agacagtcat  20040
ggattcttag tttctgtttc tggttgagcc agcagggtcc cttcctcatc cctcttttct  20100
gcttatcact agagacagaa actaaaacca tgactttagg ctgctgagag cctaaaacaa  20160
aacgacagca agagaaggtg ggttggacca gcttgcctgt gacttcaggc acttcatctt  20220
tactgggcac tgggtgaatg acagtgtggg gagggggtctt cataacacgg caatcagcag 20280
cccactgtgc ccaggagact cgcctgtggt cctggttatc aaccacagcc ctttccagtc  20340
tcaaaaatgt ccccgctggg acagcaagtt acatcgtcgc tacaagtcct gtctcctggg  20400
agatgcagtc cagcagcact acatcctctg agcagcaggt gccaagtggg atgaactgga  20460
taaggactgc attcggggaa acgccgtgt gaaaggaaat acacaggaag gaggtggcaa   20520
cgggtgggaa gccactagac cacgacgcga ttctgcccca gtgaaggcga ggggatagcc  20580
tgggcctaga tcgctgtgag gtctatggaa gtttccacaa gcttgctggg tagttctcga  20640
ggcaaactcg gaagggagt cccttgtctc cctggaacgg atctttcttg gcatctctgt   20700
cacactcatt aggtgggcct ggtgtcaacc ccatttgcag gccaccccaa acttgatcaa  20760
aggtccgctt ctggcacccc atacctgtc ctacaggaaa tacagggaca ggctcccaat   20820
aacaacaccc agcacggtgc catcaacacc accacgcaca cggggctca acggaacaga    20880
catctccgct tcttcaatga agacactgga gggaaattgc ttacaaggcg cttaagagac  20940
ctattaagca aacttgatgt gtggacctgc ggcggatccc gattctataa ggccaactgc  21000
acaaaaccac gagaccccct gaggactgcg ccattggctg ggtccccgat gatatgaaag  21060
```

```
aacggtggtt catttgagcg ggtgatgttt ttgcggtttc ctttagaggc acacgtgaaa   21120
catgacgggt gaaaggattc aaagtctggg atttgcttca aagcaacgca gggatggcgt   21180
gggggatgga tggggcagga agggccttga aactggtgct ggaggcttcc cagggctgcc   21240
ctggagccca gtgcgtcctc caccggccag actgtacaac ggttggatcc tgtgtccact   21300
gctaggaccc aggctccacg agcacgggct tgtgtggcac acggatgcac cctaagtcct   21360
ggcacagaga ctgctcaaca aaggcctcgg tgcttttgtg tatgtttgaa attttccata   21420
ataaaatgaa aaatgggaaa atgggaaaac aaaaatggca gcactactta ccctctgcag   21480
agttttgtcc gcttcacgcc agtgggtggc agtcgtttcc tctgccctgg ccttccatcg   21540
tttccccccct accctcttca cccacccaac agcccctgt ggtcctggca gctgtgggcc   21600
tttccttgag gtcaaggtgt ggagtcctgg ggagggctca gggaggccac cgacccgggt   21660
gtggattctg ggagaagcct gtgggatgtc cctccctggg tgaccacggc aatgtgcccc   21720
ctcctgtccc ttggccaagg ccagttccct gagccctgca gccccaagcc acagctggtc   21780
cactgacccc agttgagcct ggtcctcatc agaccagctg accctttga ccccgctac    21840
agactcggct ttgaccttgg ctgctgagga gccccccacct ggactgaggc tgcagctggc  21900
gagagaggag ccctgagctc ctctgataag aagggacctg gccagcctga cgtttgagac   21960
ccaggcatcc cggtagcctg ggtgtcctgt tgccgtggtt attcaggagc cacccactct   22020
gggacaacac cagctgctcc cacctcgcag ggctcccacg gctctgtccc aaccactcct   22080
ttctgaagga aggggtgcct ctgcgcccta aagaaaccgg gggagcccca caaccccctcc  22140
cccaccagga cactaaaagg cagctttcgg tacagtgaga catcaaagcc tcctaggccc   22200
tgagtcaaag gtatagccgt gtaatatccc agtgccagct ctccggctgc ggggagcctg   22260
gcgcaaagct tccaagcctt ccttgttcct ttcaagagcc gctcttagaa ttcaggtgag   22320
cggagacctg cagggcctcc ccagtgcggg caaaacccaa agctagcgag agggcagcct   22380
ccaggcacct ctcactaact cctcccagag gccgttgagg tgggtctggt caaacccatt   22440
tgcaagttaa cccacttgcc ctgggctgcc cagctgccac gttagtggag atctgagcgt   22500
ggtggcctgc gcaggagccc atgccctcag ccccacagcc ggtgctctct ggtcagacca   22560
cctcagccta gccccacacc cagcacttac cccagccctc gggatgggtc agcagcctcc   22620
agcctgcagc ttccaagcca gcgagtagcc ctgtctggac aacccaccag cccaccacct   22680
cctggaggat gccccagcc tcacaaggtg tcccaatggc tccgctatca acggcctggc   22740
tgcactccag atctcaccca gacccaccct acggaggagg cagcagggtt tgaggagtag   22800
tgaccacgga agtctggccg tcacctggga agtgtaggtg ataggagcca ctggtaaaca   22860
gaactgattt atttataaag ttcacgctcc cttgaagagg tgtgccccac acaggcttct   22920
ccctagcaga gcagcagtgc ccacaaaccc accccagggt gggctgtcac gggggcctca   22980
cgccagggac cccgccccctc agggactgct cgtgtccaga tcttggccag catggaaaac   23040
tccagatagt gggggcaggg gtccaggtca tctttattac gccccaggtc aagggttctt   23100
tgtacaaaaa taggtctccg tttgccagca gtgtccctcc agcagctcaa gttaatgtgt   23160
agaaaatgga ttctctgtgc ccttagaaaa tcctctcccc tccggaaaaa tctccaagtg   23220
ttggtgcccc ccgccccact gcagtcgaga agctgtgggg aggggcggcg tcggaggaag   23280
ccgccagccc ttatggggcc agctccaagc ccgtttccac cgcggcattg gtcaggctgg   23340
gccggacgaa cgaggcggcg tcggcggtgc ggggggtggt gggtgggtcc ccggctcgct   23400
gggggcggag cgcgggccgg tccacctggc gggctccccg gcgatgagcg cgccggccgc   23460
```

```
tcgctcggct tccggggctg aggctgcggg gggaaggtgg ggaaccaaac gcgcgtcaac   23520
gcgggcgcgg gcccggggca gacccccgccc gggccggccc tgcccgcacc tcccccaagc   23580
gaactcggca gtttcgtttg ctcggttggt tttggagtct tgagtccgtg ggtgccgcga   23640
ctcggtctga gacacggcgg gggcggggcg ggcgctcgga gccgcggtga gtcagggctc   23700
cgcgcccgcc gactcatttc tgccgccccg gcccgggagc gcgatttgca atgcaaagtc   23760
accccgcctc cagcacccca atctgcccca ggatccgcca gcactagaga cctcaacggc   23820
ccgacggccg ctcccctccc ctcgtctacc cctccctcgt cggcggctga gccgcgaggg   23880
gaagttttgc aatcccggac aaacaaacgc cggtcttgca cgggcttgaa aaactttggg   23940
ggaaatgaag agtgagcgaa atcgaagcca tcgctcgggc ctggcgctcg gctccgcggg   24000
ctcctggggg cgcgacccgc cgggcctgcc caccccgtcc ctcaccccg gccccggcc     24060 ctccctcctc cctgcctccc ggctgttacc tcataggtcg agggcgctca gtagcccct    24120 aaccagctga agaagtcgag tagctcgcgc tccgcaggac tcagcgcgcc ttcgcagccg   24180
ctgtcgtccg acgagtaggc ggaacgcggg gagccgggct ccgagctgcc cccgcggccc   24240
ggggacgaag aagcgcggga gggcgaggcg gcgaccgggg tggtccctgg cggcccgcgg   24300
ggcgcagacg gccgcacggc ctgcggcctc agccctcccg ccagcgcgtt gcgcacggcg   24360
tcgtgctcgg ccagcaggcg ctgcagcgcg cggatgtact ccacggctga gcgcagcgtc   24420
tccaccttgc tcagcttctt gctggcgccg ccgtgcggca cgtgctgccg cagcgcctgg   24480
aagcccaagt tcaccagctt cacgcggttg cgctcgcgct cattgcgccg cgctacggcc   24540
gctgcgccgc ctccggtctc tgcggtggcc ggtcgccgcc gccggctgca gcgcaacagt   24600
tccggggacg cgggtctccg ccgggcagcg cagccgacag ggacgggggg cgcagggggc   24660
gcggacctgg gcagtgtgcc gccgtccatc gcgcctgcat ccacccgccc gctccaggtc   24720
ccggcgcgcc gcaggaaggt gcaggcagag gaaccggagg cgacggggaa aactgtggcg   24780
ccccaagggg gcttctggca cggcgccgcc aggcaactcc ccagggcacg cgtcctaggt   24840
cgtctggagc ccggggatag gaggcctagt ggtggcaggc cgtacgcgcc agggagcgtg   24900
ggacgctcgt gtcccgcgcg tgcggccgga ctctcccagg tctccgcagg cgcggcgcag   24960
gcggctggtt tttaaatgta tagataaccc tcctccgcgc cgccgccgtc gcctttctca   25020
cgccctcctt cctttcgcctc gcctcccgc cacgcttcgc cctccccctc gcgcgatcac   25080
attctgtaag gcccaaagcg tgcgcatgtc cccctagccc atcccccgga cgcagtccac   25140
agatccccag tgcgcccaac tggcgaaatc tgcgagttcc cggtgcgccc cctgctcccg   25200
gcaggtgctt agtgcgcccc caaagcaagg tacgcaggtc ctgggttgag ccttcccgta   25260
cccccaccct aaccccgcgc gcagcccgc cagtcccaag agccgccaga ccttcgcacg   25320
cgcagcgcgc gctgtgggag ggaaggcgcg gccctggcga caacacggct gttcgggagg   25380
cgcgcaagat cccggggc agcacgcgcc gcgcagccca cacccacgcc ccaccctcct    25440
ggggccgagg aggcggggc cagggtctca gccaatcgtg ggccaccgt ttggccaatc    25500 gcgcagggcg cggctccacg cccggcccca ttgaggaagc gcgtacgcgt ggcgcgtggc   25560
tcacggggag catcgctaac aaagctgggt tcctgctggg ccccgccctg ctcctcgccc   25620
ccgcgactgg gctgggcgcg ctgtcccta gcgcagctat gtcccgagcg cgccccacc    25680 tgtgcgttaa tctactggga atggggggtgg actgcgcctt acctggggcg gggtggggct   25740
taaggagtgg tcgagactga                                               25760
```

<210> SEQ ID NO 14

<211> LENGTH: 38360
<212> TYPE: DNA
<213> ORGANISM: Homo sapiens

<400> SEQUENCE: 14

```
tgtgcaaggg accttcagag gaggaaaggg aggaaacagg tcaacctctc acggcaggca    60
aggcaagaca cccctggtt tgaggggtc ttctgcaaat ttcagggagt tgaacctcat    120
acaaacctcc ggtagtaaga aaatattca gagttctcct ttcccttctt ctcgggggaa    180
gaaagaggct aagctccact ccgcttgtcc cttccctagg ggaaggggaa ggagaaggga    240
gaatagcagc ataagcgact ggcagaggca gggaaagacc ggcagaaagg aaagagaaac    300
tgggagagga agtcagagag agagagagac aaagagggag tcaaagagag agaaagagag    360
agacagagag tcagagagag agaaagagag agacagagac aaagagggag ttagagagag    420
aaaagagag acagagagta agagagagag agtcagagag agagaaagag aagtagtaaa    480
gagaaaacag tgtaccctat tccttaaaa gccagggtaa attaaaaccc tataattgat    540
cattgaagat cttctctgtg accctagaac actccaatac tgcctgtaaa gaagcaagac    600
gagtcacacc agtgactgca agaccctaga gctattaacc agttagtcca aactacccac    660
cctgttgtta cagtaataga tgtaaaagat gccttctggg cttgtccatt tgcagaggac    720
agccaggacc tatatgcctt tgagtgagaa gaccctcact ccggtggaaa atggtaatac    780
caatagacgg tcttacccca agggtttacg gagtctccaa atttatttgg tcaaatattc    840
aaataagtca tttaattagc aaaggtaaac agaaaattga gcttgaatgg attgaaggca    900
tcacattctt gcctctgctg gagactaaat aagagcttag aaaattttgg gattagttgt    960
atggataccg tcgtctatgg gtagactcat gccctaaaaa caaaactctt acacaaaaag   1020
ctcacacgag acagaccaaa cccctcatg tggcaattac cagaaatcca acaggtggga   1080
aggttaaaac atctattagt aactgcccct gtcctagctt tactctcctt aagcagccat   1140
tccaccttgt tggtggtgta aacaacggcg tagcccaaaa acactgaggc cactgacaac   1200
ccatagcctt cctaatcaaa aatccttaac ccagtaaccc gcggatggtc caaatgcatt   1260
caatctgtag cagcaacttc tttgctgaca gaagaaagta gaaaaataac tttgagaaga   1320
aacctcattg tgagcacacc tcaccaggtc agaactatcc taagtcaaaa aaaaaaaaa   1380
aaaaagaaaa gcaaaaaggt agcttactaa ctcaaaaaat ttaaaatatg aagcgattct   1440
gtcagaaaaa gatgatttaa cattaaccac tgatcattcc cttaacccag caggtttgct   1500
aacagggggat ctaactctta atgaattacc atacaaaggt ccaaccagac ctagaaggaa   1560
ctcccttcaa gacaggacaa tagatggttc ctcccaggtg aatgagggaa aaagccacaa   1620
tgggtattca ttaagtaatg gggaaatagg agtagagtta ggaaaattgc ctaggagttg   1680
gggagttgtt tgcactgagc caagccttaa gatactgaca gaatcaggaa ggagtcattg   1740
tgaaaagtga agtagagttt acctcctcaa aagactttcc tcccccatct aatcaggaat   1800
aaatagtaac ttctcttagt agcaaaatgt attcaaagac cagcgctaac attcttaaat   1860
atctgctaga cgtaataaag aaatcaatgt actttatgtc cttagctccc acaatttagt   1920
ctaaatgttt gctctggcat gcttatactg gtccaggcaa gcattaggtc ctatcctgtt   1980
cctcttcctt gtttgtgtct cacatgtccg tgtgaaaaga ccaccaaaca ggctttgtgt   2040
gagcaacaag gctgtgtatt tcacctgggt gcaggcgggc tgagtccgaa aagagagtca   2100
gcaaagggtg gtggattatc attagttcct acaggttttg gggtaggcgg ttgggttagg   2160
agcaatgttt tgccagcagg gggtggatct cgcagagtac attctcaagg gtggggagaa   2220
```

```
ttacaacgaa ccttcttaag ggttggggag attacagagt acattgatca gttagggtgg    2280
ggcagaaaca gatcacaatg gtggaatgtc atcagttaag gctattttca cttcttttgt    2340
ggatctttgg ttgcttcggg ccatctggat gtatacgtgc aggtcacagg ggatatgatg    2400
gtttagcttg ggcccagagg cctgacagtt tgaaggtgtt tttaccttc tcagcattcc     2460 acgagttact tcttcctttg ttctcctctg cctttgcctc ttttaaaaag ttctaagttg    2520
ctagccagtc gggacaaatg cagaatgtca ggcctctgag cccaagctaa gccatcgcat    2580
cccctgtgac ttgcacgtat atacgcccag atggcctgaa gtaactgaag aatcacaaaa    2640
gaagtgaata tgccctgccc caccttacct gatgacattc caccacaaaa gaagtgtaaa    2700
tggccggtcc ttgccttaag tgatgacatt accttgtgaa atcccttctc ctggctcatc    2760
ctggctcaaa aatctccccc actgagcacc ttgcgacccc ccactctgct cgccagagaa    2820
caactccact ttgactgtaa ttttcctttaa tctacccaaa tcctataaaa cggccccacc    2880
cttatctccc ttcgctgact gtcttttcgg actcagcccg cctgcaccca ggtgaaataa    2940
acagccgcgt tgctcacaca aagcctgttt ggtggtctct tcacacggac gcgcgtgaaa    3000
cagaatgtga ggtcccgttc cagccaatgg aaaccagaca cagcagtagg gtggacgcgt    3060
caggttataa atgaccctgt ctcctttgct cagtgtactc tcgtggcaaa actgctgccg    3120
agtgtaccct ttctacagaa agtataaaaa tgaccttgcg taggaaatta aatttatgtt    3180
caagtgccat ttctttatgg caccggggag caagcatttc aaacatcatt tgtaccaatt    3240
ctaagttaaa tttggactaa acaaggtctt attaatagca aaggataatt gaaatcccaa    3300
acttacaagg ttttcaacaa agtaaagtt tgctaaaagt taacagtata acatgtatta    3360
tcctaacttc taatgttgtg accttaggct gtctagtcca cagacataaa ggaagttcgc    3420
tttggaaaag aatggttatc atctttgaga gaaaaaaat tgtttcgaag gtttaagcaa    3480
gttttgaaat attcattgta aaggaaacat attggctaaa gttaaagggg tatcttccag    3540
tttttctgtg aactggacat taaaataaaa gcccagtggg tttttcttaa agcgctaacc    3600
tgctctttaa caaaaattac gaaaggttaa aaattataaa agtttaaaaa aagagtctgg    3660
aaatctcacc ttgtggtcag accttaaaat tggatacata tgtctacaag gttttattaa    3720
aatgaagttt aacacgaata acacactaat gtaaaggtga aatttagctg atctggtata    3780
aaatcacaca ggaagcactg tcaaatataa aatggtgttt ggctttcttt ggtctaaaaa    3840
ctaataaaaa taggtactaa aggaaatttc tcagcaagaa ggcactaagg actataaaat    3900
ccactgctga tgtccccacc tttaaaacaa agatcaatt tttagaaatg atatacttgg    3960
tttatcctcc acccttaaaa caaaaggtct tctagcacag gccctgccct gagagtttcc    4020
agtacatcag caccagcctg gggatcccgt tctcatcaaa gggtggaaag aagggaaact    4080
ggagccagcc tgggaaggac cctgccttgt gctgctgact accgagattg ctattcgtac    4140 aacgaaagg gggtggacac gtcccaccag agtcaagcaa gcaccattat caacagaatc    4200
atgggccatt gtttctggat caagccctac caaattaaag ctaaggaaag ctgagtctat    4260
ctctttcctt tcctttccta acccagtgcc tatatccatg actattccta ccactagcaa    4320
ctctaacccc actttagaga gtttctgtgg tttgggagca gaggtcactg aagggatcc    4380 tataggcttc aaggtgcgct ttgttctccc tcctccacct cctacgactg cccctttccc    4440
aaacctacaa catcaaacta tgcctcgcct catgccaaat gacacaagca agttcttaga    4500
agtagaaata ggagacccaa ggcaaaccct agcattgaa agagggtata aagacataaa    4560
tgccggttaa aacggattaa atatcccgtt cgcactttaa gcaaaagtga ccattaagct    4620
```

-continued

```
tgtgggcgcg gtaggccaga ggctcaggat gcctcctttc cactgggacg gtcctcaaat    4680
caagcggaca tggagtgcgt ggtagctctt ttcgaagatt ccaccacctg gaataacgaa    4740
ttgtgccaag ctctttctct gctatttcct gaagttcagt gccctgtggg tcagccccg    4800
agggccatcc agccttcatc ttccaaaacc aattttacct cgtgtctcca acaacgaggg    4860
gaaaaaactt ggcattcctt ggagacttaa aaggttgcag taaagtcagg cacctccaaa    4920
agctgaccca tcggtctgcc cttattcatc cctgagcgga tgtatggtgg tattatggag    4980
gacctttact ggacactctg ccaaataatg agagcagtac tgatgctgta gttcagttgg    5040
ctatcccttt tactctggca tttcatcaac cagaaaaaga aaaaaaaatg tagcctcaat    5100
tcttacctct ttaacaacgc taataagtat actctttctt cgtaggtgtt atgtcgtacc    5160
atacatccag gagttcatca aaacaactaa gccaagacat gctaagaaag tttgaagagg    5220
aaaactatac agtaaaagag gagggaattg taggaagtaa aaagtttctg cttcaaagtt    5280
cccccttctt gttaaagaata aatcataagt cttagaaata atagattctt ttaaagacta    5340
atttcttca agcctccttg ctttgtgcta atagctcttt gttaagccct atcctatgta    5400
actgttggac atgctcacag acacattcca gctcacagcc tatgccctt ccttaattgg    5460
aaatgttatt gcttcctgaa acctttgta agcaacttct tgttcttcc ttgcacttac    5520
ctatttagga aagtttcaaa tcgggtatca gtttaagata gtgaggtccc actccagcca    5580
atggatgcag gacacagcag taaggacaac ccaaatgcgt aagggataaa tacatctgct    5640
tttcctttgt tcaggtgtgc tctcaccatt gttccatctg cagttgagca ccctttctgc    5700
agaaagtaaa gatggccttg ctgagagatc ttttgtctct gtgctgactc ttcttcgcag    5760
caccgattat ctatttctaa caattttggt atttctaaca ggcccacaca cactgtgtgg    5820
gccaagctgc ttcactcagt ccactgatca aatgctcatc tcatcctcac agacacaccc    5880
aggatactgc ttgaccaaat atctggacaa cccatggccc agtcaagtcg acagaccaaa    5940
tgaactgtca cagacagctt ctgtccttgg aacggggtgg gattccacgg actctctccc    6000
ttcacagtgg agatgctcag tcagcaagct gccagaagtt cagagctggg aagatataa    6060
agaggactgg gcatggaagc tgcaggaact agtcaggaac tgggagtacc taggagtcag    6120
ctcctgagtg tgcaggatca tggtgaaata gaaagttaga gaaggaagag tgtgtcaata    6180
tcagagcatt gtcttatagc acaggactta accctctcct aaggttccag ggagacagtg    6240
ccaaatcatc acttgagtgg tgcttagaag cttcagggca aaagagccaa ccctaagtac    6300
atttgtctac tggggctgcc atcacaaagc accgcagaca gggtggctta tacaacagac    6360
tcattgtctc acaatcctgg cggctggagt ccaagatcaa ggttttgcaa ggctagctcc    6420
tcctgaggcc tctcttggct tgtagatgac cggggccttc tctctgtgtc ctcacagggt    6480
cttccctcag tgcgtgtccg tgtcctcacc tcctcttgta agactccagt cctatgagat    6540
taggaccac tgtcatgaac tcatttactg ttgattacct ttgttttatg ttttttgttt    6600
ttttgagaca gggtcagtct ctgtcaccca ggctggagtg cagtggtgca atcatggctc    6660
actgcagcct caaactcctg ggctcaagga atcctcccac ctcaatctcc caagtagctg    6720
ggactacaga tgcataccac tgtgcctggg tgtattagtc tgttattgca cagctataaa    6780
gaaatacctg agagtgggta acttataaag aaaggaggtt taattggctc acggttcata    6840
gctgcttctg gggaggcctc aggaaagttt cagtcatggt ggaaggtgaa ggggaagcag    6900
acacgtctta cacggccaga cagttcctcc tacactggct gacactctct cctgccacct    6960
tgtgaagaag gtgcctgctt cctttctgc catgactgta agtttcctga ggcctcccca    7020
```

```
gccatgtggg actgtgagtc aattaaacct cctttgttta taaattgccc agtctccggt    7080
agtatcttta taacagtgtg aggatgagct aatacacaca ggaagcagca atgccatcaa    7140
agagccaggg gccttgactg gcagaactag tgagaccatc accaaaacat ggcattcctt    7200
gggcaaggca ggtgcgcagc cagcaaggta ttgcttaatc tacatgatca aaagacatca    7260
ggatggttgt tcaggaggct gagaacagcc atcctattat ggctgagttg tgtcccctca    7320
aaatttatat actgaagtct taaccccca ggacctcagt gtgtaagtat ttggagaaag    7380
ggcctttaaa gatgtagtta aattaaaatg aagacattag ggtgggccct aatccaatct    7440
gactggtgtc cttgtaagaa gaggagatga ggacacatgc agaggcatga ccacatgagg    7500
acacagggag aaggtggcca tctgcaaatc aaggagtgag gcctcgggag gaaccagcac    7560
taccaacacc ttgatctcgg acttccagtc tccagaacca tgagatgatg aaagtctgtg    7620
tttaagctgc ccagtctgtg atattgtttt gcaaccctaa tagatgaata catacccca    7680 tgaaaaagca tgatctcttg cccagtttct gcacctgaga cagttttcaa acccaaaccc    7740
cactgattga aggagggatt aggtcccagg aggacggacc ctgcagtacc atagcaggct    7800
cccccagtcc ttccccaccc caccactaaa ggtgtatttc agtaactgtg cactaggaaa    7860
agggcaatgc ccagggctgg gggactccgg gaccaagttg acactgagag ctggagtcaa    7920
ggtaccatca tgggcccact agagtagggc gtatggaggc cagcaaagtg caatcctggt    7980
ccacctctag ctcacactga gtcatccctt tgcattccca gaatgctgca tattccccca    8040
gaccctaaaa gtacactcag acaatcttgg tagttggcag aatcctcacg taggctcatt    8100
gtcctgtagg gtaaaaacta tcatagtgtt accaagtaga aacttctgaa actgcccacc    8160
accttagcca aggcaataca ccaaaaagaa aatctcattg gtggggaatg gcagagatgt    8220 gggcccttt ggaagacttg aaggttgcag gtgaggcgat tcccatcatc tcccccattt    8280
tccagagaat gctaacagac tactgtcaac ttgtgatggg aaattttatg cgtccacttc    8340
actgggccat ggtgcccaga tgtttggtta aacattattc tgggtgtgtc tgcaaggtgt    8400
ttctggatat gcttagcatt tgaatctgtg gactgagaaa agcaggtcac tctctctggt    8460
aaaggtgggc ctcatccaat cagttgaagg tctgactaaa acaaaaagat taagcaagag    8520
aaaattcgct ctccctgcct gtcttagtct gtttatgttg ctataaagga atattggagc    8580
ctgggtaatt gataaagaaa agaggtttat ttggctcatg gttctgcagg ctgtacaaga    8640
aacatgacat ctgcatctgc tgctggtgag ggcctcaggc tgcttccact cctgacagaa    8700
gatgaagggg agccagtgtg tgcagaggtc acatggtgag agaaacaagt gaacatggga    8760
ctgccaggtt gttttcaaca accagctgtc agggaactc agagtgagaa ctcactcact    8820
accatgagga tggcaccaag ccatccatga gggatctgcc ctcacaaccc aaacacccccc    8880 attagacacc acctccagca ctgaggacca aatttcaaca tgattgatag cccagctcaa    8940
agagccgctt gtctttgagc tgggatatca gtgttctgcc ttcacactca gattggaact    9000
tacaccatca gctctcctgg gtctccagct tgcagatggc agatggggat actttccaac    9060
ctccataatc acaggagcca attccccta aaaagcccct gtgtatatgt acagctaatc    9120
ccaagctcca ctgagcagta gcccagtgga ttgttgctgt gccagctgtg ctatatttgc    9180
tggagcagag ggctgtggaa tggggtacat gttaagcacc cattagtggg tggatttgtt    9240
ctatgccatc cctatttaaa aagagccctg gacaccttt gggggacatc atcattctgc    9300
ccaccacccc gggacaggag gcacatgaat gaactcacag gtgtggccat gagaggtgaa    9360
gagcttggta tcacgtgttc attcccaaca gagagcatcc accagggagc cactaagcaa    9420
```

```
ccagttagac agaatggccg cagtccttga cttcagccag cctctgtccc cgaccacctg   9480
agtgctggcc ccctgggtgc atgcatggag cagctttggt ggtagaaagg gatgctgacc   9540
atgaaatcaa cagcacagct ccacccacca aggctggtct agccactgct gccacaaatg   9600
cccaacctgt ctgcaacatg ggctgctgag aagcccccac taggcactat ccatagagaa   9660
agttgacaag gcaacagaag catccatccc attggggggca gcaattcaac tccactagaa   9720
ttgacacata acccaggctg atccccaggc cttattaagt gttgatccac caaacagggc   9780
atgcgtagca gtgccttgga ccaagggacc cactttacaa cacagggagg aggtgcagcc   9840
atggcacatg gcacatggca catggccatg gcatctgctg gtcctatcac agcccacacc   9900
actcagacgc agccagcacc acagagcagg ggagcagcct tttcagagct ccatgaaggc   9960
cccagcgtgg gggtgatact gttcaaggat ggggtgtcac attgtggaac tcagtagtca  10020
ctccaactca acagccacca tggggtgcta tgtccccaac aggcctcgga accaaggggc  10080
agaagcagca gcggcccctg taccaccact gccagtgacc tgctgtgggt tttgtgcatg  10140
ctgttccctc cactctaggc tgccagtccg gggtcgtggt ttccacaggg gacaacgcca  10200
ccagtggaca gataggagac ccactgaaat ttaggctaca gccgatgcct tgtcactttg  10260
gattatttgt ccctggagac caacagtcat gacaacgagc ccccaaactg ggagggaggt  10320
gggccgtggc catcaggagg cagtagaact gctactccat gaggggacag gaaagaatac  10380
atttggtgcc tggtgatcca agtggtggga cttgggggac ttggtgttcc ctcaactgct  10440
ttattcatga gtggacaagt acaacagcca tggcctgagc agggatggtg accagggccc  10500
cagacccctc actgaggagg gtcccagttg gcccactggg taggccacag agactagaag  10560
aggtgcccac tgacagggaa ggaaccaaac atgagtcagg gaagaacaag ggtcatgaca  10620
gccatggcca agacgctatg gggcacaggc tgtagttggc tgtttctcta aacttgtaaa  10680
cccaggtatt agtcagcgtt ctccagagaa tcagaacccc aggatatata catacagaca  10740
tatgagagga tttatgaggg gaatcggctc acatgattat gcaggctgag aagtctcatg  10800
acaggctgtc tgcaagctgg aaacctagag aagctggtgc ggggctcatt ccaagtccaa  10860
aggcctcaga accaggggag cggattgtgt aactctgagt ccgaggccaa aggcctgaaa  10920
actggtggtg gtggagtggc tactggtgtg agtcccagag cacaatggct ggagaacccg  10980
gagttccgat gtcacagtc aggagaagat gggttgccta gccctggaga aaggagaat  11040 tcgtcattcc ctgcctttt tctctctcta ggccctcaac ctattggatg gtgccaacca  11100
catcaagtga gggtagatct tccttattca gtccatggat tcaaataaca atctctttca  11160
aatctaccct cacagatacc cagaaataat gctttgcaag atgtgatggt taattttggg  11220
tgtcaacttt actagattaa gtgatacccca ggtatctgga aaagcattat ttctgggtgt  11280
gtctgtaata taggttggat gtcaccctct accccctacc caaatctcat gttgaattgt  11340
aatccttcat gctggaggtg gggcctggtg ggaggtgatt ggatcacgag gtggatcctt  11400
catagcttga tgatgtcctc atggcagtca taagatcagg ctgtttgaaa gtgtgtggca  11460
cctcccccac ctctctcttg ctcctgcttt tgccatgtga tgtgcctatt cccccttttgc  11520 cttccaccat gattggaagt ttcctgaggc gtccccagaa gcagatgctt ctatgcttcc  11580
tgtacagcct gcagaactgt gagccaatta aacctctttt cttataaatt atccagtctc  11640
ttttatctca ggtctttctt ttcttttctt ttcttttctt ttctttcttt tctttctctt  11700
ctctttctct ttcttttctt ttctttcttt ctgtctttct ttctttcaga cagatttccc  11760
tcagtctcct acagtgcagt ggcgcaatct cagctcactg caacctccac atcccaggtt  11820
```

```
caagccattt tgtgcctca gcctctcgag tagctgggat tacagtcatg caccactgtg   11880
cccagctaat tttgtgtttt tggtagacac agggtttctc catgctggcc aggcttgtct   11940
caaactcctg acctcaggtg atccacctgc cttggcccct caaagtgctg ggattatagc   12000
caccatgcct ggccccaggt atttttttac aggagtgcaa gaatggccta atacagaaac   12060
ttggtaccag ggagaaagat atttctataa agatatctga aaatgtggaa gcaacttttgc  12120 aactgggtta caggcagaag ttggaagatc ttgaaaggct cacaagaaga gaggaagatg   12180
aaggaaagtt tggaacctct tagagactgg ttaaatggct gtgaccaaaa tgctaatagt   12240
gatatggaca gtgaaggaca ggctgatgaa gtctcagatg gaaatgagaa acttatttgg   12300
aactacagca aaagtcacat gtgttatgcc ttagcaaaca cttgactgca tcctgttcat   12360
gccttaggga tctgtggaag tttgagcttg agagtgatga ctcaaggtat ctggcagaag   12420
atatttctag gcagcaaagc attcaagatg tggcctggct gcttctaaca acctacacac   12480
agatgcggga gcaaagaaat gacctaaagt tggaatttac atttaaaagg aaagcagagt   12540
gtaaacattt aaaaaaattt gcagcctggt caagtggtag agaaagaaac gcttttttca   12600
ggaaataaat tcaagcacac tctggagcta ccgcttacta gagaaatttg cacaactgaa   12660
acagagccaa gtgctaatat ccaaagacaa tggggaaaag gcctcaaagg catttcagaa   12720
acttccaaag aagcccctcc catcacaagc tcagaggcct aggaggaaag aatggtttca   12780
tggaccaaac ccagggccca gtgccctgca cagccttggg acactgttcc ccacatctcg   12840
gccactctgg gttcagcctc agctaaaacg ggtccaggta caacttgggc tgccattaca   12900
gctccagaga gtgcaagcca taagccttgg cagcttccgt gtagtgttaa acctgcagcc   12960
acacagaatg taaagtgaa ggaggcttag gagcctccac ctagatttca gaggatgtat   13020
ggaaaagcct gggtgcccag gaggaagcct gccacagggg cagttacctc acagagaacc   13080
tctactaagg cagtgcaggg ggggaatgtg gggctgagg ccccacacag agtctccagt    13140
ggggcacttc ctagtggacc catgggaagg aagggggcca ctgtcctcca ggccccagga   13200
tggtagatcc actggaagct tgcactctgc acatagaaaa gcagcaggca ctcaacaacc   13260
tgtgacagca gccacaagag ctgcaccctg cagagataca ggggcagagt ggcccaaggc   13320
ctggggtggc acacccctcg caccagcatg ccctggaaat gggacatgga gtcaaaggag   13380
actaccctag agctttaaga tttaatgact gccctgctgg gttttggact tgtatgcagc   13440
ctgtagtccc tttcttttgg ccaatttctc ccttttggaa catgaatgtt tacccaatgc   13500
ccatatcccc aatgtatctc agaagtaaat aactttttta atttacagg cttgtagatg    13560 gaagggactt gccttgactc agttgagaca ttgaacttt gagttaatgc tgaaatgagt     13620
gaagactttg gaggactatt aggaaggtat gattgtattc ggcaacagga gaaggatatg   13680
agatttggag gcccaggggc taaatgatat agtttggatg tcctttccaa acttcatgtt   13740
gaacagtaat ctccaatgtt ggaagtggag ccttggtggg aggtgattgg atcacagggg   13800
cagatcccac atggcttggt gatgtccttg atctggacac aagatctggc tgtttaaaag   13860
tgtgtggcac ctccccccac ctctctcttg ctcatgcttt tgccatgtga catgcctgct   13920 cccccttttgc cttttgccat gattggaagc ttcctgaggc ctccccagaa gcagatgctg   13980
ctgtgcttcc tatacagcct gcagaaacat gagccaatta catctgtttt cttataaatt   14040
acccagttgc aggtctttcc taatagcagt gcaatgacag cctaatacag tctgtgaagg   14100
tgttctcaga agacatcggc acttgaatca gtggactgag tgtcttagtc catttgtgct   14160
gctataagaa aatgcctgaa actgggtact ttatagagaa gataaactta ttttctcaca   14220
```

```
gttctggagg ccgggaagtt caagatcaag gtgccagcaa gtatattgtc tggtgaggga    14280
ccctatctct gcgtccaaga tggtgtgttg tggcagcctt ctccagaggg aacgaatgct    14340
ggggtcctcg catggaggat agtggaagag caatacaggg tgaactgtcc ttgaagcctt    14400
tttgacaggg tagtaattca gttatgagga cagagcctgc ataacttaat cacttcccaa    14460
aagccctact tcttaatacc accacaatgg gattacattt caacatgaat ttctaggggg    14520
tatgttcaaa tcatagcatt ctactcctag tcccccaaaa tgtatgacct tatcacatta    14580
aaaatacata cattccatcc cagtaactcc aaaagtctta actcattcca gcatcaactt    14640
taaaatcaaa gtccaaagtc ttatttaaac atcgtctaca tcagatatga ttgacactct    14700
aggtaacatt catcttgagg caaattgctc tccagctgta aacctatgaa atcaaacaag    14760
ttacatgctt ccaaaatatc atggtaggac agacagggga tagatatttc cattgcaaaa    14820
gggaacacta ggaaagaaaa aagcgataat agatcccaag taaatccaaa atccaacaag    14880
gcaagcaaaa tcagatcttg aaacttgaca atgatctcct ttgactccct gtcatgcctt    14940
ccagataccc tagggtggga gttgggcccc aagtctcca ggtggtcctg cccccatggc    15000
tttgccggct gtggctccca agcatgacag tccctgctt ttggctgtcc caggctggag    15060
ttgcacagca gtgtttctac tggcttgtgg ttgagggggc cctgaccca tggctctatt    15120 aggccatgcc tccatagcac gtgctctgtg tgtgcctgca gaagatgctg ccaaggcgta    15180
ttgcctgtgc ctctggaggg gcagcctgag ccacacctgg gcccatgtga gccatagctg    15240
aggcagctga ggagtgctac actggaatgc agggagcaga gacttgaggc agtactgggc    15300
atgaaggccc aaggtcccat aggtactcag ggaccctcca gagccctggg ttcctccctt    15360
gactccattc tgccctcaaa gcaaatgcag ggagcagaga cttgaggcag tactgggcat    15420
gaaggcctaa ggtcctgtag gtacccaggg accgtccaga gccctgggtt cctcccttga    15480
ctcccttctg ccctcaaagc cctagaactc taagcctgtg atggccatgg cagcctggaa    15540
gagctttgag atgccgtcag ggcctttctt ccattgtctt aacggacagc acctgacttc    15600
cctctatcgc caggaatctt atcaaatggt ccctgggcca cacccttttgt tttctctcct    15660 acacgcgtgg ccaagctgag actcttccaa acctttaagt tctgcttctc ttttgattat    15720
agattctgtc tttaactcat ttctctcttt cttgcatttt accatacaca gttgagagaa    15780
gccatgcagc tcccttagcg ttttgcttag agatttcttc ctctgaatat tctagttcat    15840
cactgttaaa ttctgcctcc cacaaagccc tcaggcacag acacaattca gcctagttcc    15900
ttaccacttt gtaacaggaa cggtctttcc tccagattcc aataagatat tccttgctgt    15960
gatctaacac ttcatcttta ctattcatat ttctaccagc attgggatca tgattactta    16020
aacatttctc ttttttttt agatggagcc ttgctctgtc gcccaggctg gagtgcagtg    16080
gtgggatctc ggctcactgc aagctccacc tcccgggttc acgccattct cctgcctcag    16140
cctcccgagt agctgggact accggcgccc gccaccacgc ccagctaatt ttttgtattt    16200
ttagtagaga cggggtttca ccgtgttagc caggataatc tctatctcct gaccttgtga    16260
tccgcccacg tcgcctccc aaagtgctgg gattacaggc gtgagccacc gcgcccggcc    16320
cacttaaaca ttcctaagaa gactgaggct ctgtctacag atctcctctt cttctaaacc    16380
tgcaccagaa ttgcctttaa tactctgttc atagccattt aggcttttc tgccatgcac    16440 tctgaaacac ttccagactc taccagcagt ttgaaatctg cttccacatt ttcaggtatt    16500
tataacatca acaccccact tatgtttagc aaattatgtc tccgtccctt tgtgcggcca    16560
taataaaata cctgtaactt ggtcattct acaacagatt tattatgtca cagtacggga    16620
```

-continued

```
ggctggaaaa agtgcaagat caggacactg gctgttttgg tgtctggtga gggtcccagt   16680
ctcttcttca agatgaagac ttgttgctgc ctctcctgaa ggggacaaat gctgtgtcac   16740
cacactgtgg atagtggaag agcaatacaa ggtgaactgt ctctgaagcc tttttttataa  16800
gagcgttggt ccattcatga ggactgagcc ctcatgactt aatcacttct caaaaaacgc   16860
taccgcttaa taccaccaca gcggggatta agtttaaata taatgtttgg aggccaggtg   16920
cagtggctca tgcctgtaat cccagcactt gggagggtg aggcgggcag atcgcttgag   16980
gtcatcagtt caagaccagc ctggccaaca tggagaaact ctatctctac aaaatacaaa   17040
aattaactgg gcgtggtggt gcgtgcacac ctatggtccc agctactcgg gaggttgagg   17100
catggcttaa agccaggagg ttgcagtgag ctgagatcgc gccactgcac tccagcctgg   17160
gcaacagact gagactctgt ctcaaaaaaa aaaaaaaaa acttggagaa ggcaaattca    17220
aagcacgaca gtagagaagg tccatcctcg cccaacgtga gtgggcactg tccaatcagc   17280
agtgggccca gataaggaaa aaaggtagaa gaaaggcgaa ctctccctct ctgcctctcc   17340
ccactctccc ttctgcagct gggacaccca tcttctcttg cctttggata tcagaactcc   17400
agattcttca gccttcgcac tctgagactt gtaccagtgg cctccgggtc tcaggccttc   17460
agctgcagac tgagagttac ccaactggct ttcctgattg acgcttagac tgtaccacat   17520
aaatggcttc cctggtcccc agcttgcaga tggcctattg tgggaatttt cagcctctgt   17580
aatcattgta atcatatgag cccattccca taataaatcc cttctcatgt atctatgtat   17640
ctatacctgt atcaatccta tttctttctt ttttttttt ttgagacaga gtcttgctct   17700
gtcacccagg ctggagtgca gtggcgtgtt ctcagctcaa tgcaacctcc gcctcccagg   17760
ttcaggcgat tctcctgcct cagcctcccg agtagctggg actacaggca cccgccacca   17820
cgcccagcta attttttgtat ttttagtaga gacggggttt catcatgttg gccaggatag   17880
tctccatctc ttggcctcgt gattcacccg cctcggcctc ccagagtgct gggattacag   17940
gcgtaagcca gcacacctgg cctcgatgct atttctatcc tatcggttct gtttacctga   18000
agaaccctaa cataggtttt ggtatcagga tgattctaga gaaacagaat cataagaatg   18060
agttttctga atgtgtattg tgtttttcgg aattggtttt ctaatatgac ttgacttaaa   18120
agtgagaaga actctacttc caacagtaca caggacactg atggtccatg gtgtgaatag   18180
tttatgaaaa tatgcaaatt tctgcattgt atactcctag taaaccactt acaagaggca   18240
aggagcttag tgactctgta tatgatattt tcgaacattt gtggaaaacc agggaatata   18300
gtgacgtggg ctggttacca gttggttgct ggacaaagtg atgaaatcac aggatgtgct   18360
cagtgattca aattcccagt tccagctctg tataaataac ctgtgagtgg ctgagtgaac   18420
cctgaaggag aacctccttt cctgtagccc tggggccaag actgctgaaa agcaaccaca   18480
agtcctcgtc ctgaaactgg atgaattaca acgcaagttg aactctcagc cttgcgggt   18540
gtccactgtt ccagtgaggg cattggctgg gaaacagagg atcctgtaag ttgggatgaa   18600
gacatatgga aggaccctga tgaagctggg gacggtcagc ctctaagtta ggatgagtca   18660
ttttgtcagc agaagcagcc tccctgcacc cagtggcagt gctacaccca ccccagtgc    18720
tacaccctc ccccagtggt actggccttt ccaccttctc tgaggcatta atctgtgttg   18780
cctgaggaaa gggtaaggac ttcccctaag gcagttgctg attctcctcg ggtccctccc   18840
ccaacccttc cctttgcttt aagacctata acaagactca cagcccagca ggcccctgaa   18900
ggtgaggccc acagtgtgac acaggaggag gcgagccaca ccccagaaga gccactcgac   18960
ctctctgatt tatacagaca gacacctggg agcatgagtg ggaacggacg ttgggtgtag   19020
```

```
ggcactgggg gaggaacatg gaggtggagg gaccaggtgt gcaggcatgt ccaccaagta  19080
gagcctgaat tccaggctgc aactcaggga cttggaaaag ctctaactgg ctggtcggtt  19140
gaaacatgga tcaaaggatg cctgcagtga gcgagctgga gatgcctaaa ctcccttggc  19200
ttaacataga ggaaggggtt caaaggctca ttcccaaagg agatcagaat gtgacaatga  19260
aaacctcctc acctaccctg ggagggccca aaacgcagac ctttcacaac agggatcccc  19320 aacccccgg gccatggact ggtactggtc catggcctgt taggaactgg gccacacagc  19380
aggaggtgag cggtgggtga gtgagtgaaa tccgtattta tagccactcc ccatcacttg  19440
catgaccacc tgagcttggc ctcctgtcag atcagcagca gcatcagatt ctcataggag  19500
tgcaaaccct actgtgaact gcacatacga aggatctagg ctgcaacgct ccttatgaga  19560
atctaatgcc tgatgatgtg tggctgtctc ccatcctccc cagatgggac tgtctagttg  19620
caggaaatcg agcgcaggcc tcccactgat tctacatgat ggcgagttgt ataattattt  19680
ccttacatat tacaatgtaa taataataca gataaagtga acaataaatg taatgtgttt  19740
gaatcatccc aaaaccatcc tccaactccg ggtctgtgga aaaatattct gccatgaaac  19800 tagtcccctca tgccaaaaag gttgaggact gctgtctcac aacactgaaa tatagacttg  19860
tgagggagcc cagtctcctt gaagagctct gagattgttc ttctctgtag gccagactca  19920
ctgtgggaac tgcagtcaat caactgagaa acttacatgt gatgggaata attggatcct  19980
ggggtagcag tggccaagtg ggggcattca agcaccaaag gcaaagttgg catggttacc  20040
atgatagaca gcagaggcaa agtagcagtc agacctgagt tacaggtcca acccatgtag  20100
acctatggca ctggctggtt accatgtttt tcctagcagt gaaacagatg ggaagcctgc  20160
tcaattccta ctggatacaa gcagaaaact tacagatcaa gtggacaaaa ctctaagtcc  20220
aatcataaaa acagagaatc atggcctcag tctttcacag acttgagcca gtctatgaac  20280
ccagaaagag tgaaagaaag gctgggtacc cttgaggaag gaccccagga tggccaaaaa  20340
tgtatatata ctgttaattc tttccctggt cttctccaaa ggggtctatg gccttctatc  20400
tgtgtaactg tgtattggaa aaagaaaat aatgtggcat ttcaggacga ttggacactg  20460
gctctgtcct gacattgatt ttaggagatg ctggaacgac actgtggccc tccagttagg  20520
gaggggctta gggagccagg tgatcaatgg agttttagct caggtctgac tctgtgggtc  20580
cagcgggtac ccagcccatc ctgtggtcat cttcccagct ccagatgtgt aagtggaaca  20640
gacacactca gcagccagca gagtccccac atgcgtcccg tgacctggtg tgtgaaggct  20700
actgtggtgg gaaaggccaa gtggaagcca ttagagaggt ctctacctag aaccgtcagt  20760
caaaagccat cccacatccc tggagggact gcagacatca gtgccaccac caaggacttg  20820
agaggtgcag gggcggcgat ccccaccaca gcccattctc cccacctatt cggcccacag  20880
gggagacagg tgggtcctgg agaatgacag gggactgtcc taagtttgac tccagctgca  20940
gctgctgggc cagacgaggt tccatcgctt gagcaaatta gcacatctcc tgctccctgg  21000
tgcgaagctc ttgatccagc aaatgcgttc tcctccaccc ccgtccacag ggcccagcag  21060
aagccaggcc agcgatgcac cctcgccgcc ccacctgagg ggcctctcgc ctctccagcc  21120
cgtgtcagag gtaattctca ggagtctcga tcacctctcc cttccccagg atgtcacact  21180
ggcccattac actggtgaca tcatgttgat gggacgtaag gcacaagaag tagcctccat  21240
cctagacttg ttggtgtcgg agggtgggga ataaacccaa ctggaattca gagccttcta  21300
cctcagggaa atttccagtg gtgtgaggcc tgttctaagg tgaaggacag gttgttgcag  21360 ctgaacccctc ctacaaccaa aagagaagaa cggcactaag tgggcctgtc tgatgtgggg  21420
```

```
ttgacacgtt ctttctcttt gaggtgtcca actctgtcca tttactgagt gatttgaaaa    21480
gctgctagtt agttttaagc atggcccaga gcaagagaag tctctgcagt aggtccaggc    21540
tctgtgcatg ccgctctgcc acgtgggcca catgacccgg cagatccact ggtgcctggg    21600
gtgtcagtgg cagacagaga ccctgtgtgg agtctttgcc aggcccctgt aggtgaatca    21660
cggctcaggc ctttaggatt ttggaggaag gtcctgtcat cattcacaga taacccactc    21720
tccttcagag aaacagctct tgccctgctt ctgggccttt gtagaaatta aacacttggc    21780
agtgtgaatc tataatccca gcactttggg aggctgaggt gggcaggtca cctgaggtca    21840
ggagttcaag accagcctgg ccaacatggc gaaaccctgt ctctactaaa aatacaaaat    21900
tagccaggtg tggtggcgag tgcctgtaat accagctact gggaggtgg aggcacgaga    21960 atcagttgaa cccgggaggc ggaggttgca gtgagccaaa atggtgccgc tgcactccag    22020
cctgggtgac agagggagac tctgtctcat aaaaaaagaa aagaaaagaa agaaaaaaag    22080
aaaaggaaac taaactagac aagggccacc aagttaccac gtgacttgaa tggctcatca    22140
tgatctgggg actttctgac ccacgtagcc ataaagtcgt gtgcacagca gtgctgcatc    22200
agccagtgga agcaggggat aggtgatcag gcccaagcag gtcctgaagg cacaaggaag    22260
ttacgtgaag tagtggccca aagcctgtgg ccccactgct gctcccctgc cttctccctc    22320
cctgtctgca cctgtggctg catggggagt tcctctgatt agttgacgga ggaagagaag    22380
actcaggccg gacttacaaa tggttctgct cagtatgcag acactaccgg aaagtggaca    22440
gctgcagccc tgtagcccct gggggatatc cctcagacag tggtgaagag gaatcttccc    22500
cgtgggtaga acttccggca tgcacctgtg tgtgctccgc ttagaaggag cagatgtgtg    22560
atgatatttc attcatggct gttgccagta atttaagtgg atggaggtgc ttgaaaggaa    22620
catgattgga aaattggtga tgaagaaatg tgtggaagag atgtatagat agccctttct    22680
gaacatgcta atgacatcca gatatttgtg tcccatgtga atgctcacca aagggtgacc    22740
tcagcagagg acttcagtaa tcaggtggac agcatgagct actctatgga caccagtgag    22800
ccttttccca gccacccctc tcatcaccca gtgagctcct gagcgaagtg gctgtggtgg    22860
cagggatgga ggttgtgcgt gggctcagca acatggactt ccactgacca aggccaagct    22920
gagtaccacc agcactgtat gcccagtgtg ccagcagcag agaccaacac tcagcctgat    22980
aagctccatt cctgagtgat cagcccagtg cctgggggca ggtgggtgac actgacagc    23040 tcccatcatg gaaggggcgc tgaggctcca ttccccagcg tgttgagccc ggtgcctggg    23100
ggcgggtggg tgacactgga cggttcccat catgggaggg gcgctggttt gttctcactg    23160
ggataggcgc ctgccatgga tatggatttg tcttccctgc acacagtgct tctgtcgtca    23220
ctaccatctg tgggctcaga actcctcatc taatgccgtg ctgtccacac agcattgctt    23280
tgacgaagga actcactttg cagccaaaga agcgtggcag tgggctcatg ctcgtggtat    23340
tcacgggtct taccgtgttc tccatcatcc tgaagcagct ggcgtgatag aacggtggaa    23400
tgggcttttg cagacacagc tccagcacaa gctgggtggc agtcccttgc agggctgggg    23460
caaggtgctg ctccaggagg ctgtccgtgc tctgaatcag tgtccaatat gtggagctgt    23520
ctctcccaca gtcaggattc acccgtccgg gaaccaaggg gcagaagtgg gagtggcacc    23580
acccaccatc agccccagtg acccactagc agtgttttg tttcctgttc ccatgacttt    23640
acgctctgct ggcctagggg ccttggttcc aaggtgagga atgctgccac caggagacac    23700
aacaatgact ccattgaact ggaagttaag gtggcacctg ggcagttggg gctcctcaag    23760
cctcagaatc aacaggccga taagagagtt tggatgctgg ctggggattg atccagagga    23820
```

```
cccaggggac atcgaactgc actccacacc agaggtgcgg aagagcacgg ggaatgcagg   23880
aggcccctta gggcttcttt aagtgtaacc acaccctgtg gttaagatcc ctggggccag   23940
gctcggtggc tcacgcctgt aatcccagca ctttgggagg ccgaggcggg cggatcacga   24000
ggtcaggaga ttcagaccat cctggctaac acggtgaaac cccatctcta ctaaaaatac   24060
caaaaaatta gccgggcatg gtggcaggca cctgtagtcc cagctacttg tgaggctgaa   24120
gcaggagaat ggcgtgaacc cgggaggcgg agcttgcagt gagccgagat cgcgccactg   24180
caccccagcc tgggcgacag agcaagactc cgtctcaaaa ataaaaaata ataataaaaa   24240
aataatccct gggaaagcac agcaatgcaa gtttccttag gaaactacag caaggccgag   24300
acccttaagc actgaggcct tgggtcacct ggccaggtac agaaccacta ccggctgagg   24360
tgcttgctga gggcaaaggg actacagaat gggcagtggt tataaacacc aggtactcct   24420
gtagcttggc cagtagcaga atgaggatt gcaactttca cgagtgtttc ctctccattt    24480
tgttaagaaa gcatttgtgc atatgtgtac ataagttaag caaatatctg ttttctttcc   24540
tctcttactc ctttatcatg taacataaga tctattgatt ttgtctcagt atcaaggtat   24600
cgtgaatttt acatgacagt attgaggtcg tgcgatatcg ggagagtcga catcactcga   24660
ggacttcacc tcctcttcca gggaaggagt cagtgcgtgt ctggttgtat gcgggacagt   24720
catcacatgt tagttggaac catgaccttg ctgctgtcta tttggagatg aagtacggtt   24780
taaggaggtg tgtatgggtt ccaagctgac aaggagtgaa cttgtgacgg ttcgtttcag   24840
ctgtcaactt gactggatga agggatatcc agagagcatg aaagcattat ctctgggtgt   24900
gcctgtgagg gcatttccgg agagactggc gattgaatcc gtgggctgaa taaggaagat   24960
ctgtcttcac ccaaagtggg agggcaccat ccaatccact gagggcccag gcagaacggg   25020
aagatgaatt cgtgctctct tgctctctct tcccccacca gagctgggac acccacctcc   25080
tactgccctt agacatcaga actcctggtt ctctgggctt tggaccctgg aacttatacc   25140
agtggcccct ctgactgcga gttacactgt cggcctccct ggttctcaga tcttcaggct   25200
tgaactgagc cacactacca gcctccctgg gtctccagct tgcacagaca gggcaaatca   25260
tgggacttct cagtctccat actcatgtga gccgattccc atcataaacc cccttttcttc  25320 catccatcca tccatccatc catccatcca tccatccatc catccagcta tctatctagc   25380
taccgagcta gctacctgta tctttactta tctctatcta tgtctaccta tatctatatc   25440
tctgtctaca tctctatatc tatctgatct atctctatct ctatggtaat ctcaatctgt   25500
ctgtctgtct gtccgtctct ctgtctatct gtctccctcc ctgtctgtct atctgcctgt   25560
ctgcctgcct gtctatctgt ctgtctgcct gtctgcctgt ctgtctgcct gtctgcctgt   25620
ctatctgact gtctgcctgc ctatctgtct gtctgtctgt ctttatctct atggatctgt   25680
acttatttat ctatctcatt ccgtgtatct gtctctatat ctatacatct acatcatgga   25740
ggactatggt agatgctcac tgctgtgcac tgcaccgtcc ctcccagcgg gaccacagca   25800
ctggtccagc cagctgccca cagctctcag cttgctcctc ccgaggaaat gccctcagcc   25860
aaaggcagct gcctcaccca tggcttctcc ctgccctgga agccacctct acccaatgaa   25920
tggtcgatgg aggaagcaac aggtcaggtc cttcacctga attcatggcc tctctaaagg   25980
gccccttcag ctccaaaagc acccgaggca tcatcagaaa ccttctttgc gagtggagca   26040
cagctcagct gccccacct gctccttccc tctctcacag cctttgtccc caagagcact    26100
tgccacttta cccttgacct acatgtctct atctggcagt gtctcttggg gaaccgaacc   26160
tcagacagtt tgcaagcaac aaattccaaa ggtcgtgcct gggcctggag ctctgctgac   26220
```

```
atggaagcca tgcccacctg ggacctgagg gtgtttcttg tctcacaggc ctgatattga    26280
gtggtgtgca tctgcatacc caggtggttg ttaaaacaca gaacggcttc catgctggtt    26340
gaacgacccc taccttgagc ctccaggtgt cccccagagg ccaccccggt tccttccccc    26400
agggtccaag cagggcacga cagacagctt ctggaacatc actcaatgcc gtggccagcc    26460
ccattctgat gggtctgcac caatcggggc tgcttgttaa gcatgactaa agtctcctgc    26520
agtcgtctgc taggactgcc acagcaaagc gccacagtct ggcagccttc acagagacat    26580
ttatctcccc agccctgggg gcctcaagtc caagctcaag ttgttgttgg ggctggttcc    26640
ttcgggggct acgaggtggc ctctgcccag tccctccagc ctctgcccag tccctccagc    26700
ctctggggct cccaggcagc ctcgtgtttc ttggctcgtg gagcatcact ctaatctctg    26760
ccttcacctt cacatggcgt ccttcctgtg tgtgcgtctg catccaactt ccctgttcc     26820 taaggtcacc ggtcagatct gagcaggata ctaatggcca tatcttagtt acatctgcag    26880
tgaccctatt tccaaataag gtcacatatg aggcactgaa ggtcgggact gcaacatgct    26940
tgttctccta tcatggaatc agaccagcag gtgggtcaca ttccgccaga gggagagtgg    27000
gcagacgccc aaagggctgg atgtatacag ctccaggaag aaccgcagtt gcagctgctt    27060
ggacaggtgt gggcactcac agcctcccat gacagccctg gctgggggct ccatccacag    27120
cccctggtgg ggtggggcaa ggcccttcct tctgacccac aggaccttgg acccctgggg    27180
cactgcagag ggactcaggg tcagaccagc agcctttgac atggccaaga gtgaaagtga    27240
tggggaccca cgagccatca gagctctgtc tccagagcct gcacagggag tgttgggaca    27300
aggagcaaag gaatcgggag cacatcaagg caggcaccag atttggaaga acgccccggg    27360
ggaggtgctc ccaggcgagt ggggcagagg gcagtctcct cctgggcttc cctgggtccc    27420
agcccggccc ggctgggcgt cccactgtct ttggtgtggt gtgctccctg cctgtggccc    27480
tgtgatggga gtcctgcttc tctaaacagt gagaccctca cagaacccgt cagcatgtcc    27540
aaagcacctg gaggagaaaa gatttgtctc ctcattcgtc actaggttca tggttgaggc    27600
tctcacagca aaagacagat taacaagaga aaagcagaca catttattca atataagttt    27660
catctcgtat aggagccttc ggaaatgagg acccagcact tcgggaggcc gaggtggaca    27720
gaccatttga agtcaggagt tccgagacca gcctggccaa catggtgaaa ccccatctct    27780
actaaaaata caaaattagc cgggcatggt ggcatgtgcc tgcagtccca gctaccgggg    27840
tggctgaggc aggagacttg cttgaacccg ggaggtggag gttgcagtga ccgagatca    27900 cgccattaca cttcagccag ggtgacagag tgaaactccg tctcaaaaaa aaaaaaaaa    27960 agaaaaagaa aaggaaaaag aaatgaggac ccaagggaag agggaaaccc gtgtattttt    28020
atgtggagtt tgatggagag tcatgcagag tgtgattgga ttagacaaag tgggtgtact    28080
cgtccgttct tgcactgtat aaagaatact tgagactgcg taattcataa agaaaggagg    28140
tttacttggc ttacagttcc ccaggctgta cagaaagcat ggtgctggca tccacatggc    28200 ttctggggc gggctcagga aacttacaat catggcggaa ggcaaaggag gagctggcac    28260
ttcacgtggc cggagcagga ggaagcccag agggagagag gggaggtgcc atatgccttt    28320
aaacaagcag gtctcatgag aactcactat cacgagaaca gcactggggg gaaatccacc    28380
cccatgagcc aatcacctcc agcaggcccc acctccagca ttggggatta caattcaaca    28440
tgagatttag gcaggtacac agatccaaac cgtatcaggg tgtggcctaa tggtgataca    28500
ctggggagac ttggcctgtg gtcttagtcc atcgtgtgct gttagaacag aaaaccacag    28560
actggctaac ttattggccc ctggtcctag aggctgggag gtccgagatc gacaggccac    28620
```

```
ctctggcaag ggtctttgtg ctgccttatc ccatgacaga agggcaaaga gagggagaga   28680
gagacagcca gagagaaggg gaccaaactc atccttctgt cagagcccgc tcccacgaca   28740
atgatgttag tccatcatga ttacagagat gggggacaca ttcagaccac agcagccccc   28800
tcaacccgca cacactgcac attgagggga gggccgggag actggaagga acatcagag   28860 tctggagaag accaccagga tcaccagggc tatgctctca cccggcaccc agcaccgagg   28920
ggctcatggg aaacaagacg ggtctctcgg tgcacgagtg ctgggcacac atagtccacc   28980
gtgcatcctg ggctgatgat ctggaccctg gtcctgtgca gccctggggt ggggctccag   29040
gctgagatca gccacgtctg ggggaggaga cagtgttccc agtctcacct tgccccacgg   29100
actctgacag ggggttgaaga agcaaggagg ctccaaggac tggggagggg gagtctggcc   29160
gacgatctag gagcatcaag gcgcctgctc cctctcggcg tgcccggtc ctgtaggtgg   29220 tcagttatgc aatgccactg ccttcctacc tcacaaggag ggtgggtgga ctcagaagcc   29280
aggcccaggc ttccttcttg gctcaggcaa ggaacatagg gggctttgag ctttgcttat   29340
tcatttaaca actgaacccc tagtctgtgc caggccccca tttaaatggt ccctgggata   29400
cagcagggtc cagaatgggc ccagaccctg ccccatagc tgaccttctg gagagcctga   29460
ggagtgaggg gtgccctcca ggcacggcag acggggcagg ctctgcattc ggggctcca   29520 gctgctttcc caccacccac ccactccacc cgagcccttc tgggtcagct gggctcctgg   29580
ctctgcccgc tgggggtgca agacgccaag ttccttcctg gacagtgaga gaaccatgcc   29640
aaaaagaaat gaaaggaagg cagacggcga gatgagggag agggtgggca cccagccagg   29700
gaccgcagag acgaggagga ggcacagaga cccactgtcc ccagccactg ccagtgaggc   29760
tggcccaggg ccaggggctg ggcgtccctg gcatgcatgt ggctcccagt gcccccacgt   29820
ccaacaggag tggggcggcc ccctcttctg ccacatcccc atcccacctc ccattccatt   29880
cactggtctc attttaagt ttttctctcc cagttattca ggattgattt ggagagcaga   29940
gcgatggctg caggtggctc ttcatttcc ttcacctaag aagcaaacca tcatccaccc   30000
caagcttgtc tctccagcct gccccctaca tgaggacaac ctccctcctc ttccacggtg   30060
gcgctgttcc cactggaggc ccaggcttgg ccatccgttc attcttggag tcctcaagag   30120
attgtcagct ctgcagtggg gagcagccgc tgtcaaagac cctggaactt cctccctgct   30180
gcgtccacca acccccactg cccgctgggc actcccaacc tgaaacaagc ttgctcgctg   30240
caaaagcctc acctctgacc caacttccca ctcccaggat acccaacctg gccttccctc   30300
tggatacccc tgtgggctcc cctctgctga tgggttcccc tctccagctg tggcttccct   30360
ctgctgatgg ggtcccctct ccagctgggg ctccctccac tgatggggtt ccctctacag   30420
ctgtggctct ctccactgat ggggtcccct ccagctgg ggctccctcc actgatgtgg   30480
tcccctcttc agcttgggct ccctccactg atggggtccc ctcttcagct ggggctcctc   30540
tccactgaca gggtctcctt tccatctggg gctcccttgg ctgatgaagt cccttctcca   30600
ggtgaggctg ctctctgctg acagggtccc ctctccagct aggtctcctc tctgttgata   30660
gggtcccctc tccgggtggg ctcccctctg ctgacgggt cctctgatgg ggtccctact   30720 ccagggggc tcccctccat agatgagctc cccttcctgg gttgggtgac cctccgccc   30780 tatctgtgtc tgcaggttgg ggctaggcag tgctggccag catctgacaa cctcccctttt   30840 ctgttcttgg gcactgctca cttattcagg tctcagccag gcagcccctc caatggtaat   30900
cttcagagtc cccttcagca acacagcttc ccctctgtgg cccagctcat gctgaagtaa   30960
acaaggcaat gtcattaacg gctggtatca gcttgtacgg ggaaccagtg gccccagaag   31020
```

```
cctctgggga ggcccaggct gtgaggatca ggggtccgga agagcctcta gagcgggaga    31080
aagaggcctc aggggtccct cctcacaggg gatggtgaca acacggtagg gaatggaggg    31140
gtcagggctg ggtccaggac acggtgaccc tggccagaaa aggccgggcc tggctggcac    31200
ccgcacgaag ggaacggagc cagtgtggaa aagcaggccc cgtcctcttt ctgcactccc    31260
agccccttta aactacacac agcttgtagg aaggggatca gaggcccctg ggcgtcccat    31320
ggctatgctg cacctgggga catgaagcct agggtagctc agccagctct ggtcacggct    31380
gacagacagc ctcaccccaa cagcctcacc catccctcct cagggaacag ggtcctaaca    31440
agctgctttc cccatcccag tgttgaacaa aaactcatgg gtttagacaa gagtgaaggt    31500
gactcctcca ccacccatcc cacctccagc aggcagccac ccccaaaatt attgatttat    31560
taataaatca atgacaggtg ccagccagcc ccacctgtcc ccaacctgca aatgcagaca    31620
ggggtcactt ggtccaggga gaggagaccc tcagtggagg ggagacaccc tggagagggg    31680 acccatcag caaaggggag ccccagctgg agacagtaaa taggcagact attcactgtc    31740
ttccccctca agccaggccc acagagtcac agagtatagc caccagcctc ctgggcccac    31800 ccggaggcc ccaaccacac tcccctgct cagctcagcc cggatttctg gattctgctg     31860
cctgccaggg atcctgagga ggagatggta tcagagcctc accagcccttt ctcataccca    31920 ggagtcctca tgatgataac agtgtgtgcg ccaggctgtg caggtgctgg ccgggatcct    31980
ctgaggggac gagatctcca tgggagggca ccactctgat gtccatcctg ggcttccgtg    32040
gccctgcctg gccactgccc gctgctcttg gtcaagatca tggaccctca gaggccaacc    32100
aggcctcagc ctgtgcctac agcatcctct ctactgccgg gcttctgaat tgctccttcc    32160
tcctgtctcc cacccagagc aagaacgaag gggaggcccc cagagccctg cagcgccggg    32220
agagactccc atccccaccc cgcatgccat caacacaaac tgccggagag tttaggggat    32280
cccacgactt ggggtctcca aagagacccc cgggacatct catcgagacc ccctgggca     32340 ctgcatgctc aggcttccca cccctggccc acccatgggg gtgtgccag tcccgcatct     32400 cacccatat ccatgcatgc atgcatgaac ctgaaagcac cccacaccct ctggtgctca     32460
gtcctcccct cctccctggg gtccctccc ctccctgccc ccaagccttt gcatcccct     32520 gcaaacctca aaggggaa ctatttctgt cctgaaagca gagagggccc ttttcttggg     32580
acctctccgc catctctgcc tccactccca gctgctgtca gctctggcct ggcccctgca    32640
ggaagcaatc actggtctcc ctgtttccca tctggcccca aggtctgttc ttgcccttcg    32700
accagagagg tttgaaagca caactcgggc cctgcgtgcc ctgctcccca gggctccaca    32760
cctctgagca cccgcgcagt aacggaggct cccagccccg cctcgcccca gggtcccctc    32820
caacactctc tggccttggg cctttgctat acccgggggcc tggaagggcc ccctcatccc    32880
ccaagtgtca ggcaaaggtc tcagagcact gtccctgccc ggcgtgcttg gtcctgactg    32940
ctaggcccca aatcattcct tttcccatta cctcttggtt tctctgtagc tggggtcact    33000
accccaaatt cttgaattga ctgacgtgtc caactatttc atgttttccc cctctacact    33060
gggagcccta caagggcagg gcccctggg caagaatagt gccagccagg agcccctgga    33120
gaagatagct acacatgtgc cccaggcccc agatggcact cagccctgcc tgtcaatgct    33180
ggacataggg cagttttat cctggctttc tacacaagga ggaaagacta accatgccag     33240
cgggcagcgg ccggatcacg tatgtcagta gaactctgac ccctgagaag cctggaagcc    33300
aaaccacacc tctgtagcaa tcacgccaca gactcaggcc acggctaacg gctgccagtt    33360
cacctatttt tgcccccaac tcaagaccaa ctggaggaag gcaaatatgt ccctgacgaa    33420
```

```
gggtggccgc ctccagcctc cccagcccag agcctcagcc tccccagccc actgcctcca    33480
gcaacacaca tctgaagcct tctctgttgg ttggttttat tggtatttg gaagattgtt     33540 tgttttttgt tatgagatgg agcctcgctc tgtccccag gctggagtgc agtggcgcga     33600
tctcggctca ctgcaagctc cgcctcctgg gttcaagcca ttctcctgtc tcagcctccc    33660
gagtagctgg gactacaggc acccgccacc gtgccaggct gattttttg tattttagt      33720 agagacgggg tttcaccatg ttagccatga tggtcttgat ctcctgacct catgatctgg    33780
ccatctcggc ctcccaaagt gctgggatta caggcgtgag ccactgcacc tggcctttgg    33840
aaggtctttt tatcctttat tgagataaaa ttcttatgac ataaaactta gcataaactg    33900
tagacttagt tggtgtgact ttagagtagt ctcagaattg tgcaaccatc accactgcct    33960
acttttagaa cattttcaac atcccaaaga cagaaccccg taggcacctg ttagcagcca    34020
ctccccaccc agtccacgaa gccccaggca gccactcacc aatctacttt ccattaattt    34080
gcccattcta aacacttgaa aaaaatggta tcacaatggt cttttgggtt tggcttcttt    34140
ccctcagcat catacccca aagttcatcc atgttgtagc tcgtatcggt acttcattca     34200
tttttatggc tgaataatat tccactgtat ggatagaccg atattttgtt tatttattta    34260
ttcattgatg aacatttgaa ttgttccac ttttagcta ttaaaactag tgctggctgc      34320
gtgcagttgc tcatgcctgt aatcctagca cttgggagg atgaggcagg cggatcactt     34380
gaggccaaga gtttgagacc agcctggcca acatggtgaa accccatct ctaataaaaa     34440 tacaacaatt agccagacac ggtcatgcgt gcctgtaatc tcagctactc aggaggctga    34500
ggcaggggaa tctcttgaat ccggggggca gaggttgcag tgagccaaga tcgcgccact    34560
gcactccagc ctgggcaaca gaccaagact ctgtctcaaa aaacaaaaca aacaaaaca    34620 aaacaaacca gtactgctat gaacatgcat gtgcatattg ttatacagac atatgctttc    34680
atttctcttg gatacacaca cacacacaca cacacacaca cacacacaca cacacacacg    34740
tatatctagg actggaattg ctgatttta tggaaactct atatttagca ttttgagaaa     34800
cggccagtct gttttccgaa gtggctgcac tattttgcat tcccaccagc aatgaaggag    34860
ggttccaatt tctccatacc tctgccaaca cttgttattg tctgtctctt ttatttatag    34920
ccatcttgat gggtgcatcg tggtatctcg ctgtgttttg atttgcattt ccctgatgac    34980
taatgatggg gacatctttt catgagctta tcggtcatat gtacatcttc tttggagcaa    35040
gctctattct aatcctttgc ccatcattaa aggtaggtgg tttgtcttct tgttgataag    35100
ttagagttct ttacatgttt agatactagt cccttatcaa atagatgatt cacaaatgtt    35160
tgctgtcatt tcttgggttg tctttccact tccttgatgg tgtcttttca cgcacaaatg    35220 ttttagctt tggccaagtc caattatct atttttcct ttgttgcctg tgcttttggt       35280
agtgtatatt aaaaaccatt gtttaacaca aggtcaccaa gatttattcc tatgttcttt    35340
cctaaggatt ttattttc ttttcttttt ttttcttttt tttgagacaa agtctctctc      35400
tgtcgccaaa gctggagtgc aacggcacaa tctcagctca ctgcaacccc tgcctcctgg    35460
gttcaagcga ttcttctgcc tcagcctccc gagtagctgg gattacaggc gcccaccacc    35520
atgcccagct aattttgtg ttttagcag agacggggtt tcaccatgtt ggccaggctg     35580
gactcaaact cctgatctca ggtgatccac tcgcctcggc ctcccaaact gctgggatta    35640
caggtgtgag ccactgcgcc tggccttcct aaggatatca taatttagt gcttacattt      35700 aggtctacga tccattttga gttaattttt gtgcacagca tgaggtaggg gtccaacttc    35760
attcttttgc acatggatat ctagttgtcc cagcaccatt ttctgaaaag actattcctt    35820
```

```
cccccattga attgtcttgg tacccttgtc aaaaatcaac tgatggccgg tctgaaggta    35880
gtgagttatc tcaattgatt gttcacagtc agttacagat ggaacacctc gttctactct    35940
ttcccgcctt ctcactgctg cacttgaaca gtctttaaaa aaatcaattg accataaatg    36000
caaggatttg ttcttggagt ctcaacttta ctgcattgat ctgtaggtct atccttatgc    36060
cagtaccaca ttgtcttgat tactgtagct ttgcagtaag tttgaatcag gaaatgtgag    36120
ccctccggtt ttgctcttct cttttctaga tgttttggct attctgaaac ccttgtattt    36180
ccttatgaat ttgaggatca gcttgtaaaa agacagatgg gattttgata gagattgtga    36240
agctatagat gaattcggga gtttggccat cttaacatta tgtctcctga tccatgactg    36300
caggatatct ttccatttaa ttcgatactc tttgattcct ttcaaaaata ttttgtattt    36360
ttcagtacac aagttttatg catcttttgt tgcatttatt tctaggtatg ttcttttttgc   36420 caatattata aatgagattg tcttcttcac ttcattttttg gatggttcat tgctagtgta   36480
tagaaataaa atcgatgttt gtatattgat cttgtatcct gccacattgc tatgcatgtt    36540 tattagttttt aagggtttta gtggattttc tatatataat gtcatataat cagcaaatag   36600
aaagtttaat gtcttagtcc ttttgagctg ccacaacaga ctaccataaa ctgagtggct    36660
tataaacaac acaaatgtat ttcccacagt tctggagact gggatgtcca agatcaagac    36720
acccgtaggt ttggtgtctg gtcggggcct acttctgggt tcatagatga ctgtcttctc    36780
gctgtgtccc ccccatagtg aaaggaaggg gcccagggtc tttctaaggc ttcttttata    36840
aggacactaa tccaatatag gaaggctctg ccctcataac ctaatctccc aaaggcctca    36900
cttccaaatt ccatcacctg gggagtaaga atttcaacac tgggggaca cagatattca    36960 gacatagcat ttttcttctt cctttctaat atgggtgccc ttgacatctt tttcttacct    37020
aattgccctg ccagagcctt ccagacagtg ttgaatggaa gtggggagca ttcacccac    37080 cttactcctg atcataggg aagaactatc cggctttcac cactgagcac cacgttagct    37140
ggggtatttt tgtcagcgct ctttatcagg tggaggcagg tcccttctat ttctagtgag    37200
ttcagtgctt ttttttttttt ttaatcaggg aagagtgtga gcttgtgttt gggtgccttc    37260
cctgcgtctg ttgagatgat cttacggttt ctgtctctta ttctattgat atggcgtatt    37320
tattaccttg gttgcttttt ggatgttgat aacatccaaa ctcttctgcc accccttta    37380 atagaaagct gtacaactcc ccaacctgcc tgggcgtgtc tgcccaagat gagtgctagt    37440
ggccgactcc ctgctagagt gagcactgca taaacagcct ctgcttgtcc tcatttgagt    37500
gatcttcatg tattccacga gaaatcaagg cacaggggtc tcatggtctc atgaatggct    37560
ccaccaactg aaggtgtgct ccatcggggc tgtgagtcac ctcacgccag gcagaaaggt    37620
ctctctgtca aacatggctt caaggaacca gggacctggt tcctcccaca ggccaggccc    37680
tgcccctaag tgcaatggga atatatgcac atgtcacctg tcccaaaatg ctgggagatg    37740
gcacttctgc agatgggaa actgagggac cagcccgaag tcacggggag ggaagactc    37800 ctacacacag ggaggagaag aacccagccg ggctgcaaac gcctgcccgtt cctcaacgtg    37860 cctccggctg tgcccacatc gctccagcag ctctgccttc ctcaggcata agccttctca    37920 gggcaggga ggcccaggga gcggcgctcc catcccaggc cgggctgctg agcaagcccc    37980
tcccctttct cccctcatcc tctgacagag tccacctgaa tatttgtcct ggagccagga    38040
tggaagctcc accaggccca gctaacaaca ggaacccttt cagacgcact tctgggtgcg    38100
tactgtgcca gtatcacaca gacacaagcc atgtccttgt cagccatggg atccccaagg    38160
tccccatgag gtcacaccag tgggccactg ggaagggcac ttcagatgtg gagctcccat    38220
```

```
gggccaggcc ctgcgaagtg gtcctcctac cccctcatag ccagtcttcc ctgtgagcct    38280
gcaagtgact gtgaatgtga gttccactct ggagctaaga cgggctgctg cccccgcaat    38340
cagatgtcag gcccatgaag                                                38360
```

ISOLATED GENOMIC POLYNUCLEOTIDE FRAGMENTS FROM THE P15 REGION OF CHROMOSOME 11

This application claims priority under 35 U.S.C. 119(e) from provisional application Ser. No. 60/244,705, filed Oct. 31, 2000, the contents of which are incorporated herein by reference.

FIELD OF THE INVENTION

The invention is directed to isolated genomic polynucleotide fragments located in the p15 region of chromosome 11.

BACKGROUND OF THE INVENTION

Chromosome 11 contains genes encoding, for example, KCNQ1, a voltage-gated potassium channel; IPL, a homolog of a mouse apoptosis-inducing entity; human achaete-scute homolog 2 (HASH2), human SMS3, human tumor suppressing subtransferable candidate 6 (TSSC6), human ribosomal protein L26 (RIBO26), cluster of differentiation antigen 81 (CD81) and tumor suppressing subtransferable candidate 4 (TSSC4). Human achaete-scute homolog 2 (HASH2), human SMS3, human tumor suppressing subtransferable candidate 6 (TSSC6), human ribosomal protein L26 (RIBO26), cluster of differentiation antigen 81 (CD81) and tumor suppressing subtransferable candidate 4 (TSSC4) are discussed in further detail below. Genes for the latter six proteins are located in the p15 region of chromosome 11, a region known to be associated with the Beckwith-Wiedemann Syndrome (Itoh et al. Am. J. Genet. 92, 111-6, 2000) and some childhood tumors.

Beckwith-Wiedemann Syndrome is characterized by pre and postnatal overgrowth up to 160% of normal birthweight, macroglossia, hypoglycemia, hemihypertrophy and childhood tumors, such as Wilm's tumor (Reik et al., 1998, Trends Genet. 13:330-334). This syndrome appears to be associated with deregulation of imprinting. Imprinted genes are genes that are predominantly expressed from one of the parental chromosomes. There appears to be two imprinted subdomains, since the imprinted gene domain of 11p15 contains at least two imprinted subdomains (Lee et al., 1999, Hum. Mol. Genet. 8:683-690). Mosaicism may also play some role in the Beckwith-Wiedemann Syndrome phenotype and may explain the variable phenotypes in Beckwith-Wiedemann Syndrome patients (Itoh et al., 2000, Am. J. Med. Genet. 92:111-116).

Human Achaete-scute Homolog 2 (HASH2)

HASH2 is a basic helix-loop-helix protein that serves as a critical transcription factor for the development of the trophectoderm. Mice deficient in the HASH2 homolog, MASH2, die 10 days postcoitum due to placental failure (Guillemot et al., Nature 371, 333-6, 1994).

Human Tumor Suppressing Subtransferable Candidates 4 and 6 (TSSC4 and TSSC6)

Both TSSC 4 and TSSC6 are believed to function as tumor-suppressing proteins in that the genes are among the genes of a subchromosomal fragment that suppresses in vitro growth of the rhabdomyosarcoma cell line RD (Koi et al., Science 260, 361-4, 1993).

Human Ribosomal Protein L26 (RIBO26)

RIBO26 is one of the approximately 80 proteins that compose the human ribosome (Kenmochi, N. et al., Genome Res. 8, 509-23, 1998). It has been found in mice to be induced by LPS and IFN gamma but is down regulated by TNF-alpha (Segade et al., 1996, Life Sci. 58:277-285).

Human Cluster of Differentiation Antigen 81 (CD81)

CD81 (also called TAPA1) binds the E2 envelope protein of the human hepatitis C virus and is believed to play a role in hepatitis C infection (Pileri et al., Science 282, 938-41, 1998). CD81 also appears to play a role in T cell activation (Witherden et al., 2000, J. Immunol. 165:1902-1909).

OBJECTS OF THE INVENTION

Although cDNAs encoding the above-disclosed proteins have been isolated, their precise locations and exon/intron/regulatory element organizations on chromosome 11 have not been determined. Furthermore, genomic DNA encoding these polypeptides have not been isolated. Noncoding sequences play a significant role in regulating the expression of polypeptides as well as the processing of RNA encoding these polypeptides.

There is clearly a need for obtaining genomic polynucleotide sequences encoding these polypeptides. Therefore, it is an object of the invention to isolate such genomic polynucleotide sequences.

There is also a need to develop means for identifying mutations, duplications, translocations, polysomies and mosaicism associated with Beckwith-Wiedemann syndrome.

SUMMARY OF THE INVENTION

The invention is directed to an isolated genomic polynucleotide, said polynucleotide obtainable from human chromosome 11 having a nucleotide sequence at least 95% identical to a sequence selected from the group consisting of:

(a) a polynucleotide encoding a polypeptide selected from the group consisting of human achaete-scute homolog 2 (HASH2) depicted in SEQ ID NO:1, human SMS3 depicted in SEQ ID NO:2, human tumor suppressing subtransferable candidate 6 (TSSC6) depicted in SEQ ID NO:3, ribosomal protein L26 (RIBO26) depicted in SEQ ID NO:4, cluster of differentiation antigen 81 (CD81) depicted in SEQ ID NO:5, and tumor suppressing subtransferable candidate 4 (TSSC4) depicted in SEQ ID NO:6;

(b) a polynucleotide selected from the group consisting of SEQ ID NO:7 which Encodes human HASH2 depicted in SEQ ID NO:1, SEQ ID NO:8 which encodes human SMS3 depicted in SEQ ID NO:2, SEQ ID NO:9 which encodes human TSSC6 1 depicted in SEQ ID NO:3, SEQ ID NO:10 which encodes ribosomal protein L26 (RIBO26) depicted in SEQ ID NO:4, SEQ ID NO:11 which encodes human CD81 depicted in SEQ ID NO:5 and SEQ ID NO:12 which encodes human TSSC4 depicted in SEQ ID NO:6;

(c) a polynucleotide which is a variant of SEQ ID NOS:7, 8, 9, 10, 11 or 12, (d) a polynucleotide which is an allelic variant of SEQ ID NOS:7, 8, 9, 10, 11 or 12:

(e) a polynucleotide which encodes a variant of SEQ ID NOS:1, 2, 3, 4, 5, or 6;

(f) a polynucleotide which hybridizes to any one of the polynucleotides specified in (a)-(e) and (g) a polynucleotide that is a reverse complement to the polynucleotides specified in (a) to (f), as well as nucleic acid constructs, expression vectors and host cells containing these Polynucleotide sequences.

The polynucleotides of the present invention may be used for the manufacture of a gene therapy for the prevention, treatment or amelioration of a medical condition by adding an amount of a composition comprising said polynucleotide effective to prevent, treat or ameliorate said medical condition.

The invention is further directed to obtaining these polypeptides by (a) culturing host cells comprising these sequences under conditions that provide for the expression of said polypeptide and (b) recovering said expressed polypeptide.

The polypeptides obtained may be used to produce antibodies by (a) optionally conjugating said polypeptide to a carrier protein;

(b) immunizing a host animal with said polypeptide or peptide-carrier protein conjugate of step (b) with an adjuvant and (c) obtaining antibody from said immunized host animal.

The invention is further directed to polynucleotides that hybridize to noncoding regions of said polynucleotide sequences as well as antisense oligonucleotides to these polynucleotides as well as antisense mimetics. The antisense oligonucleotides or mimetics may be used for the manufacture of a medicament for prevention, treatment or amelioration of a medical condition. The invention is further directed to kits comprising these polynucleotides and kits comprising these antisense oligonucleotides or mimetics.

In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to diagnose a pathological condition in a subject comprising (a) determining the presence or absence of a mutation in the polynucleotides of the present invention and (b) diagnosing a pathological condition or a susceptibility to a pathological condition based on the presence or absence of said mutation.

The invention is also directed to an isolated polynucleotide from the p15 region of human chromosome 11 selected from the group consisting of SEQ ID NOS: 13 and 14. SEQ ID NO:13 consists of nucleotide sequence immediately preceding the HASH2 gene; SEQ ID NO:14 consists of the gap between the RIBO26 and CD81 genes. Both of these polynucleotides are located in the imprinted subdomains of 11p15. Oligonucleotides derived from these sequences may be used to identify mutations, duplications, translocations, polysomies and mosaicism associated with Beckwith-Wiedemann syndrome. Furthermore, oligonucleotides derived from SEQ ID NO:13 may also be used as a marker for the HASH2 gene and SEQ ID NO:14 may be used as a marker for the RIBO26 and/or CD81 gene.

DETAILED DESCRIPTION OF THE INVENTION

The invention is directed to isolated genomic polynucleotide fragments that encode HASH2, human SMS3, human TSSC6, human RIBO26, human CD81 and human TSSC4, which in a specific embodiment are the HASH2, SMS3, TSSC6, RIBO26, CD81 and TSSC4 genes, as well as vectors and hosts containing these fragments and polynucleotide fragments hybridizing to noncoding regions, as well as antisense oligonucleotides to these fragments.

As defined herein, a "gene" is the segment of DNA involved in producing a polypeptide chain; it includes regions preceding and following the coding region, as well as intervening sequences (introns) between individual coding segments (exons).

As defined herein "isolated" refers to material removed from its original environment and is thus altered "by the hand of man" from its natural state. An isolated polynucleotide can be part of a vector, a composition of matter or can be contained within a cell as long as the cell is not the original environment of the polynucleotide.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand.

The HASH2 gene is 17290 base pairs in length and contains a single exon (see Table 1 below). The HASH2 gene is situated in genomic clone AC002536 at nucleotides 17081-34370. The SMS3 gene is 25970 base pairs in length and contains 3 exons (Table 2). The SMS3 gene is situated in genomic clone AC002536 at nucleotides 34371-60340. The TSSC6 gene is 30196 base pairs in length and contains 9 exons (Table 3). The TSSC6 gene is situated in genomic clone AC002536 at nucleotides 51731-81926. The RIBO26 gene is 21630 base pairs in length and contains a single exon (see Table 4 below for location of the exon). As will be discussed in further detail below, the RIBO26 gene is situated in genomic clone AC002536 at nucleotides 77701-99330. The CD81 gene is 37113 base pairs in length and contains 8 exons (Table 5). SEQ ID NO:11 which contains the CD81 gene begins at nucleotide 120961 in genomic clone AC002536 and extends to nucleotide 19180 in the downstream genomic clone AC003693. Clones AC002536 (140977 base pairs) and AC003693 (155074 base pairs) have a 2084 base pair overlap. The TSSC4 gene is 15540 base pairs in length and contains a single exon (Table 6). The TSSC4 gene is situated within nucleotides 3641-19180 (see SEQ ID NO:12) in geomic clone AC003693.

The polynucleotides of the invention have at least a 95% identity and may have a 96%, 97%, 98% or 99% identity to the polynucleotides depicted in SEQ ID NOS:7, 8, 9, 10, 11 or 12, as well as the polynucleotides in reverse sense orientation, or the polynucleotide sequences encoding the HASH2, SMS3, TSSC6, RIBO26, CD81 or TSSC4 polypeptides depicted in SEQ ID NOS:1, 2, 3, 4, 5 or 6 respectively.

A polynucleotide having 95% "identity" to a reference nucleotide sequence of the present invention, is identical to the reference sequence except that the polynucleotide sequence may include, on average, up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are:Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identify, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total numbers of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time, the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for purposes of the present invention.

A polypeptide that has an amino acid sequence at least, for example, 95% "identical" to a query amino acid sequence is identical to the query sequence except that the subject polypeptide sequence may include, on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted (indels), deleted, or substituted with another amino acid. These alterations of the reference sequence may occur at the amino or carboxy terminal positions of the reference amino acid sequence or anywhere between those terminal positions, interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutlag et al. (Com. App. Biosci. (1990) 6:237-245). In a sequence alignment, the query and subject sequence are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

The invention also encompasses polynucleotides that hybridize to the polynucleotides depicted in SEQ ID NOS: 7, 8, 9, 10, 11 or 12. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5× SSC, 0.1% SDS, 0.25% milk, and no formamide; or 40% formamide, 5× SSC, 0.5% SDS). Moderate stringency hybridization conditions correspond to a higher temperature of 55° C., e.g., 40% formamide, with 5× or 6× SCC. High stringency hybridization conditions correspond to the highest temperature of 65° C., e.g., 50% formamide, 5× or 6× SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the variant polypeptides may differ from the amino acid sequences depicted in SEQ ID NOS:1, 2, 3, 4, 5 or 6 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the HASH2, SMS3, TSSC6, RIBO26, CD81 and TSSC4 genes. These include but are not limited to an intron, a 5'-non-coding region, a 3'-non-coding region and splice junctions (see Tables 1-6), as well as transcription factor binding sites (see Table 7). The polynucleotide fragments may be a short polynucleotide fragment which is between about 8 nucleotides to about 40 nucleotides in length. Such shorter fragments may be useful for diagnostic purposes. Such short polynucleotide fragments are also preferred with respect to polynucleotides containing or hybridizing to polynucleotides containing splice junctions. Alternatively larger fragments, e.g., of about 50, 150, 500, 600 or about 2000 nucleotides in length may be used.

TABLE 1

Exon/Intron Regions of the human achaete-scute homolog 2 (HASH2) gene, 17290 bp, reference cDNA accession number U77629; reverse strand coding.

| Exon | Location (nucleotide no./amino acid no.) |
|---|---|
| 1 | 7031-7609 |
|   | 193-1 |
|   | stop codon 7028-7030 |

TABLE 2

Exon/Intron Regions of the human SMS3 gene, 25970 bp, reference cDNA accession number AB029488; reverse strand coding.

| Exon | Location (nucleotide no./amino acid no.) |
|---|---|
| 3 | 18962-19210 |
|   | 132-50 |
| 2 | 20023-20118 |
|   | 49-18 |
| 1 | 21261-21311 |
|   | 17-1 |
|   | stop codon 18959-18961 |

TABLE 3

Exon/Intron Regions of the human tumor suppressing subtransferable candidate 6 (TSSC6) gene, 30196 bp, reference cDNA accession number NM_005705; plus strand coding.

| Exon | Location (nucleotide no./amino acid no.) |
|---|---|
| 1 | 5011-5100 |
|   | 1-30 |
| 2 | 6249-6347 |
|   | 31-63 |
| 3 | 10879-10953 |
|   | 64-88 |
| 4 | 15797-15898 |
|   | 89-122 |
| 5 | 16628-16714 |
|   | 123-151 |
| 6 | 18372-18455 |
|   | 152-179 |
| 7 | 18719-18811 |
|   | 180-210 |
| 8 | 19488-19664 |
|   | 211-270 |
| 9 | 20005-20064 |
|   | 271-290 |
|   | stop codon 20065-20067 |

TABLE 4

Exon/Intron Regions of the human ribosomal protein L26 gene, 21630 bp, reference cDNA accession number AF083248; reverse strand coding.

| Exon | Location (nucleotide no./amino acid no.) |
|---|---|
| 1 | 11490-11924 |
|   | 145-1 |
|   | stop codon 11487-11489 |

TABLE 5

Exon/Intron Region of the human CD81 gene, 37113 bp, reference accession number NM_004356; plus strand coding.

| Exon | Location (nucleotide no./amino acid no.) |
|---|---|
| 1 | 10471-10536 |
| | 1-22 |
| 2 | 23333-23446 |
| | 23-60 |
| 3 | 27015-27113 |
| | 61-93 |
| 4 | 27893-27964 |
| | 94-117 |
| 5 | 28334-28441 |
| | 118-153 |
| 6 | 28790-28891 |
| | 154-187 |
| 7 | 29549-29635 |
| | 188-216 |
| 8 | 29725-29784 |
| | 217-236 |
| | stop codon 29785-29787 |

TABLE 6

Exon/Intron Region of the human tumor suppressing subtransferable candidate 4 (TSSC4) gene, 15540 bp, reference cDNA accession number NM_005706; plus strand coding.

| Exon | Location (nucleotide no./amino acid no.) |
|---|---|
| 1 | 13982-14968 |
| | 1-329 |
| | stop codon 14969-14971 |

TABLE 7

TRANSCRIPTION FACTOR BINDING SITES

| BINDING SITES | HASH2 | SMS3 | TSSC6 | RIBO26 | CD81 | TSSC4 |
|---|---|---|---|---|---|---|
| AP1FJ_Q2 | | 14 | 8 | 10 | 16 | |
| AP1_C | 4 | 6 | 8 | 10 | 8 | |
| AP1_Q2 | 4 | 7 | 5 | 10 | 6 | |
| AP1_Q4 | | | 4 | | 5 | 5 |
| AP4_Q5 | 30 | 44 | 55 | 12 | 71 | |
| AP4_Q6 | 14 | 22 | 26 | 4 | 34 | |
| ARNT_01 | 7 | 4 | | | 6 | |
| BRN2_01 | 5 | | | 4 | | |
| CDPCR3HD_01 | | | | 5 | 8 | |
| CEBPB_01 | | 9 | 5 | 13 | 4 | |
| CETS1P54_01 | | | | | 5 | |
| CMYB_01 | 4 | | | | | |
| CP2_1 | | 4 | 5 | | | |
| CREB_02 | | | | | 4 | |
| CREB_Q4 | | | | | 4 | |
| CREL_01 | 5 | 11 | 11 | | 7 | |
| DELTAEF1_01 | 42 | 49 | 67 | 57 | 84 | |
| E47_01 | | | 6 | | 17 | |
| FREAC7_01 | | 4 | 6 | | | |
| GATA1_02 | 6 | 7 | 6 | 9 | 11 | |
| GATA1_03 | 8 | 7 | 4 | 15 | 5 | |
| GATA1_04 | 9 | 16 | 10 | 11 | 10 | |
| GATA1_05 | | 5 | 7 | 5 | | |
| GATA1_06 | 4 | 7 | | | | |
| GATA2_02 | 7 | 12 | 6 | 8 | 4 | |
| GATA2_03 | | 6 | | | | |
| GATA3_02 | 4 | 6 | | | | |
| GATA3_03 | | 4 | | | | |
| GATA_C | 6 | 13 | 5 | 7 | 7 | |
| GC_01 | | | | | 7 | |
| GFI1_01 | | 6 | | | | |
| HFH2_01 | | | 4 | 4 | | |
| HFH3_01 | 5 | | 9 | 7 | 4 | |
| HFH8_01 | | | | 4 | 5 | |

TABLE 7-continued

TRANSCRIPTION FACTOR BINDING SITES

| BINDING SITES | HASH2 | SMS3 | TSSC6 | RIBO26 | CD81 | TSSC4 |
|---|---|---|---|---|---|---|
| IK1_01 | | | 4 | | | |
| IK2_01 | 22 | 24 | 34 | 33 | 56 | |
| LMO2COM_01 | 21 | 33 | 41 | 18 | 57 | 7 |
| LMO2COM_02 | 13 | 15 | 10 | 11 | 14 | |
| LYF1_01 | 5 | 7 | | 4 | 6 | |
| MAX_01 | 4 | | | | | |
| MYCMAX_02 | 4 | | | | | |
| MYOD_01 | | | | | 4 | |
| MYOD_Q6 | 13 | 13 | 22 | 5 | 34 | 11 |
| MZF1_01 | 73 | 106 | 136 | 63 | 211 | 21 |
| NF1_Q6 | | 5 | 6 | | 6 | |
| NFAT_Q6 | 23 | 33 | 20 | 39 | 16 | |
| NKX25_01 | 6 | 4 | 4 | 7 | 4 | |
| NKX25_02 | | | | 4 | | |
| NMYC_01 | 14 | 15 | 4 | 10 | | |
| OCT1_02 | | | | 6 | | |
| PADS_C | | | 6 | | 4 | |
| RORA1_01 | | 4 | | | | |
| S8_01 | 5 | 25 | 15 | 23 | 7 | |
| SOX5_01 | 5 | 9 | 5 | 8 | 11 | |
| SP1_Q6 | 6 | | | | 11 | |
| SRY_02 | | 4 | | 6 | 9 | |
| STAT_01 | 5 | | | | 5 | |
| TATA_01 | | | | 6 | | |
| TCF11_01 | 24 | 27 | 27 | 43 | 43 | 9 |
| USF_01 | 14 | 16 | 4 | 10 | 12 | 4 |
| USF_C | 14 | 16 | 4 | 10 | 12 | 6 |
| USF_Q6 | | 10 | | | 6 | |
| VMYB_02 | 9 | 5 | | 4 | 11 | |

Abbreviations: HASH2, human achaete-scute homolog 2; TSSC6, tumor suppressing subtransferable candidate 6; RIBO26, ribosomal protein L26; CD81, cluster of differentiation antigen 81; and TSSC4, tumor suppressing subtransferable candidate 4.

In a specific embodiment, such noncoding sequences are expression control sequences. These include but are not limited to DNA regulatory sequences, such as promoters, enhancers, repressors, terminators, and the like, that provide for the regulation of expression of a coding sequence in a host cell. In eukaryotic cells, polyadenylation signals are also control sequences.

In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. A transcriptional control sequence is "operatively linked" to a polynucleotide encoding a heterologous polypeptide sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the DNA sequence under the control of the expression control sequence and production of the desired product encoded by the polynucleotide sequence. If a gene that one desires to insert into a recombinant DNA molecule does not contain an appropriate start signal, such a start signal can be inserted upstream (5') of and in reading frame with the gene.

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

Expression of Polypeptides

Isolated Polynucleotide Sequences

The human chromosome 11 genomic clone of accession number AC002536 has been discovered to contain the HASH2 gene, the SMS3 gene, the TSSC6 gene, the RIBO26, part of the CD81 gene by Genscan analysis (Burge et al., 1997, J. Mol. Biol. 268:78-94), BLAST2 and TBLASTN analysis (Altschul et al., 1997, Nucl. Acids Res. 25:3389-3402), in which the sequence of AC002536 was compared to the HASH2 cDNA sequence, accession number U77629, the human SMS3 cDNA sequence accession number AB029488, TSSC6 cDNA sequence accession number NM_005705, and the RIBO26 cDNA sequence, accession number AF083248. The remainder of the CD81 gene and the TSSC4 gene were found by similar means in the downstream clone AC003693. The accession numbers for the CD81 and TSSC4 cDNAs are, respectively, NM_004356 and NM_005706.

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) or long range PCR may be used. In a specific embodiment, 5'- or 3'- non-coding portions of each gene may be identified by methods including but are not limited to, filter probing, clone enrichment using specific probes and protocols similar or identical to 5'- and 3'- "RACE" protocols which are well known in the art. For instance, a method similar to 5'- RACE is available for generating the missing 5'- end of a desired full-length transcript. (Fromont-Racine et al., 1993, Nucl. Acids Res. 21:1683-1684).

Once the DNA fragments are generated, identification of the specific DNA fragment containing the desired HASH2 gene, the SMS3 gene, the TSSC6 gene, the RIBO26 gene, the CD81 gene, the TSSC4 gene, SEQ ID NO:13 or SEQ ID NO:14 may be accomplished in a number of ways. For example, if an amount of a portion of the HASH2 gene, the SMS3 gene, the TSSC6 gene, the RIBO26 gene, the CD81 gene or the TSSC4 gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in SEQ ID NOS:7, 8, 9, 10, 11, 12, 13 or 14. Preferably, a fragment is selected that is highly unique to the polynucleotides of the invention. Those DNA fragments with substantial homology to the probe will hybridize. As noted above, the greater the degree of homology, the more stringent hybridization conditions can be used. In one embodiment, low stringency hybridization conditions are used to identify a homologous HASH2, SMS3, TSSC6, or RIBO26 polynucleotide. However, in a preferred aspect, and as demonstrated herein, a nucleic acid encoding a polypeptide of the invention will hybridize to a nucleic acid derived from the polynucleotide sequence depicted in SEQ ID NOS:7, 8, 9, 10, 11 or 12 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the HASH2, SMS3, the TSSC6, RIBO26, CD81 or TSSC4 polypeptide.

A gene encoding HASH2, SMS3, TSSC6, RIBO26, CD81 or TSSC4 polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the HASH2 gene (nucleotides 7028-7609 of SEQ ID NO:7), SMS3 gene (nucleotides 18959-21311 of SEQ ID NO:8), TSSC6 gene (nucleotides 5011-20067 of SEQ ID NO:9), RIBO26 gene (nucleotides 11487-11924 of SEQ ID NO:10), CD81 gene (nucleotides 10471-29787 of SEQ ID NO:11) or TSSC4 gene (nucleotides 13982-14971 of SEQ ID NO:12) operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The invention is further directed to a nucleic acid construct comprising expression control sequences derived from SEQ ID NOS: 7, 8, 9, 10, 11 or 12 and a heterologous polynucleotide sequence. "Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences which regulate the expression of the polynucleotide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the prokaryotic beta-lactamase gene (Villa-Komaroff et al., 1978, *Proc. Natl. Acad. Sci. USA* 75: 3727-3731), as well as the tac promoter (DeBoer et al., 1983, *Proc. Natl Acad. of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8: 423-488.

Eukaryotic promoters may be obtained from the genomes of viruses such as polyoma virus, fowlpox virus, adenovirus, bovine papilloma virus, avian sarcoma virus, cytomegalovirus, a retrovirus, hepatitis-B virus and SV40. Alternatively, heterologous mammalian promoters, such as the actin promoter or immunoglobulin promoter may be used.

The constructs of the invention may also include enhancers. Enhancers are cis-acting elements of DNA, usually from about 10 to about 300 bp that act on a promoter to increase its transcription. Enhancers from globin, elastase, albumin, alpha-fetoprotein, and insulin enhancers may be used. However, an enhancer from a virus may be used; examples include SV40 on the late side of the replication origin, the cytomegalovirus early promoter enhancer, the polyoma enhancer on the late side of the replication origin and adenovirus enhancers.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region, which codes for an amino acid sequence linked to the amino terminus of the polypeptide which can direct the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the polynucleotide of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. An example of suitable selectable markers for mammalian cells are those that enable the identification of cells competent to take of the nucleic acids of the present invention, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980).

The vectors of the present invention preferably contain an element(s) that permits stable integration of the vector into the host cell genome or autonomous replication of the vector in the cell independent of the genome of the cell.

For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional polynucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a polynucleotide sequence of the present invention may be inserted into the host cell to increase production of the gene product. An increase in the copy number of the polynucleotide sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, or a *Streptomyces* cell, e.g., *Streptomyces lividans* or *Streptomyces murinus*, or gram negative bacteria such as *E. coli* and *Pseudomonas sp.*

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian cell (e.g., human cell), an insect cell, a plant cell or a fungal cell. Mammalian host cells that could be used include but are not limited to human Hela, embryonic kidney cells (293), lung cells, H9 and Jurkat cells, mouse NIH3T3 and C127 cells, Cos 1, Cos 7 and CVI, quail QC1-3 cells, mouse L cells and Chinese Hamster ovary (CHO) cells. These cells may be transfected with a vector containing a transcriptional regulatory sequence, a protein coding sequence and transcriptional termination sequences by lipid-mediated, calcium phosphate mediated or DEAE-dextran mediated transfection (reviewed in Sambrook and Russell, Molecular Cloning, A Laboratory Mannual, Cold Spring Harbor Laboratroy Press, Cold Spring Harbor, N.Y., 2001). Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells. The polynucleotide may be directly introduced into the eukaryonic cell via electroporation, bolistics, or polybrene (reviewed in Sambrook and Russell, supra).

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). The fungal host cell may also be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980). The fungal host cell may also be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming Fusarium species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182-187, Academic Press, Inc., New York; Ito et al., 1983, *Journal of Bacteriology* 153: 163; and Hinnen et al., 1978, Proc. e Natl Acad. f Sci.s USA 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, the presence of the HASH2 and RIBO26 protein may be detected using standard transcription assays. The presence of TSSC4 and TSSC6 may be detected by assaying for tumor suppressor activity in rhabdomyosarcoma cells (Koi et al., 1993, Science 260:361-364). The presence of CD81 may be detected by assaying for binding to E2 hepatitis C protein (Allander et al., 2000, J. Gen. Virol. 81:2451-2459).

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Antibodies

According to the invention, the HASH2, SMS3, TSSC6, RIBO26, CD81 or TSSC4 polypeptides produced according to the method of the present invention may be used as an immunogen to generate any of these antibodies. Such antibodies include but are not limited to polyclonal, monoclonal, chimeric, single chain, Fab fragments, and an Fab expression library.

Various procedures known in the art may be used for the production of antibodies. For the production of antibody, various host animals can be immunized by injection with the polypeptide thereof, including but not limited to rabbits, mice, rats, sheep, goats, etc. In one embodiment, the polypeptide or fragment thereof can optionally be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the HASH2, SMS3, TSSC6, RIBO26, CD81 or TSSC4 polypeptide, any technique that provides for the production of antibody molecules by continuous cell lines in culture may be used. These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for the HASH2, SMS3, TSSC6, RIBO26, CD81 or TSSC4 polypeptide together with genes from a human antibody molecule of appropriate biological activity can be used; such antibodies are within the scope of this invention.

According to the invention, techniques described for the production of single chain antibodies (U.S. Pat. No. 4,946,778) can be adapted to produce polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for the HASH2, SMS3, TSSC6, RIBO26, CD81 or TSSC4 polypeptides.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a particular polypeptide, one may assay generated hybridomas for a product which binds to a particular polypeptide fragment containing such epitope. For selection of an antibody specific to a particular polypeptide from a particular species of animal, one can select on the basis of positive binding with the polypeptide expressed by or isolated from cells of that species of animal.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Uses of Polynucleotides

Diagnostics

Polynucleotides containing noncoding regions of SEQ ID NOS:7, 8, 9, 10, 11, 12, 13 or 14 may be used as probes for detecting mutations from samples from a patient. Genomic DNA may be isolated from the patient. A mutation(s) may be detected by Southern blot analysis, specifically by hybridizing restriction digested genomic DNA to various probes and subjecting to agarose electrophoresis. Alternatively, these polynucleotides may be used as PCR primers and be used to amplify the genomic DNA isolated from the patients. Additionally, primers may be obtained by routine or long range PCR that yield products containing contiguous intron/exon sequence and products containing more than one exon with intervening intron. The sequence of the amplified genomic DNA from the patient may be determined using methods known in the art. Such probes may be between 10-100 nucleotides in length and may preferably be between 20-50 nucleotides in length. Specifically, probes derived from SEQ ID NOS: 13 or 14 may be used to identify mutations duplications, translocations, polysomies and mosaicism associated with Beckwith-Wiedemann syndrome.

Thus the invention is thus directed to kits comprising these polynucleotide probes. In a specific embodiment, these probes are labeled with a detectable substance.

Antisense Oligonucleotides and Mimetics

The antisense oligonucleotides or mimetics of the present invention may be used to decrease levels of a polypeptide. For example, HASH2 is required for development of the trophoblast. Therefore, the HASH2 antisense oligonucleotides of the present invention could be used as an antifertility agent. RIBO026 is expressed in abundance in small cell tumors of the lung. RIBO026 antisense sequences could be used to inhibit small cell tumor growth. CD81 plays a role in T cell activation, and its antisense sequences may help control autoimmune disorders in which T cell activation is uncontrolled. CD81 also binds the human hepatitis C virus; thus CD81 antisense sequences may, by reducing CD81 expression, reduce the infectivity of the human hepatitis C virus. The TSSC4 and 6 proteins act as tumor suppressors. Therefore, antisense sequences may act as antiapoptosis agents.

The HASH2, SMS3, TSSC6, RIBO26, CD81 and TSSC4 genes are all situated in a region of chromosome 11 known to be associated with the Beckwith-Wiedemann Syndrome. Thus, antisense sequences of any of these six genes may provide means of managing patients with the Beckwith-Wiedemann Syndrome. Furthermore, antisense oligonucleotides of SEQ ID NOS:13 or 14 may be used for the same purpose.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ as found to be effective in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, HASH2 is necessary for development of the trophoblast, RIBO26 is a component of the ribosome, TSSC6 and TSSC4 are involved in repressing tumor growth, and CD81 is involved in T cell activation. Therefore, the HASH2 gene may be used to treat some forms of infertility. The CD81 gene may be used in patients whose ability to activate T cells is impaired. CD81 also binds the human hepatitis C virus, thus gene therapy designed to yield a secretable form of CD81 may, by binding the virus in an excretable form, reduce the spread of hepatitis C. Given the tumor suppressing actions of TSSC6 and TSSC4, their genes may be used to prevent tumor growth. RIBO26 may be used to treat disorders in which ribosome assembly is defective. The SMS3 gene is situated within the Beckwith-Wiedemann Syndrome locus and may thus be useful for treatment of patients in which the SMS3 gene is nonfunctional.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," *Science*, 247, 1465-1468, 1990; and Wolff, Jon A, "Human dystrophin expression in mdx mice after intramuscular injection of DNA constructs," *Nature*, 352, 815-818, 1991. As used herein, vectors are agents that transport the gene into the cell without degradation and include a promoter yielding expression of the gene in the cells into which it is delivered. As will be discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes:

a) Biological agents derived from viral, bacterial or other sources.

b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous poly A addition signals. Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN" and LIPOFECTACE", which are formed of cationic lipids such as N-[1-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, Nature 337:387 (1989)). Intravenous injection of cationic lipid-plasmid complexes into mice has been shown to result in expression of the DNA in lung (Brigham et al., Am. J. Med. Sci.298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J -P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is $N^4$-spermine cholesteryl carbamate (GL-67) disclosed in U.S. Pat. No. 5,767,099. Additional preferred lipids include $N^4$-spermidine cholestryl carbamate (GL-53) and 1-($N^4$-spermidine) -2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class I molecule complexed to beta2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Various references are cited herein, the disclosure of which are incorporated by reference in their entireties.

What is claimed is:

1. An isolated genomic polynucleotide, said polynucleotide obtainable from the p15 region of human chromosome 11 selected from the group consisting of:
   (a) the polynucleotide of SEQ ID NO:11;
   (b) a polynucleotide fragment of (a) that comprises nucleotides 10471-29787 of SEQ ID NO:11 and
   (c) the full complement of (a) or (b).

2. A nucleic acid construct comprising the polynucleotide of claim 1.

3. An expression vector comprising the polynucleotide of claim 1.

4. A recombinant host cell comprising the polynucleotide of claim 1.

5. A method for obtaining human cluster of differentiation antigen 81 comprising:
   (a) culturing the recombinant host cell of claim 4 under conditions that provide for the expression of obtaining human cluster of differentiation antigen 81 and
   (b) recovering said human cluster of differentiation antigen 81.

6. An isolated polynucleotide consisting of an intron fragment of SEQ ID NO:11 or its complementary sequence, wherein said intron fragment or its complementary sequence is at least 20 nucleotides in length.

7. A composition comprising the polynucleotide of claim 1 and a carrier or diluent.

8. A composition comprising the polynucleotide of claim 6 and a carrier or diluent.

9. A kit comprising the polynucleotide of claim 1.

10. A kit comprising the polynucleotide of claim 6.

11. The isolated polynucleotide of claim 6, wherein said intron is selected from the group consisting of nucleotides 10537-23332, 23447-27014, 27114-27892, 27965-28333, 28442-28789, 28892-29548 and 29636-29724 of SEQ ID NO:11 or reverse strand thereof.

12. The polynucleotide according to claim 1, wherein said polynucleotide encodes a polypeptide depicted in SEQ ID NO:5.

13. An isolated polynucleotide consisting of 50-2000 contiguous nucleotides in sequence segments of an intron region of SEQ ID NO:11, or its complementary sequence.

14. An isolated polynucleotide consisting of an intron region of SEQ ID NO:11, or its complementary sequence.

15. A kit comprising the isolated polynucleotide of claim 13.

16. A composition comprising the isolated polynucleotide of claim 13.

17. A composition comprising the isolated polynucleotide of claim 14.

18. A kit comprising the isolated polynucleotide of claim 14.

* * * * *